(12) United States Patent
Bayne et al.

(10) Patent No.: US 8,013,001 B2
(45) Date of Patent: Sep. 6, 2011

(54) MODULATORS OF LXR

(75) Inventors: Christopher D. Bayne, Honolulu, HI (US); Alan T. Johnson, Kaneohe, HI (US); Shao Po Lu, San Diego, CA (US); Raju Mohan, Encinitas, CA (US); Michael C. Nyman, San Diego, CA (US); Edwin J. Schweiger, San Diego, CA (US); William C. Stevens, Jr., La Jolla, CA (US); Haixia Wang, San Diego, CA (US); Yinong Xie, Mission Viejo, CA (US)

(73) Assignee: Exelixis, Inc., South San Francisco, CA (US)

( * ) Notice: Subject to any disclaimer, the term of this patent is extended or adjusted under 35 U.S.C. 154(b) by 159 days.

(21) Appl. No.: 12/337,591

(22) Filed: Dec. 17, 2008

(65) Prior Publication Data

US 2010/0056582 A1  Mar. 4, 2010

Related U.S. Application Data

(60) Division of application No. 10/899,458, filed on Jul. 24, 2004, now Pat. No. 7,482,366, which is a continuation-in-part of application No. 10/327,813, filed on Dec. 20, 2002.

(60) Provisional application No. 60/342,707, filed on Dec. 21, 2001.

(51) Int. Cl.
A61K 31/4412 (2006.01)
C07D 213/64 (2006.01)

(52) U.S. Cl. ........ 514/345; 546/286; 546/290; 546/301; 546/302

(58) Field of Classification Search .................. 546/286, 546/290, 301, 302; 514/345
See application file for complete search history.

(56) References Cited

U.S. PATENT DOCUMENTS

| | | |
|---|---|---|
| 3,576,814 A | 4/1971 | Seidel et al. |
| 3,710,795 A | 1/1973 | Higuchi et al. |
| 3,951,982 A | 4/1976 | Goel et al. |
| RE28,819 E | 5/1976 | Thompson |
| 3,954,734 A | 5/1976 | Doub et al. |
| 4,028,084 A | 6/1977 | McNulty et al. |
| 4,044,126 A | 8/1977 | Cook et al. |
| 4,053,470 A | 10/1977 | Doub et al. |
| 4,093,730 A | 6/1978 | Butti et al. |
| 4,108,630 A | 8/1978 | Johnson et al. |
| 4,137,408 A | 1/1979 | Kaltenbronn et al. |
| 4,159,202 A | 6/1979 | Furrer et al. |
| 4,231,938 A | 11/1980 | Monaghan et al. |
| 4,328,245 A | 5/1982 | Yu et al. |
| 4,346,227 A | 8/1982 | Terahara et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,444,784 A | 4/1984 | Hoffman et al. |
| 4,559,354 A * | 12/1985 | Fuhrer et al. .................. 514/357 |
| 4,585,894 A | 4/1986 | Johnson et al. |
| 4,681,893 A * | 7/1987 | Roth ............................. 514/422 |
| 5,033,252 A | 7/1991 | Carter |
| 5,052,558 A | 10/1991 | Carter |
| 5,070,012 A | 12/1991 | Nolan et al. |
| 5,071,773 A | 12/1991 | Evans et al. |
| 5,112,839 A | 5/1992 | Gericke et al. |
| 5,145,966 A | 9/1992 | Aumueller et al. |
| 5,157,037 A | 10/1992 | Schuetz et al. |
| 5,177,080 A | 1/1993 | Angerbauer et al. |
| 5,194,438 A | 3/1993 | Schuetz et al. |
| 5,221,623 A | 6/1993 | Legocki et al. |
| 5,254,543 A | 10/1993 | Hanko et al. |
| 5,273,995 A | 12/1993 | Roth |
| 5,283,173 A | 2/1994 | Fields et al. |
| 5,298,429 A | 3/1994 | Evans et al. |
| 5,323,907 A | 6/1994 | Kalvelage |
| 5,326,767 A | 7/1994 | Schuetz et al. |
| 5,332,750 A | 7/1994 | Mederski et al. |

(Continued)

FOREIGN PATENT DOCUMENTS

CA  1 115 278 A1  12/1981

(Continued)

OTHER PUBLICATIONS

Sokolovskaya et al. (Chemistry of Heterocyclic Compounds 1977, 13(7), 723-727; translated from Khimiya Geterotsiklicheskikh Soedinenii 1977, 7, 897-901).*
Byrn et al., Chapter 11 Hydrates and Solvates in Solid-State Chemistry of Drugs (2nd Ed.), 1999, 233-247.*
A.M. Rouhi, Chem. & Eng. News, Feb. 24, 2003, 81(8), 32-35.*
Gong et al. Expert Opin. Ther. Targets 2004, 8(1), 49-54.*
Bennett et al. Expert Opin. Ther. Patents 2006, 16(12), 1673-1699.*
Michael et al. Mini-Reviews in Medicinal Chemistry 2005, 5(8), 729-740.*

(Continued)

Primary Examiner — Jason M Nolan
(74) Attorney, Agent, or Firm — McDonnell Boehnen Hulbert & Berghoff LLP

(57) ABSTRACT

Compounds of the invention, such as compounds of formula (I):

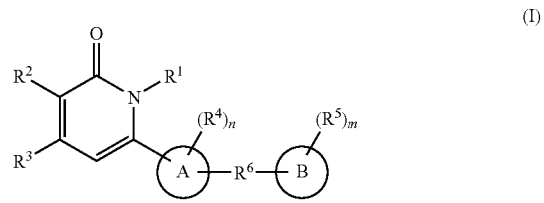

where n, m, A, B, $R^1$, $R^2$, $R^3$, $R^4$ and $R^5$ are defined herein, are useful as modulators of the activity of liver X receptors. Pharmaceutical compositions containing the compounds and methods of using the compounds are also disclosed.

34 Claims, No Drawings

U.S. PATENT DOCUMENTS

| | | |
|---|---|---|
| 5,332,833 A | 7/1994 | Sekiya et al. |
| 5,354,772 A | 10/1994 | Kathawala |
| 5,356,911 A | 10/1994 | Mueller-Gliemann et al. |
| 5,378,711 A | 1/1995 | Schuetz et al. |
| 5,378,720 A | 1/1995 | Hlasta et al. |
| 5,380,868 A | 1/1995 | Gallenkamp et al. |
| 5,399,566 A | 3/1995 | Katano et al. |
| 5,407,948 A | 4/1995 | Fey et al. |
| 5,410,066 A | 4/1995 | Gallenkamp et al. |
| 5,439,927 A | 8/1995 | Sekiya et al. |
| 5,466,233 A | 11/1995 | Weiner et al. |
| 5,466,701 A | 11/1995 | Hlasta et al. |
| 5,468,614 A | 11/1995 | Fields et al. |
| 5,484,890 A | 1/1996 | Johnson et al. |
| 5,504,070 A | 4/1996 | Bihovsky et al. |
| 5,514,825 A | 5/1996 | Vuligonda et al. |
| 5,543,534 A | 8/1996 | Vuligonda et al. |
| 5,571,696 A | 11/1996 | Evans et al. |
| 5,591,858 A | 1/1997 | Vuligonda et al. |
| 5,598,269 A | 1/1997 | Kitaevich et al. |
| 5,599,823 A | 2/1997 | Muller-Gliemann et al. |
| 5,599,967 A | 2/1997 | Vuligonda et al. |
| 5,605,915 A | 2/1997 | Vuligonda et al. |
| 5,607,967 A | 3/1997 | Friedman et al. |
| 5,612,363 A | 3/1997 | Mohan et al. |
| 5,618,503 A | 4/1997 | Johnson et al. |
| 5,618,844 A | 4/1997 | Gowravaram et al. |
| 5,618,931 A | 4/1997 | Beard et al. |
| 5,618,943 A | 4/1997 | Vuligonda et al. |
| 5,624,922 A | 4/1997 | Johnson et al. |
| 5,625,041 A | 4/1997 | Johnson et al. |
| 5,648,503 A | 7/1997 | Vuligonda et al. |
| 5,648,514 A | 7/1997 | Johnson et al. |
| 5,650,289 A | 7/1997 | Wood |
| 5,654,469 A | 8/1997 | Vuligonda et al. |
| 5,659,042 A | 8/1997 | Gillett et al. |
| 5,667,973 A | 9/1997 | Fields et al. |
| 5,674,713 A | 10/1997 | McElroy et al. |
| 5,683,888 A | 11/1997 | Campbell |
| 5,684,022 A | 11/1997 | Shuto et al. |
| 5,693,641 A | 12/1997 | Buckman et al. |
| 5,696,233 A | 12/1997 | Evans et al. |
| 5,698,571 A | 12/1997 | Audia et al. |
| 5,710,004 A | 1/1998 | Evans et al. |
| 5,723,620 A | 3/1998 | Vuligonda et al. |
| 5,723,666 A | 3/1998 | Vuligonda et al. |
| 5,726,173 A | 3/1998 | Mohan et al. |
| 5,726,198 A | 3/1998 | Mohan et al. |
| 5,728,553 A | 3/1998 | Goodey et al. |
| 5,728,697 A | 3/1998 | Mohan et al. |
| 5,728,846 A | 3/1998 | Vuligonda et al. |
| 5,731,308 A | 3/1998 | Mohan et al. |
| 5,731,311 A | 3/1998 | Mohan et al. |
| 5,741,657 A | 4/1998 | Tsien et al. |
| 5,741,896 A | 4/1998 | Vuligonda et al. |
| 5,747,542 A | 5/1998 | Vuligonda et al. |
| 5,753,635 A | 5/1998 | Buckman et al. |
| 5,760,276 A | 6/1998 | Beard et al. |
| 5,763,635 A | 6/1998 | Vuligonda et al. |
| 5,773,594 A | 6/1998 | Johnson et al. |
| 5,808,083 A | 9/1998 | Johnson et al. |
| 5,808,124 A | 9/1998 | Beard et al. |
| 5,814,645 A | 9/1998 | Kanellakopulos et al. |
| 5,843,746 A | 12/1998 | Tatsumi et al. |
| 5,846,970 A | 12/1998 | Buckman et al. |
| 5,846,972 A | 12/1998 | Buckman et al. |
| 5,855,654 A | 1/1999 | Willingham et al. |
| 5,859,005 A | 1/1999 | Mohan et al. |
| 5,863,914 A | 1/1999 | Mohan et al. |
| 5,863,930 A | 1/1999 | Dressel et al. |
| 5,869,497 A | 2/1999 | Johnson et al. |
| 5,877,207 A | 3/1999 | Klein et al. |
| 5,883,255 A | 3/1999 | Berges et al. |
| 5,888,830 A | 3/1999 | Mohan et al. |
| 5,935,984 A | 8/1999 | Goldmann et al. |
| 5,945,340 A | 8/1999 | Francis et al. |
| 5,951,121 A | 9/1999 | Takahashi |
| 5,952,345 A | 9/1999 | Klein et al. |
| 5,955,108 A | 9/1999 | Sutton et al. |
| 5,955,604 A | 9/1999 | Tsien et al. |
| 5,958,954 A | 9/1999 | Klein et al. |
| 5,962,473 A | 10/1999 | Johnson et al. |
| 5,994,375 A | 11/1999 | Kochanny et al. |
| 5,998,471 A | 12/1999 | Johnson et al. |
| 5,998,655 A | 12/1999 | Vuligonda et al. |
| 6,008,204 A | 12/1999 | Klein et al. |
| 6,025,382 A | 2/2000 | Bastian et al. |
| 6,028,033 A | 2/2000 | Hill et al. |
| 6,051,731 A | 4/2000 | Vuligonda et al. |
| 6,054,470 A | 4/2000 | Betageri et al. |
| 6,071,912 A | 6/2000 | Kochanny et al. |
| 6,087,505 A | 7/2000 | Vuligonda et al. |
| 6,090,810 A | 7/2000 | Klein et al. |
| 6,117,987 A | 9/2000 | Johnson et al. |
| 6,156,784 A | 12/2000 | Betageri et al. |
| 6,166,088 A | 12/2000 | Kochanny et al. |
| 6,184,215 B1 | 2/2001 | Elias et al. |
| 6,187,814 B1 | 2/2001 | Elias et al. |
| 6,187,933 B1 | 2/2001 | Vuligonda et al. |
| 6,204,054 B1 | 3/2001 | Sutton et al. |
| 6,221,808 B1 | 4/2001 | Schmidt et al. |
| 6,228,848 B1 | 5/2001 | Klein et al. |
| 6,242,454 B1 | 6/2001 | Kochanny et al. |
| 6,251,921 B1 | 6/2001 | Bastian et al. |
| 6,252,090 B1 | 6/2001 | Vasudevan et al. |
| 6,255,330 B1 | 7/2001 | Goldmann et al. |
| 6,265,350 B1 | 7/2001 | Schnatterer et al. |
| 6,268,365 B1 | 7/2001 | Betageri et al. |
| 6,274,091 B1 | 8/2001 | Mohan et al. |
| 6,284,768 B1 | 9/2001 | Betageri et al. |
| 6,291,677 B1 | 9/2001 | Vasudevan et al. |
| 6,294,503 B1 | 9/2001 | Gupta et al. |
| 6,303,785 B1 | 10/2001 | Vasudevan et al. |
| 6,313,107 B1 | 11/2001 | Vasudevan et al. |
| 6,316,503 B1 | 11/2001 | Li et al. |
| 6,344,182 B1 | 2/2002 | Sutton et al. |
| 6,344,561 B2 | 2/2002 | Vuligonda et al. |
| 6,348,186 B1 | 2/2002 | Sutton et al. |
| 6,350,774 B1 | 2/2002 | Bach et al. |
| 6,355,806 B1 | 3/2002 | Johnson et al. |
| 6,359,135 B1 | 3/2002 | Vasudevan et al. |
| 6,369,225 B1 | 4/2002 | Vasudevan et al. |
| 6,369,261 B1 | 4/2002 | Johnson et al. |
| 6,380,201 B1 | 4/2002 | Johnson et al. |
| 6,380,256 B1 | 4/2002 | Vasudevan et al. |
| 6,387,892 B1 | 5/2002 | Vasudevan et al. |
| 6,387,919 B1 | 5/2002 | Davis et al. |
| 6,387,951 B1 | 5/2002 | Vasudevan et al. |
| 6,391,901 B1 | 5/2002 | Chirgadze et al. |
| 6,399,774 B1 | 6/2002 | Vasudevan et al. |
| 6,416,957 B1 | 7/2002 | Evans et al. |
| 6,444,471 B1 | 9/2002 | Johnson |
| 6,465,663 B2 | 10/2002 | Vuligonda et al. |
| 6,469,028 B1 | 10/2002 | Klein et al. |
| 6,479,035 B1 | 11/2002 | Cripps et al. |
| 6,495,552 B2 | 12/2002 | Vasudevan et al. |
| 6,521,624 B1 | 2/2003 | Klein et al. |
| 6,531,599 B2 | 3/2003 | Vasudevan et al. |
| 6,538,149 B1 | 3/2003 | Vuligonda et al. |
| 6,555,690 B2 | 4/2003 | Johnson et al. |
| 6,603,019 B2 | 8/2003 | Vasudevan et al. |
| 7,482,366 B2 | 1/2009 | Bayne et al. |
| 2002/0072073 A1 | 6/2002 | Medina et al. |
| 2003/0181420 A1 | 3/2003 | Bayne et al. |
| 2005/0080111 A1 | 4/2005 | Bayne et al. |
| 2008/0119488 A1 | 5/2008 | Bayne et al. |

FOREIGN PATENT DOCUMENTS

| | | |
|---|---|---|
| CA | 2 077 412 A1 | 3/1993 |
| CA | 2 084 857 A1 | 6/1993 |
| CH | 00477475 A1 | 8/1969 |
| CN | 1289803 A1 | 4/2001 |
| DD | 244341 A1 | 4/1987 |
| DE | 01189994 B1 | 4/1965 |
| DE | 2637477 A1 | 2/1978 |
| DE | 2824341 A1 | 12/1978 |
| DE | 4309552 A1 | 9/1994 |

| | | |
|---|---|---|
| DE | 4313747 A1 | 11/1994 |
| DE | 4407488 A1 | 9/1995 |
| DE | 4414648 A1 | 11/1995 |
| DE | 19518739 A1 | 11/1996 |
| DE | 19627421 A1 | 1/1998 |
| DE | 19729061 A1 | 1/1999 |
| EP | 0 018 305 A1 | 10/1980 |
| EP | 0 051 813 B1 | 5/1982 |
| EP | 0 140 646 B1 | 5/1985 |
| EP | 0 176 064 A1 | 4/1986 |
| EP | 0 294 995 B1 | 12/1988 |
| EP | 0 339 105 A1 | 11/1989 |
| EP | 0 350 691 B2 | 1/1990 |
| EP | 0 406 656 B1 | 1/1991 |
| EP | 0 487 745 A | 6/1992 |
| EP | 0 500 297 A1 | 8/1992 |
| EP | 0 530 702 A1 | 3/1993 |
| EP | 0 542 059 A | 5/1993 |
| EP | 0 546 420 A1 | 6/1993 |
| EP | 0 547 708 A1 | 6/1993 |
| EP | 0 548 680 A1 | 6/1993 |
| EP | 0 551 572 B1 | 7/1993 |
| EP | 0 557 843 A2 | 9/1993 |
| EP | 0 594 019 A1 | 4/1994 |
| EP | 0 594 022 A1 | 4/1994 |
| EP | 0 624 583 B1 | 11/1994 |
| EP | 0 626 378 A1 | 11/1994 |
| EP | 0 705 600 A1 | 4/1996 |
| EP | 0 842 934 A1 | 5/1996 |
| EP | 0 733 629 A1 | 9/1996 |
| EP | 0 747 049 A1 | 12/1996 |
| EP | 0 747 055 A2 | 12/1996 |
| EP | 0 755 934 A1 | 1/1997 |
| EP | 0 797 995 A2 | 10/1997 |
| EP | 0 802 192 A1 | 10/1997 |
| EP | 0 824 917 A2 | 2/1998 |
| EP | 0 832 650 A2 | 4/1998 |
| EP | 0 838 458 A1 | 4/1998 |
| EP | 0 853 610 | 7/1998 |
| EP | 0 856 255 A2 | 8/1998 |
| EP | 0 859 661 B1 | 8/1998 |
| EP | 0 922 045 B1 | 6/1999 |
| EP | 0 931 786 A2 | 7/1999 |
| EP | 0 948 478 B1 | 10/1999 |
| EP | 1 006 108 A1 | 6/2000 |
| EP | 1 006 112 A1 | 6/2000 |
| EP | 1 031 578 A2 | 8/2000 |
| EP | 1 082 958 A2 | 3/2001 |
| EP | 1 226 832 A2 | 7/2002 |
| EP | 1 239 672 A2 | 9/2002 |
| EP | 1 300 396 A1 | 4/2003 |
| GB | 2345058 A1 | 6/2000 |
| JP | 51-122075 A1 | 10/1976 |
| JP | 53-025578 A | 3/1978 |
| JP | 53-050179 | 5/1978 |
| JP | 64-9979 A1 | 1/1989 |
| JP | 12-61371 A1 | 10/1989 |
| JP | 2124871 A1 | 5/1990 |
| JP | 8208516 A1 | 8/1996 |
| JP | 2001-302637 A1 | 10/2001 |
| WO | WO 91/19697 A1 | 12/1991 |
| WO | WO 9206085 A1 * | 4/1992 |
| WO | WO 92/07856 A1 | 5/1992 |
| WO | WO 93/10143 A1 | 5/1993 |
| WO | WO 93/11154 A1 | 6/1993 |
| WO | WO 93/16698 A1 | 9/1993 |
| WO | WO 93/20818 A1 | 10/1993 |
| WO | WO 93/23040 A1 | 11/1993 |
| WO | WO 93/23041 A1 | 11/1993 |
| WO | WO 94/00494 A1 | 1/1994 |
| WO | WO 94/21632 A1 | 9/1994 |
| WO | WO 95/02596 A1 | 1/1995 |
| WO | WO 95/22966 A1 | 8/1995 |
| WO | WO 95/27700 A1 | 10/1995 |
| WO | WO 95/28984 A1 | 11/1995 |
| WO | WO 96/03378 A1 | 2/1996 |
| WO | WO 96/11000 A1 | 4/1996 |
| WO | WO 96/11006 A1 | 4/1996 |
| WO | WO 96/12181 A1 | 4/1996 |
| WO | WO 96/12701 A1 | 5/1996 |
| WO | WO 96/20930 A1 | 7/1996 |
| WO | WO 96/22021 A1 | 7/1996 |
| WO | WO 96/37481 A1 | 11/1996 |
| WO | WO 96/37515 A1 | 11/1996 |
| WO | WO 96/38421 A1 | 12/1996 |
| WO | WO 96/40256 A1 | 12/1996 |
| WO | WO 96/40257 A1 | 12/1996 |
| WO | WO 96/40258 A2 | 12/1996 |
| WO | WO 96/41639 A1 | 12/1996 |
| WO | WO 97/09297 A1 | 3/1997 |
| WO | WO 97/10896 A1 | 3/1997 |
| WO | WO 97/25033 A1 | 7/1997 |
| WO | WO 97/29067 A1 | 8/1997 |
| WO | WO 97/31947 A1 | 9/1997 |
| WO | WO 97/48672 A2 | 12/1997 |
| WO | WO 98/00366 A1 | 1/1998 |
| WO | WO 98/07723 A1 | 2/1998 |
| WO | WO 98/07725 A1 | 2/1998 |
| WO | WO 98/17115 A1 | 4/1998 |
| WO | WO 98/25875 A1 | 6/1998 |
| WO | WO 98/32444 A1 | 7/1998 |
| WO | WO 98/39284 A1 | 9/1998 |
| WO | WO 98/48804 A1 | 11/1998 |
| WO | WO 98/58922 A1 | 12/1998 |
| WO | WO 99/23075 A1 | 5/1999 |
| WO | WO 99/31066 A1 | 6/1999 |
| WO | WO 99/33821 A1 | 7/1999 |
| WO | WO 99/40062 A1 | 8/1999 |
| WO | WO 99/52893 A1 | 10/1999 |
| WO | WO 99/55676 A1 | 11/1999 |
| WO | WO 99/65901 A1 | 12/1999 |
| WO | WO 00/02556 A | 1/2000 |
| WO | WO 00/17334 A2 | 3/2000 |
| WO | WO 00/25134 A1 | 5/2000 |
| WO | WO 00/37075 A | 6/2000 |
| WO | WO 00/37077 A1 | 6/2000 |
| WO | WO 00/39102 A | 7/2000 |
| WO | WO 00/40965 A1 | 7/2000 |
| WO | WO 00/49992 A2 | 8/2000 |
| WO | WO 00/54759 A | 9/2000 |
| WO | WO 00/57915 A1 | 10/2000 |
| WO | WO 00/66611 A | 11/2000 |
| WO | WO 00/73277 A1 | 12/2000 |
| WO | WO 00/78972 A2 | 12/2000 |
| WO | WO 01/03705 A1 | 1/2001 |
| WO | WO 01/15676 A2 | 3/2001 |
| WO | WO 01/19342 A1 | 3/2001 |
| WO | WO 01/22964 A1 | 4/2001 |
| WO | WO 01/37805 A1 | 5/2001 |
| WO | WO 01/42215 A1 | 6/2001 |
| WO | WO 01/47493 A1 | 7/2001 |
| WO | WO 01/60818 A1 | 8/2001 |
| WO | WO 01/82917 A2 | 11/2001 |
| WO | WO 01/96308 A1 | 12/2001 |
| WO | WO 02/18361 A2 | 3/2002 |
| WO | WO 02/26727 A2 | 4/2002 |
| WO | WO 02/36581 A1 | 5/2002 |
| WO | WO 02/083143 A1 | 10/2002 |
| WO | WO 02/085397 A1 | 10/2002 |
| WO | WO 02/089800 A2 | 11/2002 |
| WO | WO 02/090355 A1 | 11/2002 |
| WO | WO 02/098856 A2 | 12/2002 |
| WO | WO 03/002559 A2 | 1/2003 |
| WO | WO 03/002561 A1 | 1/2003 |
| WO | WO 03/059884 A | 7/2003 |
| WO | WO 2004/103974 A1 | 5/2004 |
| WO | WO 95/03803 A1 | 2/2005 |

OTHER PUBLICATIONS

Schafer et al. Drug Discovery Today 2008, 13 (21/22), 913-916.*
Horig et al. Journal of Translational Medicine 2004, 2(44).*
Zhao et al. Journal of Endocrinology 2010, 204, 233-240.*
Shiba et al.: N-vs. 0-(S-) PTC Alkylation of 3-Cyano-4, 6-Dimethyl-2-Oxo (Thioxol-l, 2-Dihydropyridinen, Phosphorus, Sulfur, and Silicon, 158:91-95 (2000).
Siddiq: "The Effect of the Substituents on the Carbonyl Absorptions of 2H-Pyrid-2-Ones and 2H-Thiopyran-2-Ones", Pakistan J. Sci. Ind. Res., 31(1):6-10 (1988).

Sinal et al.: "Targeted Disruption of the Nuclear Receptor FXR/BAR Impairs Bile Acid and Lipid Homeostasis", Cell, 102:731-744 (2000).

Soliman et at.: "Synthesis of Some Substituted Pyridones from Chalcones", J. Serb. Chem. Soc., 56(7):377-381 (1991).

Song et al.: "Ubiquitous Receptor: Structures, Immunocytochemical Localization, and Modulation of Gene Activation by Receptors for Retinoic Acids and Thyroid Hormones", Ann. New York Acad. of Sciences, 761:38-49 (1995).

Standeven et al.: "Specific Antagonist of Retinoid Toxicity in Mice", Toxicology Appl. Pharm., 138:169-175 (1996).

Standeven et al.: Retinoid-Induced Epiphyseal Plate Closure in Guinea Pigs, Fundamental Appl. Toxicology, 34:91-98 (1996).

Standeven et al.: "Retinoid-Induced Hypertriglyceridemia in Rats Is Mediated by Retinoic Acid Receptors", Fundamental Appl. Toxicology, 33:264-271 (1996).

STN Abstract 1990:400185, Document No. 113:185 for Kul'nevich, V. et al., "Synthesis and antiviral activity of N-alkyl-3-cyano-2-pyridones and 3-cyano-2-alkoxypyridines," Khim. -Farm, Zh., 24(2): 132-4 (1990).

STN Abstract 1985:45743, Document No. 102:45743 for Tsoi et at., "Synthesis of 1-Alkyl-4, 6-Dimethyl-2-Oxo: Micotinonitriles", Farm, Inst, Perm, USSR Deposited Doc., VINITI:3802-3883 (1983).

STN Abstract 1998:100985, Document No. 128:192569 for Kosulina et al., "Synthesis and anthelmintic activity of new 2-pyridinone derivatives," Khim. -farm. Zh., 31(4): 30-32 (1997).

Teng et al.: "Identification of Highly Potent Retinoic Acid Receptor a-Selective Antagonists", J. Med. Chem., 40:2245-2451 (1997).

Tominaga et al.: "Synthesis and Reactions of 6-Aryl-and 6-Styryl-3-cyano-4-methylthio-2H-pyran-2-ones", Chem. Pharm. Bull., 32(9):3384-3395 (1984).

Tomkins, G.M.: "The Metabolic Code", Science, 189:760-763 (1975).

Tonkikh et al.: "4(3H)-Quinazolinones Containing Heterocyclic Group in Position", Chemistry of Heterocyclic Compounds, 36(7):822-829 (2000).

Tsien, R.Y.: "The Green Fluorescent Protein", Annu. Rev. Biochem., 67:509-544 (1998).

Tsoi et al.: "Synthesis of 1-Alkyl-4, 6-Dimethyl-2-Oxo: Micotinonitriles", Farm, Inst, Perm, USSR Deposited Doc., VINITI:3802-3883 (1983).

Turnder et al., "Insulin resistance, impaired glucose tolerance and non-insulin-dependent diabetes, pathologic mechanisms and treatment: Current status and therapeutic possibilities", Progress in Drug Research, 51:3-94 (1998).

Urizar et al.: "The Farnesoid X-activated Receptor Mediates Bile Acid Activation of Phospholipid Transfer Protein Gene Expression", J. Biol. Chem., 275(50):39313-39317 (2000).

Vanallan et al.,: "Reactions of Some 4-Methylene-4H-Pyran Derivatives with Primary and Secondary Amines", J. Heterocycl. Chem., 7(3):495-507 (1970).

Wan et al., "Hepatocyte-Specific Mutation Establishes Retinoid X Receptor a as a Heterodimeric Integrator of Multiple Physiological Processes in the Liver", Mol. Cell. Biol., 20(12):4436-4444 (2000).

Whitlow et al.: "Crystallographic analysis of potent and selective factor Xa inhibitors complexed to bovine trypsin", Acta Cryst., D55:1395-1404 (1999).

Willy et al.: "LXR, a nuclear receptor that defines a distinct retinoid response pathway", Genes & Development, 9:1033-1045 (1995).

Wright et al.: "UKPDS 28: A Randomized Trial of Efficacy of Early Addition of Metformin in Sulfonylurea-Treated Type 2 Diabetes", Diabetes Care, 21(1):87-92 (1998).

Xu et al.: "Polymer Supported Bases in Solution-Phase Synthesis. 2. A Convenient Method for N-Alkylation Reactions of Weakly Acidic Heterocycles", Biooroganic & Med. Chem. Ltrs., 8:1089-1092 (1998).

Yalpani, M.: "Cholesterol-lowering drugs", Chemistry & Industry, pp. 85-89 (1996).

Zapata et al.: Estudio Cinetico de la Hidrolisis Acida de la 1-Bencilidenamino-4,6-Difenil-2-Piridonan, Hidroeists, 80:526-530 (1984).

Zayed et al.: "Synthesis of Some new N'-Substituted N-Aminopyridine Derivatives", Pharmazie, 40:725-726 (1985).

Zhang et al.: "AT, Receptor Blockers Prevent Sympathetic Hyperactivity and Hypertension by Chronic Ouabain and Hypertonic Saline", Am. J. Physiol. Heart Circ. Physiol., 280:H1318-H1323 (2001).

Zhou et al.: "Nuclear Receptors Have Distinct Affinities for Coactivators: Characterization by Fluorescence Resonance Energy Transfer", Mol. Endocrinol., 12(10):1594-1604 (1998).

Hafez et al.: "Synthesis of Azo-Sulfa Drugs Based on 2-Pyridinone and 2-Pyridinethione", Journal of the Chinese Chemical Society, vol. 40, 1993, 289-296.

El-Kholy et al.: "Pyrone Series. Part XI. Reactivity of 4,6-Diaryl-2-Pyrones and Cyclo-Propane Derivatives Obtained from 2-Pyrazolines", J. Chem. Soc. C, (11):1578-1584 (1970).

El-Hashash et al.: "Behaviour of 3-Nitrobenzal-p-Isopropyl or p-Chloro-aceptophenones Toward Oxygen and Carbon Nucleophiles and Some Studies with the Products", J. Chem. Soc. Pak., 9(2):229-234 (1987).

Ehm: "Uber die Kondensation von N-Substituierten Acetessigsaure-amiden zu a-Pyridonderivaten und uber davon abgeleitete Verbindungen", Liebigs Ann. Chem., 10:1642-1660 (1977).

Bomika et al.: "Alkylation of 3-Cyano-2-Oxopyridine Derivatives", Khimiya Geterotsiklicheskikh Soediinenii, 8:899-902 (1976).

Disepio et al.: "Identification of the AP1-Antagonism Domain of Retinoic Acid Receptors", Mol. Cell Biol. Res. Comm., 1:7-13 (1999).

Coniff et al.: "Multicenfer, Placebo-Controlled Trial Comparing Acarbose (BAY g 5421) With Placebo, Tolbutamide, and Tolbutamide-Plus-Acarbose in Non-Insulin-Dependent Diabetes Meltitus", Am. J. Med., 98:443-451 (1995).

Coniff et al.: "Acarbose: A Review of US Clinical Experience", Clinical Therapeutics, 19(1):16-26 (1997).

Chiba et al.: "Distinct Retinoid X Receptor-Retinoic Acid Receptor Heterodimers Are Differentially Involved in the Control of Expression of Retinoid Target Genes in F9 Embryonal Carcinoma Cells", Mol. Cell. Biol., 17(6):3013-3020 (1997).

Chiasson et al.: "The Efficacy of Acarbose in the Treatment of Patients with Non-Insulin-dependent Diabetes Mellitus", Ann. Internal Med.,121:928-935 (1994).

Chiang et al.: "Farnesoid X Receptor Responds to Bile Acids and Represses Cholesterol 7a-Hydroxylase Gene (CYP7A 1) Transcription", J. Biol. Chem., 275(15):10918-10924 (2000).

Chen et al.: "Synthesis and Fluorescence Behaviour of Some 3-Cyano-4-Substituted-6-Pyrenyl-2-Pyridone Derivatives", Dyes and Pigments, 27(3):249-259 (1995).

Database CAPLUS on ACS, AN 1988:167259, Jure, M. et al., "1-Methyl-6-phenyl-4-trifluoromethyl-3-cyano-2-pyridone and its properties", Latvijas PSR Zinatnu Akademijas Vestis, Kimijas Serija, (5):627-631 (1987).

Database Caplus on ACS, AN 1987:458776, Gutcait, A. et al., "Synthesis, structure, and properties of 1-amino-6-phenyl-4-trifluoromethyl-3-cyano-2-pyridone", Latvijas PSR Zinatnu Akademijas Vestis, Kimijas Serija, 5:607-12 (1986).

Carpenter et al.: "Configuring Radioligand Receptor Binding Assays for HTS Using Scintillation Proximity Assay Technology", Meth. Mol. Biol., vol. 190, Book: High Throughput Screening: Methods and Protocols, Humane Press Inc., Totowa, New Jersey, pp. 31-49 (2002).

Cade et al.: Lack of Biological Activity of Preproendothelin [110-130] in Several Endothelin Assays, Life Sciences, 47 (23):2079-2103 (1990).

Buckman et al.: "Design, Synthesis, and Biological Activity of Novel Purine and Bicyclic Pyrimidine Factor Xa Inhibitors", Bioorganic & Med. Chem. Ltrs, 8:2235-2240 (1998).

Buckman et al.: "Automated Parallel Solid-Phase Synthesis of Non-Peptide CCR1 Receptor Antagonists", Combinatorial Chem. & High Throughput Screening, 5:249-251 (2002).

Bronstein et al.: "1,2-Dioxetanes: Novel Chemiluminescent Enzyme Substrates. Applications to Immunoassays", J. Bioluminescence and Chemiluminescence, 4:99-111 (1989).

Alajarin et al., "Nuevas Reacciones de las Aldiminas Derivadas de la 1-Amino-4,6-Difenil-2-Piridona", Alaes de Quimica, 74(4), 1978, 625-627.

Aggarwal et al., "Reaction of α-Ketoketene S, N-Acetals with Cyanoacetamide: A New General Method for Substituted and Fused 4-9N-Alkylamino-, N-Arylamino-, or N-Morpholino)-3-Cyano-2(1H)-Pyridones", Synthesis, vol. 3, 1982, 214-216.

Buysens, K. J. et al.: "Intramolecular Diels-Alder Reactions of 2(1H)-Pyrazinones: Synthesis of New Furo/Pyrano-pyridinones and -pyridines," Tetrahedron, vol. 51, No. 45, 1995 pp. 12463-12478, XP004104713.

Borch, R.F. et al.: "New synthesis of substituted 2(1H)-pyridones. Synthesis of a potential camptothecin intermediate," J. Org. Chem., vol. 37, No. 8, 1972, pp. 1141-1145.

Pelton, P.D. and Demarest, K.T.: "Nuclear Receptors as Potential Targets for Modulating Reverse Cholesterol Transport," Current Topics in Medicinal Chemistry, vol. 5, 2005, pp. 265-282.

Kurihara, Takushi et al., "Synthesis of C-nor-4,6-Secocamptothecin and Related Compounds," Journal of Heterocyclic Chemistry, 1993, vol. 30, No. 3, pp. 643-652.

Noguchi, Michihiko, et al., "Reaction of 1, 3, 6-Trimethylpyrimidine-2, 4 (1H, 3H)-Dione-5-Carbaldehyde with Aldimines," Chemistry Express, 1989, vol. 4, No. 8, pp. 503-506.

Van Allan, J.A., et al., "Reactions of Some Pyranylidene Esters with Amines," Journal of Heterocyclic Chemistry, 1971, vol. 8, No. 5, pp. 803-807.

An Office Action dated Dec. 16, 2009 in the corresponding Canadian Application No. 2,469,435, listing CAS registry numbers.

STN Columbus printout generated on Jun. 25, 2010, pp. 1-172.

Hoberg, Heinz et al.: "Nickel(0)-katalysierte [2+2+2]-Cycloaddition von Alkynen mit Isocyanaten zu 2-Oxo-1,2-dihydrophyridinen," Synthesis, 1982, No. 4, pp. 324-325.

Kuzuya, Masayuki et al.: "The Structure-Reactivity-Chemoselectivity Relationship on the Reactions of 1-Unsubstituted Tautomeric 2-Pyridones with Benzyne," Bulletin of the Chemical Society of Japan, 1985, vol. 58, No. 4, pp. 1149-1155.

Sladowska, Helena: "Investigations on the Synthesis and Properties of Some N-Arylpiperazinylalkyl Derivatives of Imides of 3, 4-Pyridinedicarboxylic Acids," Farmaco, 1963, vol. 48, No. 1, pp. 85-94.

Jahine, H. et al.: "Reactions with 3-Chloro & 3-Hydrazino-4-benzyl-6-phenylpyridazines," Indian Journal of Chemistry, Section B: Organic Chemistry Including Medicianl Chemistry, 1977, vol. 15B, No. 4, pp. 352-355.

Hobhkob, M.C. et al., Zhurnal Organicheskoi Khimii, 1996, vol. 32, No. 5, pp. 667-674.

Musante, Carlo and Fatutta, Silvana—Sul furoil-piruvato di etile: composti eterociclici contenenti il nucleo del furano (*),: Gazzetta Chimica Italiana, 1958, vol. 88, pp. 879-898.

Fatutta, Silvana: "Benzofuroll-2-piruvato di etile ealcuni soul prodotti di condensazlone," Gazzetta Chimica Italiana, 1959, vol. 89, pp. 964-978.

Ariegnn, V. et al.: "Cercetari asupra unor N.R.-x-piridone, Nota II. Derivati sulfonamidlici ai x-piridonei," Farmacia, 1971, vol. 19, No. 3, pp. 129-133.

Sladowska, Helena: "Badania Nadsynteza I Wlasciwosciamio-I N-Arylopiperazyny-Lopropylowych Pochodnych Estru Etylowego Kwasu 3-CYJA-No-2-Hydroksy-6-Metylopirydyno-4-kARBOKSYLOWEGO," Acta Poloniae Pharmaceutca, 1992, vol. 49, No. 1-2, pp. 61-65.

Office Action mailed on Nov. 14, 2008 in U.S. Appl. No. 10/327,813.

Final Office Action mailed on May 1, 2008 in U.S. Appl. No. 10/327,813.

Office Action mailed on Oct. 17, 2007 in U.S. Appl. No. 10/327,813.

Final Office Action mailed on Mar. 26, 2007 in U.S. Appl. No. 10/327,813.

Office Action mailed on Aug. 15, 2006 in U.S. Appl. No. 10/327,813.

Office Action mailed on Feb. 7, 2006 in U.S. Appl. No. 10/327,813.

Office Action mailed on Jul. 5, 2005 in U.S. Appl. No. 10/327,813.

Office Action mailed on Sep. 2, 2004 in U.S. Appl. No. 10/327,813.

Agarwal et al., "AGN193109 Is a Highly Effective Antagonist of Retinoid Action in Human Ectocervical Epithelial Cells", J. Biol. Chem., 271(21), 1996, 12209-12212.

Berger et al., "Secreted Placental alkaline phosphatase: a powerful new quantitative indicator of gene expression in eukaryotic cells", Gene, 66:I-10 (1988).

Barrett-Connor, E., "Epidemiology, Obesity, and Non-Insulin-Dependent Diabetes Mellitus", Epidemiol. Rev., 11:172-181 (1989).

Bapat et al., "Pyridines as Leaving Groups in Synthetic Transformations: Nucleophilic Displacements of Amino Groups, and Novel Preparations of Nitriles and Isocyanates", Tetrahedron Letters, 31:2691-2694 (1976).

Bantick et al. , "New Non-Peptide Angiotensin II Receptor Antagonists. 1 : Structure-Activity Relationships of a Series of 2(1H)-Pyridinones", Bioorganic & Medicinal Chemistry Letters, 4(1):121-126 (1994).

Balicki et al., "Novel Pyrethroid Insecticides III* Synthesis of Some N-(1-Pyridyl) Substituted Amides of Cyclopropanecarboxylic Acids", Bulletin of the Polish Academy of Sciences Chemistry, 37(7-8):269-275 (1986).

Arques et al., "Some Synthetic Applications of 1-Amino-4,6-Diphenylpyridine-2-Thione", Anales de Quimica, 77:248-250 (1981).

Aranyos et al., "Novel Electron-Rich Bulky Phosphine Ligands Facilitate the Palladium-Catalyzed Preparation of Diaryl Ethers", J. Am. Chem. Soc., 121:4369-4378 (1999).

Ansel, H.C., Chapter 6, "Peroral Solids, Capsules, Tablets, and Controlled-Release Dosage Forms", Book: Introduction to Pharmaceutical Dosage Forms, Lea & Febiger, Philadelphia, 4th Ed., Lea & Febiger, Philadelphia, p. 126 (1985).

Ali et al., "Action of Grignard Reagents on 2-Alkylthio-s-triazolo[1,5-b)isoquinolin-5 (1OH)-ones & Their Derivatives", Indian Journal of Chemistry, 13:1145-1148 (1975).

Alejandre-Duran et al., "Study on the Mutagenicity of Nifurtimox and Eight Derivatives with the L-Arabinose Resistance Test of *Salmonella typhimurium*", Mutation Research, 206:193-200 (1988).

Alberti et al., "Structural characterisation of the mouse nuclear oxysterol receptor genes LXRa and LXRB", Gene, 243:93-103 (2000).

Alajarin et al. , "Preparation of Fused Meso-Ionic Compounds from 1-Amino-4,6-Diphenyl-2-Pyridone", Tetrahedron Letters, 21:4025-4026 (1980).

Alajarin et al., 1-Amino-4,6-Difenil-2-Pyridone in Organic Synthesis: Conversion of Benzylic Alcohols and Benzylamines into Benzonitril and Conversion of Aryl Methyl Ketones into Aroyl Cyanides, Anales de Quimica, 77:338-341 (1980).

El-Kholy et al.: "Prone Series. X. Reactivity of 4,5,6-Triaryl-2-Pyridones and the Corresponding Thio-Analogues", J. Chem. Soc. ,C, (15):1950-1954 (1969).

El-Kholy et al.: "Reactivity of 3-Amino-, 3-Halogeno-, and 3-Nitro-2-Pyrones and Thiopyrones", J. Heterocycl. Chem., 12(1):129-133 (1975).

El-Mobayed et al.: "Reactions with 6-Acetyl 3, 5-Diarylcyclohexen-1-Ones and 2-Hydroxy 4, 6-Diaryl Nicotinonitrile Synthesised by Michael Reactions from 3-Nitrobenzal-p-isopropyl Acetophenones and some Studies with the Products", Egypt. J. Pharrn. Sci., 30(1-4):329-337 (1989).

Elgemeie et al.: "Synthesis of Several N-Substituted Amino-2-Pyridones", Organic Preparations and Procedures, 26(4):465-497 (1994).

Elgemeie et al.: "Novel Synthesis of Pyridine-2(1H)Thiones, N-Amino-2-Pyridones and Pyridazine Derivatives", Organic Preparations and Procedures Int., 23(5):645-650 (1991).

Elgemeie et al.: "Reactions of Acylthiosemicarbazides with b-Diketones: Novel Synthesis of N-(1-Pyridyl)thiourea Derivatives", J. Chem. Research, (S):87 (1993).

Elmoghayer et al.: "Activated Nitriles in Heterocyclic Synthesis. Part III (1). Synthesis of N-Amino-2-Pyridone, Pyranopyrazole and Thiazolopyridine Derviatives", J. Heterocyclic Chem., 21:1885-1887 (1984).

Evans et al.: "Synthesis of Diaryl Ethers through the Copper-Promoted Arylation of Phenols with Arylboronic Acids. An Expedient Synthesis of Thyroxine", Tetrahedron Ltrs., 39:2937-2940 (1998).

Evans, R.M.: "The Steriod and Thyroid Hormone Receptor Superfamily", Science, 240:889-895 (1988).

Faid-Allah: "Synthesis of Pyridones and Dihydropyridines from Pyrylium Salts and Nitriles from Adimines", Croatica Chemica ACTA, 60(4):717-733 (1987).

Flier, J.S.: "Insulin Receptors and Insulin Resistance", Ann. Rev. Med., 34:145-160 (1983).

Furukawa et al.: "Synthesis of 5-(Alkylaminocarbonyl)-4,6-Dimethyl-2-Pyridones from N-Alkyl-3-Oxobutanamides", Synthesis, 12:1715-1717 (1998).

Garcia et al.: "Morbidity and Mortality in Diabetics In the Framingham Population: Sixteen Year Follow-up Study", Diabetes, 23(2):105-111 (1974).

Glass, C.K.: "Differential Recognition of Target Genes by Nuclear Receptor Monomers, Dimers, and Heterodimers", Endocrine Rev., 15(3):391-407 (1994).

Glickman et al.: "A Comparison of ALPHAScreen, TR-FRET, and TRF as Assay Methods for FXR Nuclear Receptors", J. Biomol. Screening, 7(1):3-10 (2002).

Gorman et al.: "Recombinant Genomes Which Express Chloramphenicol Acetyltransferase in Mammalian Cells", Mot. Cell. Biol., 2(9):1044-1051 (1982).

Gutcait et al.: "Synthesis, structure and properties of 1-amino-6-phenyl-4-trifluoromethyl-3-cyano-2-pyridone," Lativijas PSR Zinatnu Akademijas Vestis, Kimijas Serija (5):607-612 (1986).

Haffner, S.M.: "Management of Dyslipidemia in Adults With Diabetesn, Diabetes Care", 21(1):160-178 (1998).

Hayashi et al.: "Syntheses and Anti-tumor Activity of N-Heterocyclic Compounds Having the Cyclic Hydrazide Structure", Yakugaku Zasshi, 98(11):1560-1565 (1978).

Hayashi et al.: "2-Amino-3-Phyenylisocarbostyril", Yakugaku Zasshi, 94(10):1322-1327 (1974).

Heyman et al.: "9-Cis Retinoic Acid Is a High Affinity Ligand for the Retinoid X Receptor", Cell, 68:397-406 (1992).

Howard et al.: "Lipoprotein Composition in Diabetes Meltitus", Atherosclerosis, a:153-162 (1978).

Issac: "Model Studies Related to Synthesis and 1,4-Dipolar Cycloaddition Reactions of Mesoionic Heterocycles", Bull. Chem. Soc. Jpn., 72:503-509 (1999).

IUPAC-IUB Commission on Biochemical Nomenclature Abbreviated Nomenclature of Synthetic Polypeptides (Polymerized Amino Acids): Revised Recommendations, Biochem., 11(5):942-944-(1972).

Iwamoto et al.: "Effect of Combination Therapy of Troglitazone and Sulphonylureas in Patients with Type 2 Diabetes Who Were Poorly Controlled by Sulphonylurea Therapy Alone", Diabetic Medicine, 13:365-370 (1996).

Janowski et al.: "An oxysterol signalling pathway mediated by the nuclear receptor LXRa", Nature, 383:728-731 (1996).

Johnson et al.: "High Affinity Retinoic Acid Receptor Antagonists: Analogs of AGN 193109", Bioorganic & Med. Chem. Ltrs, 9:573-576 (1999).

Johnson et al.: "Identification of Retinoic Acid Receptor B Subtype Specific Agonists", J. Med. Chem., 39 (26):5027-5030 (1996).

Johnson et al.: "Synthesis and Characterization of a Highly Potent and Effective Antagonist of Retinoic Acid Receptors", J. Med. Chem., 38:4764-4767 (1995).

Johnson et al.: "Synthesis and Biological Activity of High-Affinity Retinoic Acid Receptor Antagonists", Bioorganic & Med. Chem., 7:1321-1338 (1999).

Joslin, E.P.: "Arteriosclerosis and Diabetes", Ann. Clin. Med., 5(12):1061-1080 (1927).

Jurado et al.: "Genetic Differences Between the Standard Ames Tester Strains TA100 and TA98", Mutagenesis, 8(6):527-632 (1993).

Jurado et al.: "Role of Classical Nitroreductase and 0-Acetyltransferase on the Mutagenicity of Nifurtimox and Eight Derivatives in *Salmonella typhimurium*", Environmental and Molecular Mutagenesis, 26:86-93 (1995).

Jure, M. et al.: "1-Methyl-6-phenyl-4-trifluoromethyl-3-cyano-2-pyridone and its properties", Latvijas PSR Zinatnu Akademijas Vestis, Kimijas Serija, (5):627-631 (1987).

Kain, S.R.: "Use of Secreted Alkaline Phosphatase as a Reporter of Gene Expression in Mammalian Cells", Book: Methods in Molecular Biology, vol. 63: Recombinant Protein Protocols: Detection and Isolation, Humana Press Inc., Totowa, New Jersey, pp. 49-60 (1997).

Kaplan et al. (Eds.): "Chapter 10: Cardiovascular Diseases", Book: Health and Human Behavior, McGraw-Hill, Inc., pp. 206-242 (1993).

Katritzky et al.: "Heterocycles in Organic Synthesis, Part 23. 1-Amino-4,6-diphenyl-2-pyridone: a New Reagent for the Conversion of Aldehydes into Nitriles", J. Chem. Soc., Perkins Trans., 1(8):1957-1960 (1979).

Katritzky et al.: "1-Chloromethyl-3,5-Dimethylpyrazole Hydrochloride. A Useful Synthetic Intermediate", Can. J. Chem., 67:1144-1147 (1989).

Katritzky et al.: "Preparation of Some Novel Pyridone Derivatives", Pakistan J. Sci. Ind. Res., 21(1):1-4 (1978).

Katritzky et al.: "a-(4,6-Diphenyl-2-oxo-1-pyridyl)benzyl-lithiums and their Reactions with Electrophiles", J. Chem. Soc. Perkins 1:2851-2855 (1980).

Kislyi et al.: "Investigation of the Regioselectivity of Alkylation of 3-Nitropyridin-2(1H)-ones", Russian Chemical Bulletin, International Edition, 50(3):460-463 (2001).

Klein et al.: "Identification and Functional Separation of Retinoic Acid Receptor Neutral Antagonists and Inverse Agonists", J. Biol. Chem., 271(37):22692-22696 (1996).

Knowler et al.: "Obesity in the Pima Indians: its magnitude and relationship with diabetes", Am J. Clin. Nutr., 53:1543S-1551S (1991).

Kochhar et al.: The use of a retinoid receptor antagonist in a new model to study vitamin A-dependent developmental eventsn, Int. J. Dev. Biol., 42:601-608 (1 998).

Koller et al.: "The Preparation of Substituted 1(2H)-Isoquinolinones From Polylithiated 2-(2-Methylphenyl) hydrazinecarboxylic Acid Esters", Synthetic Communications, 26(9):1763-1774 (1996).

Kosulina et al.: "Synthesis and anthelmintic activity of new 2-pyridinone derivatives," Khim. -farm. Zh. 31(4):30-32 (1997).

Kumar et al.1: "Keten Dithioacetals Part II. Reaction of 30Cyano-4-Methylthio-2(1H)-Pyridones with Hydrazine and Guanidine: Synthesis of Novel Substituted and Fused Pyrazolo [4,3-c]Pyridone and Pyrido[4,3-d]Pyrimidine Derivatives", J, Chem. Soc., Perkins Trans, 1(8):857-862 (1978).

Kul'Mevocj, V. et al.: "Synthesis and antiviral activity of N-alkyl-3-cyano-2-pyridones and 3-cyano-2-alkoxypyridines," Khim. -Farm. Zh., 24(2):132-4 (1990).

Kuthan et al.: "Ome 3-Cyano-4, 6-Diaryl-2-Pyridones with Luminiscent Properties", Collection Czechoslov. Chem. Commun., 44:2409-2416 (1979).

Kwiterovick, P.O.: "State-of-the-Art Update and Review: Clinical Trials of Lipid-Lowering Agents", Am. J. Cardiology, 82(12A):3U-I7U (1998).

Laakso et al.: "Epidemiology of macrovascular disease in diabetes", Diabetes Reviews, 5(4): 294-375 (1997).

Lehmann et al.:"Activation of the Nuclear Receptor LXR by Oxysterols Defines a New Hormone Response Pathway", J. Biol, Chem., 272(6):3137-3140 (1997).

Levin et al.: "9-Cis retinoic acid stereoisomer binds and activates the nuclear receptor RXRa", Nature, 355:359-361 (1992).

Lisovenko et al.: "Intermolecular Cyclodimerization of Aroyl(Imidoyl)Ketenes Generated by Thermolysis of 5-Aryl-4-Imidoyl-2,3-Dihydro-2,3-Furandiones", Chemistry of Heterocyclic Compounds, 37(10): 1314-1316 (2001).

Lorenzo et al.: "Reactividad de N,N'Biheterociclos Frente A Reactivos Nucleofilos", Anales de Quimica, 77:351-354 (1980).

Mahler et al.: "Clinical Review 102: Type 2 Diabetes Mellitus: Update on Diagnosis, Pathophysiology, and Treatment", J. Clin. Endocrin. & Metab., 84(4):1165-1171 (1999).

Mangalsdorf et al.: "Characterization of three RXR genes that mediate the action of 9-cis retinoic acid", Genes & Development, 6:329-344 (1992).

Mangelsdorf et al.: "The RXR Heterodimers and Orphan Receptors", Cell, 83:841-850 (1996).

Martinez-Ortiz et al.: "Contribucion al Estudio Polarografico de la 1-Bencilidenamino-4,6-Difenil-2-Piridona", An. Univ. Murcia, Cienc., Volume Date 1980-1982, 39-40(1-4): 147-157 (1983).

Martinez-Ortiz et al.: "Electrochemical Behavior of 1-(o-Nitrobenzylidene) Amino-4,6-Diphenyl-2-Pyridone", Port Electrochem Acta, 3:147-159 (1985).

Martinez-Ortiz et al.: "Electrochemical Behaviour of Aldimines Derived from 1-Amino-4,6-Diphenyl-2-Pyridone", J. Electroanal. Chem., 154:193-203 (1983).

Mester et al.: "NMR Studies in the Heterocyclic Series XXX-Carbon-13 NMR Study of 5-Nitrofurfural Derivatives", Magn. Reson. Chem., 25(8):737-739 (1987).
Mester et al.: "Activity Against Trypanosoma Cruzi of New Analogues of Nifurtimox", Arch. Pharm. (Weinheim), 320: 115-120 (1987).
Mester et al.: "Quantitative Structure Activity Relationships of 5-Nitrofuran Derivatives", Chromatographia, 30 (3/4):191-194 (1990).
Mishnev et al.: "Molecular and Crystal Structure of 1-(2-Hydroxybenzilidene)Amino-6-Phenyl-4-Trifluoromethyl-3-Cyano-2-Pyridone" Letvijas PSR Zinatu akademijas Vestis. Kimijas Serija (2):168-171 (1987).
Mohan et al.: "Synthesis and Biological Activity of Angiotensin II Analogues Containing a Val-His Replacement ValψICH(CONH2)NH)His", J. Med. Chem., 34:2402-2410 (1991).
Mohen et al.: "Solid Phase Synthesis of N-Substituted Amidinophenoxy Pyridines as Factor XA Inhibitors", Bioorganic & Med. Chem. Ltrs, 8:1877-1882 (1998).
Molina et al.: "Fused Mesoionic Heterocycles", Tetrahedron Letters, 24(33):3523-3526 (1983).
Molina et al.: "Reaccion de 4,6-difenil-2-piridonas N-sustituidas con 1-fluoro-2, 4-dinitrobenceno", An. Univ, Murcia Clinic, Ciene., Volume Date 1980-1982, 39-40(1-4):227-236 (1983).
Molina et al.: "Heterocyclization Reactions with Carbodiimides Synthesis of Fused 1,2,4-Triazoles", Heterocycles, 24(12):3363-3368 (1986).
Molina et al.: "Influencia de Ia Temperatura Sobre la Naturalezed de Los Productos de Termolisis de Los Derivados N-Acilados de la 1-Amino-4, 6-Difenil-2-Piridona", Anales de Quimica, 24:1125-1127 (1978).
Molina et al.: New Synthesis of Pyrazole and Isoxazole Derivativesn, J.Heterocyclic Chem., 21:461-464 (1984).
Molina et al.: "Preparation Y Propiedades de Aldimines Derivadas de la 1-Amino-4,6-Difenil-2-Piridona Y Benzaldehidos Orto-Sustituidos", Anales de Quimica, 75(9-10):739-44 (1979).
Molina et al.: "Fused Mesoionic Heterocycles: Synthesis of 1,3,4-Oxadiazolo[3,3-a] Pyridine and 1,3,4-Thiadiazolo [3,2-a]Pyridine Derivatives", J. Chem. Soc. Perkins Trans, 1(2):351-355 (1982).
Molina et al.: "Fused Mesoionic Heterocycles: Synthesis of 1,3,4-Triazolo[3,2-a]Pyridine Derivatives", J. Chem. Soc. Perkin Trans., 1(8):1891-1897 (1984).
Moraga et al.: "Genotoxicity Testing of Antiparasitic Nitrofurans in the Drosophila Wing Somatic Mutation and Recombination Test", Metagenesis, 4(2):I05-110 (1989).
Mukherjee et al.: "Ligand and coactivator recruitment preferences of peroxisome proliferator activated receptor a", J. Steroid Biochem. Mol. Biol., 81:217-225 (2002).
Nagpal et al.: "Tazarotene-Induced Gene 1 (TIG1), a Novel Retinoic Acid Receptor-Responsive Gene in Skin", J. Invest. Dermatal., 106(5):269-274 (1996).
Nakib et al.: "A Novel Synthetic Route to 2,3,4-Trisubstituted 6-Pheynl-Pyridines", J. Chem. Research, S:146-147 (1988).
Ng et al.: "Design, Synthesis, and Biological Activity of Novel Factor Xa Inhibitors: 4-Aryloxy Substituents of 2,6-Diphenoxypyridines", Bioorganic & Med.. Chem., 10:657-666 (2002).
Nogrady, T.: "Pro-Drugs and Soft Drugs", Medicinal Chemistry: A Biochemical Approach, Oxford University Press, New York, pp. 388-394 (1985).
O'Malley (Ed.): "Editorial: Did Eucaryotic Steroid Receptors Evolve from Intracrine Gene Regulators?", Endocrinology, 125(3):1119-1120 (1989).
Owicki, J.C.: "Fluroescence Polarization and Anisotrophy in High Throughput Screening: Perspectives and Primer", J. Biomol. Screening, 5(5):297-306 (2000).
Peet et al.: "The LXRs: a new class of oxysterol receptors", Curr. Opin. Genetics Develop., 8:571-575 (1998).
Peet et al.: "Cholesterol and Bile Acid Metabolism Are Impaired in Mice Lacking the Nuclear Oxysterol Receptor LXRa", Cell, 93:693-704 (1998).

Phillips et al.: "Design, Synthesis, and Activity of a Novel Series of Factor Xa Inhibitors: Optimization of Arylamidine Groups", J. Med. Chem., 45:2484-2493 (2002).
Phillips et al.: "Discovery of N-[2-[5-[Amino(imino)methyl]-2-hydroxyphenoxyl]-3,5-difluoro-6-13-(4,5-dihydro-1-methyl-1H-imidazol-2-yl)phenoxy]pyridfin-4-yl]-N-methylglycine(ZK-807834): A Potent, Selective, and Orally Active Inhibitor of the Blood Coagulation Enzyme Factor Xa", J. Med. Chem., 41:3557-3562 (1998).
Physicians' Desk Reference: PDR, Oradell, N.J.:Medical Economics Co. "Hormones", p. 216 (2000).
Pierce et al.: "Preparation and Antiinflammatory Activity of 2- and 4-Pyridones", J. Med. Chem., 25:131-136 (1982).
Rastogi et al.: "Keten SS-Acetals. Part 10. Reaction of α-Oxoketen SS-Acetals with N-Alkylcyanoacetamides: a New General Method for Substituted and Fused 2, 7-Dialkyl-8-amino-5-cyano-2,7-napthyridine-1,6(2H,7H)-Diones", J. Chem. Soc., Perkin Trans, 1(6):554-558 (1978).
Reaven et al.: "Insulin Resistance and Human Disease: A Short History", J. Basic and Clin. Phys. and Pharm., 9:387406 (1998).
Reaven, G.M.: "Pathophysiology of Insulin Resistance in Human Disease", Physiol. Reviews, 75(3):473-486 (1995).
Rees et al.: "An N-Arninopyridone-Pyridazine Rearrangement; A New Decarbonylation Reaction", J. Chem. Soc. D, Chemical Communications, (8):377 (1969).
Rees et al.: "Reactive Intermediates. Part XVIII. An N-Aminopyridone-to-Pyridazine Rearrangement; a New Decarbonylation Reaction", J. Chem. Sco. Perkin Trans., 1(6):77-82 (1972).
Ried et al., "Uber Struktur and Reaktionen von Phenylcyclobutendion-Enamin- 1:1-Addukten", Liebigs Ann. Chem., 762:1-12 (1972).
Ried et al.: "3-Hydroxy-Pyridone-(2) aus Phenylcyclobutendion and Enaminen", Liebigs Ann. Chem., 725:230-233 (1969).
Salman: "New Heterocyclic Synthesis from Cyanopyridine Derivatives", Comman. Fac. Sci. Univ. Ank. Series B, 44:57-66 (1998).
Salman: "Synthesis and Reaction of Cyanopyridone Derivatives and their Potential Biological Activities", Pharmazie, 54:178-183 (1999).
Saunders et al: "Expression of oestrogen receptor beta (ERβ1) protein in human breast cancer biopsies", British J. Cancer, 86(2):250-256 (2002).
El-Kholy et al.: "Prone Series. IX. Some Reactions of 1 -Amino-4,5,6-Triaryl-2-Pyridones", J. Chem. Soc., C, (6):974-978 (1969).
Morissette et al. Advanced Drug Delivery Reviews 2004, 56, 275-300.
Accession No. 1931:43141, Basu, Umaprasanna, abstract of "B-Diketones in ring formation. III", J. INdian Chem. Soc. (1931), vol. 8, pp. 119-128.
Accession No. 1994:557497. Elgemeie et al, CAPLUS abstract of "Synthesis of several N-substituted amino-2-pyridones." Organic Preparations & Procedures Int. (1994). vol. 26(4). pp. 465-468.
Accession No. 1995:468947, Attia, Adel et al, abstract of "Synthesis of some N-hexopyranosyl-2-pyridones and -2-pyridinethiones," Carbohydrate Research (1995), vol. 268 (No. 2), pp. 295-300.
Accession No. 1999:185916, Salman, Asmaa, abstract of "Synthesis and reacion of cyanopyridone derivatives and their potential biological activities," Pharmazie (1999), vol. 54 (No. 3), pp. 178-183.
Accession No. 2000:879315. Tonkikh et al, Caplus abstract of "4(3H)-Quinazolines containinga beterocyclic group in position 3." Chemistry of Het. Compounds (2000). vol. 36(7). pp. 822-829.
Vivekananda, S.A. et al, "Electron-impact Mass Spectral Study of 2-Allyloxy-6-phenyl-4-trifuoromethyl Pyridines and N-allyl-6-phenyl-4-trifluoromethyl-2-(1H)-pyridones," Rapid Comm. Mass Spec. (1998), vol. 12, pp. 651-657.
N.T.A. Dawood, et al.: "Synthesis of Some Pyridone Derivatives," Bolletino Chimico Farmaceutico, vol. 140, No. 3, 2001, pp. 149-154.
Galal E. H. Elgemeie, et al.: "Reactions of Acylthiosernicarbazides with B-Diketones," J. Chem. Research, vol. 3, 1993, p. 87.

* cited by examiner

MODULATORS OF LXR

CROSS REFERENCE TO RELATED APPLICATIONS

This application is a divisional of U.S. patent application Ser. No. 10/899,458, which is a continuation-in-part of the U.S. patent application Ser. No. 10/327,813, filed Dec. 20, 2002, which claims the benefit of priority to U.S. Provisional Patent Application Ser. No. 60/342,707, filed Dec. 21, 2001, the disclosures of which are incorporated herein in their entireties.

FIELD OF THE INVENTION

Compounds, compositions and methods for modulating the activity of liver X receptors (LXRs) are provided. In particular, pyridone derivatives are provided for modulating the activity of LXRs.

BACKGROUND OF THE INVENTION

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al. (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression. There are three RXR genes (see, e.g., Mangelsdorf et al. (1992) *Genes Dev.* 6:329-344), coding for RXRα, -β, and -γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol.* 20:4436-4444.

Orphan Nuclear Receptors

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for farnesoid X receptor (FXR).

Since it is known that products of intermediary metabolism act as transcriptional regulators in bacteria and yeast, such molecules may serve similar functions in higher organisms (see, e.g., Tomkins (1975) *Science* 189:760-763 and O'Malley (1989) *Endocrinology* 125:1119-1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and farnesylated proteins.

LXRα and LXRβ

LXRα is found predominantly in the liver, with lower levels found in kidney, intestine, spleen and adrenal tissue (see, e.g., Willy, et al. (1995) *Gene Dev.* 9(9):1033-1045). LXRβ is ubiquitous in mammals and was found in nearly all tissues examined. LXRs are activated by certain naturally occurring, oxidized derivatives of cholesterol (see, e.g., Lehmann, et al. (1997) *J. Biol. Chem.* 272(6):3137-3140). LXRα is activated by oxycholesterol and promotes cholesterol metabolism (Peet et al. (1998) *Cell* 93:693-704). Thus, LXRs appear to play a role in, e.g., cholesterol metabolism (see, e.g., Janowski, et al. (1996) *Nature* 383:728-731).

Nuclear Receptors and Disease

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see, e.g., International Patent Application Publication No. WO 00/17334). Activity of nuclear receptors, including LXRs, FXR and PPAR, and orphan nuclear receptors, has been implicated in physiological processes including, but not limited to, bile acid biosynthesis, cholesterol metabolism or catabolism, and modulation of cholesterol 7α-hydroxylase gene (CYP7A1) transcription (see, e.g., Chiang et al. (2000) *J. Biol. Chem.* 275:10918-10924), HDL metabolism (see, e.g., Urizar et al. (2000) *J. Biol. Chem.* 275:39313-39317 and International Patent Application Publication No. WO 01/03705), and increased cholesterol efflux and increased expression of ATP binding cassette transporter protein (ABC1) (see, e.g., International Patent Application Publication No. WO 00/78972).

Thus, there is a need for compounds, compositions and methods of modulating the activity of nuclear receptors, including LXRs, FXR, PPAR and orphan nuclear receptors. Such compounds are useful in the treatment, prevention, or amelioration of one or more symptoms of diseases or disorders in which nuclear receptor activity is implicated.

SUMMARY OF THE INVENTION

Compounds for use in compositions and methods for modulating the activity of nuclear receptors are provided. In particular, compounds for use in compositions and methods for modulating liver X receptors (LXRα and LXRβ), FXR, PPAR and/or orphan nuclear receptors are provided. In certain embodiments, the compounds are N-substituted pyridone compounds. In one embodiment, the compounds provided herein are agonists of LXR. In another embodiment, the compounds provided herein are antagonists of LXR. Agonists that exhibit low efficacy are, in certain embodiments, antagonists.

Accordingly, one aspect of this invention is directed to compounds of formula (I):

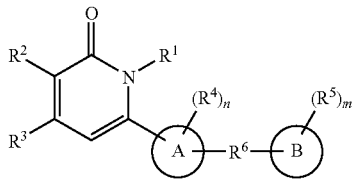

wherein:
n is 1 to 4;
m is 1 to 4;

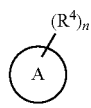

is aryl or heteroaryl;

is aryl, heterocyclyl or heteroaryl;
$R^1$ is hydrogen, aralkyl or heteroarylalkyl;
$R^2$ is hydrogen, cyano, —$R^7$—$N(R^8)_2$, —$R^7$—$N(R^8)S(O)_2R^{10}$ or —$R^7$—$N(R^8)C(NR^8)N(R^8)_2$;
$R^3$ is hydrogen, alkyl, alkenyl, aralkyl, aralkenyl, haloalkyl, haloalkenyl, cycloalkyl, cycloalkylalkyl, heterocyclyl, heterocyclylalkyl, heteroaryl or heteroarylalkyl;
each $R^4$ is independently hydrogen, halo, alkyl or haloalkyl;
each $R^5$ is independently selected from the group consisting of hydrogen, halo, nitro, alkyl, alkenyl, aryl, aralkyl, aralkenyl, haloalkyl, haloalkenyl, cycloalkyl, cycloalkylalkyl, heterocyclyl, heterocyclylalkyl, heteroaryl, heteroarylalkyl, —$R^7$—CN, —$R^7$—$N(R^8)_2$, —$R^7$—$OR^8$, —$R^7$—O—$R^9$—$C(O)OR^8$, —$R^7$—$C(O)R^{11}$, —$R^7$—$C(O)OR^8$, —$R^7$—$C(O)N(R^8)_2$, —$R^7$—$C(O)N(R^8)OR^8$, —$R^7$—$C(O)N(R^8)N(R^8)_2$, —$R^7$—$C(O)N(R^8)$—$R^9$—$C(O)OR^8$, —$R^7$—$C(S)N(R^8)_2$, —$R^7$—$N(R^8)C(O)R^8$, —$R^7$—$N(R^8)C(O)OR^{10}$, —$R^7$—$S(O)_tR^8$ (where t is 0 to 2) and —$R^7$—$S(O)_2N(R^8)_2$;
$R^6$ is —$OR^7$—, —$N(R^8)$—, a direct bond, a straight or branched alkylene chain, a straight or branched alkenylene chain or a straight or branched alkynylene chain;
each $R^7$ is independently selected from a direct bond, a straight or branched alkylene chain or a straight or branched alkenylene chain;
each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl;
each $R^9$ is independently selected from a straight or branched alkylene chain or a straight or branched alkenylene chain;
each $R^{10}$ is independently selected from alkyl, aryl, aralkyl or cycloalkylalkyl; and
$R^{11}$ is hydrogen, alkyl, aryl, aralkyl, cycloalkyl, cycloalkylalkyl, heterocyclyl, heterocyclylalkyl, heteroaryl or heteroarylalkyl;
as an isomer, a mixture of stereoisomers, a racemic mixture thereof of stereoisomers, or as a tautomer;
or as a pharmaceutically acceptable salt, prodrug, solvate or polymorph thereof.

Another aspect of this invention is directed to methods of treating, preventing, or ameliorating the symptoms of a disease or disorder that is modulated or otherwise affected by nuclear receptor activity or in which nuclear receptor activity is implicated, comprising administering to a subject in need thereof an effective amount of a compound of formula (I) as set forth above, or a pharmaceutically acceptable derivative thereof.

Another aspect of this invention is directed to methods of reducing cholesterol levels in a subject in need thereof, comprising administering an effective amount of a compound of formula (I) as set forth above, or a pharmaceutically acceptable derivative thereof.

Another aspect of this invention is directed to methods of treating, preventing, or ameliorating one or more symptoms of a disease or disorder which is affected by cholesterol, triglyceride, or bile acid levels, comprising administering to a subject in need thereof an effective amount of a compound of formula (I) as set forth above, or a pharmaceutically acceptable derivative thereof.

Another aspect of this invention is directed to methods of modulating nuclear receptor activity, comprising contacting the nuclear receptor with a compound of formula (I) as set forth above, or a pharmaceutically acceptable derivative thereof.

Another aspect of this invention is directed to methods of modulating cholesterol metabolism, comprising administering an effective amount of a compound of formula (I) as set forth above, or a pharmaceutically acceptable derivative thereof.

Another aspect of this invention is directed to methods of treating, preventing or ameliorating one or more symptoms of hypocholesterolemia in a subject in need thereof, comprising administering an effective amount of a compound of formula (I) as set forth above, or a pharmaceutically acceptable derivative thereof.

Another aspect of this invention is directed to methods of increasing cholesterol efflux from cells of a subject, comprising administering an effective amount of a compound of formula (I) as set forth above, or a pharmaceutically acceptable derivative thereof.

Another aspect of this invention is directed to methods of increasing the expression of ATP-Binding Cassette (ABC1) in the cells of a subject, comprising administering an effective amount of a compound of formula (I) as set forth above, or a pharmaceutically acceptable derivative thereof.

Another aspect of this invention is directed to in vitro methods for altering nuclear receptor activity, comprising contacting the nuclear receptor with a compound of formula (I) as set forth above, or a pharmaceutically acceptable derivative thereof.

Another aspect of this invention is directed to methods of reducing cholesterol levels in a subject in need thereof, comprising administering an effective amount of a compound of formula (I) as set forth above, or a pharmaceutically acceptable derivative thereof.

Another aspect of this invention is directed to pharmaceutical compositions comprising a pharmaceutically acceptable excipient and a compound of formula (I) as set forth above.

DETAILED DESCRIPTION OF THE INVENTION

Definitions

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

As used in the specification and appended claims, unless specified to the contrary, the following terms have the meaning indicated.

"Alkyl" refers to a straight or branched hydrocarbon chain radical consisting solely of carbon and hydrogen atoms, containing no unsaturation, having from one to twelve carbon atoms, preferably one to eight, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, the alkyl radical may be optionally substituted by one or more substituents selected from the group consisting of halo, cyano, nitro, —$OR^8$, —$N(R^8)_2$, —$C(O)R^8$, —$C(O)OR^8$, —$C(O)N(R^8)_2$, —$N(R^8)C(O)OR^{10}$, —$N(R^8)C(O)R^8$, —$N[S(O)_tR^8]_2$ (where t is 0 to 2), —$N(R^8)S(O)_tR^8$ (where t is 0 to 2), —$S(O)_pOR^8$ (where p is 1 to 2), —$S(O)_tR^8$ (where t is 0 to 2), and —$S(O)_pN(R^8)_2$ (where p is 1 to 2) where each $R^8$ and $R^{10}$ is as defined above in the Summary of the Invention. Unless stated otherwise specifically in the specification, it is understood that for radicals, as defined below, that contain a substituted alkyl group that the substitution can occur on any carbon of the alkyl group.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by one or more substituents selected from the group consisting of halo, cyano, nitro, —$OR^8$, —$N(R^8)_2$, —$C(O)R^8$, —$C(O)OR^8$, —$C(O)N(R^8)_2$, —$N(R^8)C(O)OR^{10}$, —$N(R^8)C(O)R^8$, —$N[S(O)_tR^8]_2$ (where t is 0 to 2), —$N(R^8)S(O)_tR^8$ (where t is 0 to 2), —$S(O)_pOR^8$ (where p is 1 to 2), —$S(O)_tR^8$ (where t is 0 to 2), and —$S(O)_pN(R^8)_2$ (where p is 1 to 2) where each $R^8$ and $R^{10}$ is as defined above in the Summary of the Invention. Unless stated otherwise specifically in the specification, it is understood that for radicals, as defined below, that contain a substituted alkenyl group that the substitution can occur on any carbon of the alkenyl group.

"Aryl" refers to refers to aromatic monocyclic or multicyclic ring system containing from 6 to 19 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heteroaryl, heteroarylalkyl, heterocyclyl, heterocyclylalkyl, —$R^7$—$OR^8$, —$R^7$—$N(R^8)_2$, —$R^7$—$C(O)R^8$, —$R^7$—$C(O)OR^8$, —$R^7$—$C(O)N(R^8)_2$, —$R^7$—$N(R^8)C(O)OR^{10}$, —$R^7$—$N(R^8)C(O)R^8$, —$R^7$—$N[S(O)_tR^8]_2$ (where t is 0 to 2), —$R^7$—$N(R^8)S(O)_tR^8$ (where t is 0 to 2), —$R^7$—$S(O)_pOR^8$ (where p is 1 to 2), —$R^7$—$S(O)_tR^8$ (where t is 0 to 2), and —$R^7$—$S(O)_pN(R^8)_2$ (where p is 1 to 2) where each $R^8$, $R^7$ and $R^{10}$ is as defined above in the Summary of the Invention.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl radical(s) and the alkyl radical may be optionally substituted as described above.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain. The alkylene chain may be optionally substituted by one or more substituents selected from the group consisting of halo, cyano, nitro, aryl, cycloalkyl, heteroaryl, heterocyclyl, —$OR^8$, —$N(R^8)_2$, —$C(O)R^8$, —$C(O)OR^8$, —$C(O)N(R^8)_2$, —$N(R^8)C(O)OR^{10}$, —$N(R^8)C(O)R^8$, —$N[S(O)_tR^8]_2$ (where t is 0 to 2), —$N(R^8)S(O)_tR^8$ (where t is 0 to 2), —$S(O)_pOR^8$ (where p is 1 to 2), —$S(O)_tR^8$ (where t is 0 to 2), and —$S(O)_pN(R^8)_2$ (where p is 1 to 2) where each $R^8$ and $R^{10}$ is as defined above in the Summary of the Invention. The alkylene chain may be attached to the rest of the molecule through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. The alkenylene chain may be optionally substituted by one or more substituents selected from the group consisting of halo, cyano, nitro, aryl, cycloalkyl, heteroaryl, heterocyclyl, —$OR^8$, —$N(R^8)_2$, —$C(O)R^8$, —$C(O)OR^8$, —$C(O)N(R^8)_2$, —$N(R^8)C(O)OR^{10}$, —$N(R^8)C(O)R^8$, —$N[S(O)_tR^8]_2$ (where t is 0 to 2), —$N(R^8)S(O)_tR^8$ (where t is 0 to 2), —$S(O)_pOR^8$ (where p is 1 to 2), —$S(O)_tR^8$ (where t is 0 to 2), and —$S(O)_pN(R^8)_2$ (where p is 1 to 2) where each $R^8$ and $R^{10}$ is as defined above in the Summary of the Invention.

"Alkynylene" and "alkynylene chain" refer to a straight or branched divalent hydrocarbon chain linking the rest of the molecule to a radical group, consisting solely of carbon and hydrogen, containing at least one triple bond and having from two to twelve carbon atoms, e.g., ethynylene, propynylene, n-butenylene, and the like. The alkynylene chain is attached to the rest of the molecule through a single bond and to the radical group through a triple bond or a single bond. The points of attachment of the alkynylene chain to the rest of the molecule and to the radical group can be through one carbon or any two carbons within the chain. The alkynylene chain may be optionally substituted by one or more substituents selected from the group consisting of halo, cyano, nitro, aryl, cycloalkyl, heteroaryl, heterocyclyl, —$OR^8$, —$N(R^8)_2$, —$C(O)R^8$, —$C(O)OR^8$, —$C(O)N(R^8)_2$, —$N(R^8)C(O)OR^{10}$, —$N(R^8)C(O)R^8$, —$N[S(O)_tR^8]_2$ (where t is 0 to 2), —$N(R^8)S(O)_tR^8$ (where t is 0 to 2), —$S(O)_pOR^8$ (where p is 1 to 2), —$S(O)_tR^8$ (where t is 0 to 2), and —$S(O)_pN(R^8)_2$ (where p is 1 to 2) where each $R^8$ and $R^{10}$ is as defined above in the Summary of the Invention.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^7$—$OR^8$, —$R^7$—$N(R^8)_2$, —$R^7$—$C(O)R^8$, —$R^7$—$C(O)OR^8$, —$R^7$—$C(O)N(R^8)_2$, —$R^7$—$N(R^8)C(O)OR^{10}$, —$R^7$—$N(R^8)C(O)R^8$, —$R^7$—$N[S(O)_tR^8]_2$ (where t is 0 to 2), —$R^7$—$N(R^8)S(O)_tR^8$ (where t is 0 to 2), —$R^7$—$S(O)_pOR^8$ (where p is 1 to 2), and —$R^7$—$S(O)_tR^8$ (where t is 0 to 2), —$R^7$—$S(O)_pN(R^8)_2$ (where p is 1 to 2) where each $R^8$, $R^7$ and $R^{10}$ is as defined above in the Summary of the Invention.

"Cycloalkylalkyl" refers to a radical of the formula —$R_aR_d$ where $R_a$ is an alkyl radical as defined above and $R_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above, e.g., 2-bromoethynyl, 3-bromoprop-1-enyl, and the like.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, nitro, aryl, aralkyl, cycloalkyl, cycloalkylalkyl, heterocyclyl, heterocyclylalkyl, heteroaryl, heteroarylalkyl, —$R^7$—$OR^8$, —$R^7$—$N(R^8)_2$, —$R^7$—$CN$, —$R^7$—$C(O)R^8$, —$R^7$—$C(O)OR^8$, —$R^7$—$C(O)N(R^8)_2$, —$R^7$—$N(R^8)C(O)OR^{10}$, —$R^7$—$N(R^8)C(O)R^8$, —$R^7$—$N[S(O)_tR^8]_2$ (where t is 0 to 2), —$R^7$—$N(R^8)S(O)_tR^8$ (where t is 0 to 2), —$R^7$—$S(O)_pOR^8$ (where p is 1 to 2), —$R^7$—$S(O)_tR^8$ (where t is 0 to 2), and —$R^7$—$S(O)_pN(R^8)_2$ (where p is 1 to 2) where each $R^8$, $R^7$ and $R^{10}$ is as defined above in the Summary of the Invention. For purposes of this invention, the term "N-heterocyclyl" refers to heterocyclyl radicals as defined above containing at least one nitrogen atom in ring.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The heterocyclyl radical and the alkyl radical may be optionally substituted as defined above.

"Heteroaryl" refers to a 3- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxazepinyl, oxazolyl, oxiranyl, phenazinyl, phenothiazinyl, phenoxazinyl, phthalazinyl, phthalimidyl pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, nitro, aryl, aralkyl, cycloalkyl, cycloalkylalkyl, heterocyclyl, heterocyclylalkyl, heteroaryl, heteroarylalkyl, —$R^7$—$OR^8$, —$R^7$—$N(R^8)_2$, —$R^7$—$CN$, —$R^7$—$C(O)R^8$, —$R^7$—$C(O)OR^8$, —$R^7$—$C(O)N(R^8)_2$, —$R^7$—$N(R^8)C(O)OR^{10}$, —$R^7$—$N(R^8)C(O)R^8$, —$R^7$—$N[S(O)_tR^8]_2$ (where t is 0 to 2), —$R^7$—$N(R^8)S(O)_tR^8$ (where t is 0 to 2), —$R^7$—$S(O)_pOR^8$ (where p is 1 to 2), —$R^7$—$S(O)_tR^8$ (where t is 0 to 2), and —$R^7$—$S(O)_pN(R^8)_2$ (where p is 1 to 2) where each $R^8$, $R^7$ and $R^{10}$ is as defined above in the Summary of the Invention. For purposes of this invention, the term "N-heteroaryl" refers to heteroaryl radicals as defined above containing at least one nitrogen atom in ring.

"Heteroarylalkyl" refers to a radical of the formula —$R_aR_f$ where $R_a$ is an alkyl radical as defined above and $R_f$ is a heteroaryl radical as defined above, and if the heteroaryl is a nitrogen-containing heteroaryl, the heteroaryl may be attached to the alkyl radical at the nitrogen atom. The heteroaryl radical and the alkyl radical may be optionally substituted as defined above.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals as defined herein and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable derivative" refers to pharmaceutically acceptable salts as defined herein and also includes esters, prodrugs, solvates and polymorphs of the compounds of the invention.

"Therapeutically effective amount" refers to that amount of a compound of formula (I) which, when administered to a mammal, preferably a human, is sufficient to effect treatment, as defined below, for a disease-state associated the nuclear receptor activity. The amount of a compound of formula (I) which constitutes a "therapeutically effective amount" will vary depending on the compound, the condition and its severity, and the age of the mammal to be treated, but can be determined routinely by one of ordinary skill in the art having regard to his own knowledge and to this disclosure.

"Modulating" or "modulate" refers to the treating, prevention, suppression, enhancement or induction of a function or condition. For example, the compounds of the present invention can modulate hyperlipidemia by lowering cholesterol in a human, thereby suppressing hyperlipidemia.

"Treating" or "treatment" as used herein covers the treatment of a disease or condition associated with the nuclear receptor activity as disclosed herein, in a mammal, preferably a human, and includes:

(i) preventing a disease or condition associated with the nuclear receptor activity from occurring in a mammal, in particular, when such mammal is predisposed to the disease or condition but has not yet been diagnosed as having it;

(ii) inhibiting a disease or condition associated with the nuclear receptor activity, i.e., arresting its development; or (iii) relieving a disease or condition associated with the nuclear receptor activity, i.e., causing regression of the condition.

The compounds of formula (I), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The chemical naming protocol and structure diagrams used herein employ and rely on the chemical naming features as utilized by the ChemDraw program (available from Cambridgesoft Corp., Cambridge, Mass.). In particular, the compound names were derived from the structures using the Autonom program as utilized by Chemdraw Ultra or ISIS base (MDL Corp.).

For example, a compound of formula (V) wherein n and m are each 1, Y is sulfur, $R^1$ is 2,4-difluorobenzyl, $R^2$ is cyano, $R^3$ is trifluoromethyl, $R^4$ is hydrogen,

B is pyridin-3-yl, $R^5$ is piperazin-1-yl and $R^6$ is a direct bond, i.e., a compound of the following formula:

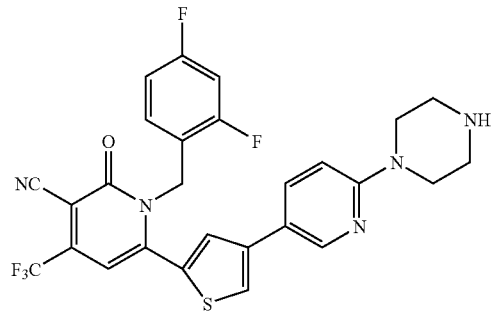

is named herein as 1-(2,4-Difluoro-benzyl)-2-oxo-6-[4-(6-piperazin-1-yl-pyridin-3-yl)-thiophen-2-yl]-4-trifluoromethyl-1,2-dihydro-pyridine-3-carbonitrile.

The term "atherosclerosis" refers to process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery heart disease or ischemic heart disease), cerebrovascular disease including ischemic stroke, multi-infarct dementia, and peripheral vessel disease, including intermittent claudication, and erectile dysfunction.

The term "dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL) (less than 40 mg/dL)).

As used herein, "$EC_{50}$" refers to a dosage, concentration or amount of a particular test compound that elicits a dose-dependent response at 50% of maximal expression of a particular response that is induced, provoked or potentiated by the particular test compound.

The term "hyperlipidemia" refers to the presence of an abnormally elevated level of lipids in the blood. Hyperlipidemia can appear in at least three forms: (1) hypercholesterolemia, i.e., an elevated LDL cholesterol level (120 mg/dL and above); (2) hypertriglyceridemia, i.e., an elevated triglyceride level; (150 mg/dL and above) and (3) combined hyperlipidemia, i.e., a combination of hypercholesterolemia and hypertriglyceridemia.

As used herein, "$IC_{50}$" refers to an amount, concentration or dosage of a particular test compound that achieves a 50% inhibition of a maximal response, such as modulation of nuclear receptor, including the LXRα or LXRβ activity, in an assay that measures such response.

As used herein, "LXR α" refers to all mammalian forms of such receptor including, for example, alternative splice isoforms and naturally occurring isoforms. Representative LXR α species include, without limitation the rat (Genbank Accession NM_031627) (SEQ ID NOS: 1-2), mouse (Genbank Accession BC012646) (SEQ ID NOS: 3-4), and human (GenBank Accession No. U22662) (SEQ ID NOS: 5-6) forms of the receptor.

As used herein, "LXR β" refers to all mammalian forms of such receptor including, for example, alternative splice isoforms and naturally occurring isoforms. Representative LXR β species include, without limitation the rat (GenBank Accession NM 031626) (SEQ ID NOS: 7-8), mouse (Genbank Accession NM_009473) (SEQ ID NOS: 9-10), and human (GenBank Accession No. U07132) (SEQ ID NOS: 11-12) forms of the receptor.

As used herein "LXR" or "LXRs" refers to both LXRα and LXRβ.

The terms "obese" and "obesity" refers to a Body Mass Index (BMI) greater than 27.8 kg/m$^2$ for men and 27.3 kg m$^2$ for women (BMI equals weight (kg)/height (m$^2$).

Utility of the Compounds of the Invention

The compounds of the invention exhibit valuable pharmacological properties in mammals, and are particularly useful as selective LXR agonists, antagonists, inverse agonists, partial agonists and antagonists, for the treatment, or prevention of diseases associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

These diseases include, for example, hyperlipidemia, dyslipidemia, hypercholesterolemia, atherosclerosis, atherosclerotic cardiovascular diseases, hyperlipoproteinemia, (see, e.g., Patent Application Publication Nos. WO 00/57915 and WO 00/37077), hyperglycemia, insulin resistance, diabetes, lipodystrophy, obesity, syndrome X (US Patent Application No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp. 189-196), optic nerve and retinal pathologies (i.e., macular degeneration, retinitis pigmentosa), repair of traumatic damage to the central or peripheral nervous system (*Trends in Neurosciences* (1994), Vol. 17, pp. 525-530), prevention of the degenerative process due to aging (*American Journal of Pathology* (1997), Vol. 151, pp. 1371-1377), Parkinson's disease or Alzheimer's disease (see, e.g., International Patent Application Publication No. WO 00/17334; *Trends in Neurosciences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem.* (1996), Vol. 33, No. 2, pp. 148-150), and autoimmune diseases (*J. Lipid Res*. (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a patient with atherosclerosis or atherosclerotic cardiovascular disease manifest by clinical signs of such disease, wherein the methods comprise administering to the patient a therapeutically effective amount of a compound or composition of the present invention.

Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a patient at risk for such an event. The patient may already have atherosclerotic cardiovascular disease at the time of administration, or may be at risk for developing it. Risk factors for developing atherosclerotic cardiovascular disease events include increasing age (65 and over), male gender, a family history of atherosclerotic cardiovascular disease events, high blood cholesterol (especially LDL or "bad" cholesterol over 100 mg/dL), cigarette smoking and exposure to tobacco smoke, high blood pressure, diabetes, obesity and physical inactivity.

Also contemplated herein is the use of a compound of the invention, or a pharmaceutically acceptable derivative thereof, in combination with one or more of the following therapeutic agents in treating atherosclerosis: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzafibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In one embodiment compounds of the invention are used in combination with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®); see, U.S. Pat. No. 4,346,227); fluvastatin sodium (LESCOL®); see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulas of these and additional HMG-CoA reductase inhibitors that can be used in combination with the compounds of the invention are described at page 87 of M.

Yalpani, "Cholesterol Lowering Drugs," *Chemistry & Industry*, pp. 85-89 (5 Feb. 1996). In presently preferred embodiments, the HMG-CoA reductase inhibitor is selected from lovastatin and simvastatin.

The compounds of the present invention can also be used in methods for decreasing hyperglycemia and insulin resistance, i.e., in methods for treating diabetes (International Patent Application Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a patient in need of such treatment.

Additionally the instant invention also provides a method for preventing or reducing the risk of developing hyperglycemia, insulin resistance, diabetes or syndrome X in a patient, comprising the administration of a prophylactically effective amount of a compound or composition of the present invention to a patient at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, *Textbook of Endocrinology*, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. *Ann. Chim. Med.* (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., *Diabetes* (1974), Vol. 23, pp. 105-11 (1974); and Laakso, M. and Lehto, S., *Diabetes Reviews* (1997), Vol. 5, No. 4, pp. 294-315). Several lipoprotein abnormalities have been described among diabetic subjects (Howard B., et al., *Arteriosclerosis* (1978), Vol. 30, pp. 153-162).

The compounds of the invention can also be used effectively in combination with one or more additional active diabetes agents depending on the desired target therapy (see, e.g., Turner, N. et al., *Prog. Drug Res.* (1998), Vol. 51, pp. 33-94; Haffner, S., *Diabetes Care* (1998), Vol. 21, pp. 160-178; and DeFronzo, R. et al. (eds.), *Diabetes Reviews* (1997), Vol. 5, No. 4). A number of studies have investigated the benefits of combination therapies with oral agents (see, e.g., Mahler, R., *J. Clin. Endocrinol. Metab.* (1999), Vol. 84, pp. 1165-71; United Kingdom Prospective Diabetes Study Group: UKPDS 28, *Diabetes Care* (1998), Vol. 21, pp. 87-92; Bardin, C. W. (ed.), CURRENT THERAPY IN ENDOCRINOLOGY AND METABOLISM, 6th Edition (Mosby—Year Book, Inc., St. Louis, Mo. 1997); Chiasson, J. et al., *Ann. Intern. Med.* (1994), Vol. 121, pp. 928-935; Coniff, R. et al., *Clin. Ther.* (1997), Vol. 19, pp. 16-26; Coniff, R. et al., *Am. J. Med.* (1995), Vol. 98, pp. 443-451; Iwamoto, Y. et al., *Diabet. Med.* (1996), Vol. 13, pp. 365-370; Kwiterovich, P., *Am. J. Cardiol* (1998), Vol. 82 (12A), pp. 3U-17U). These studies indicate that diabetes and hyperlipidemia modulation can be further improved by the addition of a second agent to the therapeutic regimen.

Accordingly, the compounds of the invention may be used in combination with one or more of the following therapeutic agents in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO$_4$); antiglucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

Further provided by this invention are methods of using the compounds of the invention to treat obesity, as well as the complications of obesity. Obesity is linked to a variety of medical conditions including diabetes and hyperlipidemia. Obesity is also a known risk factor for the development of type 2 diabetes (See, e.g., Barrett-Conner, E., *Epidemol. Rev.* (1989), Vol. 11, pp. 172-181; and Knowler, et al., *Am. J. Clin. Nutr.* (1991), Vol. 53, pp. 1543-1551).

In addition, the compounds of the invention can be used in combination with agents used in treated obesity or obesity-related disorders. Such agents, include, but are not limited to, phenylpropanolamine, phentermine, diethylpropion, mazindol, fenfluramine, dexfenfluramine, pheniramine, $\beta_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

Evaluation of the Utility of the Compounds of the Invention

Standard physiological, pharmacological and biochemical procedures are available for testing the compounds to identify those that possess biological activities that modulate the activity or nuclear receptors, including the LXRs (LXRα and LXRβ). Such assays include, for example, biochemical assays such as binding assays, fluorescence polarization assays, FRET based coactivator recruitment assays (see, generally, Glickman et al., *J. Biomolecular Screening* (2002), Vol. 7, No. 1, pp. 3-10, as well as cell based assays including the co-transfection assay, the use of LBD-Gal 4 chimeras and protein-protein interaction assays, (see, Lehmann. et al., *J. Biol. Chem.* (1997), Vol. 272, No. 6, pp. 3137-3140.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., *Biomol. Screen* (2000 October), Vol. 5, No. 5, pp. 297), scintillation proximity assays (SPA) (see, for example, Carpenter et al., *Methods Mol. Biol.* (2002), Vol 190, pp. 31-49) and fluorescence resonance energy transfer energy transfer (FRET) or time resolved FRET based coactivator recruitment assays (Mukherjee et al., *J. Steroid Biochem. Mol. Biol.* (2002 July); Vol. 81, No. 3, pp. 217-25; (Zhou et al., *Mol. Endocrinol.* (1998 October), Vol. 12, No. 10, pp. 1594-604). Generally such assays can be preformed using either the full length receptor, or isolated ligand binding domain (LBD). In the case of LXRα, the LBD comprises amino acids 188-447, for LXRβ the LDB comprises amino acids 198-461, and for FXR, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, [$^3$H] 24,25 Epoxycholesterol) generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of LXR with RXRα can also be measured by fluorescence resonance energy transfer (FRET), or time resolved FRET, to monitor the ability of the compounds provided herein to bind to LXR or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor.

In addition a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor (see, for example, U.S. Pat. Nos. 5,071,773; 5,298,429 and 6,416,957). Treatment of the transfected cells with an agonist for the nuclear receptor increases the transcriptional activity of that receptor which is reflected by an increase in expression of the reporter gene which may be measured by a variety of standard procedures.

For those receptors that function as heterodimers with RXR, such as the LXRs, the co-transfection assay typically includes the use of expression plasmids for both the nuclear receptor of interest and RXR. Typical co-transfection assays require access to the full length nuclear receptor and suitable response elements that provide sufficient screening sensitivity and specificity to the nuclear receptor of interest.

Typically, the expression plasmid comprises: (1) a promoter, such as an SV40 early region promoter, HSV tk promoter or phosphoglycerate kinase (pgk) promoter, CMV promoter, Srα promoter or other suitable control elements known in the art, (2) a cloned polynucleotide sequence, such as a cDNA encoding a receptor, co-factor, or fragment thereof, ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. Genes & Development 9 1033-1045 (1995)) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example see U.S. Pat. Nos. 6,534,261 and 6,503,7171) or a strong promoter or enhancer sequence together with a targeting sequence to enable homologous or non-homologous recombination of the activating sequence upstream of the gene of interest.

Genes encoding the following full-length previously described proteins, which are suitable for use in the co-transfection studies and profiling the compounds described herein, include human LXR α (accession U22662) (SEQ ID NOS: 5-6), human LXR β (accession U07132) (SEQ ID NOS: 11-12), rat FXR (accession U18374) (SEQ ID NOS: 13-14), human FXR (accession NM_005123) (SEQ ID NOS: 15-16), human RXR α (accession NM_002957) (SEQ ID NO: 17-18), human RXR β (accession XM_042579) (SEQ ID NOS: 19-20), human RXR γ (accession XM_053680) (SEQ ID NOS: 21-22), human PPARα (accession X57638) (SEQ ID NOS: 23-24) and human PPAR δ (accession U10375) (SEQ ID NOS: 25-26). All accession numbers in this application refer to GenBank accession numbers.

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., (1987) *Mol. Cell. Biol.* 7 725-735) down stream from the herpes virus thymidine kinase promoter (located at nucleotides residues-105 to +51 of the thymidine kinase nucleotide sequence, obtained for example, from the plasmid pBLCAT2 (Luckow & Schutz (1987) *Nucl. Acid. Res.* 15 5490-5494)) which is linked in turn to the appropriate response element (RE).

The choice of hormone response element is dependent upon the type of assay to be used. In the case of the use of the full-length LXR α or LXR β a reporter plasmid comprising a known LXR RE would typically be used, such as for example in a reporter plasmid such as LXREx1-tk-luciferase, (see U.S. Pat. No. 5,747,661, which is hereby incorporated by reference). In the case of a LXR a or LXR P-LBD-Gal4 fusion, GAL4 Upstream Activating Sequences (UAS) would be used. Typically the GAL4 UAS would comprise the sequence 5'CGGRNNRCYNYNCNCCG-3' (SEQ ID NO: 27), where Y=C or T, R=A or G, and N=A, C, T or G, and would be present as a tandem repeat of 4 copies.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase (see, Berger, J., et al., *Gene* (1988), Vol. 66, pp. 1-10; and Kain, S. R., *Methods. Mol. Biol.* (1997), Vol. 63, pp. 49-60), β-galactosidase (See, U.S. Pat. No. 5,070,012, issued Dec., 3, 1991 to Nolan et al., and Bronstein, I., et al., *J. Chemilum. Biolum.* (1989), Vol. 4, pp. 99-111), chloramphenicol acetyltransferase (See, Gorman et al., *Mol. Cell. Biol.* (1982), Vol. 2, pp. 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., *Annu. Rev. Biochem.* (1998), Vol. 67, pp. 509-44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full length nuclear receptor. As with the full length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used.

A third cell based assay of utility for screening compounds of the present invention is a mammalian two-hybrid assay that measures the ability of the nuclear hormone receptor to interact with a cofactor in the presence of a ligand (see, for example, U.S. Pat. Nos. 5,667,973, 5,283,173 and 5,468, 614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene which can be measured for various reporter genes as described above. Transcription of the reporter gene is thus driven by the interaction of the interacting protein and nuclear receptor of interest in a ligand dependent fashion.

Any compound which is a candidate for activation of LXRα or LXRβ may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by LXRα or LXRβ and other nuclear receptors in vivo, using Northern-blot, RT PCR or oligonucleotide microarray analysis to analyze RNA levels. Western-blot analysis can be used to measure expression of proteins encoded by LXR target genes. Genes that are known to be regulated by the LXRs include the ATP binding cassette transporters ABCA1, ABCG1, ABCG5, ABCG8, the sterol response element binding protein 1c (SREBP1c) gene, stearoyl CoA desaturase 1 (SCD-1) and the apolipoprotein apoE gene (ApoE).

Established animal models exist for a number of diseases of direct relevance to the claimed compounds and these can be used to further profile and characterize the claimed compounds. These model systems include diabetic dyslipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDR$^{-/-}$) and atherosclerosis using both the Apo E($^{-/-}$) and LDL($^{-/-}$) mice fed a western diet. (21% fat, 0.05% cholesterol). Additionally LXR or FXR animal models (e.g., knockout mice) can be used to further evaluate the present compounds and compositions in vivo (see, for example, Peet, et al., *Cell* (1998), Vol. 93, pp. 693-704, and Sinal, et al., *Cell* (2000), Vol. 102, pp. 731-744).

Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington's Pharmaceutical Sciences,* 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state associated with the activity of a nuclear receptor in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

Compounds of the invention, or pharmaceutically acceptable derivatives thereof, may also be administered simultaneously with, prior to, or after administration of one or more of the therapeutic agents described above in the Utility of the Compounds of the Invention. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the HMG-CoA reductase inhibitor is preferred.

Embodiments of the Compounds of the Invention

One embodiment of the compounds of formula (I), as set forth above in the Summary of the Invention, is that group of compounds having the following formula (II):

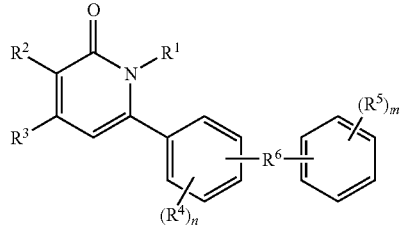

(II)

wherein n is 1 to 4; m is 1 to 4; $R^1$ is hydrogen, aralkyl or heteroarylalkyl; $R^2$ is hydrogen, cyano or —$R^7$—N($R^8$)$_2$; $R^3$ is hydrogen or haloalkyl; each $R^4$ is independently hydrogen, halo, alkyl or haloalkyl; each $R^5$ is independently selected from the group consisting of hydrogen, halo, nitro, alkyl, alkenyl, aryl, aralkyl, aralkenyl, haloalkyl, haloalkenyl, cycloalkyl, cycloalkylalkyl, heterocyclyl, heterocyclylalkyl, heteroaryl, heteroarylalkyl, —$R^7$—CN, —$R^7$—N($R^8$)$_2$, —$R^7$—O$R^8$, —$R^7$—O—$R^9$—C(O)O$R^8$, —$R^7$—C(O)$R^{11}$, —$R^7$—C(O)O$R^8$, —$R^7$—C(O)N($R^8$)$_2$, —$R^7$—C(O)N($R^8$)O$R^8$, —$R^7$—C(O)N($R^8$)N($R^8$)$_2$, —$R^7$—C(O)N($R^8$)—$R^9$—C(O)O$R^8$, —$R^7$—C(S)N($R^8$)$_2$, —$R^7$—N($R^8$)C(O)O$R^{10}$, —$R^7$—S(O)$_t R^8$ (where t is 0 to 2) and —$R^7$—S(O)$_2$N($R^8$)$_2$; $R^6$ is —O$R^7$—, a direct bond, a straight or branched alkylene chain, a straight or branched alkenylene chain or a straight or branched alkynylene chain; each $R^7$ is independently selected from a direct bond, a straight or branched alkylene chain or a straight or branched alkenylene chain; each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl; each $R^9$ is independently selected from a straight or branched alkylene chain or a straight or branched alkenylene chain; $R^{10}$ is alkyl, aryl, aralkyl or cycloalkylalkyl; and $R^{11}$ is hydrogen, alkyl, aryl, aralkyl, cycloalkyl, cycloalkylalkyl, heterocyclyl, heterocyclylalkyl, heteroaryl or heterarylalkyl; as an isomer, a mixture of stereoisomers, a racemic mixture thereof of stereoisomers, or as a tautomer; or as a pharmaceutically acceptable salt, prodrug, solvate or polymorph thereof.

Of this group of compounds, one embodiment is that subgroup of compounds wherein n is 1; m is 1 or 2; $R^1$ is aralkyl or heteroarylalkyl; $R^2$ is cyano; $R^3$ is haloalkyl; $R^4$ is hydrogen, halo, alkyl or haloalkyl; each $R^5$ is independently selected from the group consisting of hydrogen, halo, nitro, alkyl, alkenyl, haloalkyl, heterocyclyl, heteroaryl, —$R^7$—CN, —$R^7$—N($R^8$)$_2$, —$R^7$—O$R^8$, —$R^7$—O—$R^9$—C(O)O$R^8$, —$R^7$—C(O)$R^{11}$, —$R^7$—C(O)O$R^8$, —$R^7$—C(O)N($R^8$)$_2$, —$R^7$—C(O)N($R^8$)O$R^8$, —$R^7$—C(O)N($R^8$)N($R^8$)$_2$, —$R^7$—C(O)N($R^8$)—$R^9$—C(O)O$R^8$, —$R^7$—C(S)N($R^8$)$_2$, —$R^7$—N($R^8$)C(O)O$R^{10}$, —$R^7$—S(O)$_t R^8$ (where t is 0 to 2) and —$R^7$—S(O)$_2$N($R^8$)$_2$; $R^6$ is —O$R^7$—, a direct bond, a straight or branched alkylene chain or a straight or branched alkynylene chain; each $R^7$ is independently selected from a direct bond or a straight or branched alkylene chain; each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl; each $R^9$ is a straight or branched alkylene chain optionally substituted by aryl or heteroaryl; $R^{10}$ is alkyl, aryl, aralkyl or cycloalkylalkyl; and $R^{11}$ is hydrogen, alkyl, aryl, aralkyl, cycloalkyl, cycloalkylalkyl, heterocyclyl, heterocyclylalkyl, heteroaryl or heterarylalkyl.

Of this subgroup of compounds, one embodiment is that class of compounds wherein $R^6$ is —O$R^7$—.

Of this class of compounds, one embodiment is that subclass of compounds wherein $R^1$ is aralkyl optionally substituted with one or more substituents independently selected from alkyl, halo or haloalkyl.

Of this subclass of compounds, one embodiment is that set of compounds wherein n is 1; m is 1 or 2; $R^2$ is cyano; $R^3$ is trifluoromethyl; $R^4$ is hydrogen, methyl, 1-methylethyl or chloro; each $R^5$ is independently selected from the group consisting of hydrogen, halo, alkyl, alkenyl or haloalkyl.

Of this set of compounds, one embodiment is that subset of compounds wherein each $R^5$ is independently selected from hydrogen, chloro, bromo, fluoro, methyl, ethyl, 1-methylethyl, 1,1-dimethylethyl, ethenyl or trifluoromethyl.

Of the subclass of compounds set forth above, another embodiment is that set of compounds wherein n is 1; m is 1 or 2; $R^2$ is cyano; $R^3$ is trifluoromethyl; $R^4$ is hydrogen, methyl, 1-methylethyl or chloro; each $R^5$ is independently selected from the group consisting of haloalkyl, $-R^7-CN$, $-R^7-N(R^8)_2$, $-R^7-OR^8$ and $R^7-O-R^9-C(O)OR^8$ each $R^7$ is independently selected from a direct bond or methylene chain; each $R^8$ is independently selected from hydrogen, alkyl, aryl and aralkyl; and $R^9$ is a methylene chain.

Of the subclass of compounds set forth above, another embodiment is that set of compounds wherein n is 1; m is 1 or 2; $R^2$ is cyano; $R^3$ is trifluoromethyl; $R^4$ is hydrogen, methyl, 1-methylethyl or chloro; each $R^5$ is independently selected from the group consisting of heteroaryl, $-R^7-OR^8$, $-R^7-C(O)R^{11}$, $-R^7-C(O)OR^8$, $-R^7-C(O)N(R^8)_2$, $-R^7-C(O)N(R^8)OR^8$, $-R^7-C(O)N(R^8)N(R^8)_2$, $-R^7-C(O)N(R^8)-R^9-C(O)OR^8$, $-R^7-C(S)N(R^8)_2$ and $-R^7-S(O)_tR^8$ (where t is 0 to 2); each $R^7$ is independently selected from a direct bond or a straight or branched alkylene chain; each $R^8$ is independently selected from hydrogen, alkyl, haloalkyl, aryl, aralkyl, aralkenyl, cycloalkyl or heterocyclyl optionally substituted with hydroxy; $R^9$ is a straight or branched alkylene chain (optionally substituted by phenyl or imidazolyl); and $R^{11}$ is hydrogen, alkyl, aryl, aralkyl, cycloalkyl, cycloalkylalkyl, heterocyclyl, heterocyclylalkyl, heteroaryl or heterarylalkyl.

Of this set of compounds, one embodiment is that subset of compounds wherein m is 1 or 2; each $R^5$ is independently selected from $-R^7-OR^8$, $-R^7-C(O)R^{11}$, $-R^7-C(O)OR^8$, $-R^7-C(O)N(R^8)_2$, $-R^7-C(O)N(R^8)OR^8$ or $-R^7-C(O)N(R^8)N(R^8)_2$; each $R^7$ is independently selected from a direct bond or methylene; each $R^8$ is independently selected from hydrogen, methyl, ethyl, 1,1-dimethylethyl, benzyl, 2-phenylethyl, cyclohexyl or piperidinyl optionally substituted by hydroxy; and $R^{11}$ is hydrogen, alkyl, aryl, aralkyl, cycloalkyl, cycloalkylalkyl, heterocyclyl, heterocyclylalkyl, heteroaryl or heterarylalkyl.

Of the subclass of compounds set forth above, another embodiment is that set of compounds wherein n is 1; m is 1 or 2; $R^2$ is cyano; $R^3$ is trifluoromethyl; $R^4$ is hydrogen, methyl, 1-methylethyl or chloro; each $R^5$ is independently selected from the group consisting of heteroaryl, $-R^7-C(O)N(R^8)-R^9-C(O)OR^8$, $-R^7-C(S)N(R^8)_2$ and $-R^7-S(O)_tR^8$ (where t is 0 to 2); each $R^7$ is independently selected from a direct bond or a straight or branched alkylene chain; each $R^8$ is independently selected from hydrogen or alkyl, haloalkyl, aryl, aralkyl, aralkenyl, cycloalkyl or heterocyclyl; and $R^9$ is a straight or branched alkylene chain (optionally substituted by phenyl or imidazolyl).

Of this set of compounds, one embodiment is that subset of compounds wherein n is 1; m is 1; $R^2$ is cyano; $R^3$ is trifluoromethyl; $R^4$ is hydrogen or chloro; $R^5$ is $-R^7-C(O)N(R^8)-R^9-C(O)OR^8$; $R^7$ is a direct bond; each $R^8$ is independently hydrogen or alkyl; and $R^9$ is a straight or branched alkylene chain optionally substituted by phenyl or imidazolyl.

Of this set of compounds, another embodiment is that subset of compounds wherein n is 1; m is 1; $R^2$ is cyano; $R^3$ is trifluoromethyl; $R^4$ is hydrogen, methyl, 1-methylethyl or chloro; each $R^5$ is independently selected from the group consisting of phthalimidyl, $-R^7-C(S)N(R^8)_2$ and $-R^7-S(O)_tR^8$ (where t is 0 or 2); each $R^7$ is a direct bond; and each $R^8$ is independently selected from hydrogen or alkyl.

Of the class of compounds of formula (II) as set forth above, another embodiment is that subclass of compounds wherein $R^1$ is heteroarylalkyl.

Of this subclass of compounds, one embodiment is that set of compounds wherein n is 1; m is 1 or 2; $R^1$ is optionally substituted thiazol-5-ylmethyl; $R^2$ is cyano; $R^3$ is trifluoromethyl; $R^4$ is hydrogen, methyl, 1-methylethyl or chloro; each $R^5$ is independently selected from the group consisting of hydrogen, halo, alkyl, alkenyl or haloalkyl.

Of the subgroup of compounds of formula (II) set forth above, another embodiment is that class of compounds wherein $R^1$ is aralkyl optionally substituted with one or more substituents independently selected from alkyl, halo or haloalkyl; each $R^5$ is independently selected from the group consisting of hydrogen, halo, nitro, alkyl, alkenyl, haloalkyl, $-R^7-CN$, $-R^7-N(R^8)_2$, $-R^7-OR^8$, $-R^7-C(O)R^{11}$, $-R^7-C(O)OR^8$, $-R^7-C(O)N(R^8)_2$, $-R^7-N(R^8)C(O)OR^{10}$, $-R^7-S(O)_tR^8$ (where t is 0 to 2) and $-R^7-S(O)_2N(R^8)_2$; $R^6$ is a direct bond, a straight or branched alkenylene chain or a straight or branched alkynylene chain; each $R^7$ is independently selected from a direct bond or a straight or branched alkylene chain; each $R^8$ is independently selected from hydrogen, alkyl, cycloalkyl, cycloalkylalkyl or heterocyclyl; each $R^9$ is a straight or branched alkylene chain optionally substituted by aryl or heteroaryl; $R^{10}$ is alkyl, aryl, aralkyl or cycloalkylalkyl; and $R^{11}$ is hydrogen, alkyl, aryl, aralkyl, cycloalkyl, cycloalkylalkyl, heterocyclyl, heterocyclylalkyl, heteroaryl or heterarylalkyl.

Of this class of compounds, one embodiment is that subclass of compounds wherein n is 1; m is 1 or 2; $R^1$ is benzyl optionally substituted with one or more substituents independently selected from alkyl, halo or haloalkyl; $R^2$ is cyano; $R^3$ is trifluoromethyl; $R^4$ is hydrogen; each $R^5$ is independently selected from the group consisting of alkyl, trifluoromethyl, $-R^7-OR^8$ and $R^7-S(O)_tR^8$ (where t is 0 to 2); $R^6$ is a direct bond; $R^7$ is a direct bond; $R^8$ is hydrogen or alkyl; and $R^9$ is a straight or branched alkylene chain.

Of this class of compound, another embodiment is that subclass of compounds wherein n is 1; m is 1 or 2; $R^1$ is benzyl optionally substituted with one or more substituents independently selected from alkyl, halo or haloalkyl; $R^2$ is cyano; $R^3$ is trifluoromethyl; $R^4$ is hydrogen; each $R^5$ is independently selected from the group consisting of alkyl, $-R^7-C(O)R^{11}$, $-R^7-C(O)OR^8$ or $-R^7-C(O)N(R^8)_2$; $R^6$ is a direct bond; each $R^7$ is a direct bond; each $R^8$ is independently hydrogen, alkyl, aryl or aralkyl; and $R^{11}$ is hydrogen, alkyl, aryl, aralkyl, cycloalkyl, cycloalkylalkyl, heterocyclyl, heterocyclylalkyl, pyrrolidinyl or piperidinyl.

Of this class of compound, another embodiment is that subclass of compounds wherein n is 1; m is 1 or 2; $R^2$ is cyano; $R^3$ is trifluoromethyl; $R^4$ is hydrogen; each $R^5$ is independently selected from the group consisting of hydrogen, halo, alkyl, alkenyl, haloalkyl or $-R^7-OR^8$; $R^6$ is a direct bond, a straight or branched alkenylene chain or a straight or branched alkynylene chain; $R^7$ is a direct bond; and $R^8$ is hydrogen or alkyl.

Of this class of compound, another embodiment is that subclass of compounds wherein n is 1; m is 1 or 2; $R^2$ is cyano; $R^3$ is trifluoromethyl; $R^4$ is hydrogen; each $R^5$ is independently selected from the group consisting of nitro, $-R^7-N(R^8)_2$, $-R^7-OR^8$ or $-R^7-N(R^8)C(O)OR^{10}$; $R^6$ is a direct bond; each $R^7$ is a direct bond; each $R^8$ is independently selected from hydrogen or alkyl; and $R^{10}$ is alkyl.

Another embodiment of the compounds of formula (I), as set forth above in the Summary of the Invention, is that group of compounds having the following formula (III):

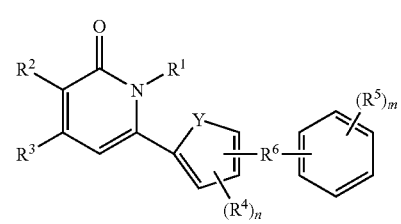

(III)

wherein Y is oxygen or sulfur; n is 1 or 2; m is 1 to 4; $R^1$ is aralkyl; $R^2$ is hydrogen, cyano, $-R^7-N(R^8)_2$, $-R^7-N(R^8)$ $S(O)_2R^{10}$ or $-R^7-N(R^8)C(NR^8)N(R^8)_2$; $R^3$ is hydrogen or haloalkyl; each $R^4$ is independently hydrogen, halo, alkyl or haloalkyl; each $R^5$ is independently selected from the group consisting of hydrogen, halo, nitro, alkyl, alkenyl, aryl, aralkyl, aralkenyl, haloalkyl, haloalkenyl, cycloalkyl, cycloalkylalkyl, heterocyclyl, heterocyclylalkyl, heteroaryl, heteroarylalkyl, $-R^7-CN$, $-R^7-N(R^8)_2$, $-R^7-OR^8$, $-R^7-OC(O)OR^8$, $-R^7-O-R^9-C(O)OR^8$, $-R^7-O-R^9-OR^8$, $-R^7-C(O)R^{11}$, $-R^7-C(O)OR^8$, $-R^7-C(O)N(R^8)_2$, $-R^7-C(O)N(R^8)OR^8$, $-R^7-C(O)N(R^8)N(R^8)_2$, $-R^7-C(O)N(R^8)-R^9-C(O)OR^8$, $-R^7-C(S)N(R^8)_2$, $-R^7-N(R^8)C(O)OR^{10}$, $-R^7-S(O)_tR^8$ (where t is 0 to 2) and $-R^7-S(O)_2N(R^8)_2$; $R^6$ is $-N(R^8)-$, a direct bond, a straight or branched alkylene chain, a straight or branched alkenylene chain or a straight or branched alkynylene chain; each $R^7$ is independently selected from a direct bond, a straight or branched alkylene chain or a straight or branched alkenylene chain; each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl; each $R^9$ is independently selected from a straight or branched alkylene chain or a straight or branched alkenylene chain; each $R^{10}$ is independently selected from alkyl, aryl, aralkyl or cycloalkylalkyl; and $R^{11}$ is hydrogen, alkyl, aryl, aralkyl, cycloalkyl, cycloalkylalkyl, heterocyclyl, heterocyclylalkyl, heteroaryl or heterarylalkyl; as an isomer, a mixture of stereoisomers, a racemic mixture thereof of stereoisomers, or as a tautomer; or as a pharmaceutically acceptable salt, prodrug, solvate or polymorph thereof.

Of this group of compounds, one embodiment is that subgroup of compounds wherein Y is oxygen or sulfur; n is 1 or 2; m is 1 to 4; $R^1$ is aralkyl optionally substituted with one or more substituents selected from the group consisting of alkyl and halo; $R^2$ is hydrogen, cyano, $-R^7-N(R^8)_2$, $-R^7-N(R^8)S(O)_2R^{10}$ or $-R^7-N(R^8)C(NR^8)N(R^8)_2$; $R^3$ is hydrogen or haloalkyl; each $R^4$ is independently hydrogen, halo, alkyl or haloalkyl; each $R^5$ is independently selected from the group consisting of hydrogen, halo, nitro, alkyl, haloalkyl, $-R^7-CN$, $-R^7-N(R^8)_2$, $-R^7-OR^8$, $-R^7-OC(O)OR^8$, $-R^7-O-R^9-C(O)OR^8$, $-R^7-O-R^9-OR^8$, $-R^7-C(O)R^{11}$, $-R^7-C(O)OR^8$, $-R^7-N(R^8)C(O)OR^{10}$, $-R^7-S(O)_tR^8$ (where t is 0 to 2) and $-R^7-S(O)_2N(R^8)_2$; $R^6$ is $-N(R^8)-$, a direct bond, a straight or branched alkylene chain, a straight or branched alkenylene chain or a straight or branched alkynylene chain; each $R^7$ is independently selected from a direct bond or a straight or branched alkylene chain; each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl; each $R^9$ is a straight or branched alkylene chain; each $R^{10}$ is independently selected from alkyl, aryl, aralkyl or cycloalkylalkyl; and $R^{11}$ is hydrogen, alkyl, aryl, aralkyl, cycloalkyl, cycloalkylalkyl, heterocyclyl, heterocyclylalkyl, heteroaryl or heterarylalkyl.

Of this subgroup of compounds, one embodiment is that class of compounds wherein Y is sulfur.

Of this class of compounds, one embodiment is that subclass of compounds wherein n is 1; m is 1 to 3; $R^1$ is benzyl optionally substituted with one or more substituents selected from the group consisting of chloro, bromo, fluoro, methyl or ethyl; $R^2$ is hydrogen, cyano, $-R^7-N(R^8)_2$, $-R^7-N(R^8)S(O)_2R^{10}$ or $-R^7-N(R^8)C(NR^8)N(R^8)_2$; $R^3$ is haloalkyl; $R^4$ is hydrogen; each $R^5$ is independently selected from the group consisting of hydrogen, halo, nitro, alkyl, haloalkyl, $-R^7-CN$, $-R^7-N(R^8)_2$, $-R^7-OR^8$, $-R^7-OC(O)OR^8$, $-R^7-O-R^9-C(O)OR^8$, $-R^7-O-R^9-OR^8$, $-R^7-C(O)R^{11}$, $-R^7-C(O)OR^8$, $-R^7-N(R^8)C(O)OR^{10}$, $-R^7-S(O)_tR^8$ (where t is 0 to 2) and $-R^7-S(O)_2N(R^8)_2$; $R^6$ is a direct bond, a straight or branched alkylene chain, a straight or branched alkenylene chain or a straight or branched alkynylene chain; each $R^7$ is independently selected from a direct bond or a straight or branched alkylene chain; each $R^8$ is independently selected from hydrogen, alkyl, alkenyl, haloalkyl, haloalkenyl, aryl, aralkyl, aralkenyl, cycloalkyl or cycloalkylalkyl; each $R^9$ is a straight or branched alkylene chain; each $R^{10}$ is independently selected from alkyl, aralkyl or cycloalkylalkyl; and $R^{11}$ is hydrogen, alkyl, aryl, aralkyl, cycloalkyl, cycloalkylalkyl, heterocyclyl, heterocyclylalkyl, heteroaryl or heterarylalkyl.

Of this subclass of compounds, one embodiment is that set of compounds wherein n is 1; m is 1 to 3; $R^1$ is benzyl optionally substituted with one or more substituents selected from the group consisting of chloro, bromo, fluoro, methyl or ethyl; $R^2$ is cyano; $R^4$ is hydrogen; each $R^5$ is independently selected from the group consisting of hydrogen, halo, alkyl, haloalkyl, $-R^7-OR^8$ and $-R^7-O-R^9-OR^8$; $R^6$ is a direct bond, a straight or branched ethylene chain, a straight or branched ethenylene chain or a straight or branched ethynylene chain; each $R^7$ is a direct bond; each $R^8$ is independently selected from hydrogen, alkyl, alkenyl, haloalkyl, haloalkenyl, aryl, aralkyl, aralkenyl, cycloalkyl or cycloalkylalkyl; and each $R^9$ is a straight or branched ethylene chain.

Of this subclass of compounds, another embodiment is that set of compounds wherein n is 1; m is 1 or 2; $R^1$ is benzyl optionally substituted with one or more substituents selected from the group consisting of chloro, bromo, fluoro, methyl or ethyl; $R^2$ is hydrogen, cyano, $-R^7-N(R^8)_2$, $-R^7-N(R^8)S(O)_2R^{10}$ or $-R^7-N(R^8)C(NR^8)N(R^8)_2$; $R^3$ is haloalkyl; $R^4$ is hydrogen; when m is 1, $R^5$ is hydrogen or $-R^7-S(O)_tR^8$ (where t is 0 to 2); or when m is 2, one $R^5$ is $-R^7-S(O)_tR^8$ (where t is 0 to 2) or $-R^7-S(O)_2N(R^8)_2$ and the other $R^5$ is independently selected from the group consisting of alkyl, halo, haloalkyl and $-R^7-OR^8$; $R^6$ is a direct bond; each $R^7$ is independently a direct bond or a straight or branched alkylene chain; each $R^8$ is independently selected from hydrogen, alkyl, haloalkyl, haloalkenyl, aryl, aralkyl, aralkenyl, cycloalkyl or cycloalkylalkyl; and $R^{10}$ is alkyl, aryl, aralkyl or cycloalkylalkyl.

Of this subclass of compounds, another embodiment is that set of compounds wherein n is 1; m is 1 or 2; $R^1$ is benzyl optionally substituted with one or more substituents selected from the group consisting of chloro, bromo, fluoro, methyl or ethyl; $R^2$ is cyano; $R^3$ is haloalkyl; $R^4$ is hydrogen; each $R^5$ is independently selected from the group consisting of halo, nitro, alkyl, $-R^7-CN$, $-R^7-N(R^8)_2$, $-R^7-OR^8$, $-R^7-OC(O)OR^8$, $-R^7-O-R^9-C(O)OR^8$, $-R^7-C(O)R^{11}$, $-R^7-C(O)OR^8$ and $-R^7-N(R^8)C(O)OR^{10}$; $R^6$ is $-N(H)-$ or a direct bond; each $R^7$ is independently a direct bond or a straight or branched alkylene chain; each $R^8$ is independently selected from hydrogen, alkyl, alkenyl, haloalkyl, haloalkenyl, aryl, aralkyl, aralkenyl, cycloalkyl or cycloalkylalkyl; each $R^9$ is a straight or branched alkylene chain; $R^{10}$ is alkyl, aryl, aralkyl or cycloalkylalkyl; and $R^{11}$ is hydrogen, alkyl, aryl, aralkyl, cycloalkyl, cycloalkylalkyl, heterocyclyl, heterocyclylalkyl, heteroaryl or heterarylalkyl.

Of the subgroup of compounds set forth above for formula (III), another embodiment is that class of compounds wherein Y is oxygen.

Of this class of compound, one embodiment is that subclass of compounds wherein n is 1; m is 1 to 3; $R^1$ is benzyl optionally substituted with one or more substituents selected from the group consisting of chloro, bromo, fluoro, methyl or ethyl; $R^2$ is cyano; $R^3$ is haloalkyl; $R^4$ is hydrogen; each $R^5$ is independently selected from the group consisting of halo, nitro, alkyl, haloalkyl, $-R^7-CN$, $-R^7-N(R^8)_2$, $-R^7-OR^8$, $-R^7-OC(O)OR^8$, $-R^7-O-R^9-C(O)OR^8$, —R⁷—O—R⁹—OR⁸, —R⁷—C(O)R¹¹, —R⁷—C(O)OR⁸, —R⁷—N(R⁸)C(O)OR¹⁰ and —R⁷—S(O)ₜR⁸ (where t is 0 to 2); R⁶ is a direct bond; each R⁷ is independently selected from a direct bond or a straight or branched alkylene chain; each R⁸ is independently selected from hydrogen, alkyl, alkenyl, haloalkyl, haloalkenyl, aryl, aralkyl, aralkenyl, cycloalkyl or cycloalkylalkyl; each R⁹ is a straight or branched alkylene chain; R¹⁰ is alkyl, aryl, aralkyl or cycloalkylalkyl; and R¹¹ is hydrogen, alkyl, aryl, aralkyl, cycloalkyl, cycloalkylalkyl, heterocyclyl, heterocyclylalkyl, heteroaryl or heterarylalkyl.

Of this subclass of compounds, one embodiment is that set of compounds wherein n is 1; m is 1 to 3; R¹ is benzyl optionally substituted with one or more substituents selected from the group consisting of chloro, bromo, fluoro, methyl or ethyl; R² is cyano; R³ is trifluoromethyl; R⁴ is hydrogen; each R⁵ is independently selected from the group consisting of halo, alkyl, haloalkyl, —R⁷—OR⁸ and —R⁷—O—R⁹—OR⁸; R⁶ is a direct bond; each R⁷ is independently a direct bond or a straight or branched alkylene chain; each R⁸ is independently selected from hydrogen, alkyl, alkenyl, haloalkyl, haloalkenyl, aryl, aralkyl, aralkenyl, cycloalkyl or cycloalkylalkyl; and each R⁹ is a straight or branched ethylene chain.

Of this subclass of compounds, another embodiment is that set of compounds wherein n is 1; m is 1 or 2; R¹ is benzyl optionally substituted with one or more substituents selected from the group consisting of chloro, bromo, fluoro, methyl or ethyl; R² is hydrogen, cyano, —R⁷—N(R⁸)₂, —R⁷—N(R⁸)S(O)₂R¹⁰ or —R⁷—N(R⁸)C(NR⁸)N(R⁸)₂; R³ is haloalkyl; R⁴ is hydrogen; when m is 1, R⁵ is hydrogen or —R⁷—S(O)ₜR⁸ (where t is 0 to 2); or when m is 2, one R⁵ is —R⁷—S(O)ₜR⁸ (where t is 0 to 2) and the other R⁵ is independently selected from the group consisting of halo, haloalkyl and —R⁷—OR⁸; R⁶ is a direct bond; each R⁷ is a direct bond; each R⁸ is independently selected from hydrogen, alkyl, haloalkyl, haloalkenyl, aryl, aralkyl, aralkenyl, cycloalkyl or cycloalkylalkyl; and R¹⁰ is alkyl, aryl, aralkyl or cycloalkylalkyl.

Of this subclass of compounds, another embodiment is that set of compounds wherein n is 1; m is 1 or 2; R¹ is benzyl optionally substituted with one or more substituents selected from the group consisting of chloro, bromo, fluoro, methyl or ethyl; R² is cyano; R³ is haloalkyl; R⁴ is hydrogen; each R⁵ is independently selected from the group consisting of halo, nitro, alkyl, —R⁷—CN, —R⁷—N(R⁸)₂, —R⁷—OR⁸, —R⁷—OC(O)OR⁸, —R⁷—O—R⁹—C(O)OR⁸, —R⁷—C(O)R¹¹, —R⁷—C(O)OR⁸ and —R⁷—N(R⁸)C(O)OR¹⁰; R⁶ is a direct bond; each R⁷ is independently a direct bond or a straight or branched alkylene chain; each R⁸ is independently selected from hydrogen, alkyl, alkenyl, haloalkyl, haloalkenyl, aryl, aralkyl, aralkenyl, cycloalkyl or cycloalkylalkyl; each R⁹ is a straight or branched alkylene chain; R¹⁰ is alkyl, aryl, aralkyl or cycloalkylalkyl; and R¹¹ is hydrogen, alkyl, aryl, aralkyl, cycloalkyl, cycloalkylalkyl, heterocyclyl, heterocyclylalkyl, heteroaryl or heterarylalkyl.

Another embodiment of the compounds of formula (I), as set forth above in the Summary of the Invention, is that group of compounds having the following formula (IV):

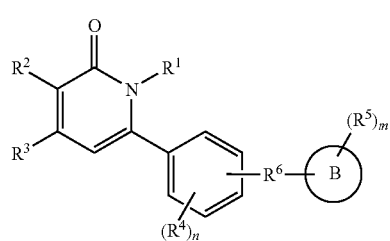

(IV)

wherein n is 1 to 4; m is 1 to 4; R¹ is aralkyl; R² is cyano or —R⁷—N(R⁸)₂; R³ is haloalkyl;

is heterocyclyl or heteroaryl; each R⁴ is independently hydrogen, halo, alkyl or haloalkyl; each R⁵ is independently selected from the group consisting of halo, alkyl, haloalkyl, —R⁷—CN and —R⁷—C(O)OR⁸; R⁶ is —O— or a direct bond; each R⁷ is independently selected from a direct bond or a straight or branched alkylene chain; and each R⁸ is independently selected from hydrogen, alkyl, aryl or aralkyl; as an isomer, a mixture of stereoisomers, a racemic mixture thereof of stereoisomers, or as a tautomer; or as a pharmaceutically acceptable salt, prodrug, solvate or polymorph thereof.

Of this group of compounds, one embodiment is that subgroup of compounds wherein R¹ is benzyl optionally substituted by one or more substituents selected from the group consisting of chloro, bromo, fluoro, methyl or ethyl;

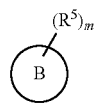

is a N-heteroaryl selected from the group consisting of indolyl and thiazolyl; each R⁵ is independently selected from the group consisting of halo, alkyl, haloalkyl, —R⁷—CN and —R⁷—C(O)OR⁸; and R⁶ is a direct bond.

Of this group of compounds, another embodiment is that subgroup of compounds wherein R¹ is benzyl optionally substituted by one or more substituents selected from the group consisting of chloro, bromo, fluoro, methyl or ethyl;

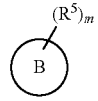

is a N-heteroaryl selected from the group consisting of indolyl, pyrimidyl, pyrazinyl, pyridinyl and thiazolyl; each R⁵ is independently selected from the group consisting of halo, alkyl, haloalkyl, —R⁷—CN and —R⁷—C(O)OR⁸; and R⁶ is —O—.

Of this group of compounds, another embodiment is that subgroup of compounds wherein R¹ is benzyl optionally substituted by one or more substituents selected from the group consisting of chloro, bromo, fluoro, methyl or ethyl;

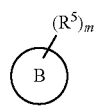

is N-heterocyclyl selected from the group consisting of piperidinyl and piperazinyl; and each R⁵ is independently selected from the group consisting of halo, alkyl, haloalkyl, —R⁷—CN and —R⁷—C(O)OR⁸.

Of this group of compounds, another embodiment is that subgroup of compounds wherein R¹ is benzyl optionally sub stituted by one or more substituents selected from the group consisting of chloro, bromo, fluoro, methyl or ethyl;

is benzodioxolyl; each $R^5$ is independently selected from the group consisting of halo, alkyl, haloalkyl, —$R^7$—CN and —$R^7$—C(O)OR$^8$; and $R^6$ is a direct bond.

Another embodiment of the compounds of formula (I), as set forth above in the Summary of the Invention, is that group of compounds having the following formula (V):

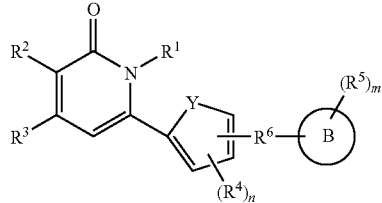

wherein n is 1 or 2; m is 1 to 4; Y is oxygen or sulfur; $R^1$ is aralkyl; $R^2$ is cyano or —$R^7$—N($R^8$)$_2$; $R^3$ is haloalkyl; each $R^4$ is independently hydrogen, halo, alkyl or haloalkyl;

is naphthyl, heterocyclyl or heteroaryl; each $R^5$ is independently selected from the group consisting of hydrogen, alkyl, alkenyl, halo, haloalkyl, heterocyclyl, —$R^7$—OR$^8$, —$R^7$—CN, —$R^7$—C(O)OR$^8$, —$R^7$—OC(O)R$^{10}$ and —$R^7$—S(O)$_t$R$^8$ (where t is 0 to 2); $R^6$ is a direct bond; each $R^7$ is independently selected from a direct bond, a straight or branched alkylene chain or a straight or branched alkenylene chain; each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl; $R^{10}$ is alkyl, aryl, aralkyl or cycloalkylalkyl; as an isomer, a mixture of stereoisomers, a racemic mixture thereof of stereoisomers, or as a tautomer; or as a pharmaceutically acceptable salt, prodrug, solvate or polymorph thereof.

Of this group of compounds, one embodiment is that subgroup of compounds wherein Y is —O—; $R^1$ is benzyl optionally substituted by one or more substituents selected from the group consisting of chloro, bromo, fluoro, methyl or ethyl; $R^3$ is haloalkyl;

is a N-heteroaryl selected from the group consisting of pyrimidinyl and pyridinyl; each $R^5$ is independently selected from the group consisting of hydrogen, alkyl, alkenyl, halo, haloalkyl, morpholinyl, piperazinyl, —$R^7$—CN, —$R^7$—OR$^8$, —$R^7$—C(O)OR$^8$, —$R^7$—OC(O)R$^{10}$ and —$R^7$—S(O)$_t$R$^8$ (where t is 0 to 2); each $R^7$ is independently a direct bond or a methylene chain; each $R^8$ is hydrogen or alkyl; and $R^{10}$ is alkyl or cycloalkylalkyl.

Of this group of compounds, another embodiment is that subgroup of compounds wherein Y is —O—; $R^1$ is benzyl optionally substituted by one or more substituents selected from the group consisting of chloro, bromo, fluoro, methyl or ethyl; $R^3$ is haloalkyl;

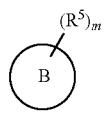

is heterocyclyl; each $R^5$ is independently selected from the group consisting of hydrogen, alkyl, alkenyl, halo, haloalkyl, —$R^7$—CN, —$R^7$—OR$^8$, —$R^7$—C(O)OR$^8$, —$R^7$—OC(O)R$^{10}$ and —$R^7$—S(O)$_t$R$^8$ (where t is 0 to 2); each $R^7$ is independently a direct bond or a methylene chain; each $R^8$ is hydrogen or alkyl; and $R^{10}$ is alkyl or cycloalkylalkyl.

Of this group of compounds, another embodiment is that subgroup of compounds wherein Y is —S—; $R^1$ is benzyl optionally substituted by one or more substituents selected from the group consisting of chloro, bromo, fluoro, methyl or ethyl; $R^3$ is haloalkyl;

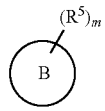

is a N-heteroaryl selected from the group consisting of pyridinyl, indolyl and pyrimidinyl; each $R^5$ is independently selected from the group consisting of hydrogen, alkyl, alkenyl, halo, haloalkyl, morpholinyl, piperazinyl, —$R^7$—CN, —$R^7$—OR$^8$, —$R^7$—C(O)OR$^8$, —$R^7$—OC(O)R$^{10}$ and —$R^7$—S(O)$_t$R$^8$ (where t is 0 to 2); each $R^7$ is independently a direct bond or a methylene chain; each $R^8$ is hydrogen or alkyl; and $R^{10}$ is alkyl or cycloalkylalkyl.

Of this group of compounds, another embodiment is that subgroup of compounds wherein Y is —S—; $R^1$ is benzyl optionally substituted by one or more substituents selected from the group consisting of chloro, bromo, fluoro, methyl or ethyl; $R^3$ is haloalkyl;

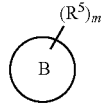

is heterocyclyl; each $R^5$ is independently selected from the group consisting of hydrogen, alkyl, alkenyl, halo, haloalkyl, —$R^7$—CN, —$R^7$—OR$^8$, —$R^7$—C(O)OR$^8$, —$R^7$—OC(O)R$^{10}$ and —$R^7$—S(O)$_t$R$^8$ (where t is 0 to 2); each $R^7$ is independently a direct bond or a methylene chain; each $R^8$ is hydrogen or alkyl; and $R^{10}$ is alkyl or cycloalkylalkyl.

Of this group of compounds, another embodiment is that subgroup of compounds wherein Y is —S—; $R^1$ is benzyl optionally substituted by one or more substituents selected from the group consisting of chloro, bromo, fluoro, methyl or ethyl; $R^3$ is haloalkyl;

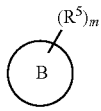

is naphthyl; and each $R^5$ is independently selected from hydrogen, alkyl, halo or haloalkyl.

Another embodiment of the compounds of formula (I), as set forth above in the Summary of the Invention, is that group of compounds having the following formula (VI):

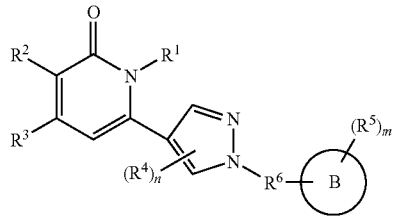

(VI)

wherein n is 1 or 2; m is 1 to 4; $R^1$ is aralkyl; $R^2$ is cyano or $-R^7-N(R^8)_2$; $R^3$ is haloalkyl; each $R^4$ is independently hydrogen, halo, alkyl or haloalkyl;

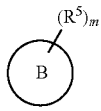

is aryl or heteroaryl; each $R^5$ is independently selected from the group consisting of hydrogen, alkyl, alkenyl, halo, haloalkyl, $-R^7-R^8-R^7-CN$, $-R^7-C(O)OR^8$, $-R^7-OC(O)R^{10}$ and $-R^7-S(O)_tR^8$ (where t is 0 to 2); $R^6$ is a direct bond or a straight or branched alkylene chain; each $R^7$ is independently selected from a direct bond, a straight or branched alkylene chain or a straight or branched alkenylene chain; each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl; and $R^{10}$ is alkyl, aryl, aralkyl or cycloalkylalkyl; as an isomer, a mixture of stereoisomers, a racemic mixture thereof of stereoisomers, or as a tautomer; or as a pharmaceutically acceptable salt, prodrug, solvate or polymorph thereof.

Of this group of compounds, one embodiment is that subgroup of compounds wherein $R^1$ is benzyl optionally substituted by one or more substituents selected from the group consisting of chloro, bromo, fluoro, methyl or ethyl; and

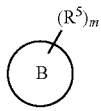

is phenyl or pyridinyl; each $R^5$ is independently selected from the group consisting of hydrogen, alkyl, halo, haloalkyl, $-R^7-OR^8$, $-R^7-CN$ and $-R^7-S(O)_tR^8$ (where t is 0 to 2); each $R^7$ is a direct bond or a straight or branched alkylene chain; each $R^8$ is hydrogen or alkyl; and $R^{10}$ is alkyl.

Of this subgroup of compounds, one embodiment is that class of compounds wherein

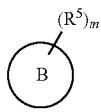

is phenyl; and each $R^5$ is independently selected from the group consisting of alkyl, halo, haloalkyl, $-R^7-OR^8$, $-R^7-CN$ and $-R^7-S(O)_tR^8$ (where t is 0 to 2);

Of this subgroup of compounds, another embodiment is that class of compounds wherein m is 1 or 2;

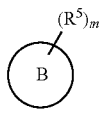

is pyridinyl; and each $R^5$ is independently selected from the group consisting of hydrogen, alkyl, halo, haloalkyl, $-R^7-OR^8$, $-R^7-CN$ and $-R^7-S(O)_tR^8$ (where t is 0 to 2).

Specific embodiments of the various groups, subgroups, classes, subclasses, set and subsets of compounds of formula (I), as set forth above, are disclosed herein in the Examples set forth herein.

Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for 1,2-dihydroxys include ketal- and acetal-forming groups. Suitable protecting groups for amino, amidino and guanidino include t-butoxycarbonyl, benzyloxycarbonyl, and the like. Suitable protecting groups for mercapto include $-C(O)-R$ (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, Protective Groups in Organic Synthesis (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of the invention, as described above in the Summary of the Invention, may not possess pharmacological activity as such, they may be administered to a mammal having a disease associated with defects in cholesterol transport, glucose metabolism, fatty acid metabolism and cholesterol metabolism, and thereafter metabolized in the body to form compounds of the invention which are pharmacologically active. Such derivatives may therefore be described as "prodrugs". All prodrugs of compounds of the invention are included within the scope of the invention.

It is understood that one of ordinary skill in the art would be able to make the compounds of the invention not specifically prepared herein in light of the following disclosure, including the Preparations and Examples, and information known to those of ordinary skill in the chemical synthesis field.

Starting materials in the synthesis examples provided herein are either available from commercial sources or via literature procedures or by methods disclosed herein. All commercially available compounds were used without further purification unless otherwise indicated. $CDCl_3$ (99.8% D, Cambridge Isotope Laboratories) was used in all experiments as indicated. $^1$H NMR spectra were recorded on a Bruker Avance 400 MHz NMR spectrometer. Significant peaks are tabulated and typically include: number of protons, multiplicity (s, singlet; d, double; t, triplet; q, quartet; m, multiplet; br s, broad singlet) and coupling constant(s) in Hertz. Chemical shifts are reported as parts per million (δ) relative to tetramethylsilane. Mass spectra were recorded on a Perkin-Elmer SCIEX HPLC/MS instrument using reverse-phase conditions (acetonitrile/water, 0.05% trifluoroacetic acid) and electrospray (ES) ionization. Abbreviations used in the examples below have their accepted meanings in the chemical literature. For example, $CH_2Cl_2$ (dichloromethane), $C_6H_6$ (benzene), TFA (trifluoroacetic acid), EtOAc (Ethyl Acetate), $Et_2O$ (diethyl ether), DMAP (4-dimethylaminopyridine), DMF (N,N-dimethylformamide) and THF (tetrahydrofuran). Flash chromatography was performed using Merck Silica Gel 60 (230-400 mesh).

The compounds of the invention can be prepared according to the methods disclosed herein or by the methods disclosed in the parent application, U.S. patent application Ser. No. 10/327,813, which is incorporated herein by reference in its entirety, or by methods known to one skilled in the art in view of the teachings of this disclosure and the afore-mentioned parent application.

Preparation of Compounds of the Invention

For purposes of illustration only, most of the formulae in the following Reaction Schemes are directed to specific embodiments of the compounds of invention. However, one of ordinary skill in the art, in view of the teachings of this specification and U.S. patent application Ser. No. 10/327,813 would reasonably be expected to be able to prepare all the compounds of the invention as set forth above in the Summary of the Invention utilizing the appropriately-substituted starting materials and methods known to one skilled in the art.

In the general descriptions immediately following each Reaction Scheme, the phrase "standard isolation procedures" is meant to include one or more of the following techniques familiar to one schooled in the art of organic chemistry: organic extraction, washing of organic solutions with dilute aqueous acid or base, use of drying agents, filtration, concentration in vacuo, followed by purification using distillation, crystallization, or solid-liquid phase chromatography. The phrase "elevated temperature" refers to a temperature above ambient temperature and the phrase "reduced temperature" refers to a temperature below ambient temperature.

A. Preparation of Compounds of Formula (B)

Compounds of formula (B) are starting materials in the preparation of the compounds of the invention and can be prepared according to methods known to one skilled in the art or by the method described below in Reaction Scheme 1, wherein $X_a$ is bromo or iodo; m is 1 to 4; each $R^{5a}$ is independently hydrogen, fluoro, chloro, alkyl, haloalkyl, —$OR^8$, —$N(R^8)_2$ or —$S(O)_tR^8$ (where each $R^8$ is as defined in the Summary of the Invention), and $R^{10a}$ is alkyl, aryl or aralkyl:

1.

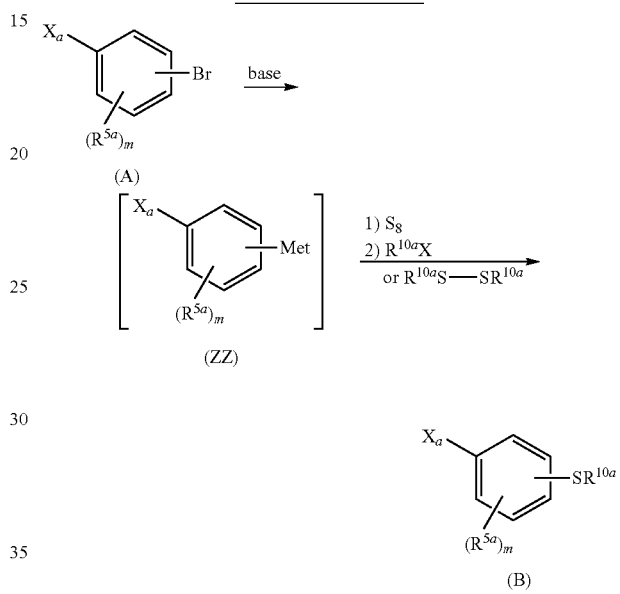

REACTION SCHEME 1

Compounds of formula (A) are commercially available or may be prepared according to methods disclosed herein or known to one skilled in the art or by methods disclosed in U.S. patent application Ser. No. 10/327,813.

In general, compounds of formula (B) are prepared by first reacting a solution of the arylhalides of formula (A) in an aprotic solvent at reduced temperature with a strong base in a metal-halogen exchange reaction to afford the organometallic reagent of formula (ZZ), which upon reaction with a source of elemental sulfur such as $S_8$, provides an intermediate arylthiol (not shown). Reaction of this arylthiol with an alkyl halide in the presence of a base provides the compound of formula (B) after isolation using standard procedures. In an alternate manner, the organometallic reagent of formula (ZZ) is reacted with various alkyl and aryl disulfides to give compounds of formula (B) using standard isolation procedures.

B. Preparation of Compounds of Formula (Ca)

Compounds of formula (Ca) are starting materials in the preparation of the compounds of the invention and can be prepared according to methods known to one skilled in the art or by the method described below in Reaction Scheme 2, wherein $X_a$ is bromo or iodo; $X_b$ is bromo, chloro or iodo; m is 1 to 4; each R is hydrogen or alkyl; each $R^{5a}$ is independently hydrogen, fluoro, chloro, alkyl, haloalkyl or —$OR^8$ (where $R^8$ is as defined in the Summary of the Invention); and $R^{10a}$ is alkyl, aryl or aralkyl:

REACTION SCHEME 2

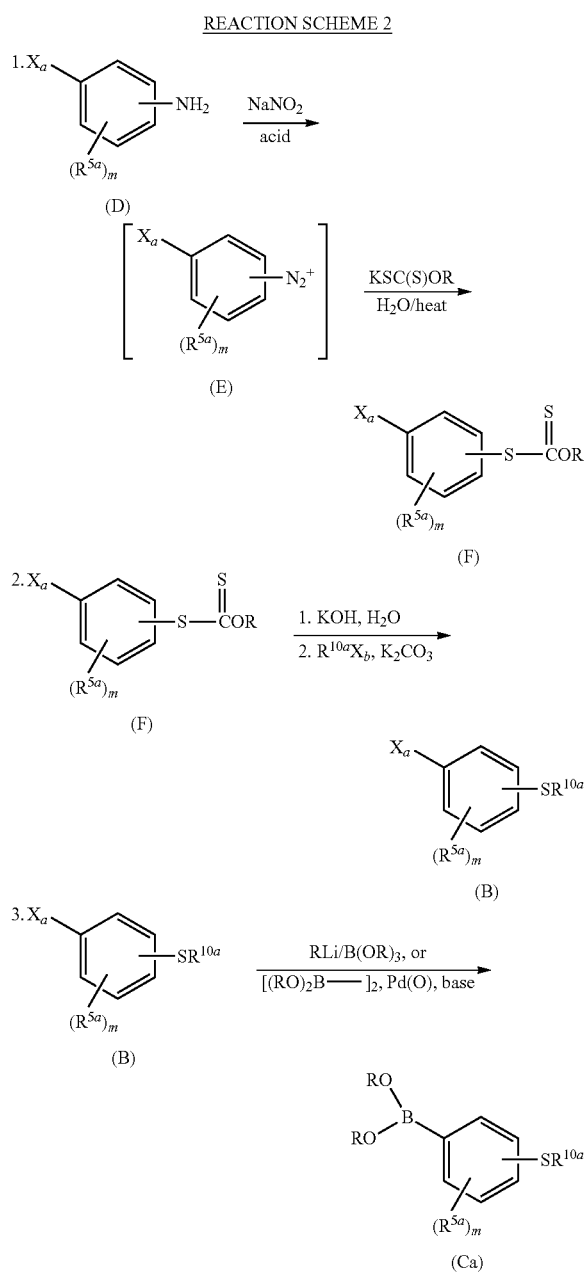

Compounds of formula (D) are commercially available or may be prepared according to methods disclosed herein or known to one skilled in the art or by methods disclosed in U.S. patent application Ser. No. 10/327,813.

In general, compounds of formula (Ca) are prepared by first exposing an aniline of formula (D) to diazotization conditions to give the aryldiazonium salt of formula (E) which, upon exposure to a source of nucleophilic sulfur such as a xanthate salt at elevated temperature, provides the compound of formula (F) after standard isolation procedures. Hydrolysis of the compound of formula (F) under basic conditions and exposure to an alkylating agent in the presence of a base then provides a compound of formula (B) using standard isolation procedures. Conversion of the compound of formula (B) to the compound of formula (Ca) is accomplished by treating the compound of formula (B) in an aprotic solvent at reduced temperature with a strong base in a metal-halogen exchange followed by reaction of the intermediate organometallic reagent (not shown) with a trialkylborate. Alternatively, compounds of formula (B) are reacted with a diboronate or dioxaborolane reagent, such as pinacolborane in a palladium mediated coupling reaction, for example a Suzuki reaction, to give compound of formula (Ca) after standard isolation procedures.

C. Preparation of Compounds of Formula (Ka)

Compounds of formula (Ka) are starting materials in the preparation of the compounds of the invention and can be prepared according to methods known to one skilled in the art or by the method described below in Reaction Scheme 3, wherein $X_b$ is bromo, chloro or iodo; m is 1 to 3; each R is hydrogen or alkyl; each $R^{5b}$ is independently hydrogen, halo, alkyl, haloalkyl, cyano, —$OR^8$, —$N(R^8)_2$, —$SR^8$, —$C(O)OR^8$, —$C(O)N(R^8)_2$; and $R^{8a}$ is alkyl, aryl or aralkyl:

REACTION SCHEME 3

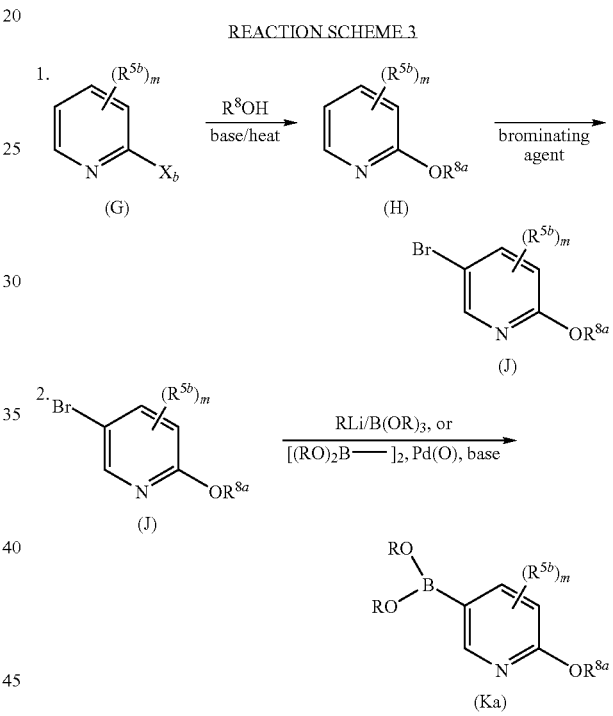

Compounds of formula (G) are commercially available or may be prepared according to methods disclosed herein or known to one skilled in the art or by methods disclosed in U.S. patent application Ser. No. 10/327,813.

In general, compounds of formula (Ka) are prepared by first reacting halopyridines of formula (G) with alcohols in the presence of base and at elevated temperature to give compounds of formula (H) after standard isolation procedures. In a subsequent step, exposure of compounds of formula (H) to a brominating agent provides halopyridines of formula (J) after standard isolation procedures. Conversion of compounds of formula (J) to compounds of formula (Ka) is then accomplished by treating the compounds of formula (J) in an aprotic solvent at reduced temperature with strong base in a metal-halogen exchange followed by reaction of the intermediate organometallic reagent (not shown) with a trialkylborate. Alternatively, compounds formula (J) are then reacted with a diboronate or dioxaborolane reagent such as pinacolborane in a palladium mediated coupling reaction, for example a Suzuki reaction, to give compounds of formula (Ka) after standard isolation procedures.

D. Preparation of Compounds of Formula (Kb)

Compounds of formula (Kb) are intermediates in the preparation of the compounds of the invention and can be prepared according to methods known to one skilled in the art or by the method described below in Reaction Scheme 4, wherein each $X_b$ is bromo, chloro or iodo; m is 1 to 3; each R is hydrogen or alkyl; each $R^{5b}$ is independently hydrogen, halo, alkyl, haloalkyl, cyano, —$OR^8$, —$N(R^8)_2$, —$SR^8$, —$C(O)OR^8$, —$C(O)N(R^8)_2$; and $R^{10a}$ is alkyl, aryl or aralkyl:

REACTION SCHEME 4

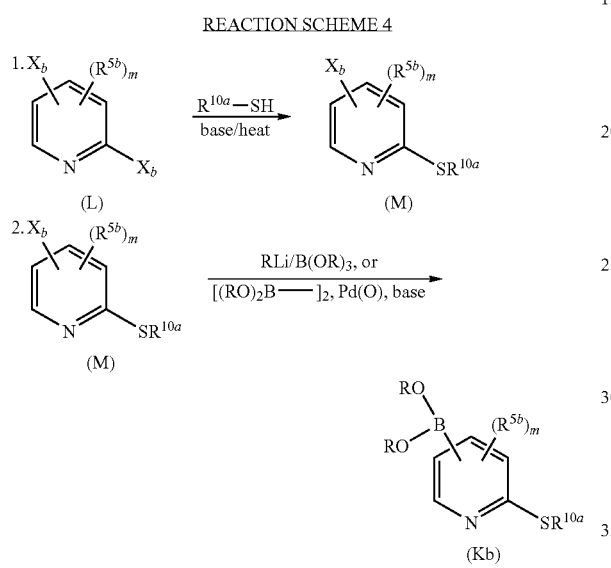

Compounds of formula (L) are commercially available or may be prepared according to methods disclosed herein or known to one skilled in the art or by methods disclosed in U.S. patent application Ser. No. 10/327,813.

In general, compounds of formula (Kb) are prepared by first reacting dihalopyridines of formula (L) with thiols in the presence of base and at elevated temperature to give sulfides of formula (M) after standard isolation procedures. Conversion of compounds of formula (M) to compounds of formula (Kb) is then accomplished by treating compounds of formula (M) in an aprotic solvent at reduced temperature with strong base in a metal-halogen exchange followed by reaction of the intermediate organometallic reagent with a trialkylborate. Alternatively, compounds (M) are reacted with a diboronate or dioxaborolane reagent such as pinacolborane in a palladium mediated coupling reaction, for example a Suzuki reaction, to give compounds of formula (Kb) after standard isolation procedures.

E. Preparation of Compounds of Formula (Cb)

Compounds of formula (Cb) are starting materials in the preparation of the compounds of the invention and can be prepared according to methods known to one skilled in the art or by the method described below in Reaction Scheme 5, wherein $X_a$ is bromo or iodo; $X_b$ is bromo, chloro or iodo; each m is 1 to 4; each R is hydrogen or alkyl; each $R^{5c}$ is independently hydrogen, fluoro, chloro, alkyl, haloalkyl, —$OR^8$, —$N(R^8)_2$; and $R^{8a}$ is alkyl, aryl or aralkyl:

REACTION SCHEME 5

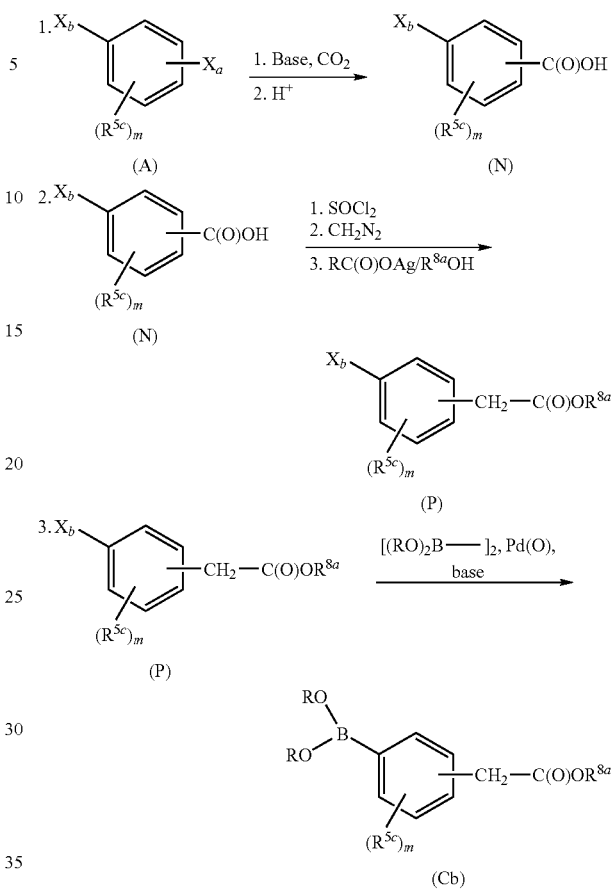

Compounds of formula (A) are commercially available or may be prepared according to methods disclosed herein or known to one skilled in the art or by methods disclosed in U.S. patent application Ser. No. 10/327,813.

In general, compounds of formula (Cb) are prepared by first reacting aryldihalides of formula (A) with strong base in an aprotic solvent at reduced temperature in a metal-halogen exchange reaction followed by carbonylation of the intermediate organometallic reagent (not shown) to give the carboxylic acids of formula (N) after standard isolation procedures. Conversion of compounds of formula (N) to compounds of formula (P) is then accomplished using the Arndt-Eistert reaction sequence, namely, preparation of the acylchloride (not shown) using standard methods, generation of the intermediate diazoketone (not shown) by treatment of the acylchloride with diazomethane at reduced temperature, followed by exposure of the diazoketone to a silver-salt of an organic acid in the presence of an alcohol and isolation using standard procedures. Palladium mediated coupling of compounds of formula (P) with a diboronate or dioxaborolane reagent such as pinacolborane provides arylboronates of formula (Cb) after standard isolation procedures.

F. Preparation of Compounds of Formula (Pb)

Compounds of formula (Pb) are starting materials in the preparation of the compounds of the invention and can be prepared according to methods known to one skilled in the art or by the method described below in Reaction Scheme 6, wherein $X_a$ is bromo or iodo; $X_b$ is bromo, chloro or iodo; m is 1 to 4; each R is alkyl or aralkyl; each $R^{5c}$ is independently hydrogen, fluoro, chloro, alkyl, haloalkyl, —OR$^8$ or —N(R$^8$)$_2$; R$^{7a}$ is alkyl, aralkyl or fluoro, and R$^{8a}$ is alkyl, aryl or aralkyl:

REACTION SCHEME 6

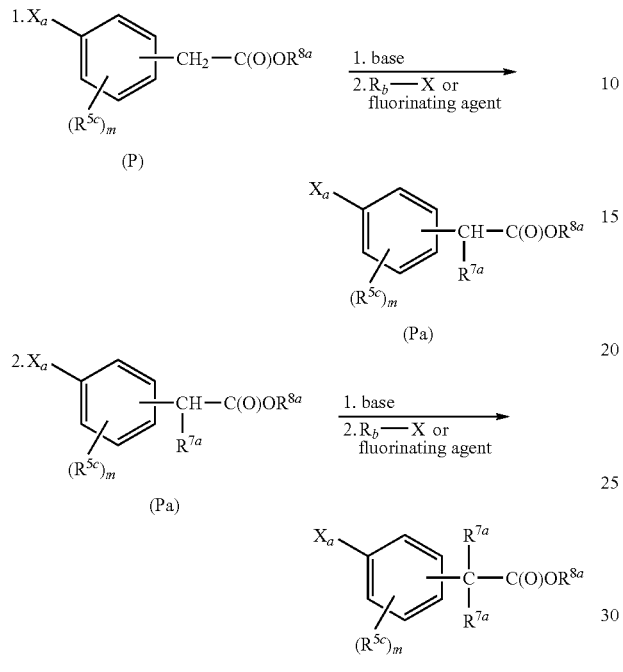

Compounds of formula (P) are commercially available or may be prepared according to methods disclosed herein or known to one skilled in the art or by methods disclosed in U.S. patent application Ser. No. 10/327,813.

In general, compounds of formula (Pb) are prepared by first treating compounds of formula (P) with a strong base in an aprotic solvent at reduced temperature followed by the addition of an alkylating or fluorinating agent to give compounds of formula (Pa). Reaction of compounds of formula (Pa) with additional base and subsequent treatment with a second portion of alkylating or fluorinating agent provides compounds of formula (Pb) after standard isolation procedures.

G. Alternate Preparation of Compounds of Formula (Cb)

Compounds of formula (Cb) are starting materials in the preparation of the compounds of the invention and can be prepared according to methods known to one skilled in the art or by the method described below in Reaction Scheme 7, wherein each m is 1 to 4; each R is hydrogen or alkyl; each R$^{5d}$ is independently hydrogen, chloro, fluoro, alkyl, haloalkyl; and R$^{8a}$ is alkyl, aryl or aralkyl:

REACTION SCHEME 7

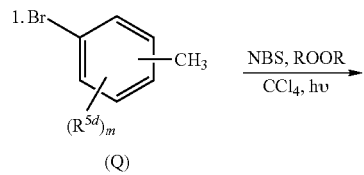

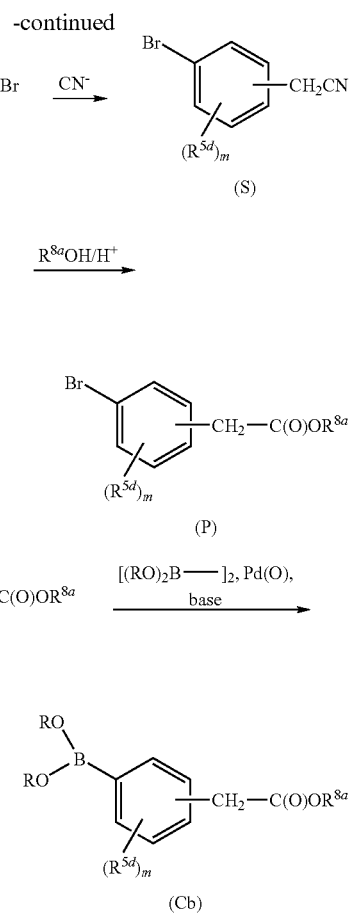

Compounds of formula (Q) are commercially available or may be prepared according to methods disclosed herein or known to one skilled in the art or by methods disclosed in U.S. patent application Ser. No. 10/327,813.

In general, compounds of formula (Cb) are prepared by first reacting substituted methylbenzenes of formula (Q) under free radical conditions in the presence of a halogenating agent to give benzyl halides of formula (R) which, upon exposure to a cyanide source, afford benzyl cyanides of formula (S) after standard isolation procedures. Treatment of an alcoholic solution of benzyl cyanides of formula (S) in the presence of strong acid provides esters of formula (P) after standard isolation procedures. Palladium mediated coupling of compounds of formula (P) with a diboronate or dioxaborolane reagent such as pinacolborane provides arylboronates of formula (Cb) after standard isolation procedures.

Alternatively, compounds of formula (Cb) are prepared by reacting compounds of formula (Pa) or compounds of formula (Pb), as described above in Reaction Scheme 6, under similar conditions as described above in Step 3 of Reaction Scheme 7 to produce compounds of formula (Cb) wherein the —CH$_2$—C(O)OR$^{8a}$ substituent is either —C(R$^{7a}$)H—C(O)OR$^{8a}$ or —C(R$^{7a}$)$_2$—C(O)OR$^{8a}$, respectively.

H. Preparation of Compounds of Formula (Ta)

Compounds of formula (Ta) are starting materials in the preparation of the compounds of the invention and can be prepared according to methods known to one skilled in the art or by the method described below in Reaction Scheme 8, wherein R is alkyl:

REACTION SCHEME 8

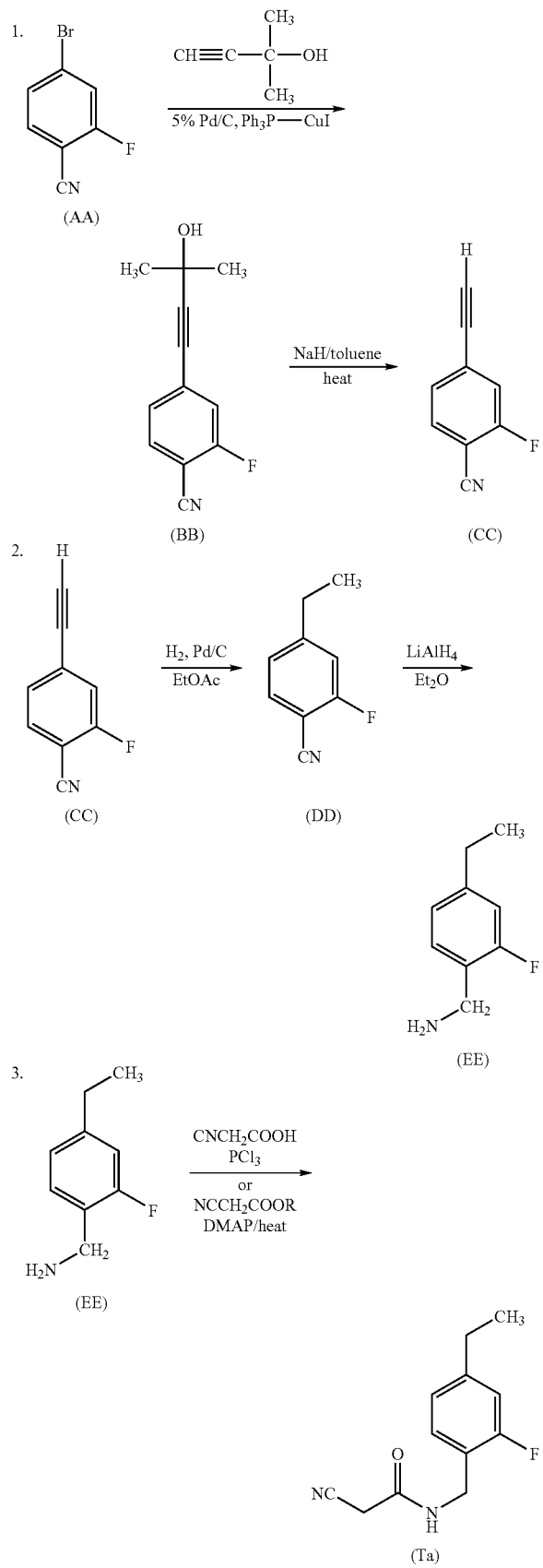

Compounds of formula (AA) are commercially available or may be prepared according to methods disclosed herein or known to one skilled in the art or by methods disclosed in U.S. patent application Ser. No. 10/327,813.

In general, compounds of formula (Ta) are prepared by first reacting the arylhalide of formula (AA) with 2-methyl-3-butyn-2-ol in the presence of palladium and a copper(I) salt to give the alkyne of formula (BB) after standard isolation procedures. Exposure of alkyne of formula (BB) to strong base at elevated temperature affords the alkyne of formula (CC) which is then, under standard conditions of catalytic hydrogenation, converted to the nitrile of formula (DD) after standard isolation procedures. Reduction of the nitrile of formula (DD) with a metalhydride reagent provides the benzylamine of formula (EE) after standard isolation procedures. Conversion of the benzylamine of formula (EE) to the compound of formula (Ta) is then accomplished by either treating a solution of the benzylamine of formula (EE) with the acylchloride prepared from cyanoacetic acid under standard conditions, in the presence of a base, or by heating a solution of the benzylamine of formula (EE) with a cyanoacetic ester in the presence of a base such as N,N-dimethylaminopyridine (DMAP) to give the compounds of formula (Ta) after standard isolation procedures.

I. Preparation of Compounds of Formula (Ua)

Compounds of formula (Ua) are starting materials in the preparation of the compounds of the invention and can be prepared according to methods known to one skilled in the art or by the method described below in Reaction Scheme 9, wherein n is 1 to 4; each R is alkyl or aralkyl; $R^{3a}$ is alkyl, aralkyl, heteroaryl, heteroarylalkyl, cycloalkyl, cycloalkylalkyl, heterocyclyl or heterocyclylalkyl; each $R^{4a}$ is hydrogen, fluoro, chloro, alkyl or haloalkyl; and is aryl or heteroaryl:

REACTION SCHEME 9

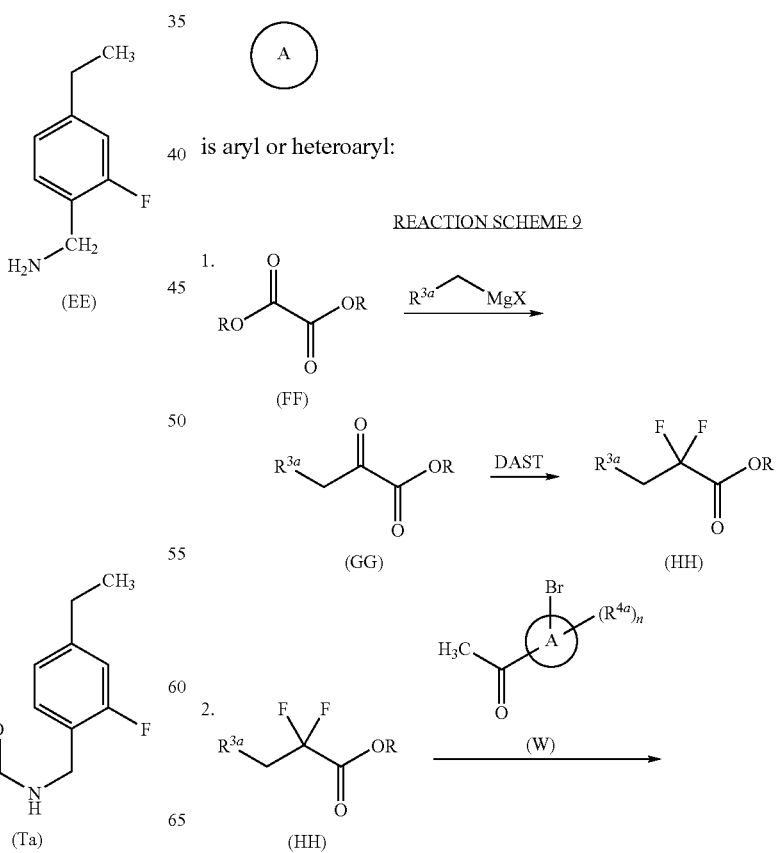

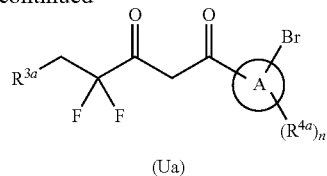

(Ua)

Compounds of formula (FF) and (GG) are commercially available or may be prepared according to methods disclosed herein or known to one skilled in the art or by methods disclosed in U.S. patent application Ser. No. 10/327,813.

In general, compounds of formula (Ua) are prepared by first treating the oxalate diesters of formula (FF) with an organometallic reagent, such as a Grignard reagent, in an aprotic solvent at reduced temperature to give the α-ketoesters of formula (GG) after standard isolation procedures. Treatment of the ketoesters of formula (GG) with a fluorinating agent, such as (diethylamino)sulfur trifluoride (DAST), affords the 2,2-difluoroesters of formula (HH) after standard isolation procedures. Reaction of 2,2-difluoroesters of formula (HH) with methylketones of formula (W) under Claisen condensation conditions provides the diketones of formula (Ua) after standard isolation procedures.

J. Preparation of Compounds of Formula (I)

Compounds of formula (Ia) are compounds of formula (I) wherein $R^6$ is a direct bond and are prepared according to methods known to one skilled in the art or by the method described below in Reaction Scheme 10, wherein n, m, $R^1$, $R^2$, $R^3$, $R^4$ and $R^5$ are as defined above in the Summary of the Invention, and

is aryl or heteroaryl and

is aryl or heteroaryl:

REACTION SCHEME 10

1.
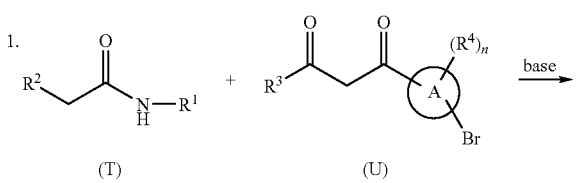

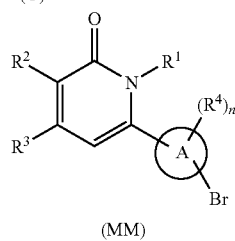

(MM)

2.
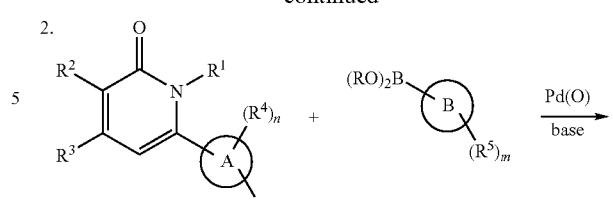

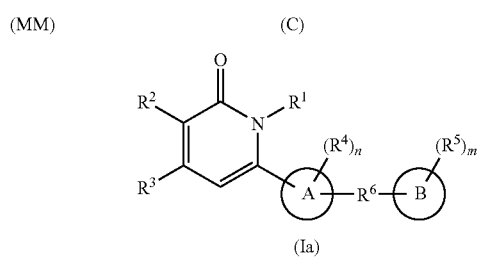

(Ia)

Compounds of formula (T) and (U) are commercially available or may be prepared according to methods disclosed herein or known to one skilled in the art or by methods disclosed in U.S. patent application Ser. No. 10/327,813.

In general, compounds of formula (Ia), which are compounds of formula (I), are prepared by first combining cyanoacetamides of formula (T) with diketones of formula (U) in the presence of base and at elevated temperature to give 2-pyridones of formula (V) after standard isolation procedures. Treatment of the pyridones of formula (V) with boronates of formula (C) under palladium-catalyzed coupling conditions (Suzuki reaction) provides the compounds of formula (Ia) after standard isolation procedures. Compounds of formula (Ia) can be further converted to various derivatives using general methods of organic chemistry known to those skilled in the art and/or by methods disclosed herein.

K. Preparation of Compounds of Formula (Ib)

Compounds of formula (Ib) are compounds of formula (I) wherein $R^6$ is a direct bond and are prepared according to methods known to one skilled in the art or by the method described below in Reaction Scheme 11, wherein R is hydrogen or alkyl, $X_b$ is bromo, chloro or iodo, and n, m, $R^1$, $R^2$, $R^3$, $R^4$ and $R^5$ are as defined above in the Summary of the Invention, and

is aryl or heteroaryl and

is aryl or heteroaryl:

REACTION SCHEME 11

1.
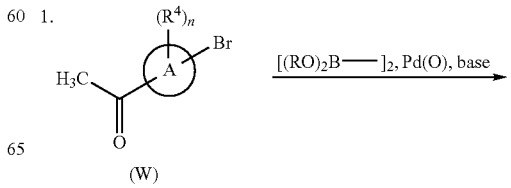

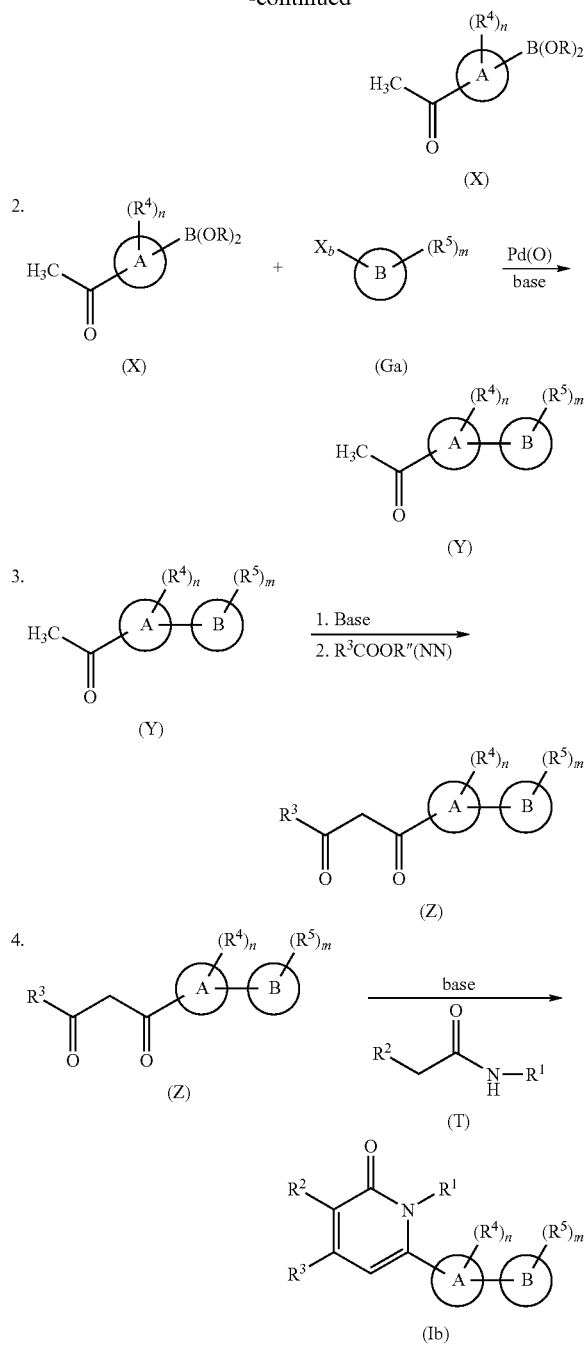

methylketones of formula (Y) in the presence of strong base, for example, under Claisen condensation conditions, provides the diketones of formula (Z) after standard isolation procedures. The diketones of formula (Z) undergo a condensation reaction with amides of formula (T) in the presence of base and at elevated temperature to give the 2-pyridones of formula (Ib) after standard isolation procedures. Compounds of formula (Ib) can be further converted to various derivatives using general methods of organic chemistry known to those skilled in the art and/or by methods disclosed herein.

L. Preparation of Compounds of Formula (Ya)

Compounds of formula (Ya) are starting materials in the preparation of the compounds of the invention and can be prepared according to methods known to one skilled in the art or by the method described below in Reaction Scheme 12, wherein each X is halo; $X_a$ is bromo or iodo; n is 1 or 2; $R^{4c}$ is hydrogen, fluoro, chloro, alkyl or haloalkyl; m, $R^1$, $R^2$, $R^3$, $R^4$ and $R^5$ are as defined above in the Summary of the Invention, and

is aryl or heteroaryl:

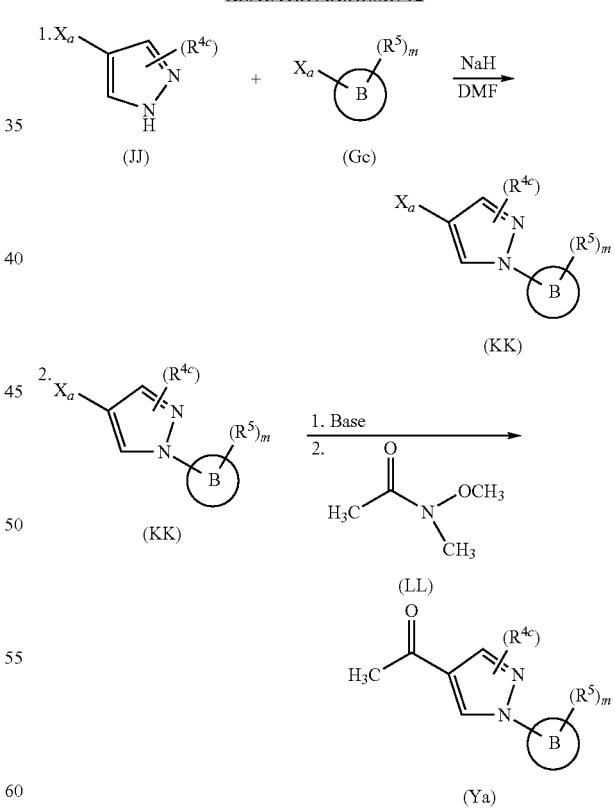

Compounds of formula (W) and (Ga) are commercially available or may be prepared according to methods disclosed herein or known to one skilled in the art or by methods disclosed in U.S. patent application Ser. No. 10/327,813.

In general, compounds of formula (Ib) are prepared by first, which are compounds of formula (I), are prepared by first treating compounds of formula (W) with a diboronate or dioxaborolane reagent such as pinacolborane under palladium mediated coupling conditions to give the boronates of formula (X) after standard isolation procedures. In a second palladium catalyzed coupling (Suzuki reaction), boronates of formula (X) are combined with halides of formula (Ga) to give methylketones of formula (Y) after standard isolation procedures. The reaction of esters of formula (NN) with Compounds of formula (JJ), (Gc) and (LL) are commercially available or may be prepared according to methods disclosed herein or known to one skilled in the art or by methods disclosed in U.S. patent application Ser. No. 10/327,813.

In general, compounds of formula (Ya) are prepared by first reacting halopyrazoles of formula (JJ) with halides of formula (Gc) in the presence of base at elevated temperatures to give the pyrazole derivatives of formula (KK) after standard isolation procedures. Treatment of the pyrazole derivatives of formula (KK) with strong base in an aprotic solvent at reduced temperature under conditions of metal-halogen exchange gives the intermediate organometallic reagent (not shown), followed by the addition of an acylating agent effective at reduced temperatures, such as the compound of formula (LL), provides the pyrazolemethylketones of formula (Ya) after standard isolation procedures.

The following specific Preparations (for intermediates) and Examples (for compounds, pharmaceutical compositions and methods of use of the invention) are provided as a guide to assist in the practice of the invention, and are not intended as a limitation on the scope of the invention.

Preparation 1

Compounds of Formula (B)

1,3-Dibromo-5-ethyl-benzene (1.54 g, 5.8 mmoles) was dissolved into anhydrous THF (20 mL) under nitrogen, and was chilled to −78° C. To this stirring solution was slowly (over 10 min) added t-BuLi (3.8 mL, 6.5 mmoles, 1.7M solution in pentane). After the addition was complete the mixture was allowed to stir at −78° C. for an additional 30 min. After this period isopropyl disulfide (1.4 mL, 8.8 mmoles) was added and the mixture was allowed to warm to ambient temperature. The reaction was then warmed to 75° C., and was stirred at this temperature for 16 hours. After this period the reaction mix was evaporated in vacuo and was purified using flash silica chromatography (0-1% EtOAc/Hexane) to yield 1-bromo-3-ethyl-5-isopropylsulfanyl-benzene (1.08 g, 72%) as a clear liquid. $^1$H-NMR (CDCl$_3$): δ 7.34-7.32 (m, 1H), 7.19-7.17 (m, 1H), 7.13-7.11 (m, 1H), 3.39 (m, J=6.6 Hz, 1H), 2.59 (q, J=7.6 Hz, 2H), 1.30 (d, J=6.6 hz, 6H), 1.22 (t, J=7.6 Hz, 3H).

Preparation 2

Compounds of Formula (F)

3-Bromo-5-trifluoromethyl-phenylamine (4.0 mL, 28.3 mmoles) was dissolved into concentrated HCl (70 mL). This solution was chilled to 0° C. and to it was slowly added a solution of sodium nitrite (2.5 g, 36.2 mmoles) in 50 mL of water. After completion of the addition enough ethanol (90%) was added (25 mL) to affect nearly complete dissolution of the resultant mixture. The mixture was stirred at 0° C. for an additional 20 minutes. After this period the heterogeneous mixture was quickly transferred (cold) to an addition funnel. The diazonium mixture was added to a solution of O-ethylxanthic acid, potassium salt (5.7 g, 35.6 mmoles) in 50 mL of water at 60° C. The mixture was next heated to 90° C. and was stirred at this temperature for 2 hours. After this period the mixture was allowed to cool to ambient temperature, and the crude xanthate (a red liquid) was removed from the bottom of the aqueous mixture via pipette. The crude product taken up in 100 mL of diethyl ether and was washed with water (2×25 mL) and brine (20 mL). The ether layer was evaporated in vacuo to yield crude xanthate. The crude product was purified using flash silica chromatography (0-1% EtOAc/Hexane) to yield 4.7 g (51% yield) of dithiocarbonic acid S-(3-bromo-5-trifluoromethyl-phenyl) ester O-ethyl ester as a red liquid. $^1$H-NMR (CDCl$_3$): δ 7.83 (d, J=5.8 Hz, 2H), 7.71 (s, 1H), 4.63 (q, J=7.1 Hz, 2H), 1.36 (t, J=7.1 Hz, 3H).

Preparation 3

Compounds of Formula (B)

Dithiocarbonic acid S-(3-bromo-5-trifluoromethyl-phenyl) ester O-ethyl ester (3.3 g, 10.3 mmoles) was dissolved into 30 mL of EtOH, 10 mL of H$_2$O, and was sealed under nitrogen. To this stirring mixture was added KOH (2.8 g, 50 mmoles) and this mix was stirred at reflux (under nitrogen) for 12 hours. After this period the reaction mixture was evaporated in vacuo and combined with 50 mL of water. The pH was adjusted to <2 using 6N HCl and the resulting mixture was extracted with diethyl ether (3×50 mL). The combined ethereal layer was washed with brine and dried over anhydrous MgSO$_4$. Following evaporation in vacuo the crude thiol was dissolved into 50 mL of acetone. Ethyl bromide (1.5 mL, 20.1 mmoles) and K$_2$CO$_3$ (5 g, 36.2 mmoles) were added, and the mixture was stirring at ambient temperature (under nitrogen) for 6 hours. After this period the mixture was gravity filtered, and evaporated in vacuo to yield crude product. The crude product was purified using flash silica chromatography (0-1% EtOAc/Hexane) to yield 1-bromo-3-ethylsulfanyl-5-trifluoromethyl-benzene (1.33 g, 45% yield) as a yellowish liquid. $^1$H-NMR (CDCl$_3$): δ 7.56 (s, 1H), 7.52 (s, 1H), 7.43 (s, 1H), 3.0 (q, J=7.3 Hz, 2H), 1.36 (t, J=7.3 Hz, 3H).

Preparation 4

Compounds of Formula (Ca)

1-Bromo-3-ethylsulfanyl-5-trifluoromethyl-benzene (1.33 g, 4.7 mmoles) was placed into a 50 mL pear-shaped flask and was sealed under nitrogen. The material was then solubilized with 25 mL of anhydrous DMSO, and the resulting solution was degassed by passing a steady stream of nitrogen through the solution for 10 min. In a separate round-bottom flask were combined bis(pinacolato)diboron (1.3 g, 5.1 mmoles), [1,1'-bis(diphenylphosphino)ferrocene]-dichloropalladium(II) complex with DCM (1:1) (0.11 g, 0.13 mmoles) and potassium acetate (1.4 g, 14.3 mmoles) with a stirring bar under nitrogen. Following degassification the bromide solution was transferred to the "catalytic" mixture and the resulting mix was stirred at 90° C. for 16 hours. After this period the reaction mix was combined with 100 mL of water and was extracted with benzene (4×30 mL). The combined benzene layer was washed with water (4×50 mL) and was dried over anhydrous Na$_2$SO$_4$. Following evaporation in vacuo the crude product was purified using flash silica chromatography (0-1% EtOAc/Hexane) to yield 2-(3-ethylsulfanyl-5-trifluoromethyl-phenyl)-4,4,5,5-tetramethyl-[1,3,2]dioxaborolane (651 mg, 41% yield) was a thick, clear liquid. Note: TLC visualization accomplished using ceric ammonium molybdate stain. $^1$H-NMR (CDCl$_3$): δ 7.89 (s, 1H), 7.83 (s, 1H), 7.60 (s, 1H), 3.01 (q, J=7.3 Hz, 2H), 1.35 (s, 12H), 1.33 (t, J=7.3 Hz, 3H).

Preparation 5

Compounds of Formula (H)

2-Chloro-3-trifluoromethyl-pyridine (4.43 g, 24.4 mmol) was dissolved in 42 ml 21% (wt.) sodium ethoxide in ethanol. The mixture was stirred at ambient temperature for 1.5 days. After this period of time, the solvent was evaporated and the residue was taken into water and extracted with dichloromethane three times. The combined extract was washed with brine, dried over sodium sulfate, and concentrated in vacuo to give 2-ethoxy-3-trifluoromethyl-pyridine as a light liquid (3.42 g, 73% yield). The crude product was used directly for the next step. $^1$H-NMR (400 MHz, CDCl$_3$): δ 1.42 (t, 3H, J=7.07), 4.49 (q, 2H, J=7.07), 6.94 (dd, 1H, J=7.45, J=5.05), 7.85 (dd, 1H, J=1.26, J=7.45), 8.30 (dd, 1H, J=1.26, J=5.06).

Preparation 6

Compounds of Formula (J)

2-Ethoxy-3-trifluoromethyl-pyridine (900 mg, 4.71 mmol) and 1,3-dibromo-5,5-dimethylhydantoin (1.35 g, 4.71 mmol) were placed in a round-bottom flask. To this mixture was slowly added 10 mL trifluoroacetic acid. The mixture was stirred at ambient temperature for overnight. More 1,3-dibromo-5,5-dimethylhydantoin (540 mg, 1.9 mmol) was added and the reaction mixture was stirred at ambient temperature for another day. After the completion of the reaction, TFA solvent was evaporated in vacuo and the resulting residue was neutralized to pH 7 by the addition of saturated NaHCO$_3$. The aqueous layer was extracted with dichloromethane three times and the combined extract was washed with brine, dried over sodium sulfate, and concentrated in vacuo to give a mixture of oil and white solid. The residue was redissolved into 20% EtOAc/Hexane, and the unsoluable white solid was filtered out. The filtrate was concentrated and then purified by column chromatography on silica gel (10% EtOAC/Hexane) to give 5-bromo-2-ethoxy-3-trifluoromethyl-pyridine as a colorless liquid (1.0 g, 79% yield). $^1$H-NMR (400 MHz, CDCl$_3$): δ 1.41 (t, 3H, J=7.07), 4.46 (q, 2H, J=7.07), 7.94 (dd, 1H, J=0.51, J=2.53), 8.34 (dd, 1H, J=0.51, J=2.53).

Preparation 7

Compounds of Formula (Ka)

A. [1,1'-bis(diphenylphosphino)ferrocene]dichloropalladium (II) complex with dichloromethane (1:1), (286 mg, 0.35 mmol), potassium acetate (1.55 g, 15.8 mmol), and bis(pinacolato)diboron (1.3 g, 5.3 mmol) were placed into a vial and degassed with stream of nitrogen for 20 min. In a separate vial, 5-bromo-2-ethoxy-3-trifluoromethyl-pyridine (945 mg, 3.5 mmol) was dissolved in 7 ml anhydrous DMSO and degassed with stream of nitrogen for 20 min. The DMSO solution of 5-bromo-2-ethoxy-3-trifluoromethyl-pyridine was added to the "catalyst" vial, and then heated at 80° C. overnight. After cooling to ambient temperature, water and ethyl acetate were added to the reaction mixture and the aqueous layer was extracted with ethyl acetate. The combined extract was washed with brine, dried over sodium sulfate, and concentrated in vacuo. The crude product was purified by column chromatography on silica gel (10→30% EtOAC/Hexane) to give 2-ethoxy-5-(4,4,5,5-tetramethyl-[1,3,2]dioxaborolan-2-yl)-3-trifluoromethyl-pyridine as solid (1.08 g, 97% yield). $^1$H-NMR (400 MHz, CDCl$_3$): δ 1.35 (s, 12H), 1.42 (t, 3H, J=7.07), 4.52 (q, 2H, J=7.07), 8.20 (d, 1H, J=1.01), 8.64 (d, 1H, J=1.26).

B. Alternatively, n-butyl lithium (1.6 M solution in hexane, 0.9 mL, 1.43 mmol) was slowly added to a solution of 5-bromo-2-ethoxy-3-trifluoromethyl-pyridine (352 mg, 1.3 mmol) in 2.6 mL anhydrous Et$_2$O at −78° C. under nitrogen. The mixture was kept at −78° C. for 1 hr, and then to this mixture was added triisopropyl borate (489 mg, 2.6 mmol). The mixture was allowed to warm to ambient temperature overnight. The reaction was quenched by water and the pH was adjusted to 5 by carefully addition of 1N aqueous HCl. Two layers were separated and the aqueous layer was extracted with ethyl acetate three times. The extract was washed with brine, dried over sodium sulfate, and concentrated in vacuo to give 2-ethoxy-3-trifluoromethylpyridine-5-boronic acid as a brown oil (240 mg, 67% yield). The product was used for the next step without purification.

Preparation 8

Compounds of Formula (M)

A. 2,5-Dibromo-pyridine (3.0 g, 12.7 mmol) and sodium thiomethoxide (0.84 g, 12 mmol) were dissolved in 18 ml anhydrous N,N-dimethylformamide. The mixture was heated at 160° C. under nitrogen for 6 hrs. After cooling to ambient temperature, water and ethyl acetate were added to the reaction mixture. The aqueous layer was extracted with ethyl acetate several times. The combined extract was washed with brine, dried over sodium sulfate, and concentrated in vacuo. The crude product was purified by column chromatography on silica gel (0→6% EtOAC/Hexane) to give 5-bromo-2-methylsulfanyl-pyridine as a white solid (2.18 g, 84% yield). $^1$H-NMR (400 MHz, CDCl$_3$): δ 2.55 (s, 3H), 7.09 (dd, 1H, J=0.7, J=8.6), 7.59 (dd, 1H, J=2.4, J=8.6), 8.50 (m, 1H).

B. Alternatively, 2-bromo-5-nitro-pyridine (1.22 g, 6.0 mmoles), TMS-acetylene (0.9 mL, 6.4 mmoles), CuI (11 mg, 0.06 mmoles) and dichlorobis(triphenylphosphine)palladium (II) (210 mg, 0.3 mmoles) were combined and flushed with dry nitrogen for 10 min. After this period the mix was solubilized with 24 mL of anhydrous triethylamine (degassed), and the mix was stirred at ambient temperature for 4 hours. After this period the reaction mix was evaporated in vacuo and purified directly using flash silica chromatography (0-10% EtOAc/Hexane) to yield 5-nitro-2-trimethylsilanylethynyl-pyridine as a brown solid. This material was dissolved into THF (10 mL) and to this solution was added 100 mg of TFAB (on silica gel, 1.0-1.5 mmole F/g resin). The solution was stirred at ambient temperature for 15 min. After this period the reaction mix was evaporated in vacuo purified directly using flash silica chromatography (0-20% EtOAc/Hexane) to yield 2-ethynyl-5-nitro-pyridine as a clear liquid. This product was combined with 10% Pd/C (90 mg) and ethanol (20 ml) and was flushed with dry nitrogen. After oxygen exclusion the stirring mix was flushed with H$_2$ and stirred under H$_2$ pressure (balloon) for 16 hours. After this period the reaction mixture was flushed with nitrogen and then filtered through Celite. The filtrate was evaporated in vacuo and purified using flash silica chromatography (0-10% MeOH/DCM w/0.1% diethylamine) to yield 6-ethyl-pyridin-3-ylamine (442 mg, 60%-3 steps) as a brownish residue. $^1$H-NMR (CDCl$_3$): δ 8.05-8.02 (m, 1H), 6.96-6.93 (m, 2H), 3.55 (br s, 2H), 2.71 (q, J=7.3 Hz, 2H), 1.25 (t, J=7.3 Hz, 3H).

C. 6-Ethyl-pyridin-3-ylamine (442 mg, 3.62 mmoles) was dissolved into 30 mL of MeOH and 3 mL of HOAc and the resulting solution was chilled to 0° C. To this stirring mixture was slowly added a solution of bromine (0.41 mL, 8.0 mmoles) in 5 mL of HOAc. The mix was then allowed to warm to ambient temperature and was stirred at this temperature for 16 hours. After this period the reaction mix was evaporated in vacuo, combined with saturated NaHCO$_3$ (15 mL), and extracted with DCM (3×20 mL). The DCM layer was dried over anhydrous Na$_2$SO$_4$ and was evaporated in vacuo to yield the crude product was a brownish solid. The crude product was purified using flash silica chromatography (0-10% EtOAc/Hexane) to yield 2,4-dibromo-6-ethyl-pyridin-3-ylamine (868 mg, 86%) as a brown solid. $^1$H-NMR (CDCl$_3$): δ 252-827.18 (s, 1H), 4.41 (br s, 2H), 2.68 (q, J=7.6 Hz, 2H), 1.24 (t, J=7.6 Hz, 3H).

D. 2,4-Dibromo-6-ethyl-pyridin-3-ylamine (105 mg, 0.38 mmoles) was combined with 80% sodium thioethoxide (50 mg, 0.48 mmoles) in anhydrous DMF (2 mL) and was stirred at 50° C. under nitrogen for 2 hours. After this period the reaction mix was combined with water (20 mL) and was extracted with EtOAc (3×20 mL). The combined EtOAc layer was washed with water (3×15 mL) and brine. After drying over anhydrous Na$_2$SO$_4$ the organic layer was evaporated in vacuo to yield crude product. The crude product was purified using flash silica chromatography (0-15% EtOAc/Hexane) to yield 4-bromo-6-ethyl-2-ethylsulfanyl-pyridin-3-ylamine (83 mg, 84%) as a clear residue. $^1$H-NMR (CDCl$_3$): δ 6.94 (s, 1H), 4.34 (br s, 2H), 2.95 (q, J=7.3 Hz, 2H), 2.68 (q, J=7.6 Hz, 2H), 1.33 (t, J=7.3 Hz, 3H), 1.24 (t, J=7.6 Hz, 3H).

E. 4-Bromo-6-ethyl-2-ethylsulfanyl-pyridin-3-ylamine (476 mg, 1.82 mmoles) was dissolved into EtOH (5 mL) and chilled to −10° C. under nitrogen. At −10° C. 48% wt. aq. HBF$_4$ (1.0 mL) was added and the temperature was further lowered to −25° C. At −25° C. isoamyl nitrite (0.256 mL, 1.9 mmoles) was slowly added (over 1 min), and the temperature was allowed to warm to −5° C. The reaction was stirred at −5° C. for 30 min. After this period the reaction mix was chilled to −25° C. and an excess of 50% aqueous H$_3$PO$_2$ (5.0 mL) was added. The mix was then allowed to warm to ambient temperature and was stirred at this temperature for 1 hour (vigorous bubbling is observed). After this period the reaction was combined with 40 mL of diethyl ether followed (carefully) by saturated NaHCO$_3$ (10 mL). The mix was then extracted with diethyl ether (2×20 mL) and the resultant ether layer was washed with brine. After drying over anhydrous MgSO$_4$ the ethereal layer was evaporated in vacuo to yield crude product. The crude product was purified using flash silica chromatography (0-10% EtOAc/Hexane) to yield 4-bromo-2-ethylsulfanyl-6-ethylpyridine (340 mg, 76%) as a golden-yellow liquid. $^1$H-NMR (CDCl$_3$): δ 7.09 (br d, J=1.3 Hz, 1H), 6.90 (br d, J=1.5 Hz, 1H), 3.0 (q, J=7.3 Hz, 2H), 2.73 (q, J=7.6 Hz, 2H), 1.39 (t, J=7.3 Hz, 3H), 1.27 (t, J=7.6 Hz, 3H).

Preparation 9

Compounds of Formula (Kb)

Palladium catalyst ([1,1'-bis(diphenylphosphino)ferrocene]dichloropalladium (II) complex with dichloromethane (1:1), 167 mg, 0.21 mmol), potassium acetate (1.81 g, 18.5 mmol, Aldrich), and bis(pinacolato)diboron (1.56 g, 6.1 mmol) were placed into a vial and degassed with stream of nitrogen for 20 min. In a separate vial, 5-bromo-2-methylsulfanylpyridine (836 mg, 4.1 mmol) was dissolved in 8 ml anhydrous DMSO and degassed with stream of nitrogen for 20 min. The DMSO solution of 5-bromo-2-methylsulfanylpyridine was added to the "catalyst" vial, and then heated at 80° C. overnight. After cooling to ambient temperature, water and ethyl acetate were added to the reaction mixture. The aqueous layer was extracted with ethyl acetate. The combined organic layers were washed with brine, dried over sodium sulfate, and concentrated in vacuo. The crude product was purified by column chromatography on silica gel (10→30% EtOAC/Hexane, 0.25% Et$_3$N in hexane) to give 2-methylsulfanyl-5-(4,4,5,5-tetramethyl-[1,3,2]dioxaborolan-2-yl)pyridine as a colorless oil (1.00 g, 97% yield).

$^1$H-NMR (400 MHz, CDCl$_3$): δ 1.35 (s, 12H), 2.58 (s, 3H), 7.16 (dd, 1H, J=1.0, J=8.0), 7.83 (dd, 1H, J=1.8, J=8.0), 8.50 (dd, 1H, J=1.7, J=1.0)

Preparation 10

Compounds of Formula (N)

1,3-Dibromo-5-isopropyl-benzene (1.57 g, 5.65 mmoles) was dissolved into anhydrous THF (50 mL) under nitrogen, and was chilled to −78° C. To this stirring solution was slowly (over 10 min) added t-BuLi (3.6 mL, 6.1 mmoles, 1.7M solution in pentane). After the addition was complete the mixture was allowed to stir at −78° C. for an additional 30 min. After this period CO$_2$ was bubbled through the stirring solution and the temperature was allowed to warm to ambient temperature. CO$_2$ bubbling was continued for 3 hours and afterwards the reaction was allowed to stir for an additional 6 hours. After this period 1H HCl (10 mL) was added and the mix was evaporated in vacuo (-THF). The resulting aqueous mixture was extracted with DCM (3×20 mL) and the organic layer was dried over anhydrous Na$_2$SO$_4$. Evaporation in vacuo yielded the crude carboxylic acid as a white solid. The crude acid (1.22 g, ~5.0 mmoles) was dissolved into C$_6$H$_6$ (20 mL) and to this was added freshly distilled thionyl chloride (0.5 mL, 6.9 mmoles). This mixture was heated to reflux and stirred at this temperature for 16 hours. After this period the reaction mix was evaporated in vacuo to yield crude 3-bromo-5-isopropyl-benzoyl chloride (1.0 g, 68%—2 steps) as a yellow liquid. $^1$H-NMR (CDCl$_3$): δ 8.08 (t, J=1.8 Hz, 1H), 7.89-7.87 (m, 1H), 7.68-7.66 (m, 1H), 2.98 (m, J=6.8 Hz, 1H), 1.28 (d, J=6.8 Hz, 6H).

Preparation 11

Compounds of Formula (P)

A. Potassium Hydroxide (1 g) was added to an erlenmeyer flask containing water (40 mL) and diethyl ether (50 mL) at 0° C. The mixture was stirred to fully solubilize the hydroxide. 1-Methyl-3-nitro-1-nitrosoguanidine (2.24 g, 15.2 mmoles) was added to this flask in aliquots to generate a solution of diazomethane in ether. A separate erlenmeyer flask was chilled to −78° C. Ether from the diazomethane "generator" was transferred via pipette to this "cold" flask. When nearly all of the ether (diazomethane) had been transferred to the "cold" flask, a solution of 3-Bromo-5-isopropyl-benzoyl chloride (796 mg, 3.0 mmoles) in 10 mL of diethyl ether was added to the "cold" flask. The "cold" flask was then allowed to warm to 0° C. and was stirred at this temperature for 2 hrs. After this period the reaction mixture was thoroughly purged using nitrogen gas (bubbling). The resulting ether solution was evaporated in vacuo and the crude product was purified using flash silica chromatography (0-10% EtOAc/Hexane) to yield the intermediate diazoketone (696 mg, 86%) as a yellow solid. $^1$H-NMR (CDCl$_3$): δ 7.66 (br t, J=1.8 Hz, 1H), 7.57-7.55 (m, 1H), 7.54-7.52 (m, 1H), 5.86 (s, 1H), 2.94 (m, J=6.8 Hz, 1H), 1.26 (d, J=6.8 Hz, 6H).

B. The diazoketone (696 mg, 2.61 mmoles) was dissolved into MeOH (20 mL) and to this solution at ambient temperature was added a solution of AgOBz (340 mg, 1.49 mmoles) in NEt$_3$ (4.2 mL). This mixture was stirred at ambient temperature for 30 min. After this period the reaction mix was filtered through Celite and evaporated in vacuo to yield crude product. The crude product was purified using flash silica chromatography (0-10% EtOAc/Hexane) to yield (3-bromo-5-isopropyl-phenyl)-acetic acid methyl ester (0.514 g, 62%—2 steps) as a yellow residue. $^1$H-NMR (CDCl$_3$): δ 7.28-7.25 (m, 2H), 7.06-7.04 (m, 1H), 3.71 (s, 3H), 3.57 (s, 2H), 2.86 (m, J=6.8 Hz, 1H), 1.23 (d, J=6.8 Hz, 6H).

Preparation 12

Compounds of Formula (Cb)

A. (3-Bromo-5-isopropyl-phenyl)-acetic acid methyl ester (0.514 g, 1.9 mmoles) was place into a 25 mL pear-shaped flask and was sealed under nitrogen. The material was then solubilized with 13 mL of anhydrous DMSO, and the resulting solution was degassed by passing a steady stream of nitrogen through the solution for 10 min. In a separate round-bottom flask were combined bis(pinacolato)diboron (0.58 g, 2.3 mmoles), [1,1'-bis(diphenylphosphino)ferrocene]-dichloropalladium(II) complex with DCM (1:1) (50 mg, 0.061 mmoles) and potassium acetate (0.56 g, 5.7 mmoles) with a stirring bar under nitrogen. Following degassification the bromide solution was transferred to the "catalytic" mixture and the resulting mix was stirred at 90° C. for 16 hours. After this period the reaction mix was combined with 60 mL of water and was extracted with benzene (4×15 mL). The combined benzene layer was washed with water (4×25 mL) and was dried over anhydrous Na$_2$SO$_4$. Following evaporation in vacuo the crude product was purified using flash silica chromatography (0-10% EtOAc/Hexane) to yield [3-isopropyl-5-(4,4,5,5-tetramethyl-[1,3,2]dioxaborolan-2-yl)-phenyl]-acetic acid methyl ester (502 mg, 83% yield) was a thick, greenish liquid. TLC visualization accomplished using ceric ammonium molybdate stain. $^1$H-NMR (CDCl$_3$): δ 269-167.58 (br s, 1H), 7.53 (br s, 1H), 7.26-7.23 (m, 1H), 3.68 (s, 3H), 3.62 (s, 2H), 2.91 (m, J=6.8 Hz, 1H), 1.34 (s, 12H), 1.25 (d, J=6.8 Hz, 6H).

B. Alternatively, a suspension of 2-(3-bromo-phenyl)-2-methyl-propionic acid methyl ester (755 mg, 2.9 mmoles), and potassium acetate (880 mg, 8.9 mmol) was prepared in DMSO (15 mL). Nitrogen was bubbled through the suspension to deoxygenate the mixture. Bis(pinacolato)diboron (980 mg, 3.8 mmol) was added to the suspension, followed by dichloro[1,1'-bis(diphenylphosphino)ferrocene)palladium (II) dichloromethane adduct (88 mg, 0.11 mmol). The mixture rapidly turned brown. The suspension was then immersed in an oil bath held at 80° C. After 20 minutes the nitrogen bubbling was discontinued. After stirring for 16 hours at 80° C., heating was discontinued, and the black reaction mixture was allowed to cool to ambient temperature. The reaction mixture was then diluted with H$_2$O (100 mL) and ether (100 mL). The aqueous layer was extracted with ether (4×20 mL), and the combined organic layers were washed with water (2×20 mL), brine (50 mL), dried over Na$_2$SO$_4$, filtered and concentrated under reduced pressure to afford a brown oil. The oil was azeotroped with toluene to remove any residual H$_2$O. The crude material was purified by flash chromatography eluting with a gradient from 0% to 14% ethyl acetate/hexane to afford 2-methyl-2-[3-(4,4,5,5-tetramethyl-[1,3,2]dioxaborolan-2-yl)-phenyl]-propionic acid methyl ester (790 mg, 88% yield) as a clear bluish oil. $^1$H-NMR (400 MHz, CDCl$_3$): δ 7.77 (1H, br s), 7.72-7.67 (1H, m), 7.43-7.39 (1H, m), 7.35-7.30 (1H, m), 3.65 (3H, s), 1.60 (6h, s), 1.34 (12H, s).

Preparation 13

Compounds of Formula (Pb)

A. A solution of (3-bromo-phenyl)-acetic acid (10.4 g, 48.5 mmol), in methanol (80 mL), was treated with trimethyl orthoformate (6.5 mL, 59.4 mmol). HCl gas was bubbled through the stirred solution for 10 minutes. The HCl addition was exothermic. After stirring for 15 minutes HPLC analysis of the solution showed complete conversion to product. After stirring for 16 hrs at ambient temperature the solution was diluted with toluene (100 mL) and concentrated under reduced pressure to afford a biphasic mixture. This liquid was diluted with toluene and concentrated under reduced pressure to afford (3-bromo-phenyl)-acetic acid methyl ester (11.2 g, quantitative yield) as a pale yellow liquid. $^1$H-NMR (400 MHz, CDCl$_3$): δ 7.46-7.38 (2H, m), 7.23-7.18 (2H, m), 3.71 (3H, m), 3.60 (2H, m).

B. Sodium hydride (2.5 g of a 60% suspension in mineral oil, 62 mmol) was placed in a flask under nitrogen. The suspension was washed with hexane (2×) then suspended in THF (30 mL), and DMF (30 mL), and cooled in an ice bath. To the cold suspension was added (3-bromo-phenyl)-acetic acid methyl ester (4.8 g, 21 mmol) dropwise as a solution in THF (10 mL). The ester containing flask was then rinsed with an additional portion of THF (10 mL) which was then added to the reaction to insure complete transfer. Iodomethane (4.0 mL, 64 mmol) was then added dropwise over several minutes. The iodomethane addition led to the formation of thick slurry at first, which slowly thinned as the reaction mixture was stirred. The ice bath was removed and the reaction was allowed to warm to ambient temperature. After stirring for 16 hrs at ambient temperature, HPLC analysis of a quenched aliquot (HOAc) showed several peaks present. There were several product peaks visible. The reaction was quenched by the addition of methanol (10 mL). The methanol addition did not lead to gas evolution. The reaction mixture was diluted with 1N HCl (70 mL), water (50 mL), and ether (200 mL). The aqueous layer was extracted with ether (4×50 mL), the combined organic layers were washed with brine (50 mL), dried over Na$_2$SO$_4$, filtered and concentrated under reduced pressure to afford a brown liquid. The crude material was purified by flash chromatography eluting with a gradient from 0% to 10% ethyl acetate/hexane to afford 2-(3-bromo-phenyl)-2-methyl-propionic acid methyl ester (2.93 g, 54% yield) as a clear colorless oil. $^1$H-NMR (400 MHz, CDCl$_3$): δ 7.49-7.47 (1H, m), 7.39-7.36 (1H, m), 7.27-7.24 (1H, m), 7.22-7.17 (1H, m), 3.66 (3H, s), 1.56 (6H, s).

Preparation 14

Compounds of Formula (R)

4-Bromo-2-chloro-1-methyl-benzene (2.5 mL, 18.7 mmoles) and N-bromosuccinimide (4.0 g, 22.5 mmoles) were dissolved into 50 mL of CCl$_4$. To this stirring mix was added benzoyl peroxide (0.5 g, 2.1 mmoles) and the solution was irradiated using white light. Enough light intensity was utilized to affect gentle reflux for 2 hours. After this period the mixture was cooled to ambient temperature and benzoyl peroxide (0.5 g, 2.1 mmoles) was added. Again, the mix was irradiated to reflux for a period of 2 hours. After this period the reaction mix was chilled to ambient temperature and was gravity filtered. The filtrate was evaporated in vacuo and the resulting crude residue was purified using flash silica chromatography (0-1% EtOAc/Hexane) to yield 4-bromo-1-bromomethyl-2-chloro-benzene (3.04 g, 60%) as a clear liquid. $^1$H-NMR (CDCl$_3$): δ 7.57 (d, J=2.0 Hz, 1H), 7.39 (dd, J'=8.3 Hz, J"=1.8 Hz, 1H), 7.31 (d, J=8.1 Hz, 1H), 4.53 (s, 2H).

Preparation 15

Compounds of Formula (S)

4-Bromo-1-bromomethyl-2-chloro-benzene (3.04 g, 10.7 mmoles) was dissolved into anhydrous CH$_3$CN. To this mixture (under N$_2$ at ambient temp) was added TMSCN (2.1 mL, 15.7 mmoles) followed by 1.0M TBAF (15.7 mL, 15.7 mmoles, soln in THF). The resulting mixture was stirred at ambient temperature for 15 min after which time it was evaporated in vacuo to yield crude residue. The crude residue was purified using flash silica chromatography (0-10% EtOAc/Hexane) to yield (4-bromo-2-chloro-phenyl)-acetonitrile (1.98 g, 80%) as an off-white solid. $^1$H-NMR (CDCl$_3$): δ 7.60 (d, J=2.0 Hz, 1H), 7.47 (dd, J'=8.1 Hz, J"=1.8 Hz, 1H), 7.39 (d, J=8.1 Hz, 1H), 3.79 (s, 2H).

Preparation 16

Compounds of Formula (P)

(4-Bromo-2-chloro-phenyl)-acetonitrile (1.98 g, 8.6 mmoles) was dissolved into MeOH (50 mL) and water (5 mL), and the resulting homogeneous mixture was chilled to 0° C. To this stirring (cold) mixture was slowly (carefully) added concentrated HCl (25 mL). After the addition was complete the mixture was refluxed for 16 hours. After this period the reaction mixture was combined with ice and the resulting heterogeneous mixture was extracted with diethyl ether (3×50 mL). The combined ethereal layer was washed with brine, dried over anhydrous MgSO$_4$, and evaporated in vacuo to yield clean (4-bromo-2-chloro-phenyl)-acetic acid methyl ester (2.3 g, 80%). $^1$H-NMR (CDCl$_3$): δ 7.56 (d, J=2.0 Hz, 1H), 7.37 (dd, J'=8.3 Hz, J"=2.0 Hz, 1H), 7.16 (d, J=8.3 Hz, 1H), 3.73 (s, 2H), 3.72 (s, 3H).

Preparation 17

Compounds of Formula (Cb)

(4-Bromo-2-chloro-phenyl)-acetic acid methyl ester (705 mg, 2.68 mmoles) was place into a 25 mL pear-shaped flask and was sealed under nitrogen. The material was then solubilized with 20 mL of anhydrous DMSO, and the resulting solution was degassed by passing a steady stream of nitrogen through the solution for 10 min. In a separate round-bottom flask were combined bis(pinacolato)diboron (0.82 g, 3.2 mmoles), [1,1'-bis(diphenylphosphino)ferrocene]-dichloro-palladium(II) complex with DCM (1:1) (66 mg, 0.081 mmoles) and potassium acetate (0.79 g, 8.05 mmoles) with a stirring bar under nitrogen. Following degassification the bromide solution was transferred to the "catalytic" mixture and the resulting mix was stirred at 90° C. for 16 hours. After this period the reaction mix was combined with 60 mL of water and was extracted with benzene (4×15 mL). The combined benzene layer was washed with water (4×25 mL) and was dried over anhydrous Na$_2$SO$_4$. Following evaporation in vacuo the crude product was purified using flash silica chromatography (0-10% EtOAc/Hexane) to yield [2-chloro-4-(4,4,5,5-tetramethyl-[1,3,2]dioxaborolan-2-yl)-phenyl]acetic acid methyl ester (502 mg, 83% yield) as a thick, clear residue. Note: TLC visualization accomplished using ceric ammonium molybdate stain. $^1$H-NMR (CDCl$_3$): δ 7.83-7.81 (br s, 1H), 7.65 (br d, J=7.6 Hz, 1H), 7.29 (d, J=7.3 Hz, 1H), 3.80 (s, 2H), 3.70 (s, 3H), 1.34 (s, 12H).

Preparation 18

Compounds of Formula (BB)

A mixture of 4-bromo-2-fluoro-benzonitrile (2.6 g, 13 mmol), 10% palladium on carbon (300 mg), triphenylphosphine (300 mg, 1.2 mmol), CuI (108 mg, 0.57 mmol), and K$_2$CO$_3$ (4.55 g, 33 mmol), was prepared in 1,2-dimethoxyethane (20 mL), and H$_2$O (20 mL). The resulting suspension was stirred under nitrogen for 30 minutes, and was then treated with 2-methyl-but-3-yn-2-ol (2.6 mL, 27 mmol). The reaction was then heated in an 80° C. oil bath. After stirring for 15 hours at 80° C., TLC analysis of the reaction mixture showed some of the starting 4-bromo-2-fluoro-benzonitrile remaining. A small amount of PdCl$_2$ was then added in an attempt to drive the reaction to completion. After an additional 2 hr stirring at 80° C. the TLC had changed very little. The reaction mixture was allowed to cool to ambient temperature, and was filtered through a pad of Celite. The Celite pad was washed thoroughly with EtOAc, and the filtrate was diluted with EtOAc and H$_2$O. The layers were separated and the aqueous was extracted with EtOAc (2×50 mL). The combined organic layers were washed with brine, dried over Na$_2$SO$_4$, filtered, and concentrated under reduced pressure to afford a dark oil. The crude material was purified by flash chromatography eluting with a gradient from 10% to 40% ethyl acetate/hexane to afford 2-fluoro-4-(3-hydroxy-3-methyl-but-1-ynyl)-benzonitrile (2.60 g, 98% yield) as a yellow oil. $^1$H-NMR (400 MHz, CDCl$_3$): δ 7.58-7.53 (1H, m), 7.30-7.22 (2H, m), 2.10 (1H, s), 1.62 (6H, s).

Preparation 19

Compounds of Formula (CC)

To a solution of 2-fluoro-4-(3-hydroxy-3-methyl-but-1-ynyl)-benzonitrile (2.6 g, 13 mmol) in toluene (55 mL) was added NaH (53 mg of a 60% suspension in mineral oil, 1.3 mmol). The reaction mixture was heated to reflux. After refluxing for several hours, heating was discontinued, and the cooled reaction mixture was quenched by the addition of 2M Na$_2$CO$_3$ solution. The layers were separated and the toluene layer was washed with H$_2$O (2×20 mL), brine (25 mL), dried over Na$_2$SO$_4$, filtered and concentrated under reduced pressure to afford the crude product. The crude material was purified by flash chromatography eluting with a gradient from 0% to 10% ethyl acetate/hexane to afford 4-ethynyl-2-fluoro-benzonitrile (1.25 g, 66% yield). $^1$H-NMR (400 MHz, CDCl$_3$): δ 7.61-7.57 (1H, m), 7.38-7.30 (2H, m), 3.36 (1H, s).

Preparation 20

Compounds of Formula (DD)

A solution of 4-ethynyl-2-fluoro-benzonitrile (1.29 g, 8.9 mmol) in EtOAc (30 mL) was placed in a Parr pressure bottle and palladium on carbon (130 mg of 10% on carbon) was added. The bottle was placed on the Parr hydrogenation apparatus and shaken under 10 psi of hydrogen pressure. After shaking for two hours the black suspension was filtered through a pad of Celite. The pad was washed thoroughly with EtOAc, and the combined filtrates were concentrated under reduced pressure. The residue was taken up in toluene and concentrated under reduced pressure to afford 4-ethyl-2-fluoro-benzonitrile (1.19 g, 89% yield). $^1$H-NMR (400 MHz, CDCl$_3$): δ 7.55-7.50 (1H, m), 7.11-7.03 (2H, m), 2.72 (2H, q, J=7.6 Hz), 1.26 (3H, t, J=7.6 Hz).

Preparation 21

Compounds of Formula (EE)

A solution of 4-ethyl-2-fluoro-benzonitrile (1.19 g, 8.0 mmol) in ether (70 mL) was cooled in an ice bath. To the cold, stirred solution was added LiAlH₄ (600 mg, 16 mmol). The suspension was then heated to reflux. After several hours at reflux, the suspension was allowed to cool to ambient temperature and was quenched by the careful addition of H₂O (600 μL), followed by 15% aqueous NaOH (600 μL), and finally H₂O (1.8 mL). The resulting suspension was filtered, and the solids were washed thoroughly with ether. The filtrate was concentrated under reduced pressure to afford 4-ethyl-2-fluoro-benzylamine (1.16 g, 95% yield) as a liquid. This material was used for the subsequent amide formation without further purification. ¹H-NMR (400 MHz, CDCl₃): δ 7.21 (1H, app t, J=7.6 Hz), 6.96-6.86 (2H, m), 3.85 (2H, s), 2.63 (2H, q, J=7.6 Hz), 1.22 (3H, t, J=7.6 Hz).

Preparation 22

Compounds of Formula (Ta)

Methyl cyanoacetate (1.16 mL, 13 mmol) and 4-ethyl-2-fluoro-benzylamine (1.15 g, 7.5 mmol) were combined in ethanol (20 mL). 4-(N,N-dimethylamino)pyridine (catalytic) was added and the reaction was heated in a 60° C. oil bath. After 16 hours heating, the reaction was concentrated under reduced pressure to afford crude product which was purified by flash chromatography eluting with a gradient from hexane to 60% ethyl acetate/hexane to afford 2-cyano-N-(4-ethyl-2-fluoro-benzyl)-acetamide (652 mg, 40% yield). ¹H-NMR (400 MHz, CDCl₃): δ 7.26-7.20 (1H, m), 6.98-6.90 (2H, m), 6.39 (1h, br s), 4.49 (2H, d, J=5.8 Hz), 3.38 (2H, s), 2.64 (2H, q, J=7.6 Hz), 1.23 (3H, t, J=7.6 Hz).

Preparation 23

Compounds of Formula (GG)

A. Magnesium turnings (720 mg, 30 mmol) were suspended in THF (30 mL) in a 250 mL round bottom flask fitted with a thermometer. A solution of 1-bromohexane (3.2 mL, 23 mmol) in THF (10 mL) was prepared after first drying the 1-bromohexane by passing it through a pad of activated basic alumina. About 10% of the halide solution was added to the Mg suspension, followed by a small pellet of iodine. The addition of the iodine led to an increase in the reaction temperature indicating the initiation of the Grignard reagent formation. The remaining halide solution was added dropwise over ~15 minutes. After the completion of the addition of the halide, the suspension was held at ~55° C. to complete the formation of the Grignard reagent. While the Grignard reagent was forming, a suspension of dibenzyl oxalate (5.1 g, 19 mmol) was prepared in a mixture of ether (50 mL), and THF (15 mL). This suspension was cooled to <–70° C. (internal monitoring) and then treated with the Grignard solution prepared previously at a rate sufficient to keep the internal temperature below –70° C. After stirring for 3 hours at <–70° C., the reaction was quenched by the addition of saturated aqueous NH₄Cl, followed by addition of 1 N HCl (25 mL). The cold solution was then allowed to come to ambient temperature. After ~64 hours the reaction mixture was diluted with ether and the layers were separated. The acidic aqueous layer was extracted with ether (2×50 mL). The combined organic layers were washed with saturated aqueous NaHCO₃, brine, dried over Na₂SO₄, filtered, and concentrated under reduced pressure to afford a pale brown oil. The crude material was purified by flash chromatography eluting with a gradient from 0% to 30% ethyl acetate/hexane to afford 2-oxo-octanoic acid benzyl ester (3.43 g, 73% yield) as a pale yellow oil. The material was not completely pure by NMR analysis. ¹H-NMR (400 MHz, CDCl₃): δ 7.42-7.33 (5H, m), 5.27 (2H, m), 2.82 (2H, t, J=7.3 Hz), 1.66-1.56 (2H, m), 1.35-1.23 (6H, m), 0.89-0.85 (3H, m).

B. A mixture of 2-oxobutyric acid (11.5 g, 113 mmol), and benzyl alcohol (14.0 mL, 135 mmol) in benzene (100 mL) was heated to reflux under a Dean-Stark water separator. After refluxing for 16 hrs~2 mL of water had collected in the trap (~100% of theoretical). The reaction mixture was allowed to cool to ambient temperature, and then concentrated under reduced pressure to afford a pale yellow oil. The crude material was purified by flash chromatography eluting with a gradient from 0% to 15% ethyl acetate/hexane to afford 2-oxo-butyric acid benzyl ester (13.0 g, 60% yield) as a clear colorless oil. ¹H-NMR (400 MHz, CDCl₃): δ 7.42-7.35 (5H, m), 5.28 (5H, s), 2.87 (2H, q, J=7.2 Hz), 1.12 (3H, t, J=7.2 Hz).

Preparation 24

Compounds of Formula (HH)

In a reaction vial under nitrogen, 2-oxo-butyric acid benzyl ester (12.4 g, 64.7 mmol) was treated dropwise with (diethylamino)sulfur trifluoride (10.5 mL, 79.5 mmol). The addition is exothermic and leads to a darkening of the reaction mixture. After standing at ambient temperature for ~64 hours the reaction mixture was poured onto ice (~100 g), and diluted with ether (250 mL). The layers were separated and the aqueous was extracted with ether (3×50 mL). The combined organic layers were washed with saturated NaHCO₃ solution, brine, dried over Na₂SO₄, filtered and concentrated under reduced pressure to afford a pale orange oil. The crude material was purified by flash chromatography eluting with a gradient from 0% to 20% ethyl acetate/hexane to afford 2,2-difluoro-butyric acid benzyl ester (13.0 g, 94% yield) as a pale yellow oil. ¹H-NMR (400 MHz, CDCl₃): δ 7.39-7.37 (5H, m), 5.29 (2H, s), 2.09 (2H, t of q, $J_{H-H}$=7.6 Hz, $J_{H-F}$=16.7 Hz), 1.00 (3H, t, J=7.6 Hz).

Preparation 25

Compounds of Formula (Ua)

A solution of lithium hexamethyldisilazide (2.4 mL of a 1.0M solution in THF, 2.4 mmol) was diluted with THF (2 mL) and cooled in a –78° C. bath. To this cold solution was added 1-(4-bromo-furan-2-yl)-ethanone (317 mg, 1.68 mmol) dropwise as a solution in THF (4 mL), followed by a THF (1 mL) rinse of the vial and syringe to insure complete transfer. After ~2 minutes the resulting red enolate solution was treated with a solution of 2,2-difluoro-butyric acid benzyl ester (357 mg, 1.67 mmol) in THF (4 mL), followed by a THF (1 mL) rinse of the vial and syringe to insure complete transfer. After the completion of the addition, the cooling bath was removed and the reaction was allowed to warm to ambient temperature. After stirring for 16 hrs at ambient temperature, the reaction was quenched by the addition of H₂O (10 mL), and diluted with ether (50 mL). Phosphoric acid (2M, aqueous) was added to the mixture to bring the pH below 3. The layers were separated and the aqueous was extracted with ether (3×20 mL). The combined organic layers were washed with brine, dried over Na₂SO₄, filtered, and concentrated under reduced pressure to afford a dark brown oil. The crude material was purified by flash chromatography eluting with a gradient from 0% to 30% ethyl acetate/hexane to afford 1-(4-bromo-furan-2-yl)-4,4-difluoro-hexane-1,3-dione (224 mg, 46% yield) as a red oil. The compound exists primarily in its' enolic form. $^1$H-NMR (400 MHz, CDCl$_3$): δ 14.77 (1H, br s), 7.62 (1H, s), 7.27 (2H, s), 6.45 (1H, s), 2.12 (2H, t of q, $J_{H-H}$=7.6 Hz, $J_{H-F}$=16.7 Hz), 1.05 (3H, t, J=7.6 Hz).

Preparation 26

Compounds of Formula (V)

To a solution of 1-(4-bromo-furan-2-yl)-4,4-difluoro-hexane-1,3-dione (220 mg, 0.75 mmol), and 2-cyano-N-(2,4-difluoro-benzyl)-acetamide (300 mg, 1.4 mmol) in benzene (4 mL) was added 1,8-diaza-bicycle-[5.4.0]-undec-7-ene (60 µL, 0.4 mmol). The red reaction mixture was then heated to reflux. After 3 hours, heating was discontinued and the reaction was allowed to cool to ambient temperature. After stirring at ambient temperature for 16 hours the reaction mixture was diluted with CH$_2$Cl$_2$ and purified by adsorbing the material onto silica gel, loading the resulting solid onto the column and eluting with a gradient from 0% to 30% ethyl acetate/hexane to afford 6-(4-bromo-furan-2-yl)-1-(2,4-difluoro-benzyl)-4-(1,1-difluoro-propyl)-2-oxo-1,2-dihydro-pyridine-3-carbonitrile (188 mg, 54% yield) as a yellow oil. $^1$H-NMR (400 MHz, CDCl$_3$): δ 7.62 (1H, s), 7.1-7.03 (1H, m), 6.86-6.78 (2H, m), 6.76 (1H, s), 6.64 (1H, s), 5.46 (2H, s), 2.31 (2H, t of q, $J_{H-H}$=7.6 Hz, $J_{H-F}$=16.9 Hz), 1.11 (3H, t, J=7.6 Hz).

Preparation 26

Compounds of Formula (X)

Palladium catalyst ([1,1'-bis(diphenylphosphino)ferrocene]dichloropalladium (II) complex with dichloromethane (1:1), 1.3 g, 1.59 mmol), potassium acetate (4.7 g, 47.7 mmol), and bis(pinacolato)diboron (6.05 g, 23.8 mmol) were placed into a flask and degassed with stream of N$_2$ for 20 min. In a separate flask, 1-(4-bromo-furan-2-yl)-ethanone (3.0 g, 15.9 mmol) was dissolved in 30 ml anhydrous DMSO and degassed with stream of N$_2$ for 20 min. The DMSO solution of 1-(4-bromo-furan-2-yl)-ethanone was added to the "catalyst" flask, and then heated at 80° C. overnight. After cooling to ambient temperature, water and ethyl acetate were added to the reaction mixture. The aqueous layer was extracted with ethyl acetate. The combined organic layers were washed with brine, dried over sodium sulfate, and concentrated in vacuo. The crude product was purified by column chromatography on silica gel (10→30% EtOAC/Hexane, 0.25% Et$_3$N in hexane) to give 1-[4-(4,4,5,5-tetramethyl-[1,3,2]dioxaborolan-2-yl]-furan-2-yl]-ethanone as a colorless oil (3.27 g, 87% yield). $^1$H-NMR (400 MHz, CDCl$_3$): δ 1.33 (s, 12H), 2.47 (s, 3H), 7.37 (d, 1H, J=0.60), 7.89 (d, 1H, J=0.68).

Preparation 27

Compounds of Formula (Ga)

To a solution of 4,6-dichloro-2-methylsulfanylpyrimidine (500 mg, 2.56 mmol) in anhydrous DMF (6 mL) was added sodium ethoxide (174 mg, 2.56 mmol). The reaction mixture was stirred at 70° C. for overnight. The resulting mixture was poured into 30 mL of water and was extracted with diethyl ether (20 mL×3) three times. The ether layer was separated and dried with anhydrous MgSO$_4$ and concentrated in vacuo to give crude product 4-chloro-6-ethoxy-2-methylsulfanylpyrimidine (525 mg). $^1$H-NMR (CDCl$_3$): δ 6.39 (s, 1H), 4.43 (q, J=7.1 Hz, 2H), 2.54 (s, 3H), 1.38 (t, J=7.1H, 3H).

Preparation 28

Compounds of Formula (Y)

The crude product of Preparation 27, 4-chloro-6-ethoxy-2-methylsulfanylpyrimidine, (525 mg, 2.56 mmol) was dissolved in DMF (4 mL). To this solution was added 5-acetyl-2-thiopheneboronic acid (523 mg, 3.08 mmol), PdCl$_2$dppf (209 mg, 0.26 mmol), potassium carbonate (1.06 g, 7.69 mmol) and water (0.4 mL). The reaction mixture was heated at 80° C. under nitrogen atmosphere for overnight. The reaction mixture was cooled and poured into 30 mL of water and was then extracted with diethyl ether (20 mL×3) three times. The ether layer was separated and dried with anhydrous MgSO$_4$ and concentrated in vacuo. The resulting crude product was purified by flash silica column chromatography (20% ethyl acetate in hexane) to give product 1-[5-(6-ethoxy-2-methylsulfanyl-pyrimidin-4-yl)-thiophen-2-yl]-ethanone (210 mg, 28% yield over two steps). $^1$H-NMR (CDCl$_3$): δ 7.67 (m, 2H), 6.68 (s, 1H), 4.46 (q, J=7.1 Hz, 2H), 2.60 (s, 3H), 2.59 (s, 3H), 1.40 (t, J=7.1 Hz, 3H).

Preparation 29

Compounds of Formula (Z)

A. 1-[5-(6-Ethoxy-2-methylsulfanyl-pyrimidin-4-yl)-thiophen-2-yl]-ethanone (210 mg, 0.71 mmol) was dissolved in anhydrous THF (7 mL) and cooled to −78° C. under nitrogen atmosphere. A solution of lithium bis(trimethylsilyl)amide (0.71 mL, 1.0 M) in THF was added. The reaction mixture was stirred at −20° C. under nitrogen atmosphere for 1 h. The reaction mixture was then cooled to −78° C. To this reaction mixture was added ethyl trifluoroacetate (170 µL, 1.43 mmol). The vigorously stirred solution was allowed to warm to ambient temperature overnight. The reaction mixture was poured into 20 mL of ice and water and was brought to pH=3~4 by adding 10% HCl aqueous solution. The mixture was then extracted with diethyl ether (20 mL×3) three times. The ether layer was separated and dried with anhydrous MgSO$_4$ and concentrated in vacuo to give crude product 1-[5-(6-ethoxy-2-methylsulfanyl-pyrimidin-4-yl)-thiophen-2-yl]-4,4,4-trifluoro-butane-1,3-dione (272 mg, 98% yield). $^1$H-NMR (CDCl$_3$): δ 7.81 (m, 1H), 7.68 (m, 1H), 6.70 (s, 1H), 6.47 (s, 1H), 4.47 (q, J=7.1 Hz, 2H), 2.61 (s, 3H), 1.41 (t, J=7.1 Hz, 3H).

B. Alternatively, lithium bis(trimethylsilyl)amide (1.0M solution in THF, 1.1 mL, 1.1 mmol) was slowly added to a solution of 1-[1-(3-trifluoromethyl-pyridin-2-yl)-1H-pyrazol-4-yl]-ethanone (240 mg, 0.94 mmol) in 2 mL anhydrous THF at −78° C. under nitrogen. The mixture was then allowed to warm to −20° C. and kept at −20° C. to −5° C. for 3 hrs. After this period of time the mixture was cooled to −78° C. and to it was added ethyl trifluoroacetate (200 mg, 0.41 mmol). The mixture was next allowed to warm to ambient temperature overnight. 1N aqueous HCl was carefully added to adjust the pH 2. Two layers were separated and the aqueous layer was extracted with chloroform three times. The extract was washed with brine, dried over sodium sulfate, and concentrated in vacuo to give 4,4,4-trifluoro-1-[1-(3-trifluoromethyl-pyridin-2-yl)-1H-pyrazol-4-yl]-butane-1,3-dione as a yellow solid (290 mg, 88% yield). The product was used for the next step without purification. 1H-NMR (400 MHz, CDCl$_3$): δ 6.35 (s, 1H), 7.59 (dd, 1H, J=4.80, J=7.83), 8.21 (s, 1H), 8.28 (dd, 1H, J=1.77, J=3.80), 8.75 (dd, 1H, J=4.80, J=1.77), 8.76 (d, 1H, J=0.51)

Preparation 30

Compounds of Formula (KK)

Sodium hydride (60% dispersion in mineral oil, 243 mg, 6.07 mmol) was suspended in 4 mL anhydrous N,N-dimethylformamide. To this solution was added 4-iodo-1H-pyrazole (982 mg, 5.06 mmol) in 4 mL anhydrous N,N-dimethylformamide at 0° C. under nitrogen. The mixture was stirred at 0° C. for 15 min, and then allowed to warm to ambient temperature and stirred at the same temperature for 2 hrs. After this period of time, a solution of 2-chloro-3-trifluoromethyl-pyridine (1.01 g, 5.56 mmol) in 4 mL N,N-dimethylformamide was added and the mixture was heated at 90° C. for 5 hrs. After cooling off, the mixture was poured into water and extracted with ethyl acetate three times. The combined extract was washed with brine, dried over sodium sulfate, and concentrated in vacuo to give 2-(4-iodo-pyrazol-1-yl)-3-trifluoromethyl-pyridine as a white solid (1.406 g, 74% yield). The product was used for the next step without purification. $^1$H-NMR (400 MHz, CDCl$_3$): δ 7.48 (dd, 1H, J=4.80, J=8.08), 7.79 (s, 1H), 8.21 (dd, 1H, J=1.52, J=8.08), 8.27 (s, 1H), 8.67 (dd, 1H, J=1.52, J=4.80).

Preparation 31

Compounds of Formula (Ya)

Isopropylmagnesium bromide (2.0M in Et$_2$O, 1.11 ml, 2.22 mmol) was added slowly to a solution of 2-(4-iodo-pyrazol-1-yl)-3-trifluoromethyl-pyridine (627 mg, 1.85 mmol) in 3 mL anhydrous THF at 0° C. under nitrogen. The reaction mixture was stirred at the same temperature for 2 hrs, and then followed by the addition of N-methoxy-N-methyl-acetamide (286 mg, 2.78 mmol). The mixture was allowed to warm to ambient temperature overnight. Saturated ammonium chloride was added to quench the reaction. Two layers were separated and the aqueous layer was extracted with ethyl acetate. The combined extract was washed with brine, dried over sodium sulfate, and concentrated in vacuo. The crude product was purified by column chromatography on silica gel (25% EtOAC/Hexane) to give 1-[1-(3-trifluoromethyl-pyridin-2-yl)-1H-pyrazol-4-yl]-ethanone as a white solid (277 mg, 59% yield). $^1$H-NMR (400 MHz, CDCl$_3$): δ 2.53 (s, 3H), 7.57 (dd, 1H, J=5.05, J=8.08), 8.18 (s, 1H), 8.27 (dd, 1H, J=1.52, J=8.08), 8.65 (s, 1H), 8.73 (d, 1H, J=4.03).

Example 1

Compounds of Formula (Ia)

A. To a solution of 6-(4-bromo-furan-2-yl)-1-(2,4-difluoro-benzyl)-4-(1,1-difluoro-propyl)-2-oxo-1,2-dihydro-pyridine-3-carbonitrile (75 mg, 160 μmol) and 2-(3-ethylsulfanyl-5-isopropyl-phenyl)-4,4,5,5-tetramethyl-[1,3,2]dioxaborolane (73 mg, 240 μmol) in 1,2-dimethoxyethane (2.0 mL) was added K$_2$CO$_3$ (68 mg, 490 μmol) and H$_2$O (200 μL). Dichloro[1,1'-bis(diphenylphosphino)ferrocene)palladium (II) dichloromethane adduct (11 mg, 15 μmol, ~9 mol %) was added and the resulting dark mixture was sparged with nitrogen for ~5 minutes. The reaction vial was sealed with a septum that had been pierced with a needle to allow for pressure release, and immersed in an oil bath heated to 80° C. After 5½ hours stirring at 80° C., heating was discontinued and the reaction was allowed to stir at ambient temperature for 16 hrs. The reaction mixture was then diluted with ether and H$_2$O, the layers were separated, and the aqueous was extracted with ether (3×20 mL). The combined ether layers were washed with brine (20 mL), dried over Na$_2$SO$_4$, filtered and concentrated under reduced pressure to afford a dark oil. The crude product was purified by silica gel column chromatography by adsorbing the material onto silica gel from a CH$_2$Cl$_2$ solution, loading the resulting solid onto the column and eluting with a gradient from 0% to 20% ethyl acetate/hexane to afford 1-(2,4-difluoro-benzyl)-4-(1,1-difluoro-propyl)-6-[4-(3-ethylsulfanyl-5-isopropyl-phenyl)-furan-2-yl]-2-oxo-1,2-dihydro-pyridine-3-carbonitrile (40 mg, 44% yield) as a brown foam. $^1$H-NMR (400 MHz, CDCl$_3$): δ 7.85 (1H, d, J=0.8 Hz), 7.18-7.15 (2H, m), 7.12-7.03 (2H, m), 7.00 (1H, d, J=0.8 Hz), 6.87-6.79 (2H, m), 6.76 (1H, s), 5.56 (2H, s), 2.98 (2H, q, J=7.3 Hz), 2.90 (1H, heptet, J=7.1 Hz), 2.34 (2H, t of q, J$_{H-H}$=7.6 Hz, J$_{H-F}$=16.9 Hz), 1.34 (3H, t, J=7.3 Hz), 1.27 (6H, d, J=7.1 Hz), 1.13 (3H, t, J=7.3 Hz).

B. Alternatively, to 6-(5-bromo-thiophen-2-yl)-1-(2,4-difluoro-benzyl)-2-oxo-4-trifluoromethyl-1,2-dihydro-pyridine-3-carbonitrile (134 mg, 0.28 mmol) was added 2-methyl-2-[3-(4,4,5,5-tetramethyl-[1,3,2]dioxaborolan-2-yl)-phenyl]-propionic acid methyl ester (1.2 mL of a 0.47 M solution in 1,2-dimethoxyethane, 0.56 mmol). The mixture was diluted with 1,2-dimethoxyethane (1.6 mL) and nitrogen was bubbled through the solution as an aqueous solution of K$_2$CO$_3$ (0.3 mL of a 35% w/v solution in H$_2$O, 0.8 mmol) was added. The addition of the K$_2$CO$_3$ solution caused the reaction mixture to turn dark. The mixture was then treated with dichloro[1,1'-bis(diphenylphosphino)ferrocene)palladium (II) dichloromethane adduct (21 mg, 26 μmol). After several minutes the nitrogen sparge was discontinued, and the vial was immersed in an oil bath held at 80° C. After stirring for 16 hours the dark reaction was allowed to cool to ambient temperature, and diluted with ether (30 mL), and H$_2$O (10 mL). The aqueous layer was extracted with ether (1×10 ml), the combined organic layers were washed with brine (10 mL), dried over Na$_2$SO$_4$, filtered and concentrated to afford a dark oil. The crude material was purified by flash chromatography eluting with a gradient from 0% to 20% ethyl acetate/hexane to afford 2-(3-{5-[5-cyano-1-(2,4-difluoro-benzyl)-6-oxo-4-trifluoromethyl-1,6-dihydro-pyridin-2-yl]-thiophen-2-yl}-phenyl)-2-methyl-propionic acid methyl ester (72 mg, 45% yield) as an orange-yellow oil. This material was not completely pure and was further purified by preparative reverse phase LC/MS chromatography on a C-18 column. The desired fraction was collected by mass and concentrated under reduced pressure to afford 2-(3-{5-[5-cyano-1-(2,4-difluoro-benzyl)-6-oxo-4-trifluoromethyl-1,6-dihydro-pyridin-2-yl]-thiophen-2-yl}-phenyl)-2-methyl-propionic acid methyl ester (26 mg, 17% yield) as a yellow powder. $^1$H-NMR (400 MHz, CDCl$_3$): δ 7.52-7.50 (1H, m), 7.46-7.35 (3H, m), 7.29-7.26 (1H, m), 7.12-7.05 (2H, m), 6.91-6.79 (2H, m), 6.67 (1H, s), 5.46 (2H, s), 3.68 (3H, s), 1.62 (6H, s).

C. Alternatively, to 6-(4-bromo-furan-2-yl)-1-(2,4-difluoro-benzyl)-2-oxo-4-trifluoromethyl-1,2-dihydro-pyridine-3-carbonitrile (185 mg, 0.40 mmol) was added 2-methyl-2-[3-(4,4,5,5-tetramethyl-[1,3,2]dioxaborolan-2-yl)-phenyl]propionic acid methyl ester (1.7 mL of a 0.47 M solution in 1,2-dimethoxyethane, 0.8 mmol). The mixture was diluted with 1,2-dimethoxyethane (2.3 mL) and nitrogen was bubbled through the solution as an aqueous solution of K$_2$CO$_3$ (0.4 mL of a 35% w/v solution in H$_2$O, 1.0 mmol) was added. The addition of the K$_2$CO$_3$ solution caused the reaction mixture to turn dark. The mixture was then treated with dichloro[1,1'-bis(diphenylphosphino)ferrocene)palladium (II) dichloromethane adduct (33 mg, 40 µmol). After several minutes the nitrogen sparge was discontinued, and the vial was immersed in an oil bath held at 80° C. After stirring for 16 hours the dark reaction was allowed to cool to ambient temperature, and diluted with ether (30 mL), and $H_2O$ (10 mL). The aqueous layer was extracted with ether (1×10 ml), the combined organic layers were washed with brine (10 mL), dried over $Na_2SO_4$, filtered and concentrated to afford a dark oil. The crude material was purified by flash chromatography eluting with a gradient from 0% to 20% ethyl acetate/hexane to afford bright yellow product containing fractions from the column. Some of these fractions deposited yellow crystals upon standing. The crystals were collected and found to be pure 2-(3-{5-[5-cyano-1-(2,4-difluoro-benzyl)-6-oxo-4-trifluoromethyl-1,6-dihydro-pyridin-2-yl]-furan-3-yl}-phenyl)-2-methyl-propionic acid methyl ester (74 mg, 33% yield). $^1$H-NMR (400 MHz, $CDCl_3$): δ 7.89 (1H, br s), 7.41-7.28 (4H, m), 7.11-7.05 (2H, m), 6.91-6.82 (3H, m), 5.60 (2H, s), 3.67 (3H, s), 1.61 (6H, s).

D. 6-(5-Bromo-thiophen-2-yl)-1-(2,4-difluoro-benzyl)-2-oxo-4-trifluoromethyl-1,2-dihydro-pyridine-3-carbonitrile (270 mg, 0.57 mmol), 2-methylsulfanyl-5-(4,4,5,5-tetramethyl-[1,3,2]dioxaborolan-2-yl)pyridine (214 mg, 0.85 mmol), potassium carbonate (236 mg, 1.71 mmol), and tetrakis(triphenylphosphine)palladium (0) (66 mg, 0.057 mmol) were mixed with 6 ml 9:1 $DME/H_2O$ (v/v), then heated at 80° C. overnight. All solvent was removed in vacuo. The crude product was purified by column chromatography on silica gel (10→40% EtOAC/Hexane, 0.25% $Et_3N$ in hexane) to give 1-(2,4-difluoro-benzyl)-6-[5-(6-methylsulfanyl-pyridin-3-yl)-thiophen-2-yl]-2-oxo-4-trifluoromethyl-1,2-dihydro-pyridine-3-carbonitrile as an orange solid (276 mg, 93% yield). $^1$H-NMR (400 MHz, $CDCl_3$): δ 2.61 (s, 3H), 5.45 (s, 2H), 6.66 (s, 1H), 6.82 (m, 1H), 6.88 (m, 1H), 7.09 (m, 1H), 7.12 (d, 1H, J=3.9), 7.27 (m, 2H, mixed with $CDCl_3$), 7.64 (dd, 1H, J=2.4, J=8.4), 8.67 (dd, 1H, J=2.4, J=0.8).

E. 6-(4-Bromo-furan-2-yl)-1-(2,4-difluoro-benzyl)-2-oxo-4-trifluoromethyl-1,2-dihydro-pyridine-3-carbonitrile (98 mg, 0.22 mmol), 2-ethoxy-5-(4,4,5,5-tetramethyl-[1,3,2]dioxaborolan-2-yl)-3-trifluoromethyl-pyridine (125 mg, 0.54 mmol) (or corresponding 2-ethoxy-3-trifluoromethylpyridine-5-boronic acid), potassium carbonate (149 mg, 1.08 mmol), and tetrakis(triphenylphosphine)palladium (0) (25 mg, 0.1 mmol) were mixed with 2.5 ml 9:1 $DME/H_2O$ (v/v), then heated at 80° C. overnight. All solvent was removed in vacuo. The crude product was purified by column chromatography on silica gel (10→30% EtOAC/Hexane, 0.25% $Et_3N$ in hexane) to give 1-(2,4-difluoro-benzyl)-6-[4-(6-ethoxy-5-trifluoromethyl-pyridin-3-yl)-furan-2-yl]-2-oxo-4-trifluoromethyl-1,2-dihydro-pyridine-3-carbonitrile as a yellow solid (29 mg, 37% yield). $^1$H-NMR (400 MHz, $CDCl_3$): δ 1.45 (t, 3H, J=7.07), 4.53 (q, 2H, J=7.07), 5.58 (s, 2H), 6.83 (s, 1H), 6.84 (m, 1H), 6.87 (m, 1H), 7.04 (d, 1H, J=0.76), 7.13 (m, 1H), 7.87 (d, 1H, J=2.27), 7.90 (d, 1H, J=0.76), 8.38 (d, 1H, J=2.27).

F. 6-(4-Bromo-thiophen-2-yl)-1-(2,4-difluoro-benzyl)-2-oxo-4-trifluoromethyl-1,2-dihydro-pyridine-3-carbonitrile 620 mg, 1.3 mmoles), [3-(4,4,5,5-Tetramethyl-[1,3,2]dioxaborolan-2-yl)-phenyl]-acetic acid methyl ester (520 mg, 1.95 mmoles), [1,1'-bis(diphenylphosphino)ferrocene]-dichloropalladium(II) complex with DCM (1:1) (32 mg, 0.39 mmoles), and $K_2CO_3$ (540 mg, 3.91 mmoles) were combined in 6 ml of $DME/H_2O$ (9:1, degassed), and were stirred at 85° C. for 5 hours. After this period the reaction mix was evaporated and purified using flash silica chromatography (0-30% EtOAc/Hexane) to yield (3-{5-[5-cyano-1-(2,4-difluoro-benzyl)-6-oxo-4-trifluoromethyl-1,6-dihydro-pyridin-2-yl]-thiophen-3-yl}-phenyl)-acetic acid methyl ester (365 mg, 52%) as a yellow solid. $^1$H-NMR ($CDCl_3$): δ 7.64 (br d, J=1.3 Hz, 1H), 7.39-7.35 (m, 2H), 7.33 (br d, J=1.3 Hz, 1H), 7.14-7.07 (m, 1H), 6.92-6.85 (m, 1H), 6.84-6.77 (m, 1H), 6.65 (s, 1H), 5.44 (s, 2H), 3.72 (s, 3H), 3.67 (s, 2H). MS (ES+): 545.3 (M+H).

Example 2

Compounds of Formula (Ia) and Oxidation

A. 6-(5-Bromo-furan-2-yl)-1-(2,4-difluoro-benzyl)-2-oxo-4-trifluoromethyl-1,2-dihydro-pyridine-3-carbonitrile (310 mg, 0.7 mmoles), 2-(3-Ethylsulfanyl-5-trifluoromethyl-phenyl)-4,4,5,5-tetramethyl-[1,3,2]dioxaborolane (287 mg, 0.86 mmoles), tetrakis(triphenylphosphine)palladium (0) (81 mg, 0.07 mmoles), $K_2CO_3$ (450 mg, 3.3 mmoles) were combined in 12 ml of $DME/H_2O$ (9:1, degassed), and were stirred at 85° C. for 16 hours. After this period the reaction mix was evaporated and purified using flash silica chromatography (0-20% EtOAc/Hexane) to yield 1-(2,4-difluoro-benzyl)-6-[5-(3-ethylsulfanyl-5-trifluoromethyl-phenyl)-furan-2-yl]-2-oxo-4-trifluoromethyl-1,2-dihydro-pyridine-3-carbonitrile (0.23 g, 55%) as a yellow residue.

B. 1-(2,4-Difluoro-benzyl)-6-[5-(3-ethylsulfanyl-5-trifluoromethyl-phenyl)-furan-2-yl]-2-oxo-4-trifluoromethyl-1,2-dihydro-pyridine-3-carbonitrile (0.23 g, 0.39 mmoles) was dissolved into 50 mL of DCM. To this solution at 0° C. was added 60% active m-chloroperbenzoic acid (250 mg, ~2.25 equiv.). The mix was allowed to warm to ambient temperature and was stirred at this temperature for 30 min. After this period an additional 50 mL of DCM was added and this mix was washed with 1N $Na_2CO_3$ (4×20 mL) and brine. The resulting DCM layer was dried over anhydrous $Na_2SO_4$ and was evaporated in vacuo to yield the crude product. The crude product was purified using flash silica chromatography (0-40% EtOAc/Hexane) to yield 1-(2,4-difluoro-benzyl)-6-[5-(3-ethanesulfonyl-5-trifluoromethyl-phenyl)-furan-2-yl]-2-oxo-4-trifluoromethyl-1,2-dihydro-pyridine-3-carbonitrile (205 mg, 86% yield) as a yellow solid. $^1$H-NMR ($CDCl_3$): δ 8.26 (s, 1H), 8.12 (s, 1H), 7.91 (s, 1H), 7.14-7.07 (m, 1H), 7.06 (d, J=3.8 Hz, 1H), 6.98 (d, J=3.8 Hz, 1H), 6.92-6.85 (m, 1H), 6.84-6.77 (m, 1H), 6.81 (s, 1H), 5.53 (s, 2H), 3.19 (q, J=7.3 Hz, 2H), 1.35 (t, J=7.3 Hz, 3H). MS (ES+): 617.1.

Example 3

Hydrolysis of Compounds of Formula (I)

A. (3-{5-[5-Cyano-1-(2,4-difluoro-benzyl)-6-oxo-4-trifluoromethyl-1,6-dihydro-pyridin-2-yl]-thiophen-3-yl}-phenyl)-acetic acid methyl ester (0.988 g, 1.81 mmoles) was dissolved into THF (20 mL) and water (6 mL). To this homogeneous mixture was then added LiOH hydrate (152 mg, 3.62 mmoles). This mix was then stirred at 30° C. for 2 hours. After this period the reaction mixture was acidified to pH ~3 using 1H HCl and was evaporated in vacuo. The resulting residue was extracted with DCM (3×15 mL) and the resulting organic layer was dried over anhydrous $Na_2SO_4$ and evaporated in vacuo to yield crude product. The crude product was purified using flash silica chromatography (0-5% MeOH/DCM) to yield (3-{5-[5-cyano-1-(2,4-difluoro-benzyl)-6-oxo-4-trifluoromethyl-1,6-dihydro-pyridin-2-yl]-thiophen-3-yl}-phenyl)-acetic acid (625 mg, 65%) as a yellow solid. $^1$H-NMR ($CDCl_3$): δ 7.64 (br d, J=1.5 Hz, 1H), 7.41-7.38 (m, 2H), 7.32-7.30 (m, 1H), 7.13-7.06 (m, 1H), 6.90-6.84 (m, 1H), 6.82-6.75 (m, 1H), 6.64 (s, 1H), 5.43 (s, 2H), 3.70 (s, 2H). MS (ES+): 531.1 (M+H).

Example 4

Compounds of Formula (Ib)

A. 1-[5-(6-Ethoxy-2-methylsulfanyl-pyrimidin-4-yl)-thiophen-2-yl]-4,4,4-trifluoro-butane-1,3-dione (128 mg, 0.32 mmol) and 2,4-difluorobenzyl cyanoacetamide (82 mg, 0.39 mmol) were suspended in 2 mL of benzene. To the above reaction mixture was added DBU (24 µL, 0.16 mmol). The mixture was sealed in a vial and stirred at 90° C. for overnight. The reaction mixture was concentrated in vacuo and the resulting residue was purified by flash silica column chromatography (30% ethyl acetate in hexane) to yield product 1-(2,4-difluoro-benzyl)-6-[5-(6-ethoxy-2-methylsulfanyl-pyrimidin-4-yl)-thiophen-2-yl]-2-oxo-4-trifluoromethyl-1,2-dihydropyridine-3-carbonitrile (70 mg, 38% yield). $^1$H-NMR (CDCl$_3$): δ7.57 (m, 1H), 7.10 (m, 1H), 7.09 (m, 1H), 6.87 (m, 1H), 6.79 (m, 1H), 6.65 (s, 1H), 6.64 (s, 1H), 5.41 (s, 2H), 4.47 (q, J=7.1 Hz, 2H), 2.55 (s, 3H), 1.41 (t, J=7.1 Hz, 3H).

B. 4,4,4-Trifluoro-1-[1-(3-trifluoromethyl-pyridin-2-yl)-1H-pyrazol-4-yl]-butane-1,3-dione (143 mg, 0.41 mmol) and 2-cyano-N-(2,4-difluoro-benzyl)-acetamide (86 mg, 0.41 mmol) were suspended in 1.5 mL anhydrous benzene. To the above reaction mixture was added 1,8-diazabicyclo[5,4,0]undec-7-ene (DBU (31 mg, 0.21 mmol). The mixture was heated at 90° C. under nitrogen atmosphere for overnight. After this period of time, the mixture was evaporated in vacuo and the resulting residue was purified by column chromatography on silica gel (35% EtOAC/Hexane) to give 1-(2,4-difluoro-benzyl)-2-oxo-4-trifluoromethyl-6-[1-(3-trifluoromethyl-pyridin-2-yl)-1H-pyrazol-4-yl]-1,2-dihydro-pyridine-3-carbonitrile as a yellow solid (78 mg, 36% yield). $^1$H-NMR (400 MHz, CDCl$_3$): δ 5.42 (s, 2H), 6.61 (s, 1H), 6.82 (m, 1H), 6.89 (m, 1H), 7.12 (m, 1H), 7.58 (dd, 1H, J=4.80, J=8.08), 7.73 (s, 1H), 8.28 (dd, 1H, J=1.77, J=8.08), 8.32 (s, 1H), 8.72 (dd, 1H, J=1.77, J=4.80).

Example 5

Oxidation of Compounds of Formula (I)

A. A solution of 1-(2,4-difluoro-benzyl)-4-(1,1-difluoro-propyl)-6-[4-(3-ethylsulfanyl-5-isopropyl-phenyl)-furan-2-yl]-2-oxo-1,2-dihydro-pyridine-3-carbonitrile (39 mg, 69 µmol) in CH$_2$Cl$_2$ was cooled in an ice bath and treated with 3-chloroperoxybenzoic acid (45 mg of 77% pure material, ~200 µmol). After several minutes stirring at 0° C., the ice bath was removed and after an additional 15 minutes, TLC analysis of the reaction mixture showed the starting sulfide to be gone, and the appearance of a single product spot. The reaction mixture was quenched by the addition of 10% sodium thiosulfate solution and diluted with CH$_2$Cl$_2$ (50 mL). Saturated NaHCO$_3$ was added to bring the pH >8. The organic layer was dried over Na$_2$SO$_4$, filtered, and concentrated under reduced pressure to afford a yellow film. The crude product was purified by silica gel column chromatography by adsorbing the material onto silica gel from a CH$_2$Cl$_2$ solution, loading the resulting solid onto the column and eluting with a gradient from 30% to 50% ethyl acetate/hexane to afford 1-(2,4-difluoro-benzyl)-4-(1,1-difluoro-propyl)-6-[4-(3-ethanesulfonyl-5-isopropyl-phenyl)-furan-2-yl]-2-oxo-1,2-dihydro-pyridine-3-carbonitrile (39 mg, 94% yield) as a yellow foam. $^1$H-NMR (400 MHz, CDCl$_3$): δ 7.94 (1H, s), 7.78-7.77 (1H, m), 7.72-7.71 (1H, m), 7.53-7.51 (1H, m), 7.17-7.10 (1H, m), 7.07 (1H, s), 6.87-6.80 (2H, m), 6.74 (1H, s), 5.55 (2H, s), 3.15 (2H, q, J=7.6 Hz), 3.10-2.99 (1H, m), 2.42-2.27 (2H, m), 1.35-1.30 (9H, m), 1.14 (3H, t, J=7.6 Hz).

B. 1-(2,4-difluoro-benzyl)-4-(1,1-difluoro-propyl)-6-[4-(3-ethanesulfonyl-5-isopropyl-phenyl)-furan-2-yl]-2-oxo-1,2-dihydro-pyridine-3-carbonitrile (254 mg, 0.49 mmol) was dissolved in 5 ml mixed solvent of 5:1 DCM/MeOH (v/v), and magnesium monoperoxyphthalate hydrate (MMPP, 85% tech., 627 mg, 1.08 mmol) was slowly added portionwise. The reaction was complete at ambient temperature after 3 hrs. DCM was added to the reaction mixture, and the white precipitate was filtered and thoroughly washed with DCM. The combined organic layers were washed with saturated NaHCO$_3$, brine, and dried over sodium sulfate. After concentration in vacuo, the crude product was purified by column chromatography on silica gel (15→50% EtOAC/Hexane, 0.25% Et$_3$N in hexane) to give 1-(2,4-difluoro-benzyl)-6-[5-(6-methylsulfonyl-pyridin-3-yl)-thiophen-2-yl]-2-oxo-4-trifluoromethyl-1,2-dihydro-pyridine-3-carbonitrile as a yellow solid (154 mg, 60% yield). $^1$H-NMR (400 MHz, CDCl$_3$): δ 3.28 (s, 3H), 5.43 (s, 2H), 6.66 (s, 1H), 6.81 (m, 1H), 6.90 (m, 1H), 7.14 (m, 1H), 7.19 (d, 1H, J=3.9), 7.48 (d, 1H, J=3.9), 8.10 (dd, 1H, J=2.2, J=8.2), 8.17 (dd, 1H, J=0.7, J=8.2), 8.93 (dd, 1H, J=2.2, J=0.7).

C. 1-(2,4-Difluoro-benzyl)-6-[5-(6-ethoxy-2-methylsulfanyl-pyrimidin-4-yl)-thiophen-2-yl]-2-oxo-4-trifluoromethyl-1,2-dihydropyridine-3-carbonitrile (49 mg, 0.087 mmol) was dissolved in a mixture of dichloromethane (2 mL) and methanol (0.4 mL). To this solution was added magnesium monoperoxyphthalate hexahydrate, MMPP, (108 mg, 0.218 mmol, 80% tech.) and the mixture was stirred at ambient temperature for overnight. After this period the reaction mixture was combined with dichloromethene (20 mL) and was washed with 1M NaHCO$_3$ (2×10 mL), and brine (10 mL). The resulting organic layer was separated and dried over anhydrous Na$_2$SO$_4$ and evaporated in vacuo to yield crude product. The crude product was purified using flash silica chromatography (25-50% EtOAc/Hexane) to yield 1-(2,4-difluorobenzyl)-6-[5-(6-ethoxy-2-methanesulfonyl-pyrimidin-4-yl)-thiophen-2-yl]-2-oxo-4-trifluoromethyl-1,2-dihydro-pyridine-3-carbonitrile (42 mg, 80%) as a yellow solid. $^1$H-NMR (CDCl$_3$): δ 7.72 (m, 1H), 7.14 (m, 1H), 7.13 (m, 1H), 7.07 (m, 1H), 6.88 (m, 1H), 6.78 (m, 1H), 6.63 (s, 1H), 5.40 (s, 2H), 4.61 (q, J=7.1 Hz, 2H), 3.36 (s, 3H), 1.46 (t, J=7.1 Hz, 3H). MS (ES+): 597.2 (M+H).

Example 6

Following the procedures set forth above in the foregoing preparations and examples and in U.S. patent application Ser. No. 10/327,813, the following compounds of the invention were prepared:

1-(2,4-Dimethyl-benzyl)-6-[4-(3-isopropyl-phenoxy)-3-methyl-phenyl]-2-oxo-4-trifluoromethyl-1,2-dihydro-pyridine-3-carbonitrile, MS (ES+): 531.3 (M+H);

6-[4-(4-tert-Butyl-phenoxy)-3-methyl-phenyl]-1-(2,4-dimethyl-benzyl)-2-oxo-4-trifluoromethyl-1,2-dihydro-pyridine-3-carbonitrile, MS (ES+): 545.3 (M+H);

1-(2,4-Dimethyl-benzyl)-6-[4-(4-fluoro-phenoxy)-3-methyl-phenyl]-2-oxo-4-trifluoromethyl-1,2-dihydro-pyridine-3-carbonitrile, MS (ES+): 507.1 (M+H);

1-(2,4-Dimethyl-benzyl)-6-[4-(2,4-dimethyl-phenoxy)-3-methyl-phenyl]-2-oxo-4-trifluoromethyl-1,2-dihydro-pyridine-3-carbonitrile, MS (ES+): 517.4 (M+H);

1-(2,4-Dimethyl-benzyl)-6-[4-(2,5-dimethyl-phenoxy)-3-methyl-phenyl]-2-oxo-4-trifluoromethyl-1,2-dihydro-pyridine-3-carbonitrile, MS (ES+): 517.4 (M+H);

1-(2,4-Dimethyl-benzyl)-6-[4-(2,6-dimethyl-phenoxy)-3-methyl-phenyl]-2-oxo-4-trifluoromethyl-1,2-dihydro-pyridine-3-carbonitrile, MS (ES+): 517.4 (M+H);

6-[4-(2-Chloro-phenoxy)-3-methyl-phenyl]-1-(2,4-dimethyl-benzyl)-2-oxo-4-trifluoromethyl-1,2-dihydro-pyridine-3-carbonitrile, MS (ES+): 523.1 (M+H);

6-[4-(3-Chloro-phenoxy)-3-methyl-phenyl]-1-(2,4-dimethyl-benzyl)-2-oxo-4-trifluoromethyl-1,2-dihydro-pyridine-3-carbonitrile, MS (ES+): 523.2 (M+H);

1-(2,4-Dimethyl-benzyl)-6-[3-methyl-4-(2-trifluoromethyl-phenoxy)-phenyl]-2-oxo-4-trifluoromethyl-1,2-dihydro-pyridine-3-carbonitrile, MS (ES+): 557.4 (M+H);

1-(2,4-Dimethyl-benzyl)-6-[3-methyl-4-(3-trifluoromethyl-phenoxy)-phenyl]-2-oxo-4-trifluoromethyl-1,2-dihydro-pyridine-3-carbonitrile, MS (ES+): 557.4 (M+H);

6-[4-(3-Bromo-phenoxy)-phenyl]-1-(2,4-dimethyl-benzyl)-2-oxo-4-trifluoromethyl-1,2-dihydro-pyridine-3-carbonitrile, MS (ES+): 553.3 (M+H);

6-[4-(4-Bromo-phenoxy)-phenyl]-1-(2,4-dimethyl-benzyl)-2-oxo-4-trifluoromethyl-1,2-dihydro-pyridine-3-carbonitrile, MS (ES+): 555.2 (M+H);

6-[4-(3-Benzyloxy-phenoxy)-phenyl]-1-(2,4-dimethyl-benzyl)-2-oxo-4-trifluoromethyl-1,2-dihydro-pyridine-3-carbonitrile, MS (ES+): 581.5 (M+H);

1-(2,4-Dimethyl-benzyl)-6-[4-(2,4-dimethyl-phenoxy)-phenyl]-2-oxo-4-trifluoromethyl-1,2-dihydro-pyridine-3-carbonitrile, MS (ES+): 503.2 (M+H);

6-[4-(3,5-Bis-trifluoromethyl-phenoxy)-phenyl]-1-(2,4-dimethyl-benzyl)-2-oxo-4-trifluoromethyl-1,2-dihydro-pyridine-3-carbonitrile, MS (ES+): 611.4 (M+H);

6-(4-Benzyloxy-phenyl)-1-(2,4-dichloro-benzyl)-2-oxo-4-trifluoromethyl-1,2-dihydro-pyridine-3-carbonitrile, MS (ES+): 529.0 (M+H);

1-(2,4-Dichloro-benzyl)-2-oxo-6-(4-phenoxy-phenyl)-4-trifluoromethyl-1,2-dihydro-pyridine-3-carbonitrile, MS (ES+): 515.0 (M+H);

1-(2,4-Difluoro-benzyl)-2-oxo-6-(4-phenoxy-phenyl)-4-trifluoromethyl-1,2-dihydro-pyridine-3-carbonitrile, MS (ES+): 483.0 (M+H);

1-(2-Chloro-4-fluoro-benzyl)-2-oxo-6-(4-phenoxy-phenyl)-4-trifluoromethyl-1,2-dihydro-pyridine-3-carbonitrile, MS (ES+): 499.2 (M+H);

6-(4-Benzyloxy-phenyl)-1-(2-chloro-4-fluoro-benzyl)-2-oxo-4-trifluoromethyl-1,2-dihydro-pyridine-3-carbonitrile, MS (ES+): 513.2 (M+H);

1-(2,4-Dichloro-benzyl)-2-oxo-4-pentafluoroethyl-6-(4-phenoxy-phenyl)-1,2-dihydro-pyridine-3-carbonitrile, MS (ES+): 564.9 (M+H);

1-(2,4-Dimethyl-benzyl)-6-(3-isopropyl-4-phenoxy-phenyl)-2-oxo-4-trifluoromethyl-1,2-dihydro-pyridine-3-carbonitrile, MS (ES+): 517.5 (M+H);

1-(2,4-Dimethyl-benzyl)-6-(3-isopropyl-4-o-tolyloxy-phenyl)-2-oxo-4-trifluoromethyl-1,2-dihydro-pyridine-3-carbonitrile, MS (ES+): 531.3 (M+H);

1-(2,4-Dimethyl-benzyl)-6-[4-(2-ethyl-phenoxy)-3-isopropyl-phenyl]-2-oxo-4-trifluoromethyl-1,2-dihydro-pyridine-3-carbonitrile, MS (ES+): 545.5 (M+H);

1-(2,4-Dimethyl-benzyl)-6-[4-(2,5-dimethyl-phenoxy)-3-isopropyl-phenyl]-2-oxo-4-trifluoromethyl-1,2-dihydro-pyridine-3-carbonitrile, MS (ES+): 545.2 (M+H);

1-(2,4-Dimethyl-benzyl)-6-[4-(2,4-dimethyl-phenoxy)-3-isopropyl-phenyl]-2-oxo-4-trifluoromethyl-1,2-dihydro-pyridine-3-carbonitrile, MS (ES+): 545.3 (M+H);

1-(2,4-Dimethyl-benzyl)-6-[4-(3,4-dimethyl-phenoxy)-3-isopropyl-phenyl]-2-oxo-4-trifluoromethyl-1,2-dihydro-pyridine-3-carbonitrile, MS (ES+): 545.5 (M+H);

1-(2,4-Dimethyl-benzyl)-6-(3-isopropyl-4-m-tolyloxy-phenyl)-2-oxo-4-trifluoromethyl-1,2-dihydro-pyridine-3-carbonitrile, MS (ES+): 531.2 (M+H);

1-(2,4-Dimethyl-benzyl)-6-[3-isopropyl-4-(3-isopropyl-phenoxy)-phenyl]-2-oxo-4-trifluoromethyl-1,2-dihydro-pyridine-3-carbonitrile, MS (ES+): 559.3 (M+H);

1-(2,4-Dimethyl-benzyl)-6-[3-isopropyl-4-(4-isopropyl-phenoxy)-phenyl]-2-oxo-4-trifluoromethyl-1,2-dihydro-pyridine-3-carbonitrile, MS (ES+): 559.3 (M+H);

1-(2,4-Dimethyl-benzyl)-6-(3-isopropyl-4-p-tolyloxy-phenyl)-2-oxo-4-trifluoromethyl-1,2-dihydro-pyridine-3-carbonitrile, MS (ES+): 531.3 (M+H);

6-[4-(4-tert-Butyl-phenoxy)-3-isopropyl-phenyl]-1-(2,4-dimethyl-benzyl)-2-oxo-4-trifluoromethyl-1,2-dihydro-pyridine-3-carbonitrile, MS (ES+): 573.6 (M+H);

1-(2,4-Dimethyl-benzyl)-6-[3-isopropyl-4-(4-vinyl-phenoxy)-phenyl]-2-oxo-4-trifluoromethyl-1,2-dihydro-pyridine-3-carbonitrile, MS (ES+): 543.2 (M+H);

1-(2,4-Dimethyl-benzyl)-6-[4-(4-ethyl-2-methyl-phenoxy)-3-methyl-phenyl]-2-oxo-4-trifluoromethyl-1,2-dihydro-pyridine-3-carbonitrile, MS (ES+): 531.4 (M+H);

1-(2,4-Dimethyl-benzyl)-6-[4-(4-ethyl-2-methyl-phenoxy)-3-isopropyl-phenyl]-2-oxo-4-trifluoromethyl-1,2-dihydro-pyridine-3-carbonitrile, MS (ES+): 559.3 (M+H);

1-(2,4-Dimethyl-benzyl)-6-[4-(2-ethyl-4-methyl-phenoxy)-3-methyl-phenyl]-2-oxo-4-trifluoromethyl-1,2-dihydro-pyridine-3-carbonitrile, MS (ES+): 531.2 (M+H);

1-(2,4-Dimethyl-benzyl)-6-[4-(2-ethyl-4-methyl-phenoxy)-3-isopropyl-phenyl]-2-oxo-4-trifluoromethyl-1,2-dihydro-pyridine-3-carbonitrile, MS (ES+): 559.4 (M+H);

6-(4-Benzyloxy-3-chloro-phenyl)-1-(2,4-difluoro-benzyl)-2-oxo-4-trifluoromethyl-1,2-dihydro-pyridine-3-carbonitrile, MS (ES+): 531.1 (M+H);

6-[3-Chloro-4-(4-fluoro-phenoxy)-phenyl]-1-(2,4-difluoro-benzyl)-2-oxo-4-trifluoromethyl-1,2-dihydro-pyridine-3-carbonitrile, MS (ES+): 535.1 (M+H);

1-(2,4-Difluoro-benzyl)-6-[4-(4-fluoro-phenoxy)-phenyl]-2-oxo-4-trifluoromethyl-1,2-dihydro-pyridine-3-carbonitrile, 6-[4-(4-Dimethylamino-phenoxy)-3-methyl-phenyl]-1-(2,4-dimethyl-benzyl)-2-oxo-4-trifluoromethyl-1,2-dihydro-pyridine-3-carbonitrile, MS (ES+): 532.3 (M+H);

1-(2,4-Dimethyl-benzyl)-6-[4-(4-methoxy-phenoxy)-3-methyl-phenyl]-2-oxo-4-trifluoromethyl-1,2-dihydro-pyridine-3-carbonitrile, MS (ES+): 519.3 (M+H);

6-[4-(3-Cyano-phenoxy)-3-methyl-phenyl]-1-(2,4-dimethyl-benzyl)-2-oxo-4-trifluoromethyl-1,2-dihydro-pyridine-3-carbonitrile, MS (ES+): 514.4 (M+H);

6-[4-(4-Benzyloxy-phenoxy)-3-methyl-phenyl]-1-(2,4-dimethyl-benzyl)-2-oxo-4-trifluoromethyl-1,2-dihydro-pyridine-3-carbonitrile, MS (ES+): 595.3 (M+H);

6-[4-(3-Benzyloxy-phenoxy)-3-methyl-phenyl]-1-(2,4-dimethyl-benzyl)-2-oxo-4-trifluoromethyl-1,2-dihydro-pyridine-3-carbonitrile, MS (ES+): 595.5 (M+H);

6-[4-(3-Cyano-phenoxy)-phenyl]-1-(2,4-dimethyl-benzyl)-2-oxo-4-trifluoromethyl-1,2-dihydro-pyridine-3-carbonitrile, MS (ES+): 500.4 (M+H);

6-[4-(4-Cyano-phenoxy)-phenyl]-1-(2,4-dimethyl-benzyl)-2-oxo-4-trifluoromethyl-1,2-dihydro-pyridine-3-carbonitrile, 6-[4-(4-Dimethylamino-phenoxy)-phenyl]-1-(2,4-dimethyl-benzyl)-2-oxo-4-trifluoromethyl-1,2-dihydro-pyridine-3-carbonitrile, MS (ES+): 518.4 (M+H);

1-(2,4-Dimethyl-benzyl)-6-[4-(4-hydroxy-phenoxy)-phenyl]-2-oxo-4-trifluoromethyl-1,2-dihydro-pyridine-3-carbonitrile, MS (ES+): 491.0 (M+H);

1-(2,4-Dimethyl-benzyl)-6-[4-(3-hydroxy-phenoxy)-phenyl]-2-oxo-4-trifluoromethyl-1,2-dihydro-pyridine-3-carbonitrile, 1-(2,4-Dimethyl-benzyl)-6-[4-(4-hexyloxy-phenoxy)-phenyl]-2-oxo-4-trifluoromethyl-1,2-dihydro-pyridine-3-carbonitrile, MS (ES+): 575.5 (M+H);

1-(2,4-Dimethyl-benzyl)-6-{4-[4-(3-methyl-butoxy)-phenoxy]-phenyl}-2-oxo-4-trifluoromethyl-1,2-dihydro-pyridine-3-carbonitrile, MS (ES+): 561.3 (M+H);

1-(2,4-Dimethyl-benzyl)-6-[4-(3-hexyloxy-phenoxy)-phenyl]-2-oxo-4-trifluoromethyl-1,2-dihydro-pyridine-3-carbonitrile, MS (ES+): 575.3 (M+H);

1-(2,4-Dimethyl-benzyl)-6-{4-[3-(3-methyl-butoxy)-phenoxy]-phenyl}-2-oxo-4-trifluoromethyl-1,2-dihydro-pyridine-3-carbonitrile, MS (ES+): 561.3 (M+H);

(3-{4-[5-Cyano-1-(2,4-dimethyl-benzyl)-6-oxo-4-trifluoromethyl-1,6-dihydro-pyridin-2-yl]-phenoxy}-phenoxy)-acetic acid benzyl ester, MS (ES+): 639.1 (M+H);

(4-{4-[5-Cyano-1-(2,4-dimethyl-benzyl)-6-oxo-4-trifluoromethyl-1,6-dihydro-pyridin-2-yl]-phenoxy}-phenoxy)-acetic acid benzyl ester, MS (ES+): 639.2 (M+H);

1-(2,4-Dimethyl-benzyl)-2-oxo-6-[4-(4-phenylamino-phenoxy)-phenyl]-4-trifluoromethyl-1,2-dihydro-pyridine-3-carbonitrile, MS (ES+): 566.2 (M+H);

6-[4-(4-Benzylamino-phenoxy)-phenyl]-1-(2,4-dimethyl-benzyl)-2-oxo-4-trifluoromethyl-1,2-dihydro-pyridine-3-carbonitrile, MS (ES+): 580.3 (M+H);

1-(2,4-Dimethyl-benzyl)-6-[4-(3-hydroxymethyl-phenoxy)-phenyl]-2-oxo-4-trifluoromethyl-1,2-dihydro-pyridine-3-carbonitrile, MS (ES+): 505.1 (M+H);

6-[4-(3-Benzyloxy-phenoxy)-3-isopropyl-phenyl]-1-(2,4-dimethyl-benzyl)-2-oxo-4-trifluoromethyl-1,2-dihydro-pyridine-3-carbonitrile, MS (ES+): 623.5 (M+H);

6-[4-(4-Benzyloxy-phenoxy)-3-isopropyl-phenyl]-1-(2,4-dimethyl-benzyl)-2-oxo-4-trifluoromethyl-1,2-dihydro-pyridine-3-carbonitrile, MS (ES+): 623.2 (M+H);

1-(2,4-Difluoro-benzyl)-6-[4-(3-hydroxy-phenoxy)-phenyl]-2-oxo-4-trifluoromethyl-1,2-dihydro-pyridine-3-carbonitrile, 1-(2,4-Difluoro-benzyl)-6-[4-(4-hydroxy-phenoxy)-phenyl]-2-oxo-4-trifluoromethyl-1,2-dihydro-pyridine-3-carbonitrile, 6-[4-(3-Cyano-4-trifluoromethyl-phenoxy)-phenyl]-1-(2,4-difluoro-benzyl)-2-oxo-4-trifluoromethyl-1,2-dihydro-pyridine-3-carbonitrile, MS (ES+): 576.0 (M+H);

4-{4-[5-Cyano-1-(2,4-dimethyl-benzyl)-6-oxo-4-trifluoromethyl-1,6-dihydro-pyridin-2-yl]-2-methyl-phenoxy}-benzoic acid methyl ester, MS (ES+): 547.3 (M+H);

3-{4-[5-Cyano-1-(2,4-dimethyl-benzyl)-6-oxo-4-trifluoromethyl-1,6-dihydro-pyridin-2-yl]-2-methyl-phenoxy}-benzoic acid methyl ester, MS (ES+): 547.4 (M+H);

4-{4-[5-Cyano-1-(2,4-dimethyl-benzyl)-6-oxo-4-trifluoromethyl-1,6-dihydro-pyridin-2-yl]-phenoxy}-benzoic acid, MS (ES+): 519.2 (M+H);

3-{4-[5-Cyano-1-(2,4-dimethyl-benzyl)-6-oxo-4-trifluoromethyl-1,6-dihydro-pyridin-2-yl]-phenoxy}-N-methyl-benzamide, 3-{4-[5-Cyano-1-(2,4-dimethyl-benzyl)-6-oxo-4-trifluoromethyl-1,6-dihydro-pyridin-2-yl]-phenoxy}-N,N-dimethyl-benzamide, MS (ES+): 546.5 (M+H);

1-(2,4-Dimethyl-benzyl)-2-oxo-6-{4-[3-(piperidine-1-carbonyl)-phenoxy]-phenyl}-4-trifluoromethyl-1,2-dihydro-pyridine-3-carbonitrile, MS (ES+): 586.1 (M+H);

1-(2,4-Dimethyl-benzyl)-6-{4-[3-(3-hydroxy-piperidine-1-carbonyl)-phenoxy]-phenyl}-2-oxo-4-trifluoromethyl-1,2-dihydro-pyridine-3-carbonitrile, MS (ES+): 602.4 (M+H);

N-Benzyl-3-{4-[5-cyano-1-(2,4-dimethyl-benzyl)-6-oxo-4-trifluoromethyl-1,6-dihydro-pyridin-2-yl]-phenoxy}-benzamide, MS (ES+): 608.4 (M+H);

3-{4-[5-Cyano-1-(2,4-dimethyl-benzyl)-6-oxo-4-trifluoromethyl-1,6-dihydro-pyridin-2-yl]-phenoxy}-benzoic acid N'-phenyl-hydrazide, MS (ES+): 609.3 (M+H);

3-{4-[5-Cyano-1-(2,4-dimethyl-benzyl)-6-oxo-4-trifluoromethyl-1,6-dihydro-pyridin-2-yl]-phenoxy}-N-cyclopentyl-benzamide, MS (ES+): 586.3 (M+H);

3-{4-[5-Cyano-1-(2,4-dimethyl-benzyl)-6-oxo-4-trifluoromethyl-1,6-dihydro-pyridin-2-yl]-phenoxy}-N-methoxy-N-methyl-benzamide, MS (ES+): 562.5 (M+H);

3-{4-[5-Cyano-1-(2,4-dimethyl-benzyl)-6-oxo-4-trifluoromethyl-1,6-dihydro-pyridin-2-yl]-phenoxy}-N—((S)-1-phenyl-ethyl)-benzamide, MS (ES+): 622.4 (M+H);

3-{4-[5-Cyano-1-(2,4-difluoro-benzyl)-6-oxo-4-trifluoromethyl-1,6-dihydro-pyridin-2-yl]-phenoxy}-N,N-dimethyl-benzamide, 3-Benzyloxy-5-{4-[5-cyano-1-(2,4-dimethyl-benzyl)-6-oxo-4-trifluoromethyl-1,6-dihydro-pyridin-2-yl]-phenoxy}-benzoic acid methyl ester, 3-Benzyloxy-5-{4-[5-cyano-1-(2,4-difluoro-benzyl)-6-oxo-4-trifluoromethyl-1,6-dihydro-pyridin-2-yl]-phenoxy}-N,N-dimethyl-benzamide, MS (ES+): 660.5 (M+H);

3-{4-[5-Cyano-1-(2,4-difluoro-benzyl)-6-oxo-4-trifluoromethyl-1,6-dihydro-pyridin-2-yl]-phenoxy}-5-hydroxy-N,N-dimethyl-benzamide, MS (ES+): 570.2 (M+H);

2-Benzyloxy-5-{4-[5-cyano-1-(2,4-difluoro-benzyl)-6-oxo-4-trifluoromethyl-1,6-dihydro-pyridin-2-yl]-phenoxy}-N,N-dimethyl-benzamide, MS (ES+): 660.3 (M+H);

5-{4-[5-Cyano-1-(2,4-difluoro-benzyl)-6-oxo-4-trifluoromethyl-1,6-dihydro-pyridin-2-yl]-phenoxy}-2-hydroxy-N,N-dimethyl-benzamide, MS (ES+): 570.7 (M+H);

3-{4-[5-Cyano-1-(2,4-difluoro-benzyl)-6-oxo-4-trifluoromethyl-1,6-dihydro-pyridin-2-yl]-phenoxy}-N-methyl-benzamide, N-tert-Butyl-3-{4-[5-cyano-1-(2,4-difluoro-benzyl)-6-oxo-4-trifluoromethyl-1,6-dihydro-pyridin-2-yl]-phenoxy}-benzamide, 1-(2,4-Difluoro-benzyl)-2-oxo-6-{4-[3-(piperidine-1-carbonyl)-phenoxy]-phenyl}-4-trifluoromethyl-1,2-dihydro-pyridine-3-carbonitrile, (S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-propionic acid methyl ester, MS (ES+): 604.3 (M+H);

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-propionic acid methyl ester, MS (ES+): 604.1 (M+H);

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-methyl-butyric acid methyl ester, MS (ES+): 632.3 (M+H);

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-methyl-butyric acid methyl ester, MS (ES+): 632.5 (M+H);

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-4-methyl-pentanoic acid methyl ester, MS (ES+): 646.5 (M+H);

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-4-methyl-pentanoic acid methyl ester, MS (ES+): 646.4 (M+H);

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-phenyl-propionic acid methyl ester, MS (ES+): 680.3 (M+H);

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-phenyl-propionic acid methyl ester, MS (ES+): 680.3 (M+H);

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-(1H-imidazol-4-yl)-propionic acid methyl ester, MS (ES+): 670.1 (M+H);

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-(1H-imidazol-4-yl)-propionic acid methyl ester, MS (ES+): 670.2 (M+H);

(S)-(3-{4-[5-Cyano-1-(2,4-dimethyl-benzyl)-6-oxo-4-trifluoromethyl-1,6-dihydro-pyridin-2-yl]-phenoxy}-benzoylamino)-phenyl-acetic acid methyl ester, MS (ES+): 666.5 (M+H);

(R)-(3-{4-[5-Cyano-1-(2,4-dimethyl-benzyl)-6-oxo-4-trifluoromethyl-1,6-dihydro-pyridin-2-yl]-phenoxy}-benzoylamino)-phenyl-acetic acid methyl ester, MS (ES+): 666.3 (M+H);

1-(2,4-Dimethyl-benzyl)-6-[4-(4-methylsulfanyl-phenoxy)-phenyl]-2-oxo-4-trifluoromethyl-1,2-dihydro-pyridine-3-carbonitrile, MS (ES+): 521.1 (M+H);

1-(2,4-Dimethyl-benzyl)-6-{4-[4-(1,3-dioxo-1,3-dihydro-isoindol-2-yl)-phenoxy]-phenyl}-2-oxo-4-trifluoromethyl-1,2-dihydro-pyridine-3-carbonitrile, MS (ES+): 620.2 (M+H);

3-{4-[5-Cyano-1-(2,4-dimethyl-benzyl)-6-oxo-4-trifluoromethyl-1,6-dihydro-pyridin-2-yl]-phenoxy}-N,N-dimethyl-thiobenzamide, MS (ES+): 562.4 (M+H);

6-[3-Chloro-4-(4-methanesulfonyl-phenoxy)-phenyl]-1-(2,4-difluoro-benzyl)-2-oxo-4-trifluoromethyl-1,2-dihydro-pyridine-3-carbonitrile, MS (ES+): 595.4 (M+H);

1-(2,5-Diethyl-thiazol-4-ylmethyl)-2-oxo-6-(4-phenoxy-phenyl)-4-trifluoromethyl-1,2-dihydro-pyridine-3-carbonitrile, 1-(2,4-Difluoro-benzyl)-6-(4'-methanesulfonyl-biphenyl-3-yl)-2-oxo-4-trifluoromethyl-1,2-dihydro-pyridine-3-carbonitrile, 1-(2,4-Difluoro-benzyl)-6-(4'-methanesulfonyl-biphenyl-4-yl)-2-oxo-4-trifluoromethyl-1,2-dihydro-pyridine-3-carbonitrile, 1-(2,4-Difluoro-benzyl)-6-(4'-ethylsulfanyl-3'-trifluoromethyl-biphenyl-3-yl)-2-oxo-4-trifluoromethyl-1,2-dihydro-pyridine-3-carbonitrile, MS (ES+): 595.6 (M+H);

1-(2,4-Difluoro-benzyl)-6-(4'-ethanesulfonyl-3'-trifluoromethyl-biphenyl-3-yl)-2-oxo-4-trifluoromethyl-1,2-dihydro-pyridine-3-carbonitrile, MS (ES+): 627.4 (M+H);

1-(2,4-Difluoro-benzyl)-6-(4'-methylsulfanyl-3'-trifluoromethyl-biphenyl-3-yl)-2-oxo-4-trifluoromethyl-1,2-dihydro-pyridine-3-carbonitrile, MS (ES+): 581.3 (M+H);

1-(2,4-Difluoro-benzyl)-6-(5'-methylsulfanyl-3'-trifluoromethyl-biphenyl-3-yl)-2-oxo-4-trifluoromethyl-1,2-dihydro-pyridine-3-carbonitrile, MS (ES+): 581.2 (M+H);

1-(2,4-Difluoro-benzyl)-6-(4'-methylsulfanyl-3'-trifluoromethyl-biphenyl-4-yl)-2-oxo-4-trifluoromethyl-1,2-dihydro-pyridine-3-carbonitrile, MS (ES+): 581.1 (M+H);

1-(2,4-Difluoro-benzyl)-6-(5'-methylsulfanyl-3'-trifluoromethyl-biphenyl-4-yl)-2-oxo-4-trifluoromethyl-1,2-dihydro-pyridine-3-carbonitrile, MS (ES+): 581.4 (M+H);

1-(2,4-Difluoro-benzyl)-6-(4'-methanesulfonyl-3'-trifluoromethyl-biphenyl-3-yl)-2-oxo-4-trifluoromethyl-1,2-dihydro-pyridine-3-carbonitrile, MS (ES+): 614.2 (M+H);

1-(2,4-Difluoro-benzyl)-6-(4'-methanesulfonyl-3'-trifluoromethyl-biphenyl-4-yl)-2-oxo-4-trifluoromethyl-1,2-dihydro-pyridine-3-carbonitrile, MS (ES+): 614.2 (M+H);

1-(2,4-Difluoro-benzyl)-6-(3'-methanesulfonyl-5'-trifluoromethyl-biphenyl-4-yl)-2-oxo-4-trifluoromethyl-1,2-dihydro-pyridine-3-carbonitrile, MS (ES+): 613.1 (M+H);

1-(2,4-Difluoro-benzyl)-2-oxo-4-trifluoromethyl-6-[5'-trifluoromethyl-3'-(2-trimethylsilanyl-ethanesulfonyl)-biphenyl-3-yl]-1,2-dihydro-pyridine-3-carbonitrile, MS (ES+): 699.3 (M+H);

1-(2,4-Difluoro-benzyl)-6-(3'-ethanesulfonyl-5'-trifluoromethyl-biphenyl-3-yl)-2-oxo-4-trifluoromethyl-1,2-dihydro-pyridine-3-carbonitrile, MS (ES+): 627.2 (M+H);

1-(2,4-Difluoro-benzyl)-2-oxo-6-[3'-(propane-2-sulfonyl)-5'-trifluoromethyl-biphenyl-3-yl]-4-trifluoromethyl-1,2-dihydro-pyridine-3-carbonitrile, MS (ES+): 641.3 (M+H);

1-(2,4-Difluoro-benzyl)-6-(4'-ethoxy-3'-methanesulfonyl-biphenyl-3-yl)-2-oxo-4-trifluoromethyl-1,2-dihydro-pyridine-3-carbonitrile, 1-(2,4-Difluoro-benzyl)-2-oxo-6-[5'-(propane-1-sulfinyl)-3'-trifluoromethyl-biphenyl-3-yl]-4-trifluoromethyl-1,2-dihydro-pyridine-3-carbonitrile, MS (ES+): 625.3 (M+H);

6-[5'-(Butane-1-sulfinyl)-3'-trifluoromethyl-biphenyl-3-yl]-1-(2,4-difluoro-benzyl)-2-oxo-4-trifluoromethyl-1,2-dihydro-pyridine-3-carbonitrile, 1-(2,4-Difluoro-benzyl)-2-oxo-6-(5'-phenylmethanesulfinyl-3'-trifluoromethyl-biphenyl-3-yl)-4-trifluoromethyl-1,2-dihydro-pyridine-3-carbonitrile, MS (ES+): 673.4 (M+H);

6-(5'-Cyclopropylmethanesulfinyl-3'-trifluoromethyl-biphenyl-3-yl)-1-(2,4-difluoro-benzyl)-2-oxo-4-trifluoromethyl-1,2-dihydro-pyridine-3-carbonitrile, MS (ES+): 637.3 (M+H);

1-(2,4-Difluoro-benzyl)-2-oxo-6-[5'-(propane-1-sulfinyl)-3'-trifluoromethyl-biphenyl-4-yl]-4-trifluoromethyl-1,2-dihydro-pyridine-3-carbonitrile, MS (ES+): 624.9 (M+H);

6-[5'-(Butane-1-sulfinyl)-3'-trifluoromethyl-biphenyl-4-yl]-1-(2,4-difluoro-benzyl)-2-oxo-4-trifluoromethyl-1,2-dihydro-pyridine-3-carbonitrile, MS (ES+): 639.2 (M+H);

1-(2,4-Difluoro-benzyl)-2-oxo-6-(5'-phenylmethanesulfinyl-3'-trifluoromethyl-biphenyl-4-yl)-4-trifluoromethyl-1,2-dihydro-pyridine-3-carbonitrile, MS (ES+): 673.0 (M+H);

6-(5'-Cyclopropylmethanesulfinyl-3'-trifluoromethyl-biphenyl-4-yl)-1-(2,4-difluoro-benzyl)-2-oxo-4-trifluoromethyl-1,2-dihydro-pyridine-3-carbonitrile, MS (ES+): 637.4 (M+H);

1-(2,4-Difluoro-benzyl)-6-(5'-ethanesulfinyl-3'-trifluoromethyl-biphenyl-4-yl)-2-oxo-4-trifluoromethyl-1,2-dihydro-pyridine-3-carbonitrile, MS (ES+): 611.1 (M+H);

1-(2,4-Difluoro-benzyl)-2-oxo-6-[3'-(propane-2-sulfinyl)-5'-trifluoromethyl-biphenyl-4-yl]-4-trifluoromethyl-1,2-dihydro-pyridine-3-carbonitrile, MS (ES+): 625.3 (M+H);

1-(2,4-Difluoro-benzyl)-2-oxo-6-[3'-(propane-1-sulfonyl)-5'-trifluoromethyl-biphenyl-3-yl]-4-trifluoromethyl-1,2-dihydro-pyridine-3-carbonitrile, MS (ES+): 641.4 (M+H);

1-(2,4-Difluoro-benzyl)-2-oxo-6-[3'-(propane-1-sulfonyl)-5'-trifluoromethyl-biphenyl-4-yl]-4-trifluoromethyl-1,2-dihydro-pyridine-3-carbonitrile, MS (ES+): 641.1 (M+H);

6-[3'-(Butane-1-sulfonyl)-5'-trifluoromethyl-biphenyl-3-yl]-1-(2,4-difluoro-benzyl)-2-oxo-4-trifluoromethyl-1,2-dihydro-pyridine-3-carbonitrile, MS (ES+): 655.2 (M+H);
6-[3'-(Butane-1-sulfonyl)-5'-trifluoromethyl-biphenyl-4-yl]-1-(2,4-difluoro-benzyl)-2-oxo-4-trifluoromethyl-1,2-dihydro-pyridine-3-carbonitrile, MS (ES+): 655.1 (M+H);
1-(2,4-Difluoro-benzyl)-2-oxo-6-(3'-phenylmethanesulfonyl-5'-trifluoromethyl-biphenyl-3-yl)-4-trifluoromethyl-1,2-dihydro-pyridine-3-carbonitrile, MS (ES): 689.2 (M+H);
1-(2,4-Difluoro-benzyl)-2-oxo-6-(3'-phenylmethanesulfonyl-5'-trifluoromethyl-biphenyl-4-yl)-4-trifluoromethyl-1,2-dihydro-pyridine-3-carbonitrile, MS (ES+): 689.3 (M+H);
6-(3'-Cyclopropylmethanesulfonyl-5'-trifluoromethyl-biphenyl-3-yl)-1-(2,4-difluoro-benzyl)-2-oxo-4-trifluoromethyl-1,2-dihydro-pyridine-3-carbonitrile, MS (ES+): 653.3 (M+H);
6-(3'-Cyclopropylmethanesulfonyl-5'-trifluoromethyl-biphenyl-4-yl)-1-(2,4-difluoro-benzyl)-2-oxo-4-trifluoromethyl-1,2-dihydro-pyridine-3-carbonitrile,
1-(2,4-Difluoro-benzyl)-6-(3'-ethanesulfonyl-5'-trifluoromethyl-biphenyl-4-yl)-2-oxo-4-trifluoromethyl-1,2-dihydro-pyridine-3-carbonitrile,
1-(2,4-Difluoro-benzyl)-2-oxo-6-[3'-(propane-2-sulfonyl)-5'-trifluoromethyl-biphenyl-4-yl]-4-trifluoromethyl-1,2-dihydro-pyridine-3-carbonitrile,
1-(2,4-Difluoro-benzyl)-6-(5'-isopropyl-3'-methanesulfonyl-biphenyl-3-yl)-2-oxo-4-trifluoromethyl-1,2-dihydro-pyridine-3-carbonitrile, MS (ES+): 587.3 (M+H);
1-(2,4-Difluoro-benzyl)-6-(5'-ethyl-3'-methanesulfonyl-biphenyl-3-yl)-2-oxo-4-trifluoromethyl-1,2-dihydro-pyridine-3-carbonitrile, MS (ES+): 573.2 (M+H);
1-(2,4-Difluoro-benzyl)-6-(3'-ethanesulfonyl-5'-isopropyl-biphenyl-3-yl)-2-oxo-4-trifluoromethyl-1,2-dihydro-pyridine-3-carbonitrile, MS (ES+): 601.3 (M+H);
1-(2,4-Difluoro-benzyl)-6-(3'-methanesulfonyl-5'-trifluoromethyl-biphenyl-3-yl)-2-oxo-4-trifluoromethyl-1,2-dihydro-pyridine-3-carbonitrile, MS (ES+): 613.1 (M+H);
6-(3'-Acetyl-biphenyl-3-yl)-1-(2,4-difluoro-benzyl)-2-oxo-4-trifluoromethyl-1,2-dihydro-pyridine-3-carbonitrile,
6-(4'-Acetyl-biphenyl-3-yl)-1-(2,4-difluoro-benzyl)-2-oxo-4-trifluoromethyl-1,2-dihydro-pyridine-3-carbonitrile,
3'-[5-Cyano-1-(2,4-difluoro-benzyl)-6-oxo-4-trifluoromethyl-1,6-dihydro-pyridin-2-yl]-biphenyl-3-carboxylic acid amide,
3'-[5-Cyano-1-(2,4-difluoro-benzyl)-6-oxo-4-trifluoromethyl-1,6-dihydro-pyridin-2-yl]-biphenyl-4-carboxylic acid amide,
3'-[5-Cyano-1-(2,4-difluoro-benzyl)-6-oxo-4-trifluoromethyl-1,6-dihydro-pyridin-2-yl]-biphenyl-3-carboxylic acid dimethylamide,
3'-[5-Cyano-1-(2,4-difluoro-benzyl)-6-oxo-4-trifluoromethyl-1,6-dihydro-pyridin-2-yl]-biphenyl-4-carboxylic acid dimethylamide,
1-(2,4-Difluoro-benzyl)-2-oxo-6-[3'-(pyrrolidine-1-carbonyl)-biphenyl-3-yl]-4-trifluoromethyl-1,2-dihydro-pyridine-3-carbonitrile,
1-(2,4-Difluoro-benzyl)-2-oxo-6-[4'-(piperidine-1-carbonyl)-biphenyl-3-yl]-4-trifluoromethyl-1,2-dihydro-pyridine-3-carbonitrile,
3'-[5-Cyano-1-(2,4-difluoro-benzyl)-6-oxo-4-trifluoromethyl-1,6-dihydro-pyridin-2-yl]-biphenyl-3-carboxylic acid ethylamide,
3'-[5-Cyano-1-(2,4-difluoro-benzyl)-6-oxo-4-trifluoromethyl-1,6-dihydro-pyridin-2-yl]-biphenyl-4-carboxylic acid methylamide,
3'-[5-Cyano-1-(2,4-difluoro-benzyl)-6-oxo-4-trifluoromethyl-1,6-dihydro-pyridin-2-yl]-biphenyl-4-carboxylic acid phenylamide,
3'-[5-Cyano-1-(2,4-difluoro-benzyl)-6-oxo-4-trifluoromethyl-1,6-dihydro-pyridin-2-yl]-biphenyl-4-carboxylic acid benzylamide,
3'-[5-Cyano-1-(2,4-difluoro-benzyl)-6-oxo-4-trifluoromethyl-1,6-dihydro-pyridin-2-yl]-5-isopropyl-biphenyl-3-carboxylic acid methyl ester, MS (ES+): 567.3 (M+H);
3'-[5-Cyano-1-(2,4-difluoro-benzyl)-6-oxo-4-trifluoromethyl-1,6-dihydro-pyridin-2-yl]-5-isopropyl-biphenyl-3-carboxylic acid methyl ester;
{3'-[5-Cyano-1-(2,4-difluoro-benzyl)-6-oxo-4-trifluoromethyl-1,6-dihydro-pyridin-2-yl]-biphenyl-3-yl}-acetic acid, MS (ES+): 525.5 (M+H);
{4'-[5-Cyano-1-(2,4-difluoro-benzyl)-6-oxo-4-trifluoromethyl-1,6-dihydro-pyridin-2-yl]-biphenyl-3-yl}-acetic acid, MS (ES+): 525.4 (M+H);
{3'-[5-Cyano-1-(2,4-difluoro-benzyl)-6-oxo-4-trifluoromethyl-1,6-dihydro-pyridin-2-yl]-biphenyl-4-yl}-acetic acid, MS (ES+): 525.3 (M+H);
{4'-[5-Cyano-1-(2,4-difluoro-benzyl)-6-oxo-4-trifluoromethyl-1,6-dihydro-pyridin-2-yl]-biphenyl-4-yl}-acetic acid, MS (ES+): 591.2 (M+H);
{3-Chloro-3'-[5-cyano-1-(2,4-difluoro-benzyl)-6-oxo-4-trifluoromethyl-1,6-dihydro-pyridin-2-yl]-biphenyl-4-yl}-acetic acid methyl ester, MS (ES+): 573.2 (M+H);
{3-Chloro-3'-[5-cyano-1-(2,4-difluoro-benzyl)-6-oxo-4-trifluoromethyl-1,6-dihydro-pyridin-2-yl]-biphenyl-4-yl}-acetic acid, MS (ES+): 559.1 (M+H);
6-(3',5'-Bis-trifluoromethyl-biphenyl-3-yl)-1-(2,4-difluoro-benzyl)-2-oxo-4-trifluoromethyl-1,2-dihydro-pyridine-3-carbonitrile,
6-(3',5'-Bis-trifluoromethyl-biphenyl-4-yl)-1-(2,4-difluoro-benzyl)-2-oxo-4-trifluoromethyl-1,2-dihydro-pyridine-3-carbonitrile,
6-(3'-Chloro-4'-ethoxy-biphenyl-3-yl)-1-(2,4-difluoro-benzyl)-2-oxo-4-trifluoromethyl-1,2-dihydro-pyridine-3-carbonitrile,
1-(2,4-Difluoro-benzyl)-6-(3',4'-dimethoxy-biphenyl-4-yl)-2-oxo-4-trifluoromethyl-1,2-dihydro-pyridine-3-carbonitrile,
6-(3'-Chloro-4'-ethoxy-biphenyl-4-yl)-1-(2,4-difluoro-benzyl)-2-oxo-4-trifluoromethyl-1,2-dihydro-pyridine-3-carbonitrile,
1-(2,4-Difluoro-benzyl)-2-oxo-6-(3-phenylethynyl-phenyl)-4-trifluoromethyl-1,2-dihydro-pyridine-3-carbonitrile, MS (ES+): 491.3 (M+H);
1-(2,4-Difluoro-benzyl)-2-oxo-6-(4-phenylethynyl-phenyl)-4-trifluoromethyl-1,2-dihydro-pyridine-3-carbonitrile, MS (ES+): 491.1 (M+H);
1-(2,4-Difluoro-benzyl)-2-oxo-6-[3-((E)-styryl)-phenyl]-4-trifluoromethyl-1,2-dihydro-pyridine-3-carbonitrile, MS (ES+): 493.4 (M+H);
1-(2,4-Difluoro-benzyl)-2-oxo-6-[4-((E)-styryl)-phenyl]-4-trifluoromethyl-1,2-dihydro-pyridine-3-carbonitrile, MS (ES+): 493.4 (M+H);
6-(3'-Amino-biphenyl-3-yl)-1-(2,4-difluoro-benzyl)-2-oxo-4-trifluoromethyl-1,2-dihydro-pyridine-3-carbonitrile,
1-(2,4-Difluoro-benzyl)-6-(4'-ethoxy-3'-nitro-biphenyl-3-yl)-2-oxo-4-trifluoromethyl-1,2-dihydro-pyridine-3-carbonitrile,
6-(3'-Amino-4'-ethoxy-biphenyl-3-yl)-1-(2,4-difluoro-benzyl)-2-oxo-4-trifluoromethyl-1,2-dihydro-pyridine-3-carbonitrile, {3'-[5-Cyano-1-(2,4-difluoro-benzyl)-6-oxo-4-trifluoromethyl-1,6-dihydro-pyridin-2-yl]-4-ethoxy-biphenyl-3-yl}-carbamic acid tert-butyl ester, 1-(2,4-Difluoro-benzyl)-2-oxo-6-(5-m-tolyl-thiophen-2-yl)-4-trifluoromethyl-1,2-dihydro-pyridine-3-carbonitrile, MS (ES+): 487.2 (M+H);

1-(2,4-Dichloro-benzyl)-2-oxo-6-(5-m-tolyl-thiophen-2-yl)-4-trifluoromethyl-1,2-dihydro-pyridine-3-carbonitrile, MS (ES+): 519.2 (M+H);

1-(2,4-Dimethyl-benzyl)-2-oxo-6-(5-m-tolyl-thiophen-2-yl)-4-trifluoromethyl-1,2-dihydro-pyridine-3-carbonitrile, MS (ES+): 479.1 (M+H);

6-[5-(3-Chloro-4-ethoxy-phenyl)-thiophen-2-yl]-1-(2,4-dichloro-benzyl)-2-oxo-4-trifluoromethyl-1,2-dihydro-pyridine-3-carbonitrile, MS (ES+): 585.1 (M+H);

1-(2,4-Dichloro-benzyl)-6-[5-(4-methoxy-3-methyl-phenyl)-thiophen-2-yl]-2-oxo-4-trifluoromethyl-1,2-dihydro-pyridine-3-carbonitrile, MS (ES+): 549.2 (M+H);

1-(2,4-Dichloro-benzyl)-2-oxo-4-trifluoromethyl-6-[5-(2,4,5-trimethyl-phenyl)-thiophen-2-yl]-1,2-dihydro-pyridine-3-carbonitrile, MS (ES+): 547.4 (M+H);

1-(2,4-Dichloro-benzyl)-6-[5-(4-methoxy-2-methyl-phenyl)-thiophen-2-yl]-2-oxo-4-trifluoromethyl-1,2-dihydro-pyridine-3-carbonitrile, 6-[5-(3,5-Bis-trifluoromethyl-phenyl)-thiophen-2-yl]-1-(2,4-dichloro-benzyl)-2-oxo-4-trifluoromethyl-1,2-dihydro-pyridine-3-carbonitrile, MS (ES+): 640.9 (M+H);

1-(2,4-Dichloro-benzyl)-2-oxo-6-(5-o-tolyl-thiophen-2-yl)-4-trifluoromethyl-1,2-dihydro-pyridine-3-carbonitrile, MS (ES+): 519.1 (M+H);

1-(2,4-Dichloro-benzyl)-6-[5-(3,4-dimethoxy-phenyl)-thiophen-2-yl]-2-oxo-4-trifluoromethyl-1,2-dihydro-pyridine-3-carbonitrile, MS (ES+): 565.3 (M+H);

1-(2,4-Dichloro-benzyl)-6-[5-(3,5-dichloro-phenyl)-thiophen-2-yl]-2-oxo-4-trifluoromethyl-1,2-dihydro-pyridine-3-carbonitrile, 6-[5-(3,5-Dichloro-phenyl)-thiophen-2-yl]-1-(2,4-difluoro-benzyl)-2-oxo-4-trifluoromethyl-1,2-dihydro-pyridine-3-carbonitrile, 1-(2,4-Difluoro-benzyl)-2-oxo-6-(5-o-tolyl-thiophen-2-yl)-4-trifluoromethyl-1,2-dihydro-pyridine-3-carbonitrile, MS (ES+): 487.4 (M+H);

1-(2,4-Difluoro-benzyl)-6-[5-(3,4-dimethoxy-phenyl)-thiophen-2-yl]-2-oxo-4-trifluoromethyl-1,2-dihydro-pyridine-3-carbonitrile, MS (ES+): 533.2 (M+H);

6-[5-(3-Chloro-4-ethoxy-phenyl)-thiophen-2-yl]-1-(2,4-difluoro-benzyl)-2-oxo-4-trifluoromethyl-1,2-dihydro-pyridine-3-carbonitrile, MS (ES+): 551.1 (M+H);

1-(2,4-Difluoro-benzyl)-6-[5-(4-methoxy-3-methyl-phenyl)-thiophen-2-yl]-2-oxo-4-trifluoromethyl-1,2-dihydro-pyridine-3-carbonitrile, MS (ES+): 517.3 (M+H);

6-[5-(2-Bromo-phenyl)-thiophen-2-yl]-1-(2,4-difluoro-benzyl)-2-oxo-4-trifluoromethyl-1,2-dihydro-pyridine-3-carbonitrile, MS (ES+): 488.4 (M+H);

1-(2,4-Difluoro-benzyl)-2-oxo-4-trifluoromethyl-6-[5-(3-trifluoromethyl-phenyl)-thiophen-2-yl]-1,2-dihydro-pyridine-3-carbonitrile, MS (ES+): 541.1 (M+H);

1-(2,4-Difluoro-benzyl)-6-[5-(2-fluoro-5-trifluoromethyl-phenyl)-thiophen-2-yl]-2-oxo-4-trifluoromethyl-1,2-dihydro-pyridine-3-carbonitrile, MS (ES+): 559.1 (M+H);

1-(2,4-Difluoro-benzyl)-6-[5-(4-methoxy-3,5-dimethyl-phenyl)-thiophen-2-yl]-2-oxo-4-trifluoromethyl-1,2-dihydro-pyridine-3-carbonitrile, MS (ES+): 531.1 (M+H);

1-(2,4-Difluoro-benzyl)-6-[5-(4-hydroxy-3,5-dimethyl-phenyl)-thiophen-2-yl]-2-oxo-4-trifluoromethyl-1,2-dihydro-pyridine-3-carbonitrile, MS (ES+): 517.0 (M+H);

1-(2,4-Difluoro-benzyl)-6-[5-(4-hydroxymethyl-phenyl)-thiophen-2-yl]-2-oxo-4-trifluoromethyl-1,2-dihydro-pyridine-3-carbonitrile, MS (ES+): 502.9 (M+H);

6-[4-(3,5-Bis-trifluoromethyl-phenyl)-thiophen-2-yl]-1-(2,4-difluoro-benzyl)-2-oxo-4-trifluoromethyl-1,2-dihydro-pyridine-3-carbonitrile, 6-[4-(3-Chloro-4-ethoxy-phenyl)-thiophen-2-yl]-1-(2,4-difluoro-benzyl)-2-oxo-4-trifluoromethyl-1,2-dihydro-pyridine-3-carbonitrile, 1-(2,4-Difluoro-benzyl)-6-[4-(3,4-dimethoxy-phenyl)-thiophen-2-yl]-2-oxo-4-trifluoromethyl-1,2-dihydro-pyridine-3-carbonitrile, 1-(2,4-Difluoro-benzyl)-6-[5-(4-methoxy-3-trifluoromethyl-phenyl)-thiophen-2-yl]-2-oxo-4-trifluoromethyl-1,2-dihydro-pyridine-3-carbonitrile, MS (ES+): 571.0 (M+H);

1-(2,4-Difluoro-benzyl)-6-[5-(3-fluoro-4-trifluoromethyl-phenyl)-thiophen-2-yl]-2-oxo-4-trifluoromethyl-1,2-dihydro-pyridine-3-carbonitrile, MS (ES+): 559.2 (M+H);

1-(2,4-Difluoro-benzyl)-2-oxo-6-(5-phenylethynyl-thiophen-2-yl)-4-trifluoromethyl-1,2-dihydro-pyridine-3-carbonitrile, MS (ES+): 497.0 (M+H);

1-(2,4-Difluoro-benzyl)-2-oxo-6-(4-phenylethynyl-thiophen-2-yl)-4-trifluoromethyl-1,2-dihydro-pyridine-3-carbonitrile, MS (ES+): 497.1 (M+H);

1-(2,4-Difluoro-benzyl)-2-oxo-6-[5-((E)-styryl)-thiophen-2-yl]-4-trifluoromethyl-1,2-dihydro-pyridine-3-carbonitrile, MS (ES+): 499.3 (M+H);

1-(2,4-Difluoro-benzyl)-2-oxo-6-[4-((E)-styryl)-thiophen-2-yl]-4-trifluoromethyl-1,2-dihydro-pyridine-3-carbonitrile, MS (ES+): 499.4 (M+H);

1-(2,4-Difluoro-benzyl)-2-oxo-6-(5-phenethyl-thiophen-2-yl)-4-trifluoromethyl-1,2-dihydro-pyridine-3-carbonitrile, MS (ES+): 501 (M+H);

1-(2,4-Difluoro-benzyl)-6-[5-(3-hydroxymethyl-phenyl)-thiophen-2-yl]-2-oxo-4-trifluoromethyl-1,2-dihydro-pyridine-3-carbonitrile, 1-(2,4-Difluoro-benzyl)-6-[4-(4-methoxy-3-trifluoromethyl-phenyl)-thiophen-2-yl]-2-oxo-4-trifluoromethyl-1,2-dihydro-pyridine-3-carbonitrile, MS (ES+): 570.9 (M+H);

6-[5-(3-Chloro-4-methyl-phenyl)-thiophen-2-yl]-1-(2,4-difluoro-benzyl)-2-oxo-4-trifluoromethyl-1,2-dihydro-pyridine-3-carbonitrile, MS (ES+): 521.1 (M+H);

6-[5-(3-Chloro-4-trifluoromethyl-phenyl)-thiophen-2-yl]-1-(2,4-difluoro-benzyl)-2-oxo-4-trifluoromethyl-1,2-dihydro-pyridine-3-carbonitrile, MS (ES+): 575.3 (M+H);

6-[4-(3-Chloro-4-trifluoromethyl-phenyl)-thiophen-2-yl]-1-(2,4-difluoro-benzyl)-2-oxo-4-trifluoromethyl-1,2-dihydro-pyridine-3-carbonitrile, MS (ES+): 574.9 (M+H);

6-[4-(3-Chloro-4-methyl-phenyl)-thiophen-2-yl]-1-(2,4-difluoro-benzyl)-2-oxo-4-trifluoromethyl-1,2-dihydro-pyridine-3-carbonitrile, MS (ES+): 521.1 (M+H);

1-(2,4-Difluoro-benzyl)-6-[4-(3-methoxy-4-trifluoromethyl-phenyl)-thiophen-2-yl]-2-oxo-4-trifluoromethyl-1,2-dihydro-pyridine-3-carbonitrile, MS (ES+): 571.3 (M+H);

1-(2,4-Difluoro-benzyl)-6-[5-(3-ethoxy-4-trifluoromethyl-phenyl)-thiophen-2-yl]-2-oxo-4-trifluoromethyl-1,2-dihydro-pyridine-3-carbonitrile, MS (ES+): 585.1 (M+H);

1-(2,4-Difluoro-benzyl)-6-[5-(4-ethoxy-3-trifluoromethyl-phenyl)-thiophen-2-yl]-2-oxo-4-trifluoromethyl-1,2-dihydro-pyridine-3-carbonitrile, MS (ES+): 585.1 (M+H);

1-(2,4-Difluoro-benzyl)-6-[4-(4-ethoxy-3-trifluoromethyl-phenyl)-thiophen-2-yl]-2-oxo-4-trifluoromethyl-1,2-dihydro-pyridine-3-carbonitrile, MS (ES+): 585.1 (M+H);

1-(2,4-Difluoro-benzyl)-6-[4-(3-ethoxy-4-trifluoromethyl-phenyl)-thiophen-2-yl]-2-oxo-4-trifluoromethyl-1,2-dihydro-pyridine-3-carbonitrile, MS (ES+): 585.2 (M+H);

6-{5-[3-Chloro-4-(2,2,2-trifluoro-ethoxy)-phenyl]-thiophen-2-yl}-1-(2,4-difluoro-benzyl)-2-oxo-4-trifluoromethyl-1,2-dihydro-pyridine-3-carbonitrile, MS (ES+): 605.2 (M+H);

1-(2,4-Difluoro-benzyl)-6-[5-(3-fluoro-5-trifluoromethyl-phenyl)-thiophen-2-yl]-2-oxo-4-trifluoromethyl-1,2-dihydro-pyridine-3-carbonitrile, MS (ES+): 559.2 (M+H);

1-(2,4-Difluoro-benzyl)-6-[4-(3-fluoro-5-trifluoromethyl-phenyl)-thiophen-2-yl]-2-oxo-4-trifluoromethyl-1,2-dihydro-pyridine-3-carbonitrile, MS (ES+): 558.9 (M+H);

6-[5-(3-Chloro-4-hydroxy-phenyl)-thiophen-2-yl]-1-(2,4-difluoro-benzyl)-2-oxo-4-trifluoromethyl-1,2-dihydro-pyridine-3-carbonitrile, MS (ES+): 523.2 (M+H);

6-{5-[3-Chloro-4-(2-hydroxy-ethoxy)-phenyl]-thiophen-2-yl}-1-(2,4-difluoro-benzyl)-2-oxo-4-trifluoromethyl-1,2-dihydro-pyridine-3-carbonitrile, MS (ES+): 567.4 (M+H);

1-(2,4-Difluoro-benzyl)-6-[5-(3-ethoxy-5-trifluoromethyl-phenyl)-thiophen-2-yl]-2-oxo-4-trifluoromethyl-1,2-dihydro-pyridine-3-carbonitrile, MS (ES+): 585.2 (M+H);

1-(2,4-Difluoro-benzyl)-6-[4-(3-ethoxy-5-trifluoromethyl-phenyl)-thiophen-2-yl]-2-oxo-4-trifluoromethyl-1,2-dihydro-pyridine-3-carbonitrile, MS (ES+): 585.3 (M+H);

1-(2,4-Difluoro-benzyl)-6-[5-(3-isopropoxy-5-trifluoromethyl-phenyl)-thiophen-2-yl]-2-oxo-4-trifluoromethyl-1,2-dihydro-pyridine-3-carbonitrile, MS (ES+): 599.2 (M+H);

1-(2,4-Difluoro-benzyl)-6-[4-(3-isopropoxy-5-trifluoromethyl-phenyl)-thiophen-2-yl]-2-oxo-4-trifluoromethyl-1,2-dihydro-pyridine-3-carbonitrile, MS (ES+): 599.3 (M+H);

1-(2,4-Difluoro-benzyl)-6-[5-(3-ethoxy-5-ethyl-phenyl)-thiophen-2-yl]-2-oxo-4-trifluoromethyl-1,2-dihydro-pyridine-3-carbonitrile, MS (ES+): 545.3 (M+H);

1-(2,4-Difluoro-benzyl)-6-[4-(3-ethoxy-5-ethyl-phenyl)-thiophen-2-yl]-2-oxo-4-trifluoromethyl-1,2-dihydro-pyridine-3-carbonitrile, MS (ES+): 545.3 (M+H);

1-(2,4-Difluoro-benzyl)-6-[5-(3-ethyl-5-isopropoxy-phenyl)-thiophen-2-yl]-2-oxo-4-trifluoromethyl-1,2-dihydro-pyridine-3-carbonitrile, MS (ES+): 559.2 (M+H);

1-(2,4-Difluoro-benzyl)-6-[4-(3-ethyl-5-isopropoxy-phenyl)-thiophen-2-yl]-2-oxo-4-trifluoromethyl-1,2-dihydro-pyridine-3-carbonitrile, MS (ES+): 559.2 (M+H);

1-(2,4-Dichloro-benzyl)-6-[5-(4-methanesulfonyl-phenyl)-thiophen-2-yl]-2-oxo-4-trifluoromethyl-1,2-dihydro-pyridine-3-carbonitrile, MS (ES+): 583.1 (M+H);

1-(2,4-Difluoro-benzyl)-6-[5-(4-methanesulfonyl-phenyl)-thiophen-2-yl]-2-oxo-4-trifluoromethyl-1,2-dihydro-pyridine-3-carbonitrile, MS (ES+): 551.1 (M+H);

1-(2,4-Dimethyl-benzyl)-6-[5-(3-methanesulfonyl-phenyl)-thiophen-2-yl]-2-oxo-4-trifluoromethyl-1,2-dihydro-pyridine-3-carbonitrile, MS (ES+): 543.3 (M+H);

1-(2,4-Difluoro-benzyl)-6-[5-(4-ethanesulfonyl-phenyl)-thiophen-2-yl]-2-oxo-4-trifluoromethyl-1,2-dihydro-pyridine-3-carbonitrile, MS (ES+): 565.1 (M+H);

1-(2,4-Difluoro-benzyl)-3-dimethylaminomethyl-6-[5-(4-methanesulfonyl-phenyl)-thiophen-2-yl]-4-trifluoromethyl-1H-pyridin-2-one, MS (ES+): 583.5 (M+H);

1-(2,4-Dichloro-benzyl)-6-[5-(3-methanesulfonyl-phenyl)-thiophen-2-yl]-2-oxo-4-trifluoromethyl-1,2-dihydro-pyridine-3-carbonitrile, MS (ES+): 583.3 (M+H);

N-{1-(2,4-Difluoro-benzyl)-6-[5-(4-methanesulfonyl-phenyl)-thiophen-2-yl]-2-oxo-4-trifluoromethyl-1,2-dihydro-pyridin-3-ylmethyl}-methanesulfonamide, MS (ES+): 633.3 (M+H);

3-Diethylaminomethyl-1-(2,4-difluoro-benzyl)-6-[5-(4-methanesulfonyl-phenyl)-thiophen-2-yl]-4-trifluoromethyl-1H-pyridin-2-one, MS (ES+): 611.4 (M+H);

N-{1-(2,4-Difluoro-benzyl)-6-[5-(4-methanesulfonyl-phenyl)-thiophen-2-yl]-2-oxo-4-trifluoromethyl-1,2-dihydro-pyridin-3-ylmethyl}-guanidine, MS (ES+): 597.5 (M+H);

1-(2,4-Difluoro-benzyl)-6-[4-(4-methanesulfonyl-phenyl)-thiophen-2-yl]-2-oxo-4-trifluoromethyl-1,2-dihydro-pyridine-3-carbonitrile, 1-(2,4-Difluoro-benzyl)-6-[5-(3-methanesulfonyl-phenyl)-thiophen-2-yl]-2-oxo-4-trifluoromethyl-1,2-dihydro-pyridine-3-carbonitrile, MS (ES+): 551.2 (M+H);

1-(2,4-Difluoro-benzyl)-6-[5-(3-ethanesulfonyl-phenyl)-thiophen-2-yl]-2-oxo-4-trifluoromethyl-1,2-dihydro-pyridine-3-carbonitrile, MS (ES+): 565.4 (M+H);

6-[5-(3,5-Bis-methanesulfonyl-phenyl)-thiophen-2-yl]-1-(2,4-difluoro-benzyl)-2-oxo-4-trifluoromethyl-1,2-dihydro-pyridine-3-carbonitrile, MS (ES+): 628.9 (M+H);

1-(2,4-Difluoro-benzyl)-6-[5-(4-methylsulfanyl-3-trifluoromethyl-phenyl)-thiophen-2-yl]-2-oxo-4-trifluoromethyl-1,2-dihydro-pyridine-3-carbonitrile, MS (ES+): 587.5 (M+H);

1-(2,4-Difluoro-benzyl)-6-[5-(3-methylsulfanyl-5-trifluoromethyl-phenyl)-thiophen-2-yl]-2-oxo-4-trifluoromethyl-1,2-dihydro-pyridine-3-carbonitrile, MS (ES+): 587.2 (M+H);

1-(2,4-Difluoro-benzyl)-6-[4-(4-methylsulfanyl-3-trifluoromethyl-phenyl)-thiophen-2-yl]-2-oxo-4-trifluoromethyl-1,2-dihydro-pyridine-3-carbonitrile, MS (ES+): 586.8 (M+H);

1-(2,4-Difluoro-benzyl)-6-[4-(3-methylsulfanyl-5-trifluoromethyl-phenyl)-thiophen-2-yl]-2-oxo-4-trifluoromethyl-1,2-dihydro-pyridine-3-carbonitrile, MS (ES+): 587.1 (M+H);

1-(2,4-Difluoro-benzyl)-6-[5-(4-methyl-3-methylsulfanyl-phenyl)-thiophen-2-yl]-2-oxo-4-trifluoromethyl-1,2-dihydro-pyridine-3-carbonitrile, MS (ES+): 533.8 (M+H);

1-(2,4-Difluoro-benzyl)-6-[5-(4-methanesulfinyl-3-trifluoromethyl-phenyl)-thiophen-2-yl]-2-oxo-4-trifluoromethyl-1,2-dihydro-pyridine-3-carbonitrile, MS (ES+): 518.3 (M+H);

1-(2,4-Difluoro-benzyl)-6-[5-(5-methanesulfinyl-3-trifluoromethyl-phenyl)-thiophen-2-yl]-2-oxo-4-trifluoromethyl-1,2-dihydro-pyridine-3-carbonitrile, 1-(2,4-Difluoro-benzyl)-6-[4-(4-methanesulfonyl-3-trifluoromethyl-phenyl)-thiophen-2-yl]-2-oxo-4-trifluoromethyl-1,2-dihydro-pyridine-3-carbonitrile, MS (ES+): 620.2 (M+H);

1-(2,4-Difluoro-benzyl)-6-[4-(3-methanesulfonyl-5-trifluoromethyl-phenyl)-thiophen-2-yl]-2-oxo-4-trifluoromethyl-1,2-dihydro-pyridine-3-carbonitrile, MS (ES+): 619.1 (M+H);

1-(2,4-Difluoro-benzyl)-6-[5-(4-ethoxy-3-methanesulfonyl-phenyl)-thiophen-2-yl]-2-oxo-4-trifluoromethyl-1,2-dihydro-pyridine-3-carbonitrile, MS (ES+): 595.2 (M+H);

1-(2,4-Difluoro-benzyl)-2-oxo-6-{5-[3-(propane-1-sulfinyl)-5-trifluoromethyl-phenyl]-thiophen-2-yl}-4-trifluoromethyl-1,2-dihydro-pyridine-3-carbonitrile, 6-{5-[3-(Butane-1-sulfinyl)-5-trifluoromethyl-phenyl]-thiophen-2-yl}-1-(2,4-difluoro-benzyl)-2-oxo-4-trifluoromethyl-1,2-dihydro-pyridine-3-carbonitrile, 1-(2,4-Difluoro-benzyl)-2-oxo-6-[5-(3-phenylmethanesufinyl-5-trifluoromethyl-phenyl)-thiophen-2-yl]-4-trifluoromethyl-1,2-dihydro-pyridine-3-carbonitrile, 6-[5-(3-Cyclopropylmethanesulfinyl-5-trifluoromethyl-phenyl)-thiophen-2-yl]-1-(2,4-difluoro-benzyl)-2-oxo-4-trifluoromethyl-1,2-dihydro-pyridine-3-carbonitrile, 1-(2,4-Difluoro-benzyl)-6-[5-(3-ethanesulfinyl-5-trifluoromethyl-phenyl)-thiophen-2-yl]-2-oxo-4-trifluoromethyl-1,2-dihydro-pyridine-3-carbonitrile, 1-(2,4-Difluoro-benzyl)-2-oxo-6-{4-[3-(propane-1-sulfinyl)-5-trifluoromethyl-phenyl]-thiophen-2-yl}-4-trifluoromethyl-1,2-dihydro-pyridine-3-carbonitrile, 6-{4-[3-(Butane-1-sulfinyl)-5-trifluoromethyl-phenyl]-thiophen-2-yl}-1-(2,4-difluoro-benzyl)-2-oxo-4-trifluoromethyl-1,2-dihydro-pyridine-3-carbonitrile, 1-(2,4-Difluoro-benzyl)-2-oxo-6-[4-(3-phenylmethanesulfinyl-5-trifluoromethyl-phenyl)-thiophen-2-yl]-4-trifluoromethyl-1,2-dihydro-pyridine-3-carbonitrile, 6-[4-(3-Cyclopropylmethanesulfinyl-5-trifluoromethyl-phenyl)-thiophen-2-yl]-1-(2,4-difluoro-benzyl)-2-oxo-4-trifluoromethyl-1,2-dihydro-pyridine-3-carbonitrile, 1-(2,4-Difluoro-benzyl)-6-[4-(3-ethanesulfinyl-5-trifluoromethyl-phenyl)-thiophen-2-yl]-2-oxo-4-trifluoromethyl-1,2-dihydro-pyridine-3-carbonitrile, 1-(2,4-Difluoro-benzyl)-2-oxo-6-{4-[3-(propane-2-sulfinyl)-5-trifluoromethyl-phenyl]-thiophen-2-yl}-4-trifluoromethyl-1,2-dihydro-pyridine-3-carbonitrile, 1-(2,4-Difluoro-benzyl)-2-oxo-6-{5-[3-(propane-1-sulfonyl)-5-trifluoromethyl-phenyl]-thiophen-2-yl}-4-trifluoromethyl-1,2-dihydro-pyridine-3-carbonitrile, 6-{5-[3-(Butane-1-sulfonyl)-5-trifluoromethyl-phenyl]-thiophen-2-yl}-1-(2,4-difluoro-benzyl)-2-oxo-4-trifluoromethyl-1,2-dihydro-pyridine-3-carbonitrile, MS (ES+): 661.3 (M+H);

1-(2,4-Difluoro-benzyl)-2-oxo-6-[5-(3-phenylmethanesulfonyl-5-trifluoromethyl-phenyl)-thiophen-2-yl]-4-trifluoromethyl-1,2-dihydro-pyridine-3-carbonitrile, MS (ES+): 695.1 (M+H);

6-[5-(3-Cyclopropylmethanesulfonyl-5-trifluoromethyl-phenyl)-thiophen-2-yl]-1-(2,4-difluoro-benzyl)-2-oxo-4-trifluoromethyl-1,2-dihydro-pyridine-3-carbonitrile, 1-(2,4-Difluoro-benzyl)-6-[5-(3-ethanesulfonyl-5-trifluoromethyl-phenyl)-thiophen-2-yl]-2-oxo-4-trifluoromethyl-1,2-dihydro-pyridine-3-carbonitrile, 1-(2,4-Difluoro-benzyl)-2-oxo-6-{4-[3-(propane-1-sulfonyl)-5-trifluoromethyl-phenyl]-thiophen-2-yl}-4-trifluoromethyl-1,2-dihydro-pyridine-3-carbonitrile, 6-{4-[3-(Butane-1-sulfonyl)-5-trifluoromethyl-phenyl]-thiophen-2-yl}-1-(2,4-difluoro-benzyl)-2-oxo-4-trifluoromethyl-1,2-dihydro-pyridine-3-carbonitrile, 6-[4-(3-Cyclopropylmethanesulfonyl-5-trifluoromethyl-phenyl)-thiophen-2-yl]-1-(2,4-difluoro-benzyl)-2-oxo-4-trifluoromethyl-1,2-dihydro-pyridine-3-carbonitrile, 1-(2,4-Difluoro-benzyl)-6-[4-(3-ethanesulfonyl-5-trifluoromethyl-phenyl)-thiophen-2-yl]-2-oxo-4-trifluoromethyl-1,2-dihydro-pyridine-3-carbonitrile, 1-(2,4-Difluoro-benzyl)-2-oxo-6-{4-[3-(propane-2-sulfonyl)-5-trifluoromethyl-phenyl]-thiophen-2-yl}-4-trifluoromethyl-1,2-dihydro-pyridine-3-carbonitrile, 1-(2,4-Difluoro-benzyl)-6-[5-(3-isopropyl-5-methanesulfonyl-phenyl)-thiophen-2-yl]-2-oxo-4-trifluoromethyl-1,2-dihydro-pyridine-3-carbonitrile, MS (ES+): 593.0 (M+H);

1-(2,4-Difluoro-benzyl)-6-[4-(3-isopropyl-5-methanesulfonyl-phenyl)-thiophen-2-yl]-2-oxo-4-trifluoromethyl-1,2-dihydro-pyridine-3-carbonitrile, MS (ES+): 593.1 (M+H);

1-(2,4-Difluoro-benzyl)-6-[5-(4-methanesulfonyl-3-trifluoromethyl-phenyl)-thiophen-2-yl]-2-oxo-4-trifluoromethyl-1,2-dihydro-pyridine-3-carbonitrile, MS (ES+): 619.2 (M+H);

6-[5-(3-Ethanesulfonyl-phenyl)-thiophen-2-yl]-1-(2-fluoro-benzyl)-2-oxo-4-trifluoromethyl-1,2-dihydro-pyridine-3-carbonitrile, MS (ES+): 547.3 (M+H);

1-(2-Chloro-benzyl)-6-[5-(3-ethanesulfonyl-phenyl)-thiophen-2-yl]-2-oxo-4-trifluoromethyl-1,2-dihydro-pyridine-3-carbonitrile, MS (ES+): 563.2 (M+H);

1-(2-Fluoro-benzyl)-6-[5-(3-methanesulfonyl-phenyl)-thiophen-2-yl]-2-oxo-4-trifluoromethyl-1,2-dihydro-pyridine-3-carbonitrile, MS (ES+): 533.3 (M+H);

1-(2-Chloro-benzyl)-6-[5-(3-methanesulfonyl-phenyl)-thiophen-2-yl]-2-oxo-4-trifluoromethyl-1,2-dihydro-pyridine-3-carbonitrile, 6-[5-(3-Ethanesulfonyl-5-trifluoromethyl-phenyl)-thiophen-2-yl]-1-(2-fluoro-benzyl)-2-oxo-4-trifluoromethyl-1,2-dihydro-pyridine-3-carbonitrile, MS (ES+): 615.0 (M+H);

1-(2,4-Difluoro-benzyl)-6-[5-(3-ethyl-5-methanesulfonyl-phenyl)-thiophen-2-yl]-2-oxo-4-trifluoromethyl-1,2-dihydro-pyridine-3-carbonitrile, MS (ES+): 679.3 (M+H);

1-(2,4-Difluoro-benzyl)-6-[4-(3-ethyl-5-methanesulfonyl-phenyl)-thiophen-2-yl]-2-oxo-4-trifluoromethyl-1,2-dihydro-pyridine-3-carbonitrile, MS (ES+): 679.3 (M+H);

1-(2-Chloro-benzyl)-6-[5-(3-ethanesulfonyl-5-trifluoromethyl-phenyl)-thiophen-2-yl]-2-oxo-4-trifluoromethyl-1,2-dihydro-pyridine-3-carbonitrile, MS (ES+): 631.2 (M+H);

(3-{5-[5-Cyano-1-(2,4-difluoro-benzyl)-6-oxo-4-trifluoromethyl-1,6-dihydro-pyridin-2-yl]-furan-3-yl}-phenyl)-acetic acid, MS (ES+): 515.2 (M+H);

1-(2-Chloro-benzyl)-6-[5-(3-isopropyl-5-methanesulfonyl-phenyl)-thiophen-2-yl]-2-oxo-4-trifluoromethyl-1,2-dihydro-pyridine-3-carbonitrile, MS (ES+): 591.1 (M+H);

1-(2-Fluoro-benzyl)-6-[5-(4-methanesulfonyl-phenyl)-thiophen-2-yl]-2-oxo-4-trifluoromethyl-1,2-dihydro-pyridine-3-carbonitrile, MS (ES+): 533.2 (M+H);

1-(2-Chloro-benzyl)-6-[5-(4-methanesulfonyl-phenyl)-thiophen-2-yl]-2-oxo-4-trifluoromethyl-1,2-dihydro-pyridine-3-carbonitrile, MS (ES+): 549.1 (M+H);

1-(2,4-Difluoro-benzyl)-6-[5-(3-ethanesulfonyl-5-isopropyl-phenyl)-thiophen-2-yl]-2-oxo-4-trifluoromethyl-1,2-dihydro-pyridine-3-carbonitrile, MS (ES+): 607.3 (M+H);

1-(2,4-Difluoro-benzyl)-6-[4-(3-ethanesulfonyl-5-isopropyl-phenyl)-thiophen-2-yl]-2-oxo-4-trifluoromethyl-1,2-dihydro-pyridine-3-carbonitrile, MS (ES+): 607.3 (M+H);

6-[5-(3-Ethanesulfonyl-phenyl)-thiophen-2-yl]-1-(4-ethyl-2-fluoro-benzyl)-2-oxo-4-trifluoromethyl-1,2-dihydro-pyridine-3-carbonitrile, MS (ES+): 575.2 (M+H);

1-(4-Ethyl-2-fluoro-benzyl)-6-[5-(3-methanesulfonyl-phenyl)-thiophen-2-yl]-2-oxo-4-trifluoromethyl-1,2-dihydro-pyridine-3-carbonitrile, 1-(4-Ethyl-2-fluoro-benzyl)-6-[5-(4-methanesulfonyl-phenyl)-thiophen-2-yl]-2-oxo-4-trifluoromethyl-1,2-dihydro-pyridine-3-carbonitrile, MS (ES+): 561.2 (M+H);

6-[5-(3-Ethanesulfonyl-5-trifluoromethyl-phenyl)-thiophen-2-yl]-1-(4-ethyl-2-fluoro-benzyl)-2-oxo-4-trifluoromethyl-1,2-dihydro-pyridine-3-carbonitrile, 1-(4-Ethyl-2-fluoro-benzyl)-6-[5-(3-isopropyl-5-methanesulfonyl-phenyl)-thiophen-2-yl]-2-oxo-4-trifluoromethyl-1,2-dihydro-pyridine-3-carbonitrile, MS (ES+): 603.2 (M+H);

4-(1,1-Difluoro-propyl)-1-(2-fluoro-benzyl)-6-[5-(4-methanesulfonyl-phenyl)-thiophen-2-yl]-2-oxo-1,2-dihydro-pyridine-3-carbonitrile, MS (ES+): 543.3 (M+H);

4-(1,1-Difluoro-propyl)-1-(2-fluoro-benzyl)-6-[5-(3-methanesulfonyl-phenyl)-thiophen-2-yl]-2-oxo-1,2-dihydro-pyridine-3-carbonitrile, MS (ES+): 543.3 (M+H);

4-(1,1-Difluoro-propyl)-6-[5-(3-ethanesulfonyl-5-isopropyl-phenyl)-thiophen-2-yl]-1-(2-fluoro-benzyl)-2-oxo-1,2-dihydro-pyridine-3-carbonitrile, MS (ES+): 599.2 (M+H);

6-[5-(3-tert-Butyl-5-methanesulfonyl-phenyl)-thiophen-2-yl]-1-(2,4-difluoro-benzyl)-2-oxo-4-trifluoromethyl-1,2-dihydro-pyridine-3-carbonitrile, MS (ES+): 607.2 (M+H);

6-[4-(3-tert-Butyl-5-methanesulfonyl-phenyl)-thiophen-2-yl]-1-(2,4-difluoro-benzyl)-2-oxo-4-trifluoromethyl-1,2-dihydro-pyridine-3-carbonitrile, MS (ES+): 607.2 (M+H);

1-(2,4-Difluoro-benzyl)-6-[5-(3-ethanesulfonyl-5-ethyl-phenyl)-thiophen-2-yl]-2-oxo-4-trifluoromethyl-1,2-dihydro-pyridine-3-carbonitrile, MS (ES+): 593.3 (M+H);

1-(2,4-Difluoro-benzyl)-6-{5-[3-ethyl-5-(propane-1-sulfonyl)-phenyl]-thiophen-2-yl}-2-oxo-4-trifluoromethyl-1,2-dihydro-pyridine-3-carbonitrile, MS (ES+): 607.3 (M+H);

1-(2,4-Difluoro-benzyl)-6-{5-[3-ethyl-5-(propane-2-sulfonyl)-phenyl]-thiophen-2-yl}-2-oxo-4-trifluoromethyl-1,2-dihydro-pyridine-3-carbonitrile, MS (ES+): 607.4 (M+H);

1-(2,4-Difluoro-benzyl)-6-[4-(3-ethanesulfonyl-5-ethyl-phenyl)-thiophen-2-yl]-2-oxo-4-trifluoromethyl-1,2-dihydro-pyridine-3-carbonitrile, MS (ES+): 593.3 (M+H);

1-(2,4-Difluoro-benzyl)-6-{4-[3-ethyl-5-(propane-1-sulfonyl)-phenyl]-thiophen-2-yl}-2-oxo-4-trifluoromethyl-1,2-dihydro-pyridine-3-carbonitrile, MS (ES+): 607.2 (M+H);

1-(2,4-Difluoro-benzyl)-6-{4-[3-ethyl-5-(propane-2-sulfonyl)-phenyl]-thiophen-2-yl}-2-oxo-4-trifluoromethyl-1,2-dihydro-pyridine-3-carbonitrile, MS (ES+): 607.5 (M+H);

1-(4-Chloro-benzyl)-6-[5-(4-methanesulfonyl-phenyl)-thiophen-2-yl]-2-oxo-4-trifluoromethyl-1,2-dihydro-pyridine-3-carbonitrile, MS (ES+): 579.0 (M+H);

6-[5-(3-Ethanesulfonyl-5-isopropyl-phenyl)-thiophen-2-yl]-1-(2-fluoro-benzyl)-2-oxo-4-trifluoromethyl-1,2-dihydro-pyridine-3-carbonitrile, MS (ES+): 589.3 (M+H);

1-(2-Chloro-benzyl)-6-[5-(3-ethanesulfonyl-5-isopropyl-phenyl)-thiophen-2-yl]-2-oxo-4-trifluoromethyl-1,2-dihydro-pyridine-3-carbonitrile, MS (ES+): 605.4 (M+H);

1-(4-Chloro-benzyl)-6-[5-(3-ethanesulfonyl-5-isopropyl-phenyl)-thiophen-2-yl]-2-oxo-4-trifluoromethyl-1,2-dihydro-pyridine-3-carbonitrile, MS (ES+): 605.6 (M+H);

(3-{5-[5-Cyano-1-(2,4-difluoro-benzyl)-6-oxo-4-trifluoromethyl-1,6-dihydro-pyridin-2-yl]-thiophen-2-yl}-5-isopropyl-phenyl)-acetic acid, MS (ES+): 573.2 (M+H);

(3-{5-[5-Cyano-1-(2,4-difluoro-benzyl)-6-oxo-4-trifluoromethyl-1,6-dihydro-pyridin-2-yl]-thiophen-3-yl}-5-isopropyl-phenyl)-acetic acid, MS (ES+): 573.3 (M+H);

1-(4-Chloro-benzyl)-6-[5-(3-methanesulfonyl-phenyl)-thiophen-2-yl]-2-oxo-4-trifluoromethyl-1,2-dihydro-pyridine-3-carbonitrile, MS (ES+): 549.4 (M+H);

1-(2,4-Difluoro-benzyl)-4-(1,1-difluoro-heptyl)-6-[5-(4-methanesulfonyl-phenyl)-thiophen-2-yl]-2-oxo-1,2-dihydro-pyridine-3-carbonitrile, MS (ES+): 617.0 (M+H);

1-(2,4-Difluoro-benzyl)-4-(1,1-difluoro-heptyl)-6-[5-(3-ethanesulfonyl-phenyl)-thiophen-2-yl]-2-oxo-1,2-dihydro-pyridine-3-carbonitrile, MS (ES+): 631.4 (M+H);

1-(2,4-Difluoro-benzyl)-4-(1,1-difluoro-heptyl)-6-[5-(3-methanesulfonyl-phenyl)-thiophen-2-yl]-2-oxo-1,2-dihydro-pyridine-3-carbonitrile, MS (ES+): 617.4 (M+H);

1-(2,4-Difluoro-benzyl)-4-(1,1-difluoro-3-methyl-butyl)-6-[5-(3-methanesulfonyl-phenyl)-thiophen-2-yl]-2-oxo-1,2-dihydro-pyridine-3-carbonitrile, MS (ES+): 589.3 (M+H);

1-(2,4-Difluoro-benzyl)-4-(1,1-difluoro-3-methyl-butyl)-6-[5-(3-ethanesulfonyl-phenyl)-thiophen-2-yl]-2-oxo-1,2-dihydro-pyridine-3-carbonitrile, MS (ES+): 603.3 (M+H);

1-(2,4-Difluoro-benzyl)-4-(1,1-difluoro-3-methyl-butyl)-6-[5-(4-methanesulfonyl-phenyl)-thiophen-2-yl]-2-oxo-1,2-dihydro-pyridine-3-carbonitrile, MS (ES+): 589.4 (M+H);

4-{5-[5-Cyano-1-(2,4-difluoro-benzyl)-6-oxo-4-trifluoromethyl-1,6-dihydro-pyridin-2-yl]-thiophen-2-yl}-benzenesulfonamide, MS (ES+): 552.1 (M+H);

1-(2,4-Difluoro-benzyl)-6-[5-(3-formyl-4-methoxy-phenyl)-thiophen-2-yl]-2-oxo-4-trifluoromethyl-1,2-dihydro-pyridine-3-carbonitrile, Carbonic acid tert-butyl ester 4-{5-[5-cyano-1-(2,4-difluoro-benzyl)-6-oxo-4-trifluoromethyl-1,6-dihydro-pyridin-2-yl]-thiophen-2-yl}-phenyl ester, MS (ES+): 589.4 (M+H);

6-[5-(3-Chloro-4-cyano-phenyl)-thiophen-2-yl]-1-(2,4-difluoro-benzyl)-2-oxo-4-trifluoromethyl-1,2-dihydro-pyridine-3-carbonitrile, MS (ES+): 531.8 (M+H);

6-[5-(3-Cyano-4-ethoxy-phenyl)-thiophen-2-yl]-1-(2,4-difluoro-benzyl)-2-oxo-4-trifluoromethyl-1,2-dihydro-pyridine-3-carbonitrile, MS (ES+): 547.4 (M+H);

6-[4-(3-Cyano-4-ethoxy-phenyl)-furan-2-yl]-1-(2,4-difluoro-benzyl)-2-oxo-4-trifluoromethyl-1,2-dihydro-pyridine-3-carbonitrile, MS (ES+): 526.4 (M+H);

1-(2,4-Difluoro-benzyl)-6-[5-(4-ethoxy-3-nitro-phenyl)-thiophen-2-yl]-2-oxo-4-trifluoromethyl-1,2-dihydro-pyridine-3-carbonitrile, 6-[5-(3-Amino-4-ethoxy-phenyl)-thiophen-2-yl]-1-(2,4-difluoro-benzyl)-2-oxo-4-trifluoromethyl-1,2-dihydro-pyridine-3-carbonitrile, (2-Chloro-4-{5-[5-cyano-1-(2,4-difluoro-benzyl)-6-oxo-4-trifluoromethyl-1,6-dihydro-pyridin-2-yl]-thiophen-2-yl}-phenoxy)-acetic acid ethyl ester, MS (ES+): 609.2 (M+H);

(2-Chloro-4-{5-[5-cyano-1-(2,4-difluoro-benzyl)-6-oxo-4-trifluoromethyl-1,6-dihydro-pyridin-2-yl]-thiophen-2-yl}-phenoxy)-acetic acid, MS (ES+): 581.3 (M+H);

6-[5-(4-Amino-3-chloro-phenyl)-thiophen-2-yl]-1-(2,4-difluoro-benzyl)-2-oxo-4-trifluoromethyl-1,2-dihydro-pyridine-3-carbonitrile, MS (ES+): 522.2 (M+H);

(5-{5-[5-Cyano-1-(2,4-difluoro-benzyl)-6-oxo-4-trifluoromethyl-1,6-dihydro-pyridin-2-yl]-thiophen-2-yl}-2-ethoxy-phenyl)-carbamic acid tert-butyl ester, (5-{5-[5-Cyano-1-(2,4-difluoro-benzyl)-6-oxo-4-trifluoromethyl-1,6-dihydro-pyridin-2-yl]-thiophen-3-yl}-2-ethoxy-phenyl)-carbamic acid tert-butyl ester, 4-{5-[5-Cyano-1-(2,4-difluoro-benzyl)-6-oxo-4-trifluoromethyl-1,6-dihydro-pyridin-2-yl]-thiophen-2-yl}-benzoic acid methyl ester, MS (ES+): 531.2 (M+H);

3-{5-[5-Cyano-1-(2,4-difluoro-benzyl)-6-oxo-4-trifluoromethyl-1,6-dihydro-pyridin-2-yl]-thiophen-2-yl}-benzoic acid methyl ester, MS (ES+): 530.9 (M+H);

3-{5-[5-Cyano-1-(2,4-difluoro-benzyl)-6-oxo-4-trifluoromethyl-1,6-dihydro-pyridin-2-yl]-thiophen-2-yl}-benzoic acid, 4-{5-[5-Cyano-1-(2,4-difluoro-benzyl)-6-oxo-4-trifluoromethyl-1,6-dihydro-pyridin-2-yl]-thiophen-2-yl}-benzoic acid, 3-{5-[5-Cyano-1-(2,4-difluoro-benzyl)-6-oxo-4-trifluoromethyl-1,6-dihydro-pyridin-2-yl]-thiophen-2-yl}-5-isopropyl-benzoic acid methyl ester, MS (ES+): 573.2 (M+H);

3-{5-[5-Cyano-1-(2,4-difluoro-benzyl)-6-oxo-4-trifluoromethyl-1,6-dihydro-pyridin-2-yl]-thiophen-3-yl}-5-isopropyl-benzoic acid methyl ester, MS (ES+): 573.2 (M+H);

3-{4-[5-Cyano-1-(2,4-dimethyl-benzyl)-6-oxo-4-trifluoromethyl-1,6-dihydro-pyridin-2-yl]-phenoxy}-N,N-dimethyl-thiobenzamide, MS (ES+): 562.4 (M+H);

(3-{5-[5-Cyano-1-(2,4-difluoro-benzyl)-6-oxo-4-trifluoromethyl-1,6-dihydro-pyridin-2-yl]-thiophen-2-yl}-phenyl)-acetic acid,
(4-{5-[5-Cyano-1-(2,4-difluoro-benzyl)-6-oxo-4-trifluoromethyl-1,6-dihydro-pyridin-2-yl]-thiophen-2-yl}-phenyl)-acetic acid,
(4-{5-[5-Cyano-1-(2,4-difluoro-benzyl)-6-oxo-4-trifluoromethyl-1,6-dihydro-pyridin-2-yl]-thiophen-3-yl}-phenyl)-acetic acid,
(3-{5-[5-Cyano-1-(2,4-difluoro-benzyl)-6-oxo-4-trifluoromethyl-1,6-dihydro-pyridin-2-yl]-thiophen-2-yl}-phenyl)-acetic acid methyl ester, MS (ES+): 545.2 (M+H);
(3-{5-[5-Cyano-1-(2,4-difluoro-benzyl)-6-oxo-4-trifluoromethyl-1,6-dihydro-pyridin-2-yl]-thiophen-3-yl}-phenyl)-acetic acid methyl ester, MS (ES+): 545.3 (M+H);
(4-{5-[5-Cyano-1-(2,4-difluoro-benzyl)-6-oxo-4-trifluoromethyl-1,6-dihydro-pyridin-2-yl]-thiophen-3-yl}-phenyl)-acetic acid methyl ester, MS (ES+): 545.2 (M+H);
(3-{5-[5-Cyano-1-(2,4-difluoro-benzyl)-6-oxo-4-trifluoromethyl-1,6-dihydro-pyridin-2-yl]-thiophen-2-yl}-5-isopropoxy-phenyl)-acetic acid, MS (ES+): 589.2 (M+H);
(5-{5-[5-Cyano-1-(2,4-difluoro-benzyl)-6-oxo-4-trifluoromethyl-1,6-dihydro-pyridin-2-yl]-thiophen-2-yl}-2-methoxy-phenyl)-acetic acid methyl ester, MS (ES+): 575.4 (M+H);
(5-{5-[5-Cyano-1-(2,4-difluoro-benzyl)-6-oxo-4-trifluoromethyl-1,6-dihydro-pyridin-2-yl]-thiophen-3-yl}-2-methoxy-phenyl)-acetic acid methyl ester,
(3-{5-[5-Cyano-1-(2,4-difluoro-benzyl)-6-oxo-4-trifluoromethyl-1,6-dihydro-pyridin-2-yl]-thiophen-3-yl}-5-isopropoxy-phenyl)-acetic acid methyl ester, MS (ES+): 603.2 (M+H);
(3-{5-[5-Cyano-1-(2,4-difluoro-benzyl)-6-oxo-4-trifluoromethyl-1,6-dihydro-pyridin-2-yl]-thiophen-2-yl}-4-fluoro-phenyl)-acetic acid methyl ester, MS (ES+): 563.3 (M+H);
(3-{5-[5-Cyano-1-(2,4-difluoro-benzyl)-6-oxo-4-trifluoromethyl-1,6-dihydro-pyridin-2-yl]-thiophen-2-yl}-4-methoxy-phenyl)-acetic acid methyl ester, MS (ES+): 575.1 (M+H);
(3-{5-[5-Cyano-1-(2,4-difluoro-benzyl)-6-oxo-4-trifluoromethyl-1,6-dihydro-pyridin-2-yl]-thiophen-3-yl}-5-isopropoxy-phenyl)-acetic acid, MS (ES+): 589.2 (M+H);
(5-{5-[5-Cyano-1-(2,4-difluoro-benzyl)-6-oxo-4-trifluoromethyl-1,6-dihydro-pyridin-2-yl]-thiophen-2-yl}-2-methoxy-phenyl)-acetic acid, MS (ES+): 561.2 (M+H);
(5-{5-[5-Cyano-1-(2,4-difluoro-benzyl)-6-oxo-4-trifluoromethyl-1,6-dihydro-pyridin-2-yl]-thiophen-3-yl}-2-methoxy-phenyl)-acetic acid, MS (ES+): 561.3 (M+H);
2-(3-{5-[5-Cyano-1-(2,4-difluoro-benzyl)-6-oxo-4-trifluoromethyl-1,6-dihydro-pyridin-2-yl]-thiophen-3-yl}-phenyl)-2-methyl-propionic acid methyl ester, MS (ES+): 573.2 (M+H);
(3-{5-[5-Cyano-1-(2,4-difluoro-benzyl)-6-oxo-4-trifluoromethyl-1,6-dihydro-pyridin-2-yl]-thiophen-3-yl}-4-fluoro-phenyl)-acetic acid methyl ester, MS (ES+): 563.2 (M+H);
(3-{5-[5-Cyano-1-(2,4-difluoro-benzyl)-6-oxo-4-trifluoromethyl-1,6-dihydro-pyridin-2-yl]-thiophen-2-yl}-4-methoxy-phenyl)-acetic acid, MS (ES+): 561.2 (M+H);
(3-{5-[5-Cyano-1-(2,4-difluoro-benzyl)-4-(1,1-difluoro-heptyl)-6-oxo-1,6-dihydro-pyridin-2-yl]-thiophen-2-yl}-phenyl)-acetic acid methyl ester, MS (ES+): 611.5 (M+H);
(2-Chloro-4-{5-[5-cyano-1-(2,4-difluoro-benzyl)-6-oxo-4-trifluoromethyl-1,6-dihydro-pyridin-2-yl]-thiophen-3-yl}-phenyl)-acetic acid methyl ester, MS (ES+): 579.3 (M+H);
(2-Chloro-4-{5-[5-cyano-1-(2,4-difluoro-benzyl)-6-oxo-4-trifluoromethyl-1,6-dihydro-pyridin-2-yl]-thiophen-2-yl}-phenyl)-acetic acid methyl ester, MS (ES+): 579.4 (M+H);
(3-{5-[5-Cyano-1-(2,4-difluoro-benzyl)-6-oxo-4-trifluoromethyl-1,6-dihydro-pyridin-2-yl]-thiophen-3-yl}-phenyl)-acetic acid tert-butyl ester, MS (ES+): 587 (M+H);
(3-{5-[5-Cyano-1-(2,4-difluoro-benzyl)-4-(1,1-difluoro-3-methyl-butyl)-6-oxo-1,6-dihydro-pyridin-2-yl]-thiophen-2-yl}-phenyl)-acetic acid methyl ester, MS (ES+): 583 (M+H);
3-(3-{5-[5-Cyano-1-(2,4-difluoro-benzyl)-6-oxo-4-trifluoromethyl-1,6-dihydro-pyridin-2-yl]-thiophen-2-yl}-phenyl)-propionic acid methyl ester, MS (ES+): 559.1 (M+H);
3-(3-{5-[5-Cyano-1-(2,4-difluoro-benzyl)-6-oxo-4-trifluoromethyl-1,6-dihydro-pyridin-2-yl]-thiophen-3-yl}-phenyl)-propionic acid methyl ester, MS (ES+): 559.2 (M+H);
3-(4-{5-[5-Cyano-1-(2,4-difluoro-benzyl)-6-oxo-4-trifluoromethyl-1,6-dihydro-pyridin-2-yl]-thiophen-2-yl}-phenyl)-propionic acid methyl ester, MS (ES+): 559.1 (M+H);
3-(4-{5-[5-Cyano-1-(2,4-difluoro-benzyl)-6-oxo-4-trifluoromethyl-1,6-dihydro-pyridin-2-yl]-thiophen-3-yl}-phenyl)-propionic acid methyl ester, MS (ES+): 558.7 (M+H);
6-[5-(3,5-Bis-trifluoromethyl-phenyl)-furan-2-yl]-1-(2,4-difluoro-benzyl)-2-oxo-4-trifluoromethyl-1,2-dihydro-pyridine-3-carbonitrile, MS (ES+): 593 (M+H);
6-[5-(2-Chloro-5-trifluoromethyl-phenyl)-furan-2-yl]-1-(2,4-difluoro-benzyl)-2-oxo-4-trifluoromethyl-1,2-dihydro-pyridine-3-carbonitrile, MS (ES+): 559 (M+H);
1-(2,4-Difluoro-benzyl)-6-[5-(3,4-dimethoxy-phenyl)-furan-2-yl]-2-oxo-4-trifluoromethyl-1,2-dihydro-pyridine-3-carbonitrile, MS (ES+): 517.4 (M+H);
1-(2,4-Difluoro-benzyl)-6-[5-(4-hydroxy-3-methoxy-phenyl)-furan-2-yl]-2-oxo-4-trifluoromethyl-1,2-dihydro-pyridine-3-carbonitrile, MS (ES+): 503.3 (M+H);
6-[4-(3,5-Bis-trifluoromethyl-phenyl)-furan-2-yl]-1-(2,4-difluoro-benzyl)-2-oxo-4-trifluoromethyl-1,2-dihydro-pyridine-3-carbonitrile, MS (ES+): 593.2 (M+H);
6-[4-(3-Chloro-4-ethoxy-phenyl)-furan-2-yl]-1-(2,4-difluoro-benzyl)-2-oxo-4-trifluoromethyl-1,2-dihydro-pyridine-3-carbonitrile, MS (ES+): 535.2 (M+H);
1-(2,4-Difluoro-benzyl)-6-[5-(4-methoxy-3-trifluoromethyl-phenyl)-furan-2-yl]-2-oxo-4-trifluoromethyl-1,2-dihydro-pyridine-3-carbonitrile, MS (ES+): 555.4 (M+H);
1-(2,4-Difluoro-benzyl)-6-[5-(3-fluoro-4-trifluoromethyl-phenyl)-furan-2-yl]-2-oxo-4-trifluoromethyl-1,2-dihydro-pyridine-3-carbonitrile, MS (ES+): 543.2 (M+H);
1-(2,4-Difluoro-benzyl)-6-[5-(4-fluoro-3-trifluoromethyl-phenyl)-furan-2-yl]-2-oxo-4-trifluoromethyl-1,2-dihydro-pyridine-3-carbonitrile, MS (ES+): 542.9 (M+H);
1-(2,4-Difluoro-benzyl)-6-[4-(4-methoxy-3-trifluoromethyl-phenyl)-furan-2-yl]-2-oxo-4-trifluoromethyl-1,2-dihydro-pyridine-3-carbonitrile, MS (ES+): 555.2 (M+H);
6-[4-(3-Chloro-4-methyl-phenyl)-furan-2-yl]-1-(2,4-difluoro-benzyl)-2-oxo-4-trifluoromethyl-1,2-dihydro-pyridine-3-carbonitrile, MS (ES+): 504.8 (M+H);
6-[4-(3-Chloro-4-trifluoromethyl-phenyl)-furan-2-yl]-1-(2,4-difluoro-benzyl)-2-oxo-4-trifluoromethyl-1,2-dihydro-pyridine-3-carbonitrile, MS (ES+): 559.1 (M+H);
6-[5-(3-Chloro-4-trifluoromethyl-phenyl)-furan-2-yl]-1-(2,4-difluoro-benzyl)-2-oxo-4-trifluoromethyl-1,2-dihydro-pyridine-3-carbonitrile, MS (ES+): 559 (M+H);
1-(2,4-Difluoro-benzyl)-6-[5-(3-fluoro-5-trifluoromethyl-phenyl)-furan-2-yl]-2-oxo-4-trifluoromethyl-1,2-dihydro-pyridine-3-carbonitrile, MS (ES+): 543.1 (M+H);

1-(2,4-Difluoro-benzyl)-6-[4-(4-fluoro-3-trifluoromethyl-phenyl)-furan-2-yl]-2-oxo-4-trifluoromethyl-1,2-dihydro-pyridine-3-carbonitrile, MS (ES+): 543.4 (M+H);

6-[5-(3-Chloro-4-methyl-phenyl)-furan-2-yl]-1-(2,4-difluoro-benzyl)-2-oxo-4-trifluoromethyl-1,2-dihydro-pyridine-3-carbonitrile, MS (ES+): 504.9 (M+H);

1-(2,4-Difluoro-benzyl)-6-[4-(4-ethoxy-3-trifluoromethyl-phenyl)-furan-2-yl]-2-oxo-4-trifluoromethyl-1,2-dihydro-pyridine-3-carbonitrile, MS (ES+): 569.2 (M+H);

1-(2,4-Difluoro-benzyl)-6-[4-(3-ethoxy-4-trifluoromethyl-phenyl)-furan-2-yl]-2-oxo-4-trifluoromethyl-1,2-dihydro-pyridine-3-carbonitrile, MS (ES+): 569.2 (M+H);

1-(2,4-Difluoro-benzyl)-6-[4-(3-ethoxy-5-trifluoromethyl-phenyl)-furan-2-yl]-2-oxo-4-trifluoromethyl-1,2-dihydro-pyridine-3-carbonitrile, MS (ES+): 569.3 (M+H);

1-(2,4-Difluoro-benzyl)-6-[4-(3-isopropoxy-5-trifluoromethyl-phenyl)-furan-2-yl]-2-oxo-4-trifluoromethyl-1,2-dihydro-pyridine-3-carbonitrile, MS (ES+): 583.1 (M+H);

1-(2,4-Difluoro-benzyl)-6-[4-(3-ethoxy-5-ethyl-phenyl)-furan-2-yl]-2-oxo-4-trifluoromethyl-1,2-dihydro-pyridine-3-carbonitrile, MS (ES+): 529.4 (M+H);

1-(2,4-Difluoro-benzyl)-6-[4-(3-ethyl-5-isopropoxy-phenyl)-furan-2-yl]-2-oxo-4-trifluoromethyl-1,2-dihydro-pyridine-3-carbonitrile, MS (ES+): 543.1 (M+H);

1-(2,4-Difluoro-benzyl)-6-[5-(4-methanesulfonyl-phenyl)-furan-2-yl]-2-oxo-4-trifluoromethyl-1,2-dihydro-pyridine-3-carbonitrile, MS (ES+): 535.4 (M+H);

1-(2,4-Difluoro-benzyl)-6-[5-(4-methylsulfanyl-phenyl)-furan-2-yl]-2-oxo-4-trifluoromethyl-1,2-dihydro-pyridine-3-carbonitrile, MS (ES+): 503.2 (M+H);

1-(2,4-Difluoro-benzyl)-6-[5-(3-ethanesulfonyl-phenyl)-furan-2-yl]-2-oxo-4-trifluoromethyl-1,2-dihydro-pyridine-3-carbonitrile, MS (ES+): 549.1 (M+H);

1-(2,4-Difluoro-benzyl)-6-[4-(4-methanesulfonyl-phenyl)-furan-2-yl]-2-oxo-4-trifluoromethyl-1,2-dihydro-pyridine-3-carbonitrile, MS (ES+): 535.1 (M+H);

1-(2,4-Difluoro-benzyl)-6-[5-(4-methylsulfanyl-3-trifluoromethyl-phenyl)-furan-2-yl]-2-oxo-4-trifluoromethyl-1,2-dihydro-pyridine-3-carbonitrile, MS (ES+): 570.9 (M+H);

1-(2,4-Difluoro-benzyl)-6-[5-(3-methylsulfanyl-5-trifluoromethyl-phenyl)-furan-2-yl]-2-oxo-4-trifluoromethyl-1,2-dihydro-pyridine-3-carbonitrile, MS (ES+): 571.3 (M+H);

1-(2,4-Difluoro-benzyl)-6-[4-(4-methylsulfanyl-3-trifluoromethyl-phenyl)-furan-2-yl]-2-oxo-4-trifluoromethyl-1,2-dihydro-pyridine-3-carbonitrile, MS (ES+): 571.1 (M+H);

1-(2,4-Difluoro-benzyl)-6-[4-(3-methylsulfanyl-5-trifluoromethyl-phenyl)-furan-2-yl]-2-oxo-4-trifluoromethyl-1,2-dihydro-pyridine-3-carbonitrile, MS (ES+): 571.3 (M+H);

1-(2,4-Difluoro-benzyl)-6-[5-(4-methyl-3-methylsulfanyl-phenyl)-furan-2-yl]-2-oxo-4-trifluoromethyl-1,2-dihydro-pyridine-3-carbonitrile, MS (ES+): 518.3 (M+H);

1-(2,4-Difluoro-benzyl)-6-[5-(4-methanesulfonyl-3-trifluoromethyl-phenyl)-furan-2-yl]-2-oxo-4-trifluoromethyl-1,2-dihydro-pyridine-3-carbonitrile, MS (ES+): 604.2 (M+H);

1-(2,4-Difluoro-benzyl)-6-[4-(4-methanesulfonyl-3-trifluoromethyl-phenyl)-furan-2-yl]-2-oxo-4-trifluoromethyl-1,2-dihydro-pyridine-3-carbonitrile, MS (ES+): 604.2 (M+H);

1-(2,4-Difluoro-benzyl)-6-[4-(3-methanesulfonyl-5-trifluoromethyl-phenyl)-furan-2-yl]-2-oxo-4-trifluoromethyl-1,2-dihydro-pyridine-3-carbonitrile, MS (ES+): 603.1 (M+H);

1-(2,4-Difluoro-benzyl)-6-[5-(3-methanesulfonyl-5-trifluoromethyl-phenyl)-furan-2-yl]-2-oxo-4-trifluoromethyl-1,2-dihydro-pyridine-3-carbonitrile, MS (ES+): 603.2 (M+H);

1-(2,4-Difluoro-benzyl)-2-oxo-6-{5-[3-(propane-2-sulfonyl)-5-trifluoromethyl-phenyl]-furan-2-yl}-4-trifluoromethyl-1,2-dihydro-pyridine-3-carbonitrile, MS (ES+): 631.1 (M+H);

1-(2,4-Difluoro-benzyl)-6-[4-(3-ethanesulfonyl-5-trifluoromethyl-phenyl)-furan-2-yl]-2-oxo-4-trifluoromethyl-1,2-dihydro-pyridine-3-carbonitrile, MS (ES+): 616.9 (M+H);

1-(2,4-Difluoro-benzyl)-2-oxo-6-{4-[3-(propane-1-sulfonyl)-5-trifluoromethyl-phenyl]-furan-2-yl}-4-trifluoromethyl-1,2-dihydro-pyridine-3-carbonitrile, MS (ES+): 630.9 (M+H);

1-(2,4-Difluoro-benzyl)-2-oxo-6-{4-[3-(propane-2-sulfonyl)-5-trifluoromethyl-phenyl]-furan-2-yl}-4-trifluoromethyl-1,2-dihydro-pyridine-3-carbonitrile, MS (ES+): 631.2 (M+H);

1-(2,4-Difluoro-benzyl)-2-oxo-6-{5-[3-(propane-1-sulfonyl)-5-trifluoromethyl-phenyl]-furan-2-yl}-4-trifluoromethyl-1,2-dihydro-pyridine-3-carbonitrile, MS (ES+): 630.9 (M+H);

1-(2,4-Difluoro-benzyl)-6-[4-(3-isopropyl-5-methanesulfonyl-phenyl)-furan-2-yl]-2-oxo-4-trifluoromethyl-1,2-dihydro-pyridine-3-carbonitrile, MS (ES+): 577.3 (M+H);

1-(2,4-Difluoro-benzyl)-6-[4-(3-ethyl-5-methanesulfonyl-phenyl)-furan-2-yl]-2-oxo-4-trifluoromethyl-1,2-dihydro-pyridine-3-carbonitrile, MS (ES+): 563.1 (M+H);

1-(2,4-Difluoro-benzyl)-6-[5-(3-ethyl-5-methanesulfonyl-phenyl)-furan-2-yl]-2-oxo-4-trifluoromethyl-1,2-dihydro-pyridine-3-carbonitrile, MS (ES+): 563 (M+H);

1-(2,4-Difluoro-benzyl)-6-[4-(3-ethanesulfonyl-5-isopropyl-phenyl)-furan-2-yl]-2-oxo-4-trifluoromethyl-1,2-dihydro-pyridine-3-carbonitrile, MS (ES+): 591.2 (M+H);

1-(2-Fluoro-benzyl)-6-[4-(4-methanesulfonyl-phenyl)-furan-2-yl]-2-oxo-4-trifluoromethyl-1,2-dihydro-pyridine-3-carbonitrile, MS (ES+): 517.4 (M+H);

6-[4-(3-tert-Butyl-5-methanesulfonyl-phenyl)-furan-2-yl]-1-(2,4-difluoro-benzyl)-2-oxo-4-trifluoromethyl-1,2-dihydro-pyridine-3-carbonitrile, MS (ES+): 591.2 (M+H);

1-(2-Fluoro-benzyl)-6-[4-(3-methanesulfonyl-phenyl)-furan-2-yl]-2-oxo-4-trifluoromethyl-1,2-dihydro-pyridine-3-carbonitrile, MS (ES+): 517.2 (M+H);

6-[4-(3-Ethanesulfonyl-phenyl)-furan-2-yl]-1-(2-fluoro-benzyl)-2-oxo-4-trifluoromethyl-1,2-dihydro-pyridine-3-carbonitrile, MS (ES+): 531.2 (M+H);

1-(2,4-Difluoro-benzyl)-6-{4-[3-ethyl-5-(propane-1-sulfonyl)-phenyl]-furan-2-yl}-2-oxo-4-trifluoromethyl-1,2-dihydro-pyridine-3-carbonitrile, MS (ES+): 591.3 (M+H);

1-(2,4-Difluoro-benzyl)-6-{4-[3-ethyl-5-(propane-2-sulfonyl)-phenyl]-furan-2-yl}-2-oxo-4-trifluoromethyl-1,2-dihydro-pyridine-3-carbonitrile, MS (ES+): 591.1 (M+H);

1-(2,4-Difluoro-benzyl)-6-[5-(3-methanesulfonyl-phenyl)-furan-2-yl]-2-oxo-4-trifluoromethyl-1,2-dihydro-pyridine-3-carbonitrile, MS (ES+): 535.4 (M+H);

6-[4-(3-Chloro-4-cyano-phenyl)-furan-2-yl]-1-(2,4-difluoro-benzyl)-2-oxo-4-trifluoromethyl-1,2-dihydro-pyridine-3-carbonitrile, MS (ES+): 516.5 (M+H);

6-[4-(3-Cyano-4-ethoxy-phenyl)-furan-2-yl]-1-(2,4-difluoro-benzyl)-2-oxo-4-trifluoromethyl-1,2-dihydro-pyridine-3-carbonitrile, MS (ES+): 526.4 (M+H);

1-(2,4-Difluoro-benzyl)-6-[4-(4-ethoxy-3-nitro-phenyl)-furan-2-yl]-2-oxo-4-trifluoromethyl-1,2-dihydro-pyridine-3-carbonitrile, 6-[4-(4-Amino-3-chloro-phenyl)-furan-2-yl]-1-(2,4-difluoro-benzyl)-2-oxo-4-trifluoromethyl-1,2-dihydro-pyridine-3-carbonitrile, MS (ES+): 506.2 (M+H);

(5-{5-[5-Cyano-1-(2,4-difluoro-benzyl)-6-oxo-4-trifluoromethyl-1,6-dihydro-pyridin-2-yl]-furan-3-yl}-2-ethoxy-phenyl)-carbamic acid tert-butyl ester, (5-{5-[5-Cyano-1-(2,4-difluoro-benzyl)-6-oxo-4-trifluoromethyl-1,6-dihydro-pyridin-2-yl]-furan-2-yl}-2-ethoxy-phenyl)-carbamic acid tert-butyl ester, 3-{5-[5-Cyano-1-(2,4-difluoro-benzyl)-6-oxo-4-trifluoromethyl-1,6-dihydro-pyridin-2-yl]-furan-3-yl}-5-isopropyl-benzoic acid methyl ester, MS (ES+): 557.3 (M+H);

6-[4-(3-Amino-4-ethoxy-phenyl)-furan-2-yl]-1-(2,4-difluoro-benzyl)-2-oxo-4-trifluoromethyl-1,2-dihydro-pyridine-3-carbonitrile, (3-{5-[5-Cyano-1-(2,4-difluoro-benzyl)-6-oxo-4-trifluoromethyl-1,6-dihydro-pyridin-2-yl]-furan-3-yl}-phenyl)-acetic acid, (4-{5-[5-Cyano-1-(2,4-difluoro-benzyl)-6-oxo-4-trifluoromethyl-1,6-dihydro-pyridin-2-yl]-furan-3-yl}-phenyl)-acetic acid, (3-{5-[5-Cyano-1-(2,4-difluoro-benzyl)-6-oxo-4-trifluoromethyl-1,6-dihydro-pyridin-2-yl]-furan-3-yl}-5-isopropyl-phenyl)-acetic acid, MS (ES+): 557.4 (M+H);

(3-{5-[5-Cyano-1-(2,4-difluoro-benzyl)-6-oxo-4-trifluoromethyl-1,6-dihydro-pyridin-2-yl]-furan-3-yl}-phenyl)-acetic acid methyl ester, MS (ES+): 529.4 (M+H);

(4-{5-[5-Cyano-1-(2,4-difluoro-benzyl)-6-oxo-4-trifluoromethyl-1,6-dihydro-pyridin-2-yl]-furan-3-yl}-phenyl)-acetic acid methyl ester, MS (ES+): 529.3 (M+H);

(5-{5-[5-Cyano-1-(2,4-difluoro-benzyl)-6-oxo-4-trifluoromethyl-1,6-dihydro-pyridin-2-yl]-furan-3-yl}-2-methoxy-phenyl)-acetic acid methyl ester, MS (ES+): 559.3 (M+H);

(3-{5-[5-Cyano-1-(2,4-difluoro-benzyl)-6-oxo-4-trifluoromethyl-1,6-dihydro-pyridin-2-yl]-furan-3-yl}-5-isopropoxy-phenyl)-acetic acid, MS (ES+): 573.2 (M+H);

(3-{5-[5-Cyano-1-(2,4-difluoro-benzyl)-6-oxo-4-trifluoromethyl-1,6-dihydro-pyridin-2-yl]-furan-3-yl}-4-methoxy-phenyl)-acetic acid methyl ester, MS (ES+): 559.2 (M+H);

(3-{5-[5-Cyano-1-(2,4-difluoro-benzyl)-6-oxo-4-trifluoromethyl-1,6-dihydro-pyridin-2-yl]-furan-3-yl}-4-fluoro-phenyl)-acetic acid methyl ester, MS (ES+): 547.4 (M+H);

(5-{5-[5-Cyano-1-(2,4-difluoro-benzyl)-6-oxo-4-trifluoromethyl-1,6-dihydro-pyridin-2-yl]-furan-3-yl}-2-methoxy-phenyl)-acetic acid, MS (ES+): 545.3 (M+H);

(2-Chloro-4-{5-[5-cyano-1-(2,4-difluoro-benzyl)-6-oxo-4-trifluoromethyl-1,6-dihydro-pyridin-2-yl]-furan-3-yl}-phenyl)-acetic acid methyl ester, MS (ES+): 563.2 (M+H);

(3-{5-[5-Cyano-1-(2,4-difluoro-benzyl)-6-oxo-4-trifluoromethyl-1,6-dihydro-pyridin-2-yl]-thiophen-3-yl}-benzyl)-carbamic acid tert-butyl ester, MS (ES+): 602.4 (M+H);

3-(3-{5-[5-Cyano-1-(2,4-difluoro-benzyl)-6-oxo-4-trifluoromethyl-1,6-dihydro-pyridin-2-yl]-furan-3-yl}-phenyl)-propionic acid methyl ester, MS (ES+): 543.3 (M+H);

3-(4-{5-[5-Cyano-1-(2,4-difluoro-benzyl)-6-oxo-4-trifluoromethyl-1,6-dihydro-pyridin-2-yl]-furan-3-yl}-phenyl)-propionic acid methyl ester, MS (ES+): 543.5 (M+H);

1-(2,4-Difluoro-benzyl)-2-oxo-6-(3-thiazol-2-yl-phenyl)-4-trifluoromethyl-1,2-dihydro-pyridine-3-carbonitrile, MS (ES+): 474.2 (M+H);

5-{4-[5-Cyano-1-(2,4-difluoro-benzyl)-6-oxo-4-trifluoromethyl-1,6-dihydro-pyridin-2-yl]-phenoxy}-1H-indole-2-carboxylic acid ethyl ester, 1-(2,4-Dimethyl-benzyl)-6-[4-(1H-indol-5-yloxy)-phenyl]-2-oxo-4-trifluoromethyl-1,2-dihydro-pyridine-3-carbonitrile, MS (ES+): 514.4 (M+H);

1-(2,4-Dimethyl-benzyl)-2-oxo-6-[4-(pyrimidin-2-yloxy)-phenyl]-4-trifluoromethyl-1,2-dihydro-pyridine-3-carbonitrile, MS (ES+): 477.1 (M+H);

1-(2,4-Dimethyl-benzyl)-2-oxo-6-[4-(pyrazin-2-yloxy)-phenyl]-4-trifluoromethyl-1,2-dihydro-pyridine-3-carbonitrile, MS (ES+): 477.2 (M+H);

1-(2,4-Dimethyl-benzyl)-6-[4-(4,6-dimethyl-pyrimidin-2-yloxy)-phenyl]-2-oxo-4-trifluoromethyl-1,2-dihydro-pyridine-3-carbonitrile, MS (ES+): 505.3 (M+H);

1-(2,4-Dichloro-benzyl)-2-oxo-6-[4-(pyrazin-2-yloxy)-phenyl]-4-trifluoromethyl-1,2-dihydro-pyridine-3-carbonitrile, MS (ES+): 516.9 (M+H);

1-(2,4-Difluoro-benzyl)-2-oxo-6-[4-(pyrazin-2-yloxy)-phenyl]-4-trifluoromethyl-1,2-dihydro-pyridine-3-carbonitrile, MS (ES+): 485.3 (M+H);

1-(2,4-Dimethyl-benzyl)-6-[4-(3,6-dimethyl-pyrazin-2-yloxy)-phenyl]-2-oxo-4-trifluoromethyl-1,2-dihydro-pyridine-3-carbonitrile, MS (ES+): 505.3 (M+H);

6-[4-(3-Chloro-pyrazin-2-yloxy)-phenyl]-1-(2,4-dimethyl-benzyl)-2-oxo-4-trifluoromethyl-1,2-dihydro-pyridine-3-carbonitrile, MS (ES+): 511.2 (M+H);

6-[4-(6-Chloro-pyrazin-2-yloxy)-phenyl]-1-(2,4-dimethyl-benzyl)-2-oxo-4-trifluoromethyl-1,2-dihydro-pyridine-3-carbonitrile, MS (ES+): 511.2 (M+H);

2-{4-[5-Cyano-1-(2,4-dimethyl-benzyl)-6-oxo-4-trifluoromethyl-1,6-dihydro-pyridin-2-yl]-phenoxy}-nicotinonitrile, MS (ES+): 501.3 (M+H);

2-{4-[5-Cyano-1-(2,4-dimethyl-benzyl)-6-oxo-4-trifluoromethyl-1,6-dihydro-pyridin-2-yl]-phenoxy}-6-methyl-nicotinonitrile, MS (ES+): 515.4 (M+H);

1-(2,4-Dimethyl-benzyl)-2-oxo-4-trifluoromethyl-6-[4-(5-trifluoromethyl-pyridin-2-yloxy)-phenyl]-1,2-dihydro-pyridine-3-carbonitrile, MS (ES+): 544.3 (M+H);

1-(2,4-Dichloro-benzyl)-6-[4-(1H-indol-5-yloxy)-phenyl]-2-oxo-4-trifluoromethyl-1,2-dihydro-pyridine-3-carbonitrile, MS (ES+): 554.3 (M+H);

1-(2,4-Difluoro-benzyl)-6-[4-(1H-indol-5-yloxy)-phenyl]-2-oxo-4-trifluoromethyl-1,2-dihydro-pyridine-3-carbonitrile, MS (ES+): 522.1 (M+H);

1-(2-Chloro-4-fluoro-benzyl)-6-[4-(1H-indol-5-yloxy)-phenyl]-2-oxo-4-trifluoromethyl-1,2-dihydro-pyridine-3-carbonitrile, MS (ES+): 538.3 (M+H);

1-(2,4-Dimethyl-benzyl)-6-[3-methyl-4-(pyrazin-2-yloxy)-phenyl]-2-oxo-4-trifluoromethyl-1,2-dihydro-pyridine-3-carbonitrile, MS (ES+): 491.3 (M+H);

6-[4-(3-Chloro-pyrazin-2-yloxy)-3-methyl-phenyl]-1-(2,4-dimethyl-benzyl)-2-oxo-4-trifluoromethyl-1,2-dihydro-pyridine-3-carbonitrile, MS (ES+): 525.4 (M+H);

6-[4-(6-Chloro-pyrazin-2-yloxy)-3-methyl-phenyl]-1-(2,4-dimethyl-benzyl)-2-oxo-4-trifluoromethyl-1,2-dihydro-pyridine-3-carbonitrile, MS (ES+): 525.3 (M+H);

1-(2,4-Dimethyl-benzyl)-6-[4-(3,6-dimethyl-pyrazin-2-yloxy)-3-methyl-phenyl]-2-oxo-4-trifluoromethyl-1,2-dihydro-pyridine-3-carbonitrile, MS (ES+): 519.3 (M+H);

1-(2,4-Dimethyl-benzyl)-6-[3-isopropyl-4-(pyrazin-2-yloxy)-phenyl]-2-oxo-4-trifluoromethyl-1,2-dihydro-pyridine-3-carbonitrile, MS (ES+): 519.3 (M+H);

6-[4-(3-Chloro-pyrazin-2-yloxy)-3-isopropyl-phenyl]-1-(2,4-dimethyl-benzyl)-2-oxo-4-trifluoromethyl-1,2-dihydro-pyridine-3-carbonitrile, MS (ES+): 553.4 (M+H);

6-[4-(6-Chloro-pyrazin-2-yloxy)-3-isopropyl-phenyl]-1-(2,4-dimethyl-benzyl)-2-oxo-4-trifluoromethyl-1,2-dihydro-pyridine-3-carbonitrile, MS (ES+): 553.4 (M+H);

1-(2,4-Dimethyl-benzyl)-6-[4-(3,6-dimethyl-pyrazin-2-yloxy)-3-isopropyl-phenyl]-2-oxo-4-trifluoromethyl-1,2-dihydro-pyridine-3-carbonitrile, MS (ES+): 547.3 (M+H);

2-{4-[5-Cyano-1-(2,4-dimethyl-benzyl)-6-oxo-4-trifluoromethyl-1,6-dihydro-pyridin-2-yl]-2-isopropyl-phenoxy}-6-methyl-nicotinonitrile, MS (ES+): 557.3 (M+H);

1-(2,4-Difluoro-benzyl)-2-oxo-6-[4-(pyrimidin-2-yloxy)-phenyl]-4-trifluoromethyl-1,2-dihydro-pyridine-3-carbonitrile, MS (ES+): 485.1 (M+H);

3-{4-[5-Cyano-1-(2,4-difluoro-benzyl)-6-oxo-4-trifluoromethyl-1,6-dihydro-pyridin-2-yl]-phenoxy}-pyrazine-2-carbonitrile, MS (ES+): 510.1 (M+H);

2-{4-[5-Cyano-1-(2,4-difluoro-benzyl)-6-oxo-4-trifluoromethyl-1,6-dihydro-pyridin-2-yl]-phenoxy}-6-methyl-nicotinonitrile, MS (ES+): 523.2 (M+H);

2-{4-[5-Cyano-1-(2,4-difluoro-benzyl)-6-oxo-4-trifluoromethyl-1,6-dihydro-pyridin-2-yl]-phenoxy}-nicotinonitrile, MS (ES+): 509.2 (M+H);

6-[4-(6-Chloro-pyrazin-2-yloxy)-phenyl]-1-(2,4-difluoro-benzyl)-2-oxo-4-trifluoromethyl-1,2-dihydro-pyridine-3-carbonitrile, MS (ES+): 519.3 (M+H);

6-[3-Chloro-4-(pyrimidin-2-yloxy)-phenyl]-1-(2,4-difluoro-benzyl)-2-oxo-4-trifluoromethyl-1,2-dihydro-pyridine-3-carbonitrile, MS (ES+): 519.2 (M+H);

6-[3-Chloro-4-(pyrazin-2-yloxy)-phenyl]-1-(2,4-difluoro-benzyl)-2-oxo-4-trifluoromethyl-1,2-dihydro-pyridine-3-carbonitrile, MS (ES+): 519.2 (M+H);

2-{2-Chloro-4-[5-cyano-1-(2,4-difluoro-benzyl)-6-oxo-4-trifluoromethyl-1,6-dihydro-pyridin-2-yl]-phenoxy}-nicotinonitrile, MS (ES+): 543.3 (M+H);

1-(2,4-Dimethyl-benzyl)-6-[4-(1H-indol-5-yloxy)-3,5-dimethyl-phenyl]-2-oxo-4-trifluoromethyl-1,2-dihydro-pyridine-3-carbonitrile, 1-(2,4-Difluoro-benzyl)-6-[4-(1H-indol-5-yl)-phenyl]-2-oxo-4-trifluoromethyl-1,2-dihydro-pyridine-3-carbonitrile, MS (ES+): 506.1 (M+H);

1-(2,4-Difluoro-benzyl)-6-[3-(1H-indol-5-yl)-phenyl]-2-oxo-4-trifluoromethyl-1,2-dihydro-pyridine-3-carbonitrile, MS (ES+): 506.2 (M+H);

1-(2,4-Difluoro-benzyl)-2-oxo-6-(3-pyridin-3-yl-phenyl)-4-trifluoromethyl-1,2-dihydro-pyridine-3-carbonitrile, 1-(2,4-Difluoro-benzyl)-2-oxo-6-(3-pyridin-4-yl-phenyl)-4-trifluoromethyl-1,2-dihydro-pyridine-3-carbonitrile, 1-(2,4-Dimethyl-benzyl)-6-[4-(1H-indol-5-yloxy)-3-methyl-phenyl]-2-oxo-4-trifluoromethyl-1,2-dihydro-pyridine-3-carbonitrile, 1-(2,4-Difluoro-benzyl)-2-oxo-4-trifluoromethyl-6-[4-(5-trifluoromethyl-pyridin-2-yloxy)-phenyl]-1,2-dihydro-pyridine-3-carbonitrile, MS (ES+): 552.3 (M+H);

1-(2,4-Difluoro-benzyl)-2-oxo-4-trifluoromethyl-6-[4-(3-trifluoromethyl-pyridin-2-yloxy)-phenyl]-1,2-dihydro-pyridine-3-carbonitrile, MS (ES+): 552.3 (M+H);

1-(2,4-Difluoro-benzyl)-2-oxo-4-trifluoromethyl-6-[4-(6-trifluoromethyl-pyridin-2-yloxy)-phenyl]-1,2-dihydro-pyridine-3-carbonitrile, MS (ES+): 552.1 (M+H);

1-(2,4-Difluoro-benzyl)-6-[4-(1H-indol-6-yloxy)-phenyl]-2-oxo-4-trifluoromethyl-1,2-dihydro-pyridine-3-carbonitrile, 6-{4-[5-Cyano-1-(2,4-difluoro-benzyl)-6-oxo-4-trifluoromethyl-1,6-dihydro-pyridin-2-yl]-phenoxy}-4-trifluoromethyl-nicotinic acid methyl ester, MS (ES+): 610.1 (M+H);

1-(2,4-Dichloro-benzyl)-6-[4-(1-methyl-1H-indol-5-yloxy)-phenyl]-2-oxo-4-trifluoromethyl-1,2-dihydro-pyridine-3-carbonitrile, 5-{4-[5-Cyano-1-(2,4-dimethyl-benzyl)-6-oxo-4-trifluoromethyl-1,6-dihydro-pyridin-2-yl]-phenoxy}-1H-indole-2-carboxylic acid ethyl ester, MS (ES+): 586.2 (M+H);

1-(2,4-Dimethyl-benzyl)-2-oxo-6-[4-(piperidin-4-yloxy)-phenyl]-4-trifluoromethyl-1,2-dihydro-pyridine-3-carbonitrile, 1-(2,4-Difluoro-benzyl)-2-oxo-6-(3-piperidin-1-yl-phenyl)-4-trifluoromethyl-1,2-dihydro-pyridine-3-carbonitrile, MS (ES+): 474.2 (M+H);

4-{3-[5-Cyano-1-(2,4-difluoro-benzyl)-6-oxo-4-trifluoromethyl-1,6-dihydro-pyridin-2-yl]-phenyl}-piperazine-1-carboxylic acid tert-butyl ester, MS (ES+): 575.3 (M+H);

1-(2,4-Difluoro-benzyl)-2-oxo-6-(4-piperidin-1-yl-phenyl)-4-trifluoromethyl-1,2-dihydro-pyridine-3-carbonitrile, MS (ES+): 474.3 (M+H);

4-{4-[5-Cyano-1-(2,4-difluoro-benzyl)-6-oxo-4-trifluoromethyl-1,6-dihydro-pyridin-2-yl]-phenyl}-piperazine-1-carboxylic acid tert-butyl ester, MS (ES+): 575.4 (M+H);

4-{4-[5-Cyano-1-(2,4-dimethyl-benzyl)-6-oxo-4-trifluoromethyl-1,6-dihydro-pyridin-2-yl]-phenoxy}-piperidine-1-carboxylic acid tert-butyl ester, MS (ES+): 582.3 (M+H);

6-(3-Benzo[1,3]dioxol-5-yl-phenyl)-1-(2,4-difluoro-benzyl)-2-oxo-4-trifluoromethyl-1,2-dihydro-pyridine-3-carbonitrile, 6-(4-Benzo[1,3]dioxol-5-yl-phenyl)-1-(2,4-dimethyl-benzyl)-2-oxo-4-trifluoromethyl-1,2-dihydro-pyridine-3-carbonitrile, 1-(2,4-Difluoro-benzyl)-6-[5-(6-methoxy-pyridin-3-yl)-furan-2-yl]-2-oxo-4-trifluoromethyl-1,2-dihydro-pyridine-3-carbonitrile, MS (ES+): 488.3 (M+H);

1-(2,4-Difluoro-benzyl)-6-[5-(2,4-dimethoxy-pyrimidin-5-yl)-furan-2-yl]-2-oxo-4-trifluoromethyl-1,2-dihydro-pyridine-3-carbonitrile, MS (ES+): 519.5 (M+H);

1-(2,4-Difluoro-benzyl)-2-oxo-6-(4-pyridin-4-yl-furan-2-yl)-4-trifluoromethyl-1,2-dihydro-pyridine-3-carbonitrile, MS (ES+): 458.1 (M+H);

1-(2,4-Difluoro-benzyl)-6-[4-(6-methylsulfanyl-pyridin-3-yl)-furan-2-yl]-2-oxo-4-trifluoromethyl-1,2-dihydro-pyridine-3-carbonitrile, MS (ES+): 504.1 (M+H);

1-(2,4-Difluoro-benzyl)-6-[4-(6-methanesulfonyl-pyridin-3-yl)-furan-2-yl]-2-oxo-4-trifluoromethyl-1,2-dihydro-pyridine-3-carbonitrile, MS (ES+): 536.2 (M+H);

5-{5-[5-Cyano-1-(2,4-difluoro-benzyl)-6-oxo-4-trifluoromethyl-1,6-dihydro-pyridin-2-yl]-furan-3-yl}-2-ethoxy-nicotinonitrile, MS (ES+): 527.2 (M+H);

1-(2,4-Difluoro-benzyl)-6-[4-(6-ethoxy-pyridin-3-yl)-furan-2-yl]-2-oxo-4-trifluoromethyl-1,2-dihydro-pyridine-3-carbonitrile, MS (ES+): 502.2 (M+H);

1-(2,4-Difluoro-benzyl)-6-[4-(6-isopropoxy-5-trifluoromethyl-pyridin-3-yl)-furan-2-yl]-2-oxo-4-trifluoromethyl-1,2-dihydro-pyridine-3-carbonitrile, MS (ES+): 584.3 (M+H);

1-(2,4-Difluoro-benzyl)-6-[5-(6-methanesulfonyl-pyridin-3-yl)-furan-2-yl]-2-oxo-4-trifluoromethyl-1,2-dihydro-pyridine-3-carbonitrile, MS (ES+): 536 (M+H);

5-{5-[5-Cyano-1-(2,4-difluoro-benzyl)-6-oxo-4-trifluoromethyl-1,6-dihydro-pyridin-2-yl]-furan-3-yl}-2-ethoxy-nicotinic acid ethyl ester, MS (ES+): 574.1 (M+H);

5-{5-[5-Cyano-1-(2,4-difluoro-benzyl)-6-oxo-4-trifluoromethyl-1,6-dihydro-pyridin-2-yl]-furan-2-yl}-2-ethoxy-nicotinic acid ethyl ester, MS (ES+): 574 (M+H);

1-(2,4-Difluoro-benzyl)-6-[4-(5-methyl-6-methylsulfanyl-pyridin-3-yl)-furan-2-yl]-2-oxo-4-trifluoromethyl-1,2-dihydro-pyridine-3-carbonitrile, MS (ES+): 518.1 (M+H);

1-(2,4-Difluoro-benzyl)-6-[4-(6-methanesulfonyl-5-methyl-pyridin-3-yl)-furan-2-yl]-2-oxo-4-trifluoromethyl-1,2-dihydro-pyridine-3-carbonitrile, MS (ES+): 550.3 (M+H);

5-{5-[5-Cyano-1-(2,4-difluoro-benzyl)-6-oxo-4-trifluoromethyl-1,6-dihydro-pyridin-2-yl]-furan-3-yl}-2-methanesulfonyl-nicotinic acid methyl ester, MS (ES+): 594.3 (M+H);

1-(2,4-Difluoro-benzyl)-6-[4-(5-isopropenyl-6-methylsulfanyl-pyridin-3-yl)-furan-2-yl]-2-oxo-4-trifluoromethyl-1,2-dihydro-pyridine-3-carbonitrile, MS (ES+): 544.2 (M+H);

1-(2,4-Difluoro-benzyl)-6-[4-(6-ethoxy-5-isopropenyl-pyridin-3-yl)-furan-2-yl]-2-oxo-4-trifluoromethyl-1,2-dihydro-pyridine-3-carbonitrile, MS (ES+): 542.3 (M+H);

1-(2,4-Difluoro-benzyl)-6-[4-(5-isopropenyl-6-methanesulfonyl-pyridin-3-yl)-furan-2-yl]-2-oxo-4-trifluoromethyl-1,2-dihydro-pyridine-3-carbonitrile, MS (ES+): 576.3 (M+H);

1-(2,4-Difluoro-benzyl)-4-(1,1-difluoro-propyl)-6-[4-(6-methanesulfonyl-5-methyl-pyridin-3-yl)-furan-2-yl]-2-oxo-1,2-dihydro-pyridine-3-carbonitrile, MS (ES+): 560.2 (M+H);

1-(2,4-Difluoro-benzyl)-6-[4-(6-ethylsulfanyl-5-methyl-pyridin-3-yl)-furan-2-yl]-2-oxo-4-trifluoromethyl-1,2-dihydro-pyridine-3-carbonitrile, MS (ES+): 532.2 (M+H);

1-(2,4-Difluoro-benzyl)-6-[4-(6-ethoxy-5-isopropyl-pyridin-3-yl)-furan-2-yl]-2-oxo-4-trifluoromethyl-1,2-dihydro-pyridine-3-carbonitrile, MS (ES+): 544.4 (M+H);

1-(2,4-Difluoro-benzyl)-6-[4-(5-isopropyl-6-methanesulfonyl-pyridin-3-yl)-furan-2-yl]-2-oxo-4-trifluoromethyl-1,2-dihydro-pyridine-3-carbonitrile, MS (ES+): 578.3 (M+H);

1-(2,4-Difluoro-benzyl)-6-[4-(6-ethanesulfonyl-5-methyl-pyridin-3-yl)-furan-2-yl]-2-oxo-4-trifluoromethyl-1,2-dihydro-pyridine-3-carbonitrile, MS (ES+): 564.2 (M+H);

6-[4-(2-Chloro-pyridin-4-yl)-furan-2-yl]-1-(2,4-difluoro-benzyl)-2-oxo-4-trifluoromethyl-1,2-dihydro-pyridine-3-carbonitrile, MS (ES+): 492.2 (M+H);

1-(2-Fluoro-benzyl)-6-[4-(6-methanesulfonyl-5-methyl-pyridin-3-yl)-furan-2-yl]-2-oxo-4-trifluoromethyl-1,2-dihydro-pyridine-3-carbonitrile, MS (ES+): 532.4 (M+H);

1-(2,4-Difluoro-benzyl)-2-oxo-6-[4-(6-piperazin-1-yl-pyridin-3-yl)-furan-2-yl]-4-trifluoromethyl-1,2-dihydro-pyridine-3-carbonitrile, MS (ES+): 542.4 (M+H);

6-(5-Benzo[1,3]dioxol-5-yl-furan-2-yl)-1-(2,4-difluoro-benzyl)-2-oxo-4-trifluoromethyl-1,2-dihydro-pyridine-3-carbonitrile, MS (ES+): 501.2 (M+H);

1-(2,4-Difluoro-benzyl)-6-[5-(2,3-dihydro-benzo[1,4]dioxin-6-yl)-furan-2-yl]-2-oxo-4-trifluoromethyl-1,2-dihydro-pyridine-3-carbonitrile, MS (ES+): 515.2 (M+H);

1-(2,4-Difluoro-benzyl)-2-oxo-6-(5-pyridin-3-yl-thiophen-2-yl)-4-trifluoromethyl-1,2-dihydro-pyridine-3-carbonitrile, MS (ES+): 474.2 (M+H);

1-(2,4-Difluoro-benzyl)-2-oxo-6-(5-pyridin-4-yl-thiophen-2-yl)-4-trifluoromethyl-1,2-dihydro-pyridine-3-carbonitrile, MS (ES+): 474 (M+H);

1-(2,4-Difluoro-benzyl)-2-oxo-6-(4-pyridin-3-yl-thiophen-2-yl)-4-trifluoromethyl-1,2-dihydro-pyridine-3-carbonitrile, 1-(2,4-Difluoro-benzyl)-2-oxo-6-(4-pyridin-4-yl-thiophen-2-yl)-4-trifluoromethyl-1,2-dihydro-pyridine-3-carbonitrile, 1-(2,4-Difluoro-benzyl)-6-[4-(1H-indol-5-yl)-thiophen-2-yl]-2-oxo-4-trifluoromethyl-1,2-dihydro-pyridine-3-carbonitrile, 1-(2,4-Difluoro-benzyl)-2-oxo-6-(5-pyridin-2-yl-thiophen-2-yl)-4-trifluoromethyl-1,2-dihydro-pyridine-3-carbonitrile, MS (ES+): 474.3 (M+H);

1-(2,4-Difluoro-benzyl)-6-[5-(6-methoxy-pyridin-3-yl)-thiophen-2-yl]-2-oxo-4-trifluoromethyl-1,2-dihydro-pyridine-3-carbonitrile, MS (ES+): 504.2 (M+H);

1-(2,4-Difluoro-benzyl)-6-[5-(2,4-dimethoxy-pyrimidin-5-yl)-thiophen-2-yl]-2-oxo-4-trifluoromethyl-1,2-dihydro-pyridine-3-carbonitrile, MS (ES+): 535 (M+H);

1-(2,4-Difluoro-benzyl)-2-oxo-6-(5-pyrimidin-5-yl-thiophen-2-yl)-4-trifluoromethyl-1,2-dihydro-pyridine-3-carbonitrile, MS (ES+): 475.2 (M+H);

6-[5-(2,6-Bis-trifluoromethyl-pyridin-4-yl)-thiophen-2-yl]-1-(2,4-difluoro-benzyl)-2-oxo-4-trifluoromethyl-1,2-dihydro-pyridine-3-carbonitrile, MS (ES+): 610.2 (M+H);

1-(2,4-Difluoro-benzyl)-6-[5-(6-ethoxy-5-trifluoromethyl-pyridin-3-yl)-thiophen-2-yl]-2-oxo-4-trifluoromethyl-1,2-dihydro-pyridine-3-carbonitrile, MS (ES+): 586.2 (M+H);

1-(2,4-Difluoro-benzyl)-6-[4-(6-ethoxy-5-trifluoromethyl-pyridin-3-yl)-thiophen-2-yl]-2-oxo-4-trifluoromethyl-1,2-dihydro-pyridine-3-carbonitrile, MS (ES+): 586.1 (M+H);

1-(2,4-Difluoro-benzyl)-6-[4-(6-methylsulfanyl-pyridin-3-yl)-thiophen-2-yl]-2-oxo-4-trifluoromethyl-1,2-dihydro-pyridine-3-carbonitrile, MS (ES+): 520.3 (M+H);

1-(2,4-Difluoro-benzyl)-6-[4-(6-methanesulfonyl-pyridin-3-yl)-thiophen-2-yl]-2-oxo-4-trifluoromethyl-1,2-dihydro-pyridine-3-carbonitrile, MS (ES+): 552.2 (M+H);

5-{5-[5-Cyano-1-(2,4-difluoro-benzyl)-6-oxo-4-trifluoromethyl-1,6-dihydro-pyridin-2-yl]-thiophen-2-yl}-2-ethoxy-nicotinonitrile, MS (ES+): 543.1 (M+H);

5-{5-[5-Cyano-1-(2,4-difluoro-benzyl)-6-oxo-4-trifluoromethyl-1,6-dihydro-pyridin-2-yl]-thiophen-3-yl}-2-ethoxy-nicotinonitrile, MS (ES+): 543.2 (M+H);

1-(2,4-Difluoro-benzyl)-6-[4-(6-ethoxy-pyridin-3-yl)-thiophen-2-yl]-2-oxo-4-trifluoromethyl-1,2-dihydro-pyridine-3-carbonitrile, MS (ES+): 518.3 (M+H);

1-(2,4-Difluoro-benzyl)-6-[5-(6-ethoxy-pyridin-3-yl)-thiophen-2-yl]-2-oxo-4-trifluoromethyl-1,2-dihydro-pyridine-3-carbonitrile, MS (ES+): 518.2 (M+H);

1-(2,4-Difluoro-benzyl)-6-[5-(6-isopropoxy-5-trifluoromethyl-pyridin-3-yl)-thiophen-2-yl]-2-oxo-4-trifluoromethyl-1,2-dihydro-pyridine-3-carbonitrile, MS (ES+): 600.2 (M+H);

1-(2,4-Difluoro-benzyl)-2-oxo-6-[5-(1-oxy-pyridin-4-yl)-thiophen-2-yl]-4-trifluoromethyl-1,2-dihydro-pyridine-3-carbonitrile, MS (ES+): 490.2 (M+H);

5-{5-[5-Cyano-1-(2,4-difluoro-benzyl)-6-oxo-4-trifluoromethyl-1,6-dihydro-pyridin-2-yl]-thiophen-2-yl}-2-ethoxy-nicotinic acid ethyl ester, MS (ES+): 590.1 (M+H);

1-(2,4-Difluoro-benzyl)-6-[4-(5-methyl-6-methylsulfanyl-pyridin-3-yl)-thiophen-2-yl]-2-oxo-4-trifluoromethyl-1,2-dihydro-pyridine-3-carbonitrile, MS (ES+): 534.1 (M+H);

1-(2,4-Difluoro-benzyl)-6-[5-(5-methyl-6-methylsulfanyl-pyridin-3-yl)-thiophen-2-yl]-2-oxo-4-trifluoromethyl-1,2-dihydro-pyridine-3-carbonitrile, MS (ES+): 534.2 (M+H);

1-(2,4-Difluoro-benzyl)-6-[4-(6-methanesulfonyl-5-methyl-pyridin-3-yl)-thiophen-2-yl]-2-oxo-4-trifluoromethyl-1,2-dihydro-pyridine-3-carbonitrile, MS (ES+): 566.1 (M+H);

1-(2,4-Difluoro-benzyl)-6-[5-(6-methanesulfonyl-5-methyl-pyridin-3-yl)-thiophen-2-yl]-2-oxo-4-trifluoromethyl-1,2-dihydro-pyridine-3-carbonitrile, MS (ES+): 566.2 (M+H);

5-{5-[5-Cyano-1-(2,4-difluoro-benzyl)-6-oxo-4-trifluoromethyl-1,6-dihydro-pyridin-2-yl]-thiophen-2-yl}-2-methylsulfanyl-nicotinic acid methyl ester, MS (ES+): 578.3 (M+H);

5-{5-[5-Cyano-1-(2,4-difluoro-benzyl)-6-oxo-4-trifluoromethyl-1,6-dihydro-pyridin-2-yl]-thiophen-3-yl}-2-methylsulfanyl-nicotinic acid methyl ester, MS (ES+): 578.2 (M+H);

5-{5-[5-Cyano-1-(2,4-difluoro-benzyl)-6-oxo-4-trifluoromethyl-1,6-dihydro-pyridin-2-yl]-thiophen-2-yl}-2-methanesulfonyl-nicotinic acid methyl ester, MS (ES+): 610.2 (M+H);

5-{5-[5-Cyano-1-(2,4-difluoro-benzyl)-6-oxo-4-trifluoromethyl-1,6-dihydro-pyridin-2-yl]-thiophen-3-yl}-2-methanesulfonyl-nicotinic acid methyl ester, MS (ES+): 610.3 (M+H);

1-(2,4-Difluoro-benzyl)-6-[5-(5-isopropenyl-6-methylsulfanyl-pyridin-3-yl)-thiophen-2-yl]-2-oxo-4-trifluoromethyl-1,2-dihydro-pyridine-3-carbonitrile, MS (ES+): 560.2 (M+H);

1-(2,4-Difluoro-benzyl)-6-[5-(5-isopropenyl-6-methanesulfonyl-pyridin-3-yl)-thiophen-2-yl]-2-oxo-4-trifluoromethyl-1,2-dihydro-pyridine-3-carbonitrile, MS (ES+): 592.2 (M+H);

1-(2-Fluoro-benzyl)-6-[5-(6-methanesulfonyl-5-methyl-pyridin-3-yl)-thiophen-2-yl]-2-oxo-4-trifluoromethyl-1,2-dihydro-pyridine-3-carbonitrile, MS (ES+): 548.3 (M+H);

1-(2,4-Difluoro-benzyl)-6-[5-(6-ethoxy-5-isopropenyl-pyridin-3-yl)-thiophen-2-yl]-2-oxo-4-trifluoromethyl-1,2-dihydro-pyridine-3-carbonitrile, MS (ES+): 558.3 (M+H);

1-(4-Ethyl-2-fluoro-benzyl)-6-[5-(6-methanesulfonyl-5-methyl-pyridin-3-yl)-thiophen-2-yl]-2-oxo-4-trifluoromethyl-1,2-dihydro-pyridine-3-carbonitrile, MS (ES+): 576.2 (M+H);

1-(2-Chloro-benzyl)-6-[5-(6-methanesulfonyl-5-methyl-pyridin-3-yl)-thiophen-2-yl]-2-oxo-4-trifluoromethyl-1,2-dihydro-pyridine-3-carbonitrile, MS (ES+): 564.1 (M+H);

1-(2,4-Difluoro-benzyl)-6-[4-(6-ethoxy-5-isopropenyl-pyridin-3-yl)-thiophen-2-yl]-2-oxo-4-trifluoromethyl-1,2-dihydro-pyridine-3-carbonitrile, MS (ES+): 558.2 (M+H);

1-(2,4-Difluoro-benzyl)-6-[5-(6-ethoxy-5-isopropyl-pyridin-3-yl)-thiophen-2-yl]-2-oxo-4-trifluoromethyl-1,2-dihydro-pyridine-3-carbonitrile, MS (ES+): 560.2 (M+H);

1-(2,4-Difluoro-benzyl)-6-[5-(6-ethylsulfanyl-5-methyl-pyridin-3-yl)-thiophen-2-yl]-2-oxo-4-trifluoromethyl-1,2-dihydro-pyridine-3-carbonitrile, MS (ES+): 548.2 (M+H);

1-(2,4-Difluoro-benzyl)-6-[4-(6-ethoxy-5-isopropyl-pyridin-3-yl)-thiophen-2-yl]-2-oxo-4-trifluoromethyl-1,2-dihydro-pyridine-3-carbonitrile, MS (ES+): 560.3 (M+H);

1-(2,4-Difluoro-benzyl)-6-[5-(5-isopropyl-6-methanesulfonyl-pyridin-3-yl)-thiophen-2-yl]-2-oxo-4-trifluoromethyl-1,2-dihydro-pyridine-3-carbonitrile, MS (ES+): 594.3 (M+H);

1-(2,4-Difluoro-benzyl)-6-[5-(6-ethanesulfonyl-5-methyl-pyridin-3-yl)-thiophen-2-yl]-2-oxo-4-trifluoromethyl-1,2-dihydro-pyridine-3-carbonitrile, MS (ES+): 580.4 (M+H);

1-(2,4-Difluoro-benzyl)-6-[4-(6-ethanesulfonyl-5-methyl-pyridin-3-yl)-thiophen-2-yl]-2-oxo-4-trifluoromethyl-1,2-dihydro-pyridine-3-carbonitrile, MS (ES+): 580.5 (M+H);

4-(1,1-Difluoro-propyl)-1-(2-fluoro-benzyl)-6-[5-(6-methanesulfonyl-5-methyl-pyridin-3-yl)-thiophen-2-yl]-2-oxo-1,2-dihydro-pyridine-3-carbonitrile, MS (ES+): 558.3 (M+H);

1-(2,4-Difluoro-benzyl)-6-[4-(6-ethylsulfanyl-5-methyl-pyridin-3-yl)-thiophen-2-yl]-2-oxo-4-trifluoromethyl-1,2-dihydro-pyridine-3-carbonitrile, MS (ES+): 548.2 (M+H);

1-(2,4-Difluoro-benzyl)-6-[5-(2-methanesulfonyl-6-trifluoromethyl-pyridin-4-yl)-thiophen-2-yl]-2-oxo-4-trifluoromethyl-1,2-dihydro-pyridine-3-carbonitrile, MS (ES+): 620.3 (M+H);

Acetic acid 1-(5-{5-[5-cyano-1-(2,4-difluoro-benzyl)-6-oxo-4-trifluoromethyl-1,6-dihydro-pyridin-2-yl]-thiophen-2-yl}-2-methanesulfonyl-pyridin-3-yl)-ethyl ester, MS (ES+): 638.2 (M+H);

1-(2,4-Difluoro-benzyl)-6-[5-(2-ethanesulfonyl-6-ethyl-pyridin-4-yl)-thiophen-2-yl]-2-oxo-4-trifluoromethyl-1,2-dihydro-pyridine-3-carbonitrile, MS (ES+): 594.2 (M+H);

1-(4-Chloro-benzyl)-6-[5-(6-methanesulfonyl-5-methyl-pyridin-3-yl)-thiophen-2-yl]-2-oxo-4-trifluoromethyl-1,2-dihydro-pyridine-3-carbonitrile, MS (ES+): 564 (M+H);

1-(2,4-Difluoro-benzyl)-6-{5-[5-(1-hydroxy-ethyl)-6-methanesulfonyl-pyridin-3-yl]-thiophen-2-yl}-2-oxo-4-trifluoromethyl-1,2-dihydro-pyridine-3-carbonitrile, MS (ES+): 596.2 (M+H);

1-(2,4-Difluoro-benzyl)-6-[5-(6-morpholin-4-yl-pyridin-3-yl)-thiophen-2-yl]-2-oxo-4-trifluoromethyl-1,2-dihydro-pyridine-3-carbonitrile, 6-[5-(2-Chloro-pyridin-4-yl)-thiophen-2-yl]-1-(2,4-difluoro-benzyl)-2-oxo-4-trifluoromethyl-1,2-dihydro-pyridine-3-carbonitrile, MS (ES+): 508.1 (M+H);

1-(4-Chloro-benzyl)-6-[5-(3-ethanesulfonyl-phenyl)-thiophen-2-yl]-2-oxo-4-trifluoromethyl-1,2-dihydro-pyridine-3-carbonitrile, MS (ES+): 563.2 (M+H);

1-(2,4-Difluoro-benzyl)-2-oxo-6-[5-(6-piperazin-1-yl-pyridin-3-yl)-thiophen-2-yl]-4-trifluoromethyl-1,2-dihydro-pyridine-3-carbonitrile, MS (ES+): 558.2 (M+H);

1-(2,4-Difluoro-benzyl)-2-oxo-6-[4-(6-piperazin-1-yl-pyridin-3-yl)-thiophen-2-yl]-4-trifluoromethyl-1,2-dihydro-pyridine-3-carbonitrile, MS (ES+): 558.3 (M+H);

1-(2,4-Difluoro-benzyl)-6-[4-(6-morpholin-4-yl-pyridin-3-yl)-thiophen-2-yl]-2-oxo-4-trifluoromethyl-1,2-dihydro-pyridine-3-carbonitrile, MS (ES+): 559.3 (M+H);

6-(4-Benzo[1,3]dioxol-5-yl-thiophen-2-yl)-1-(2,4-difluoro-benzyl)-2-oxo-4-trifluoromethyl-1,2-dihydro-pyridine-3-carbonitrile, 6-(5-Benzo[1,3]dioxol-5-yl-thiophen-2-yl)-1-(2,4-difluoro-benzyl)-2-oxo-4-trifluoromethyl-1,2-dihydro-pyridine-3-carbonitrile, MS (ES+): 516.7 (M+H);

1-(2,4-Difluoro-benzyl)-6-[5-(2,3-dihydro-benzo[1,4]dioxin-6-yl)-thiophen-2-yl]-2-oxo-4-trifluoromethyl-1,2-dihydro-pyridine-3-carbonitrile, MS (ES+): 531.3 (M+H);

1-(2,4-Difluoro-benzyl)-6-[5-(2,3-dihydro-benzofuran-5-yl)-thiophen-2-yl]-2-oxo-4-trifluoromethyl-1,2-dihydro-pyridine-3-carbonitrile, MS (ES+): 515.3 (M+H);

1-(2,4-Difluoro-benzyl)-6-[4-(2,3-dihydro-benzofuran-5-yl)-thiophen-2-yl]-2-oxo-4-trifluoromethyl-1,2-dihydro-pyridine-3-carbonitrile;

1-(2,4-Dichloro-benzyl)-6-[5-(4-methyl-naphthalen-1-yl)-thiophen-2-yl]-2-oxo-4-trifluoromethyl-1,2-dihydro-pyridine-3-carbonitrile, 1-(2,4-Difluoro-benzyl)-6-(5-naphthalen-2-yl-thiophen-2-yl)-2-oxo-4-trifluoromethyl-1,2-dihydro-pyridine-3-carbonitrile, MS (ES+): 523.2 (M+H);

1-(2,4-Difluoro-benzyl)-6-(5-naphthalen-1-yl-thiophen-2-yl)-2-oxo-4-trifluoromethyl-1,2-dihydro-pyridine-3-carbonitrile, MS (ES+): 523.3 (M+H);

6-(1-Benzyl-1H-pyrazol-4-yl)-1-(2,4-difluoro-benzyl)-2-oxo-4-trifluoromethyl-1,2-dihydro-pyridine-3-carbonitrile, MS (ES+): 471.2 (M+H);

1-(2,4-Difluoro-benzyl)-2-oxo-6-(1-phenyl-1H-pyrazol-4-yl)-4-trifluoromethyl-1,2-dihydro-pyridine-3-carbonitrile, MS (ES+): 456.8 (M+H);

1-(2,4-Difluoro-benzyl)-6-(3,5-dimethyl-1-phenyl-1H-pyrazol-4-yl)-2-oxo-4-trifluoromethyl-1,2-dihydro-pyridine-3-carbonitrile, MS (ES+): 485.2 (M+H);

1-(2,4-Difluoro-benzyl)-2-oxo-6-(1-phenyl-5-trifluoromethyl-1H-pyrazol-4-yl)-4-trifluoromethyl-1,2-dihydro-pyridine-3-carbonitrile, MS (ES+): 525.1 (M+H);

1-(2,4-Difluoro-benzyl)-6-(5-methyl-1-phenyl-1H-pyrazol-4-yl)-2-oxo-4-trifluoromethyl-1,2-dihydro-pyridine-3-carbonitrile, MS (ES+): 471.2 (M+H);

1-(2,4-Dichloro-benzyl)-6-[1-benzyl-1H-pyrazol-4-yl]-2-oxo-4-trifluoromethyl-1,2-dihydro-pyridine-3-carbonitrile;

1-(2,4-Difluoro-benzyl)-6-[1-(4-methoxy-benzyl)-1H-pyrazol-4-yl]-2-oxo-4-trifluoromethyl-1,2-dihydro-pyridine-3-carbonitrile, MS (ES+): 501.3 (M+H);

6-[1-(3-Cyano-4-trifluoromethyl-phenyl)-1H-pyrazol-4-yl]-1-(2,4-difluoro-benzyl)-2-oxo-4-trifluoromethyl-1,2-dihydro-pyridine-3-carbonitrile, MS (ES+): 550.1 (M+H);

6-[1-(3-Chloro-4-cyano-phenyl)-1H-pyrazol-4-yl]-1-(2,4-difluoro-benzyl)-2-oxo-4-trifluoromethyl-1,2-dihydro-pyridine-3-carbonitrile, MS (ES+): 516.1 (M+H);

6-[1-(3-Chloro-4-ethoxy-phenyl)-1H-pyrazol-4-yl]-1-(2,4-difluoro-benzyl)-2-oxo-4-trifluoromethyl-1,2-dihydro-pyridine-3-carbonitrile, MS (ES+): 535.1 (M+H);

1-(2,4-Difluoro-benzyl)-6-[1-(4-methanesulfonyl-phenyl)-1H-pyrazol-4-yl]-2-oxo-4-trifluoromethyl-1,2-dihydro-pyridine-3-carbonitrile, MS (ES+): 535 (M+H);

1-(2,4-Difluoro-benzyl)-6-[1-(3,4-dimethoxy-phenyl)-1H-pyrazol-4-yl]-2-oxo-4-trifluoromethyl-1,2-dihydro-pyridine-3-carbonitrile, MS (ES+): 517.1 (M+H);

6-[1-(4-Cyano-3-trifluoromethyl-phenyl)-1H-pyrazol-4-yl]-1-(2,4-difluoro-benzyl)-2-oxo-4-trifluoromethyl-1,2-dihydro-pyridine-3-carbonitrile, MS (ES+): 550.3 (M+H);

1-(2,4-Difluoro-benzyl)-2-oxo-4-trifluoromethyl-6-[1-(6-trifluoromethyl-pyridin-2-yl)-1H-pyrazol-4-yl]-1,2-dihydro-pyridine-3-carbonitrile, MS (ES+): 526.3 (M+H); and 1-(2,4-Difluoro-benzyl)-2-oxo-4-trifluoromethyl-6-[1-(5-trifluoromethyl-pyridin-2-yl)-1H-pyrazol-4-yl]-1,2-dihydro-pyridine-3-carbonitrile, MS (ES+): 526.3 (M+H).

Example 7

FRET Coactivator Assay

The FRET coactivator assay measures the ability of LXR ligands to promote protein-protein interactions between the ligand binding domain (LBD) of LXR and transcriptional coactivator proteins. The assay involves the use a recombinant Glutathione-S-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought into close proximity to the allophycocyanin moiety there is little or no energy transfer and excitation of the europium chelate results in emission at 615 nm. Thus the intensity of light emitted at 665 nm gives an indication of the strength of the protein-protein interaction.

Required Materials:

1. Partially purified recombinant protein comprising glutathione-S-transferase fused in frame to the LXR-ligand binding domain (comprising amino acids 188-447 of human LXRα, or amino acids 198-461 of human LXRβ).

2. Biotinylated peptide containing a SRC-1 LXXLL receptor interaction motif (B-SRC-1)

3. Anti-GST antibody conjugated to an Europium chelate (αGST-K) (From Wallac/PE Life Sciences Cat# AD0064)

4. Streptavidin linked allophycocyanin (SA-APC) (From Wallac/PE Life Sciences CAT# AD0059A)

5. 1×FRET Buffer: (20 mM $KH_2PO_4/K_2HPO_4$ pH 7.3, 150 mM NaCl, 2.5 mM CHAPS, 2 mM EDTA, 1 mM DTT (add fresh))

6. 96 well or 384 well black multiwell plates (from LJL)

Stock Solutions:
0.5 M $KH_2PO_4/K_2HPO_4$: pH 7.3
5 M NaCl
80 mM (5%) CHAPS
0.5 M EDTA pH 8.0
1 M DTT (keep at −20° C.)

Preparation of Screening Reagents:

Prepare reaction mixture for the appropriate number of wells by combining the following reagents 5 nM/well GST-hLXRαLBD, 5 nM/well GST-hLXRβLBD, 5 nM/well Anti-GST antibody (Eu), 12 nM/well biotin-SRC-1 peptide, 12 nM/well APC-SA adjust the volume to 10 µL/well with 1×-FRET buffer.

Procedure:

Add 0.5 µL of a 1 mM stock compound (for approx. 10 µM final concentration) or solvent to each well in a 96 well or 384 well black plate (LJL).

Add 10 µl reaction mixture (prepared above) to each well of the multiwell plate.

Incubate covered or in the dark (the APC is light sensitive) at ambient temperature for 1-4 hours. After this time if reactions are not read they can be stored at 4° C. for several more hours without too much loss of signal.

Read the plate using an LJL Analyst, or similar instrument, using the following conditions:

Channel 1: Excitation is 330 nm and emission is 615. This is for Eu chelate

Channel 2: Excitation is 330 nm and emission is 665. This is for APC

For channel 1: Flashes per well=100; Integration time=1000 µs; interval between flashes=1×10 ms; Delay after flash=200 µs For channel 2: Flashes per well=100; Integration time=100 µs; interval between flashes=1×10 ms; Delay after flashes=65 µs Example 8

Scintillation Proximity Assay (SPA)

The SPA assay measures the radioactive signal generated by the binding of $^3$H-24,25-epoxycholesterol to LXRα or LXRβ. The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

Required Materials:
1. Label: $^3$H-24,25-epoxy-cholesterol (Amersham)
2. LXRα lysate: Baculovirus expressed LXRα/RXR heterodimer with RXR having a 6-HIS tag produced as a crude lysate
3. LXRβ lysate: Baculovirus expressed LXR/RXR heterodimer with RXR having a 6-HIS tag produced as a crude lysate
4. SPA beads: Ysi copper His-tag SPA beads (Amersham)
5. Plates: Non-binding surface 96-well plate (Corning)
6. Protein lysate dilution buffer: (20 mM Tris-HCl pH 7.9, 500 mM NaCl, 5 mM Imidazole).
7. 2×SPA Buffer: (40 mM $K_2HPO_4/KH_2PO_4$ pH 7.3, 100 mM NaCl, 0.05% Tween 20, 20% Glycerol, 4 mM EDTA)
8. 2×SPA Buffer w/o EDTA: (40 mM $K_2HPO_4/KH_2PO_4$ pH 7.3, 100 mM NaCl, 0.05% Tween 20, 20% Glycerol)

Stock Solutions
0.5 M $K_2HPO_4/KH_2PO_4$ pH 7.3
0.5 M EDTA pH 8.0
5 M NaCl
10% Tween-20
Glycerol Preparation of Protein Lysates Baculovirus expression plasmids for human RXR α (accession No NM_002957), LXRα (accession No U22662), LXRβ (accession No U07132) were made by cloning the appropriate full-length cDNAs into the pBacPakhis1 vector (Clontech, CA) following standard procedures. Insertion of the cDNAs into the pBAcPakhis1 vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately $1.25 \times 10^6$/ml at 27° C., in a total volume of 500 mL per 1 L sized spinner flasks, cultured under standard conditions. To prepare LXRα lysate, insect cells were co-transfected with the LXRα expression cassette at an M.O.I of 0.5 to 0.8 and with the RXR expression cassette at a M.O.I. of approximately 1.6. To prepare LXRβ lysate, insect cells were co-transfected with the LXRβ expression cassette at an M.O.I of approximately 1.6 and with the RXR expression cassette at a M.O.I. of approximately 1.6. In both cases cells were incubated for 48 hours at 27° C. with constant shaking prior to harvesting.

After incubation, cells were harvested by centrifugation and pelleted. Cell pellets were resuspended in two volumes of ice-cold freshly prepared extraction buffer (20 mM Tris pH 8.0, 10 mM Imidazole, 400 mM NaCl, containing one EDTA free protease inhibitor tablet (Roche Catalog No: 1836170) per 10 ml of extraction buffer).

Cells were homogenized slowly on ice using a Douncer to achieve 80-90% cell lysis. The homogenate was centrifuged in a pre-chilled rotor (Ti50 or Ti70, or equivalent) at 45,000 rpm for 30 minutes at 4° C. Aliquots of the supernatant were frozen on dry ice and stored frozen at −80° C. until quantification and quality control. Aliquots of the lysates were tested in the SPA assay to ensure lot to lot consistency, and via SDS-PAGE analysis after purification using Ni-NTA Resin (Qiagen) and adjusted for protein concentration and expression level prior to use in screening assays.

Preparation of Screening Reagents

[$^3$H] 24,25 Epoxycholesterol (EC) solution: For a single 384-well plate (or 400 wells), 21 μL of [$^3$H] EC (specific activity 76.5 Ci/mmol, concentration 3.2 mCi/mL) was added to 4.4 mL of 2×SPA buffer to provide for a final concentration of 200 nM. For each additional 384-well plate, an additional 19.1 μL of [$^3$H] EC was added to 4.0 mL of additional 2×SPA buffer. The final concentration of [$^3$H] EC in the well was 50 nM.

LXRα lysate (prepared as above) was diluted with protein lysate dilution buffer. 1400 μL of diluted LXRα lysate was prepared per 384-well plate, (or 200 wells) and 1120 μL of diluted LXRα lysate was prepared for each additional 384-well plate.

LXRβ lysate (prepared as above) was diluted with protein lysate dilution buffer. 1400 μL of diluted LXRβ lysate was prepared per 384-well plate, (or 200 wells) and 1120 μL of diluted LXRβ lysate was prepared for each additional 384-well plate.

SPA bead solution: For a 384-well plate (or 400 wells), 3.75 mL of 2×SPA buffer w/o EDTA, 2.25 mL of $H_2O$, and 1.5 mL of Ysi His-tag SPA beads (vortex well before taking) were mixed together. For each additional 384-well plate, an additional 3.5 mL of 2×SPA buffer w/o EDTA, 2.1 mL of $H_2O$, and 1.4 mL of Ysi His-tag SPA beads were mixed together.

Procedure:

Appropriate dilutions of each compound were prepared and pipetted into the appropriate wells of a multiwell plate.

9.1 μL of [$^3$H] EC was added to each well of column 2-23 of the multiwell plate.

5 μl of diluted LXRα lysate was added to each well of column 2-23 on odd rows of the multiwell plate.

5 μL of diluted LXRβ lysate was added to each well of column 2-23 on even rows of the multiwell plate.

17.5 μL of SPA bead solution was added to each well of column 2-23 of the multiwell plate.

The plates were covered with clear sealer and placed in an incubator at ambient temperature for 1 hour.

After incubation plates were analyzed using a luminescent plate reader (MicroBeta, Wallac) using the program n ABASE 3H_384DPM. The setting for n ABASE 3H_384DPM was:
Counting Mode: DPM
Sample Type: SPA
ParaLux Mode: low background
Count time: 30 sec.

Assays for LXRα and LXRβ were performed in the identical manner. The determined Ki represents the average of at least two independent dose response experiments. The binding affinity for each compound may be determined by non-linear regression analysis using the one site competition formula to determine the $IC_{50}$ where:

$$Y = \text{Bottom} + \frac{(\text{Top} - \text{Bottom})}{(1 + 10^{X - \log IC_{50}})}$$

The Ki is than calculated using the Cheng and Prusoff equation where:

$$Ki = IC_{50}/(1+[\text{Concentration of Ligand}]/Kd \text{ of Ligand})$$

For this assay, typically the Concentration of Ligand=50 nM and the Kd of EC for the receptor is 200 nM as determined by saturation binding.

The compounds of the invention demonstrated the ability to bind to LXRα and/or LXRβ when tested in this assay.

Example 15

Co-Transfection Assay

To measure the ability of compounds to activate or inhibit the transcriptional activity of LXR in a cell based assay, the co-transfection assay was used. It has been shown that LXR functions as a heterodimer with RXR. For the co-transfection assay, expression plasmids for LXR and RXR are introduced via transient transfection into mammalian cells along with a luciferase reporter plasmid that contains one copy of a DNA sequence that is bound by LXR-RXR heterodimers (LXRE; Willy, P. et al. 1995). Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

Required Materials
1. CV-1 African Green Monkey Kidney Cells
2. Co-transfection expression plasmids, comprising full-length LXRα (pCMX-hLXR α), LXRβ (pCMX-hLXR β), or RXRα (pCMX-RXR), reporter plasmid (LXREx1-Tk-Luciferase), and control (pCMX-Galactosidase expression vector) (Willey et al. Genes & Development 9 1033-1045 (1995)).
3. Transfection reagent such as FuGENE6 (Roche).
4. 1× Cell lysis buffer (1% Triton X 100 (JT Baker X200-07), 10% Glycerol (JT Baker M778-07), 5 mM Ditriotreitol (Quantum Bioprobe DTT03; add fresh before lysing), 1 mM EGTA (Ethylene Glycol-bis(B-Amino ethyl ether)-N,N,N', N'-Tetracetic Acid) (Sigma E-4378), 25 mM Tricine (ICN 807420) pH 7.8)
5. 1× Luciferase assay buffer (pH at 7.8) (0.73 mM ATP, 22.3 mM Tricine, 0.11 mM EDTA, 33.3 mM DTT)
6. 1× Luciferrin/CoA (11 mM Luciferin, 3.05 mM Coenzyme A, 10 mM HEPES)

Preparation of Screening Reagents

CV-1 cells were prepared 24 hours prior to the experiment by plating them into T-175 flasks or 500 cm$^2$ dishes in order to achieve 70-80% confluency on the day of the transfection. The number of cells to be transfected was determined by the number of plates to be screened. Each 384 well plate requires 1.92×106 cells or 5000 cells per well. DNA Transfection Reagent was prepared by mixing the required plasmid DNAs with a cationic lipid transfection reagent FuGENE6 (Roche) by following the instructions provided with the reagents. Optimal DNA amounts were determined empirically per cell line and size of vessel to be transfected. 10-12 mL of media was added to the DNA Transfection Reagent and this mixture was added to the cells after aspirating media from the T175 cm$^2$ flask. Cells were then incubated at least 5 hours at 37° C. to prepare screening cells.

Luciferase assay reagent was prepared by combining before use (per 10 mL):
  10 mL 1× Luciferase assay buffer
  0.54 mL of 1× Luciferrin/CoA
  0.54 mL of 0.2 M Magnesium sulfate Procedure Assay plates were prepared by dispensing 5 μL of compound per well of a 384 well plate to achieve final compound concentration of 10 μM and no more than 1% DMSO. Media was removed from the screening cells, the cells trypsinized, harvested cells by centrifugation, counted, and plated at a density of approximately 5000 cells per well in the 384 well assay plate prepared above in a volume of about 45 μL. Assay plates containing both compounds and screening cells (50 μL in total volume) were incubated for 20 hours at 37° C.

After incubation with compounds, media was removed from the cells and lysis buffer (30 μL/well) added. After 30 minutes at ambient temperature, luciferase assay buffer (30 μL/well) was added and the assay plates read on a luminometer (PE Biosystems Northstar reader with on-board injectors, or equivalent). Plates were read immediately after addition of luciferase assay buffer.

The LXR/LXRE co-transfection assay can be used to establish the $EC_{50}/IC_{50}$ values for potency and percent activity or inhibition for efficacy. Efficacy defines the activity of a compound relative to a high control ((N-(3-((4-fluorophenyl)-(naphthalene-2-sulfonyl)amino)propyl)-2,2-dimethyl-propionamide)) or a low control (DMSO/vehicle). The dose response curves are generated from an 8 point curve with concentrations differing by ½ LOG units. Each point represents the average of 4 wells of data from a 384 well plate.

The data from this assay is fitted to the following equation, from the $EC_{50}$ value may be solved:

$$Y = \text{Bottom} + (\text{Top} - \text{Bottom})/(1 + 10^{((logEC50-X)*HillSlope)})$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by ((N-(3-((4-fluorophenyl)-(naphthalene-2-sulfonyl)-amino)propyl)-2,2-dimethyl-propionamide) that is measured individually in each dose response experiment.

For the antagonist assay, a LXR agonist can be added to each well of a 384 well plate to elicit a response. The % inhibition for each antagonist is therefore a measurement of the inhibition of the activity of the agonist. In this example, 100% inhibition would indicate that the activity of a specific concentration of LXR agonist has been reduced to baseline levels, defined as the activity of the assay in the presence of DMSO only.

Compounds of the invention, when tested in this assay, demonstrated the ability to modulate the activity of LXRα and/or LXRβ.

Example 16

In Vivo Studies

In order to evaluate direct regulation of key target genes by the compounds of the invention, animals are administered a single oral dose of the test compound and tissues collected at six or fifteen hours after dose. Male C57BL/6 mice (n=8) are dosed by oral gavage with vehicle or compound. At six and fifteen hours after the dose, animals are bled via the retro orbital sinus for plasma collection. Animals are then euthanized and tissues, such as liver and intestinal mucosa are collected and snap frozen for further analysis. Plasma is analyzed for a lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα-/- or LXRβ-/-) and C57BL/6 wild-type controls are used in this same protocol.

Plasma Lipid Evaluation:

To compare the effects of compounds on plasma cholesterol and triglycerides, animals are dosed with compound for one week and plasma lipid levels are monitored throughout the study. Male C57BL/6 mice (n=8) are dosed daily by oral gavage with vehicle or compound. Plasma samples are taken on day −1 (in order to group animals), day 1, 3, and 7. Samples are collected three hours after the daily dose. On day 7 of the study, following plasma collection, animals are euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα−/− or LXRβ−/−) and C57BL/6 wild-type controls are used in this same protocol.

Cholesterol Absorption:

Evaluation of compounds to inhibit cholesterol absorption is done via measurement of labeled cholesterol in feces. Male A129 mice (n=7) are dosed daily by oral gavage with vehicle or compound for 7 days. On day 7 of the study, animals are administered [$^{14}$C]-cholesterol and [$^{3}$H]-sitostanol by oral gavage. Animals are individually housed on wire racks for the next 24 hours in order to collect feces. Feces are then dried and ground to a fine powder. Labeled cholesterol and sitostanol are extracted from the feces and ratios of the two are counted on a liquid scintillation counter in order to evaluate the amount of cholesterol absorbed by the individual animal.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following formula (II):

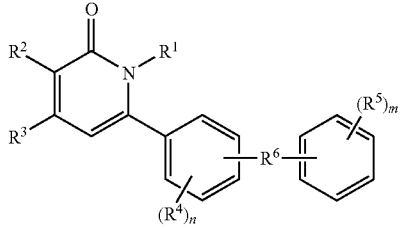

wherein:
n is 0 to 4;
m is 0 to 5;
$R^1$ is hydrogen, aralkyl or heteroarylalkyl;
$R^2$ is hydrogen, cyano or —$R^7$—N($R^8$)$_2$;
$R^3$ is haloalkyl;
each $R^4$ is independently halo, alkyl or haloalkyl;
each $R^5$ is independently selected from the group consisting of halo, nitro, alkyl, alkenyl, aryl, aralkyl, aralkenyl, haloalkyl, haloalkenyl, cycloalkyl, cycloalkylalkyl, heterocyclyl, heterocyclylalkyl, heteroaryl, heteroarylalkyl, —$R^7$—CN, —$R^7$—N($R^8$)$_2$, —$R^7$—$OR^8$, —$R^7$—O—$R^9$—C(O)$OR^8$, —$R^7$—C(O)$R^{11}$, —$R^7$—C(O)$OR^8$, —$R^7$—C(O)N($R^8$)$_2$, —$R^7$—C(O)N($R^8$)$OR^8$, —$R^7$—C(O)N($R^8$)N($R^8$)$_2$, —$R^7$—C(O)N($R^8$)—$R^9$—C(O)$OR^8$, —$R^7$—C(S)N($R^8$)$_2$, —$R^7$—N($R^8$)C(O)$OR^{10}$, —$R^7$—S(O)$_t R^8$ (where t is 0 to 2) and —$R^7$—S(O)$_2$N($R^8$)$_2$;
$R^6$ is —$OR^7$—, a direct bond, a straight or branched alkylene chain, a straight or branched alkenylene chain or a straight or branched alkynylene chain;
each $R^7$ is independently selected from a direct bond, a straight or branched alkylene chain or a straight or branched alkenylene chain;
each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl;
each $R^9$ is independently selected from a straight or branched alkylene chain or a straight or branched alkenylene chain;
$R^{10}$ is alkyl, aryl, aralkyl or cycloalkylalkyl; and
$R^{11}$ is hydrogen, alkyl, aryl, aralkyl, cycloalkyl, cycloalkylalkyl, heterocyclyl, heterocyclylalkyl, heteroaryl or heterarylalkyl;
as a stereoisomer, a mixture of stereoisomers, a racemic mixture of stereoisomers, or as a tautomer;
or as a pharmaceutically acceptable salt thereof.

2. The compound of claim 1 wherein:
n is 0 or 1;
m is 0 to 2;
$R^1$ is aralkyl or heteroarylalkyl;
$R^2$ is cyano;
$R^3$ is haloalkyl;
$R^4$ is halo, alkyl or haloalkyl;
each $R^5$ is independently selected from the group consisting of halo, nitro, alkyl, alkenyl, haloalkyl, heterocyclyl, heteroaryl, —$R^7$—CN, —$R^7$—N($R^8$)$_2$, —$R^7$—$OR^8$, —$R^7$—O—$R^9$—C(O)$OR^8$, —$R^7$—C(O)$R^{11}$, —$R^7$—C(O)$OR^8$, —$R^7$—C(O)N($R^8$)$_2$, —$R^7$—C(O)N($R^8$)$OR^8$, —$R^7$—C(O)N($R^8$)N($R^8$)$_2$, —$R^7$—C(O)N($R^8$)—$R^9$—C(O)$OR^8$, —$R^7$—C(S)N($R^8$)$_2$, —$R^7$—N($R^8$)C(O)$OR^{10}$, —$R^7$—S(O)$_t R^8$ (where t is 0 to 2) and —$R^7$—S(O)$_2$N($R^8$)$_2$;
$R^6$ is —$OR^7$—, a direct bond, a straight or branched alkenylene chain or a straight or branched alkynylene chain;
each $R^7$ is independently selected from a direct bond or a straight or branched alkylene chain;
each $R^8$ is independently selected from hydrogen, alkyl, alkenyl, haloalkyl, haloalkenyl, aryl, aralkyl, aralkenyl, cycloalkyl, cycloalkylalkyl, heterocyclyl, heterocyclylalkyl, heteroaryl or heteroarylalkyl;
each $R^9$ is a straight or branched alkylene chain optionally substituted by aryl or heteroaryl;
$R^{10}$ is alkyl, aryl, aralkyl or cycloalkylalkyl; and
$R^{11}$ is hydrogen, alkyl, aryl, aralkyl, cycloalkyl, cycloalkylalkyl, heterocyclyl, heterocyclylalkyl, heteroaryl or heterarylalkyl.

3. The compound of claim 2 wherein $R^6$ is —$OR^7$—.

4. The compound of claim 3 wherein $R^1$ is aralkyl optionally substituted with one or more substituents independently selected from alkyl, halo or haloalkyl.

5. The compound of claim 4 wherein
n is 0 or 1;
m is 0 to 2;
$R^2$ is cyano;
$R^3$ is trifluoromethyl;
$R^4$ is methyl, 1-methylethyl or chloro;
each $R^5$ is independently selected from the group consisting of halo, alkyl, alkenyl or haloalkyl.

6. The compound of claim 5 wherein each $R^5$ is independently selected from chloro, bromo, fluoro, methyl, ethyl, 1-methylethyl, 1,1-dimethylethyl, ethenyl or trifluoromethyl.

7. The compound of claim 6 selected from the group consisting of the following:

1-(2,4-Dimethyl-benzyl)-6-[4-(3-isopropyl-phenoxy)-3-methyl-phenyl]-2-oxo-4-trifluoromethyl-1,2-dihydro-pyridine-3-carbonitrile;

6-[4-(4-tert-Butyl-phenoxy)-3-methyl-phenyl]-1-(2,4-dimethyl-benzyl)-2-oxo-4-trifluoromethyl-1,2-dihydro-pyridine-3-carbonitrile;

1-(2,4-Dimethyl-benzyl)-6-[4-(4-fluoro-phenoxy)-3-methyl-phenyl]-2-oxo-4-trifluoromethyl-1,2-dihydro-pyridine-3-carbonitrile;

1-(2,4-Dimethyl-benzyl)-6-[4-(2,4-dimethyl-phenoxy)-3-methyl-phenyl]-2-oxo-4-trifluoromethyl-1,2-dihydro-pyridine-3-carbonitrile;

1-(2,4-Dimethyl-benzyl)-6-[4-(2,5-dimethyl-phenoxy)-3-methyl-phenyl]-2-oxo-4-trifluoromethyl-1,2-dihydro-pyridine-3-carbonitrile;

1-(2,4-Dimethyl-benzyl)-6-[4-(2,6-dimethyl-phenoxy)-3-methyl-phenyl]-2-oxo-4-trifluoromethyl-1,2-dihydro-pyridine-3-carbonitrile;

6-[4-(2-Chloro-phenoxy)-3-methyl-phenyl]-1-(2,4-dimethyl-benzyl)-2-oxo-4-trifluoromethyl-1,2-dihydro-pyridine-3-carbonitrile;

6-[4-(3-Chloro-phenoxy)-3-methyl-phenyl]-1-(2,4-dimethyl-benzyl)-2-oxo-4-trifluoromethyl-1,2-dihydro-pyridine-3-carbonitrile;

1-(2,4-Dimethyl-benzyl)-6-[3-methyl-4-(2-trifluoromethyl-phenoxy)-phenyl]-2-oxo-4-trifluoromethyl-1,2-dihydro-pyridine-3-carbonitrile;

1-(2,4-Dimethyl-benzyl)-6-[3-methyl-4-(3-trifluoromethyl-phenoxy)-phenyl]-2-oxo-4-trifluoromethyl-1,2-dihydro-pyridine-3-carbonitrile;

6-[4-(3-Bromo-phenoxy)-phenyl]-1-(2,4-dimethyl-benzyl)-2-oxo-4-trifluoromethyl-1,2-dihydro-pyridine-3-carbonitrile;
6-[4-(4-Bromo-phenoxy)-phenyl]-1-(2,4-dimethyl-benzyl)-2-oxo-4-trifluoromethyl-1,2-dihydro-pyridine-3-carbonitrile;
6-[4-(3-Benzyloxy-phenoxy)-phenyl]-1-(2,4-dimethyl-benzyl)-2-oxo-4-trifluoromethyl-1,2-dihydro-pyridine-3-carbonitrile;
1-(2,4-Dimethyl-benzyl)-6-[4-(2,4-dimethyl-phenoxy)-phenyl]-2-oxo-4-trifluoromethyl-1,2-dihydro-pyridine-3-carbonitrile;
6-[4-(3,5-Bis-trifluoromethyl-phenoxy)-phenyl]-1-(2,4-dimethyl-benzyl)-2-oxo-4-trifluoromethyl-1,2-dihydro-pyridine-3-carbonitrile;
6-(4-Benzyloxy-phenyl)-1-(2,4-dichloro-benzyl)-2-oxo-4-trifluoromethyl-1,2-dihydro-pyridine-3-carbonitrile;
1-(2,4-Dichloro-benzyl)-2-oxo-6-(4-phenoxy-phenyl)-4-trifluoromethyl-1,2-dihydro-pyridine-3-carbonitrile;
1-(2,4-Difluoro-benzyl)-2-oxo-6-(4-phenoxy-phenyl)-4-trifluoromethyl-1,2-dihydro-pyridine-3-carbonitrile;
1-(2-Chloro-4-fluoro-benzyl)-2-oxo-6-(4-phenoxy-phenyl)-4-trifluoromethyl-1,2-dihydro-pyridine-3-carbonitrile;
6-(4-Benzyloxy-phenyl)-1-(2-chloro-4-fluoro-benzyl)-2-oxo-4-trifluoromethyl-1,2-dihydro-pyridine-3-carbonitrile;
1-(2,4-Dichloro-benzyl)-2-oxo-4-pentafluoroethyl-6-(4-phenoxy-phenyl)-1,2-dihydro-pyridine-3-carbonitrile;
1-(2,4-Dimethyl-benzyl)-6-(3-isopropyl-4-phenoxy-phenyl)-2-oxo-4-trifluoromethyl-1,2-dihydro-pyridine-3-carbonitrile;
1-(2,4-Dimethyl-benzyl)-6-(3-isopropyl-4-o-tolyloxy-phenyl)-2-oxo-4-trifluoromethyl-1,2-dihydro-pyridine-3-carbonitrile;
1-(2,4-Dimethyl-benzyl)-6-[4-(2-ethyl-phenoxy)-3-isopropyl-phenyl]-2-oxo-4-trifluoromethyl-1,2-dihydro-pyridine-3-carbonitrile;
1-(2,4-Dimethyl-benzyl)-6-[4-(2,5-dimethyl-phenoxy)-3-isopropyl-phenyl]-2-oxo-4-trifluoromethyl-1,2-dihydro-pyridine-3-carbonitrile;
1-(2,4-Dimethyl-benzyl)-6-[4-(2,4-dimethyl-phenoxy)-3-isopropyl-phenyl]-2-oxo-4-trifluoromethyl-1,2-dihydro-pyridine-3-carbonitrile;
1-(2,4-Dimethyl-benzyl)-6-[4-(3,4-dimethyl-phenoxy)-3-isopropyl-phenyl]-2-oxo-4-trifluoromethyl-1,2-dihydro-pyridine-3-carbonitrile;
1-(2,4-Dimethyl-benzyl)-6-(3-isopropyl-4-m-tolyloxy-phenyl)-2-oxo-4-trifluoromethyl-1,2-dihydro-pyridine-3-carbonitrile;
1-(2,4-Dimethyl-benzyl)-6-[3-isopropyl-4-(3-isopropyl-phenoxy)-phenyl]-2-oxo-4-trifluoromethyl-1,2-dihydro-pyridine-3-carbonitrile;
1-(2,4-Dimethyl-benzyl)-6-[3-isopropyl-4-(4-isopropyl-phenoxy)-phenyl]-2-oxo-4-trifluoromethyl-1,2-dihydro-pyridine-3-carbonitrile;
1-(2,4-Dimethyl-benzyl)-6-(3-isopropyl-4-p-tolyloxy-phenyl)-2-oxo-4-trifluoromethyl-1,2-dihydro-pyridine-3-carbonitrile;
6-[4-(4-tert-Butyl-phenoxy)-3-isopropyl-phenyl]-1-(2,4-dimethyl-benzyl)-2-oxo-4-trifluoromethyl-1,2-dihydro-pyridine-3-carbonitrile;
1-(2,4-Dimethyl-benzyl)-6-[3-isopropyl-4-(4-vinyl-phenoxy)-phenyl]-2-oxo-4-trifluoromethyl-1,2-dihydro-pyridine-3-carbonitrile;
1-(2,4-Dimethyl-benzyl)-6-[4-(4-ethyl-2-methyl-phenoxy)-3-methyl-phenyl]-2-oxo-4-trifluoromethyl-1,2-dihydro-pyridine-3-carbonitrile;
1-(2,4-Dimethyl-benzyl)-6-[4-(4-ethyl-2-methyl-phenoxy)-3-isopropyl-phenyl]-2-oxo-4-trifluoromethyl-1,2-dihydro-pyridine-3-carbonitrile;
1-(2,4-Dimethyl-benzyl)-6-[4-(2-ethyl-4-methyl-phenoxy)-3-methyl-phenyl]-2-oxo-4-trifluoromethyl-1,2-dihydro-pyridine-3-carbonitrile;
1-(2,4-Dimethyl-benzyl)-6-[4-(2-ethyl-4-methyl-phenoxy)-3-isopropyl-phenyl]-2-oxo-4-trifluoromethyl-1,2-dihydro-pyridine-3-carbonitrile;
6-(4-Benzyloxy-3-chloro-phenyl)-1-(2,4-difluoro-benzyl)-2-oxo-4-trifluoromethyl-1,2-dihydro-pyridine-3-carbonitrile;
6-[3-Chloro-4-(4-fluoro-phenoxy)-phenyl]-1-(2,4-difluoro-benzyl)-2-oxo-4-trifluoromethyl-1,2-dihydro-pyridine-3-carbonitrile; and
1-(2,4-Difluoro-benzyl)-6-[4-(4-fluoro-phenoxy)-phenyl]-2-oxo-4-trifluoromethyl-1,2-dihydro-pyridine-3-carbonitrile, or a pharmaceutically acceptable salt of any of the foregoing.

8. The compound of claim 4 wherein:
n is 0 or 1;
m is 1 or 2;
$R^2$ is cyano;
$R^3$ is trifluoromethyl;
$R^4$ is methyl, 1-methylethyl or chloro;
each $R^5$ is independently selected from the group consisting of haloalkyl, —$R^7$—CN, —$R^7$—N($R^8$)$_2$, —$R^7$—$OR^8$ and $R^7$—O—$R^9$—C(O)$OR^8$
each $R^7$ is independently selected from a direct bond or methylene chain;
each $R^8$ is independently selected from hydrogen, alkyl, aryl and aralkyl; and
$R^9$ is a methylene chain.

9. The compound of claim 8 selected from the group consisting of the following:
6-[4-(4-Dimethylamino-phenoxy)-3-methyl-phenyl]-1-(2,4-dimethyl-benzyl)-2-oxo-4-trifluoromethyl-1,2-dihydro-pyridine-3-carbonitrile;
1-(2,4-Dimethyl-benzyl)-6-[4-(4-methoxy-phenoxy)-3-methyl-phenyl]-2-oxo-4-trifluoromethyl-1,2-dihydro-pyridine-3-carbonitrile;
6-[4-(3-Cyano-phenoxy)-3-methyl-phenyl]-1-(2,4-dimethyl-benzyl)-2-oxo-4-trifluoromethyl-1,2-dihydro-pyridine-3-carbonitrile;
6-[4-(4-Benzyloxy-phenoxy)-3-methyl-phenyl]-1-(2,4-dimethyl-benzyl)-2-oxo-4-trifluoromethyl-1,2-dihydro-pyridine-3-carbonitrile;
6-[4-(3-Benzyloxy-phenoxy)-3-methyl-phenyl]-1-(2,4-dimethyl-benzyl)-2-oxo-4-trifluoromethyl-1,2-dihydro-pyridine-3-carbonitrile;
6-[4-(3-Cyano-phenoxy)-phenyl]-1-(2,4-dimethyl-benzyl)-2-oxo-4-trifluoromethyl-1,2-dihydro-pyridine-3-carbonitrile;
6-[4-(4-Cyano-phenoxy)-phenyl]-1-(2,4-dimethyl-benzyl)-2-oxo-4-trifluoromethyl-1,2-dihydro-pyridine-3-carbonitrile;
6-[4-(4-Dimethylamino-phenoxy)-phenyl]-1-(2,4-dimethyl-benzyl)-2-oxo-4-trifluoromethyl-1,2-dihydro-pyridine-3-carbonitrile;
1-(2,4-Dimethyl-benzyl)-6-[4-(4-hydroxy-phenoxy)-phenyl]-2-oxo-4-trifluoromethyl-1,2-dihydro-pyridine-3-carbonitrile;

1-(2,4-Dimethyl-benzyl)-6-[4-(3-hydroxy-phenoxy)-phenyl]-2-oxo-4-trifluoromethyl-1,2-dihydro-pyridine-3-carbonitrile;
1-(2,4-Dimethyl-benzyl)-6-[4-(4-hexyloxy-phenoxy)-phenyl]-2-oxo-4-trifluoromethyl-1,2-dihydro-pyridine-3-carbonitrile;
1-(2,4-Dimethyl-benzyl)-6-{4-[4-(3-methyl-butoxy)-phenoxy]-phenyl}-2-oxo-4-trifluoromethyl-1,2-dihydro-pyridine-3-carbonitrile;
1-(2,4-Dimethyl-benzyl)-6-[4-(3-hexyloxy-phenoxy)-phenyl]-2-oxo-4-trifluoromethyl-1,2-dihydro-pyridine-3-carbonitrile;
1-(2,4-Dimethyl-benzyl)-6-{4-[3-(3-methyl-butoxy)-phenoxy]-phenyl}-2-oxo-4-trifluoromethyl-1,2-dihydro-pyridine-3-carbonitrile;
(3-{4-[5-Cyano-1-(2,4-dimethyl-benzyl)-6-oxo-4-trifluoromethyl-1,6-dihydro-pyridin-2-yl]-phenoxy}-phenoxy)-acetic acid benzyl ester;
(4-{4-[5-Cyano-1-(2,4-dimethyl-benzyl)-6-oxo-4-trifluoromethyl-1,6-dihydro-pyridin-2-yl]-phenoxy}-phenoxy)-acetic acid benzyl ester;
1-(2,4-Dimethyl-benzyl)-2-oxo-6-[4-(4-phenylamino-phenoxy)-phenyl]-4-trifluoromethyl-1,2-dihydro-pyridine-3-carbonitrile;
6-[4-(4-Benzylamino-phenoxy)-phenyl]-1-(2,4-dimethyl-benzyl)-2-oxo-4-trifluoromethyl-1,2-dihydro-pyridine-3-carbonitrile;
1-(2,4-Dimethyl-benzyl)-6-[4-(3-hydroxymethyl-phenoxy)-phenyl]-2-oxo-4-trifluoromethyl-1,2-dihydro-pyridine-3-carbonitrile;
6-[4-(3-Benzyloxy-phenoxy)-3-isopropyl-phenyl]-1-(2,4-dimethyl-benzyl)-2-oxo-4-trifluoromethyl-1,2-dihydro-pyridine-3-carbonitrile;
6-[4-(4-Benzyloxy-phenoxy)-3-isopropyl-phenyl]-1-(2,4-dimethyl-benzyl)-2-oxo-4-trifluoromethyl-1,2-dihydro-pyridine-3-carbonitrile;
1-(2,4-Difluoro-benzyl)-6-[4-(3-hydroxy-phenoxy)-phenyl]-2-oxo-4-trifluoromethyl-1,2-dihydro-pyridine-3-carbonitrile;
1-(2,4-Difluoro-benzyl)-6-[4-(4-hydroxy-phenoxy)-phenyl]-2-oxo-4-trifluoromethyl-1,2-dihydro-pyridine-3-carbonitrile; and
6-[4-(3-Cyano-4-trifluoromethyl-phenoxy)-phenyl]-1-(2,4-difluoro-benzyl)-2-oxo-4-trifluoromethyl-1,2-dihydro-pyridine-3-carbonitrile,
or a pharmaceutically acceptable salt of any of the foregoing.

10. The compound of claim 4 wherein:
n is 0 or 1;
m is 1 or 2;
$R^2$ is cyano;
$R^3$ is trifluoromethyl;
$R^4$ is methyl, 1-methylethyl or chloro;
each $R^5$ is independently selected from the group consisting of heteroaryl, $-R^7-OR^8$, $-R^7-C(O)R^{11}$, $-R^7-C(O)OR^8$, $-R^7-C(O)N(R^8)_2$, $-R^7-C(O)N(R^8)OR^8$, $-R^7-C(O)N(R^8)N(R^8)_2$, $-R^7-C(O)N(R^8)-R^9-C(O)OR^8$, $-R^7-C(S)N(R^8)_2$ and $-R^7-S(O)_tR^8$ (where t is 0 to 2);
each $R^7$ is independently selected from a direct bond or a straight or branched alkylene chain;
each $R^8$ is independently selected from hydrogen, alkyl, haloalkyl, aryl, aralkyl, aralkenyl, cycloalkyl or heterocyclyl optionally substituted with hydroxy;
$R^9$ is a straight or branched alkylene chain (optionally substituted by phenyl or imidazolyl); and
$R^{11}$ is hydrogen, alkyl, aryl, aralkyl, cycloalkyl, cycloalkylalkyl, heterocyclyl, heterocyclylalkyl, heteroaryl or heterarylalkyl.

11. The compound of claim 10 wherein:
m is 1 or 2;
each $R^5$ is independently selected from $-R^7-OR^8$, $-R^7-C(O)R^{11}$, $-R^7-C(O)OR^8$, $-R^7-C(O)N(R^8)_2$, $-R^7-C(O)N(R^8)OR^8$ or $-R^7-C(O)N(R^8)N(R^8)_2$;
each $R^7$ is independently selected from a direct bond or methylene;
each $R^8$ is independently selected from hydrogen, methyl, ethyl, 1,1-dimethylethyl, benzyl, 2-phenylethyl, cyclohexyl or piperidinyl optionally substituted by hydroxy; and
$R^{11}$ is hydrogen, alkyl, aryl, aralkyl, cycloalkyl, cycloalkylalkyl, heterocyclyl, heterocyclylalkyl, heteroaryl or heterarylalkyl.

12. The compound of claim 11 selected from the group consisting of the following:
4-{4-[5-Cyano-1-(2,4-dimethyl-benzyl)-6-oxo-4-trifluoromethyl-1,6-dihydro-pyridin-2-yl]-2-methyl-phenoxy}-benzoic acid methyl ester;
3-{4-[5-Cyano-1-(2,4-dimethyl-benzyl)-6-oxo-4-trifluoromethyl-1,6-dihydro-pyridin-2-yl]-2-methyl-phenoxy}-benzoic acid methyl ester;
4-{4-[5-Cyano-1-(2,4-dimethyl-benzyl)-6-oxo-4-trifluoromethyl-1,6-dihydro-pyridin-2-yl]-phenoxy}-benzoic acid;
3-{4-[5-Cyano-1-(2,4-dimethyl-benzyl)-6-oxo-4-trifluoromethyl-1,6-dihydro-pyridin-2-yl]-phenoxy}-N-methyl-benzamide;
3-{4-[5-Cyano-1-(2,4-dimethyl-benzyl)-6-oxo-4-trifluoromethyl-1,6-dihydro-pyridin-2-yl]-phenoxy}-N,N-dimethyl-benzamide;
1-(2,4-Dimethyl-benzyl)-2-oxo-6-{4-[3-(piperidine-1-carbonyl)-phenoxy]-phenyl}-4-trifluoromethyl-1,2-dihydro-pyridine-3-carbonitrile;
1-(2,4-Dimethyl-benzyl)-6-{4-[3-(3-hydroxy-piperidine-1-carbonyl)-phenoxy]-phenyl}-2-oxo-4-trifluoromethyl-1,2-dihydro-pyridine-3-carbonitrile;
N-Benzyl-3-{4-[5-cyano-1-(2,4-dimethyl-benzyl)-6-oxo-4-trifluoromethyl-1,6-dihydro-pyridin-2-yl]-phenoxy}-benzamide;
3-{4-[5-Cyano-1-(2,4-dimethyl-benzyl)-6-oxo-4-trifluoromethyl-1,6-dihydro-pyridin-2-yl]-phenoxy}-benzoic acid N'-phenyl-hydrazide;
3-{4-[5-Cyano-1-(2,4-dimethyl-benzyl)-6-oxo-4-trifluoromethyl-1,6-dihydro-pyridin-2-yl]-phenoxy}-N-cyclopentyl-benzamide;
3-{4-[5-Cyano-1-(2,4-dimethyl-benzyl)-6-oxo-4-trifluoromethyl-1,6-dihydro-pyridin-2-yl]-phenoxy}-N-methoxy-N-methyl-benzamide;
3-{4-[5-Cyano-1-(2,4-dimethyl-benzyl)-6-oxo-4-trifluoromethyl-1,6-dihydro-pyridin-2-yl]-phenoxy}-N-((S)-1-phenyl-ethyl)-benzamide;
3-{4-[5-Cyano-1-(2,4-difluoro-benzyl)-6-oxo-4-trifluoromethyl-1,6-dihydro-pyridin-2-yl]-phenoxy}-N,N-dimethyl-benzamide;
3-Benzyloxy-5-{4-[5-cyano-1-(2,4-dimethyl-benzyl)-6-oxo-4-trifluoromethyl-1,6-dihydro-pyridin-2-yl]-phenoxy}-benzoic acid methyl ester;
3-Benzyloxy-5-{4-[5-cyano-1-(2,4-difluoro-benzyl)-6-oxo-4-trifluoromethyl-1,6-dihydro-pyridin-2-yl]-phenoxy}-N,N-dimethyl-benzamide;

3-{4-[5-Cyano-1-(2,4-difluoro-benzyl)-6-oxo-4-trifluoromethyl-1,6-dihydro-pyridin-2-yl]-phenoxy}-5-hydroxy-N,N-dimethyl-benzamide;

2-Benzyloxy-5-{4-[5-cyano-1-(2,4-difluoro-benzyl)-6-oxo-4-trifluoromethyl-1,6-dihydro-pyridin-2-yl]-phenoxy}-N,N-dimethyl-benzamide;

5-{4-[5-Cyano-1-(2,4-difluoro-benzyl)-6-oxo-4-trifluoromethyl-1,6-dihydro-pyridin-2-yl]-phenoxy}-2-hydroxy-N,N-dimethyl-benzamide;

3-{4-[5-Cyano-1-(2,4-difluoro-benzyl)-6-oxo-4-trifluoromethyl-1,6-dihydro-pyridin-2-yl]-phenoxy}-N-methyl-benzamide;

N-tert-Butyl-3-{4-[5-cyano-1-(2,4-difluoro-benzyl)-6-oxo-4-trifluoromethyl-1,6-dihydro-pyridin-2-yl]-phenoxy}-benzamide; and 1-(2,4-Difluoro-benzyl)-2-oxo-6-{4-[3-(piperidine-1-carbonyl)-phenoxy]-phenyl}-4-trifluoromethyl-1,2-dihydro-pyridine-3-carbonitrile, or a pharmaceutically acceptable salt of any of the foregoing.

13. The compound of claim 4 wherein:
n is 0 or 1;
m is 1 or 2;
$R^2$ is cyano;
$R^3$ is trifluoromethyl;
$R^4$ is methyl, 1-methylethyl or chloro;
each $R^5$ is independently selected from the group consisting of heteroaryl, $-R^7-C(O)N(R^8)-R^9-C(O)OR^8$, $-R^7-C(S)N(R^8)_2$ and $-R^7-S(O)_tR^8$ (where t is 0 to 2);
each $R^7$ is independently selected from a direct bond or a straight or branched alkylene chain;
each $R^8$ is independently selected from hydrogen or alkyl, haloalkyl, aryl, aralkyl, aralkenyl, cycloalkyl or heterocyclyl; and
$R^9$ is a straight or branched alkylene chain (optionally substituted by phenyl or imidazolyl).

14. The compound of claim 13 wherein:
n is 0 or 1;
m is 1;
$R^2$ is cyano;
$R^3$ is trifluoromethyl;
$R^4$ is chloro;
$R^5$ is $-R^7-C(O)N(R^8)-R^9-C(O)OR^8$;
$R^7$ is a direct bond;
each $R^8$ is independently hydrogen or alkyl; and
$R^9$ is a straight or branched alkylene chain optionally substituted by phenyl or imidazolyl.

15. The compound of claim 14 selected from the group consisting of the following:

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-propionic acid methyl ester;

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-propionic acid methyl ester;

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-methyl-butyric acid methyl ester;

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-methyl-butyric acid methyl ester;

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-4-methyl-pentanoic acid methyl ester;

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-4-methyl-pentanoic acid methyl ester;

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-phenyl-propionic acid methyl ester;

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-phenyl-propionic acid methyl ester;

(S)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-(1H-imidazol-4-yl)-propionic acid methyl ester;

(R)-2-(3-{4-[5-Cyano-1-(2,4-dimethyl-benzyl)-6-oxo-4-trifluoromethyl-1,6-dihydro-pyridin-2-yl]-phenoxy}-benzoylamino)-3-(1H-imidazol-4-yl)-propionic acid methyl ester;

(S)-(3-{4-[5-Cyano-1-(2,4-dimethyl-benzyl)-6-oxo-4-trifluoromethyl-1,6-dihydro-pyridin-2-yl]-phenoxy}-benzoylamino)-phenyl-acetic acid methyl ester; and (R)-(3-{4-[5-Cyano-1-(2,4-dimethyl-benzyl)-6-oxo-4-trifluoromethyl-1,6-dihydro-pyridin-2-yl]-phenoxy}-benzoylamino)-phenyl-acetic acid methyl ester, or a pharmaceutically acceptable salt of any of the foregoing.

16. The compound of claim 13 wherein:
n is 0 or 1;
m is 1;
$R^2$ is cyano;
$R^3$ is trifluoromethyl;
$R^4$ is methyl, 1-methylethyl or chloro;
each $R^5$ is independently selected from the group consisting of phthalimidyl, $-R^7-C(S)N(R^8)_2$ and $-R^7-S(O)_tR^8$ (where t is 0 or 2);
each $R^7$ is a direct bond; and
each $R^8$ is independently selected from hydrogen or alkyl.

17. The compound of claim 16 selected from the group consisting of the following:

1-(2,4-Dimethyl-benzyl)-6-[4-(4-methylsulfanyl-phenoxy)-phenyl]-2-oxo-4-trifluoromethyl-1,2-dihydro-pyridine-3-carbonitrile;

1-(2,4-Dimethyl-benzyl)-6-{4-[4-(1,3-dioxo-1,3-dihydro-isoindol-2-yl)-phenoxy]-phenyl}-2-oxo-4-trifluoromethyl-1,2-dihydro-pyridine-3-carbonitrile;

3-{4-[5-Cyano-1-(2,4-dimethyl-benzyl)-6-oxo-4-trifluoromethyl-1,6-dihydro-pyridin-2-yl]-phenoxy}-N,N-dimethyl-thiobenzamide; and 6-[3-Chloro-4-(4-methanesulfonyl-phenoxy)-phenyl]-1-(2,4-difluoro-benzyl)-2-oxo-4-trifluoromethyl-1,2-dihydro-pyridine-3-carbonitrile, or a pharmaceutically acceptable salt of any of the foregoing.

18. The compound of claim 3 wherein $R^1$ is heteroarylalkyl.

19. The compound of claim 18 wherein:
n is 0 or 1;
m is 0-2;
$R^1$ is optionally substituted thiazol-5-ylmethyl;
$R^2$ is cyano;
$R^3$ is trifluoromethyl;
$R^4$ is methyl, 1-methylethyl or chloro;
each $R^5$ is independently selected from the group consisting of halo, alkyl, alkenyl or haloalkyl.

20. The compound of claim 19, i.e., namely 1-(2,5-Diethyl-thiazol-4-ylmethyl)-2-oxo-6-(4-phenoxy-phenyl)-4-trifluoromethyl-1,2-dihydro-pyridine-3-carbonitrile, or a pharmaceutically acceptable salt thereof.

21. The compound of claim 2 wherein:

R$^1$ is aralkyl optionally substituted with one or more substituents independently selected from alkyl, halo or haloalkyl;

each R$^5$ is independently selected from the group consisting of halo, nitro, alkyl, alkenyl, haloalkyl, —R$^7$—CN, —R$^7$—N(R$^8$)$_2$, —R$^7$—OR$^8$, —R$^7$—C(O)R$^{11}$, —R$^7$—C(O)OR$^8$, —R$^7$—C(O)N(R$^8$)$_2$, —R$^7$—N(R$^8$)C(O)OR$^{10}$, —R$^7$—S(O)$_t$R$^8$ (where t is 0 to 2) and —R$^7$—S(O)$_2$N(R$^8$)$_2$;

R$^6$ is a direct bond, a straight or branched alkenylene chain or a straight or branched alkynylene chain;

each R$^7$ is independently selected from a direct bond or a straight or branched alkylene chain;

each R$^8$ is independently selected from hydrogen, alkyl, cycloalkyl, cycloalkylalkyl or heterocyclyl;

each R$^9$ is a straight or branched alkylene chain optionally substituted by aryl or heteroaryl;

R$^{10}$ is alkyl, aryl, aralkyl or cycloalkylalkyl; and

R$^{11}$ is hydrogen, alkyl, aryl, aralkyl, cycloalkyl, cycloalkylalkyl, heterocyclyl, heterocyclylalkyl, heteroaryl or heterarylalkyl.

22. The compound of claim 21 wherein:

n is 0;

m is 1 or 2;

R$^1$ is benzyl optionally substituted with one or more substituents independently selected from alkyl, halo or haloalkyl;

R$^2$ is cyano;

R$^3$ is trifluoromethyl;

each R$^5$ is independently selected from the group consisting of alkyl, trifluoromethyl, —R$^7$—OR$^8$ and R$^7$—S(O)$_t$R$^8$ (where t is 0 to 2);

R$^6$ is a direct bond;

R$^7$ is a direct bond;

R$^8$ is hydrogen or alkyl; and

R$^9$ is a straight or branched alkylene chain.

23. The compound of claim 22 selected from the group consisting of the following:

1-(2,4-Difluoro-benzyl)-6-(4'-methanesulfonyl-biphenyl-3-yl)-2-oxo-4-trifluoromethyl-1,2-dihydro-pyridine-3-carbonitrile;

1-(2,4-Difluoro-benzyl)-6-(4'-methanesulfonyl-biphenyl-4-yl)-2-oxo-4-trifluoromethyl-1,2-dihydro-pyridine-3-carbonitrile;

1-(2,4-Difluoro-benzyl)-6-(4'-ethylsulfanyl-3'-trifluoromethyl-biphenyl-3-yl)-2-oxo-4-trifluoromethyl-1,2-dihydro-pyridine-3-carbonitrile;

1-(2,4-Difluoro-benzyl)-6-(4'-ethanesulfonyl-3'-trifluoromethyl-biphenyl-3-yl)-2-oxo-4-trifluoromethyl-1,2-dihydro-pyridine-3-carbonitrile;

1-(2,4-Difluoro-benzyl)-6-(4'-methylsulfanyl-3'-trifluoromethyl-biphenyl-3-yl)-2-oxo-4-trifluoromethyl-1,2-dihydro-pyridine-3-carbonitrile;

1-(2,4-Difluoro-benzyl)-6-(5'-methylsulfanyl-3'-trifluoromethyl-biphenyl-3-yl)-2-oxo-4-trifluoromethyl-1,2-dihydro-pyridine-3-carbonitrile;

1-(2,4-Difluoro-benzyl)-6-(4'-methylsulfanyl-3'-trifluoromethyl-biphenyl-4-yl)-2-oxo-4-trifluoromethyl-1,2-dihydro-pyridine-3-carbonitrile;

1-(2,4-Difluoro-benzyl)-6-(5'-methylsulfanyl-3'-trifluoromethyl-biphenyl-4-yl)-2-oxo-4-trifluoromethyl-1,2-dihydro-pyridine-3-carbonitrile;

1-(2,4-Difluoro-benzyl)-6-(4'-methanesulfonyl-3'-trifluoromethyl-biphenyl-3-yl)-2-oxo-4-trifluoromethyl-1,2-dihydro-pyridine-3-carbonitrile;

1-(2,4-Difluoro-benzyl)-6-(4'-methanesulfonyl-3'-trifluoromethyl-biphenyl-4-yl)-2-oxo-4-trifluoromethyl-1,2-dihydro-pyridine-3-carbonitrile;

1-(2,4-Difluoro-benzyl)-6-(3'-methanesulfonyl-5'-trifluoromethyl-biphenyl-4-yl)-2-oxo-4-trifluoromethyl-1,2-dihydro-pyridine-3-carbonitrile;

1-(2,4-Difluoro-benzyl)-6-(3'-ethanesulfonyl-5'-trifluoromethyl-biphenyl-3-yl)-2-oxo-4-trifluoromethyl-1,2-dihydro-pyridine-3-carbonitrile;

1-(2,4-Difluoro-benzyl)-2-oxo-6-[3'-(propane-2-sulfonyl)-5'-trifluoromethyl-biphenyl-3-yl]-4-trifluoromethyl-1,2-dihydro-pyridine-3-carbonitrile;

1-(2,4-Difluoro-benzyl)-6-(4'-ethoxy-3'-methanesulfonyl-biphenyl-3-yl)-2-oxo-4-trifluoromethyl-1,2-dihydro-pyridine-3-carbonitrile;

1-(2,4-Difluoro-benzyl)-2-oxo-6-[5'-(propane-1-sulfinyl)-3'-trifluoromethyl-biphenyl-3-yl]-4-trifluoromethyl-1,2-dihydro-pyridine-3-carbonitrile;

6-[5'-(Butane-1-sulfinyl)-3'-trifluoromethyl-biphenyl-3-yl]-1-(2,4-difluoro-benzyl)-2-oxo-4-trifluoromethyl-1,2-dihydro-pyridine-3-carbonitrile;

1-(2,4-Difluoro-benzyl)-2-oxo-6-(5'-phenylmethanesulfinyl-3'-trifluoromethyl-biphenyl-3-yl)-4-trifluoromethyl-1,2-dihydro-pyridine-3-carbonitrile;

6-(5'-Cyclopropylmethanesulfinyl-3'-trifluoromethyl-biphenyl-3-yl)-1-(2,4-difluoro-benzyl)-2-oxo-4-trifluoromethyl-1,2-dihydro-pyridine-3-carbonitrile;

1-(2,4-Difluoro-benzyl)-2-oxo-6-[5'-(propane-1-sulfinyl)-3'-trifluoromethyl-biphenyl-4-yl]-4-trifluoromethyl-1,2-dihydro-pyridine-3-carbonitrile;

6-[5'-(Butane-1-sulfinyl)-3'-trifluoromethyl-biphenyl-4-yl]-1-(2,4-difluoro-benzyl)-2-oxo-4-trifluoromethyl-1,2-dihydro-pyridine-3-carbonitrile;

1-(2,4-Difluoro-benzyl)-2-oxo-6-(5'-phenylmethanesulfinyl-3'-trifluoromethyl-biphenyl-4-yl)-4-trifluoromethyl-1,2-dihydro-pyridine-3-carbonitrile;

6-(5'-Cyclopropylmethanesulfinyl-3'-trifluoromethyl-biphenyl-4-yl)-1-(2,4-difluoro-benzyl)-2-oxo-4-trifluoromethyl-1,2-dihydro-pyridine-3-carbonitrile;

1-(2,4-Difluoro-benzyl)-6-(5'-ethanesulfinyl-3'-trifluoromethyl-biphenyl-4-yl)-2-oxo-4-trifluoromethyl-1,2-dihydro-pyridine-3-carbonitrile;

1-(2,4-Difluoro-benzyl)-2-oxo-6-[3'-(propane-2-sulfinyl)-5'-trifluoromethyl-biphenyl-4-yl]-4-trifluoromethyl-1,2-dihydro-pyridine-3-carbonitrile;

1-(2,4-Difluoro-benzyl)-2-oxo-6-[3'-(propane-1-sulfonyl)-5'-trifluoromethyl-biphenyl-3-yl]-4-trifluoromethyl-1,2-dihydro-pyridine-3-carbonitrile;

1-(2,4-Difluoro-benzyl)-2-oxo-6-[3'-(propane-1-sulfonyl)-5'-trifluoromethyl-biphenyl-4-yl]-4-trifluoromethyl-1,2-dihydro-pyridine-3-carbonitrile;

6-[3'-(Butane-1-sulfonyl)-5'-trifluoromethyl-biphenyl-3-yl]-1-(2,4-difluoro-benzyl)-2-oxo-4-trifluoromethyl-1,2-dihydro-pyridine-3-carbonitrile;

6-[3'-(Butane-1-sulfonyl)-5'-trifluoromethyl-biphenyl-4-yl]-1-(2,4-difluoro-benzyl)-2-oxo-4-trifluoromethyl-1,2-dihydro-pyridine-3-carbonitrile;

1-(2,4-Difluoro-benzyl)-2-oxo-6-(3'-phenylmethanesulfonyl-5'-trifluoromethyl-biphenyl-3-yl)-4-trifluoromethyl-1,2-dihydro-pyridine-3-carbonitrile;

1-(2,4-Difluoro-benzyl)-2-oxo-6-(3'-phenylmethanesulfonyl-5'-trifluoromethyl-biphenyl-4-yl)-4-trifluoromethyl-1,2-dihydro-pyridine-3-carbonitrile;

6-(3'-Cyclopropylmethanesulfonyl-5'-trifluoromethyl-biphenyl-3-yl)-1-(2,4-difluoro-benzyl)-2-oxo-4-trifluoromethyl-1,2-dihydro-pyridine-3-carbonitrile;

6-(3'-Cyclopropylmethanesulfonyl-5'-trifluoromethyl-biphenyl-4-yl)-1-(2,4-difluoro-benzyl)-2-oxo-4-trifluoromethyl-1,2-dihydro-pyridine-3-carbonitrile;

1-(2,4-Difluoro-benzyl)-6-(3'-ethanesulfonyl-5'-trifluoromethyl-biphenyl-4-yl)-2-oxo-4-trifluoromethyl-1,2-dihydro-pyridine-3-carbonitrile;

1-(2,4-Difluoro-benzyl)-2-oxo-6-[3'-(propane-2-sulfonyl)-5'-trifluoromethyl-biphenyl-4-yl]-4-trifluoromethyl-1,2-dihydro-pyridine-3-carbonitrile;

1-(2,4-Difluoro-benzyl)-6-(5'-isopropyl-3'-methanesulfonyl-biphenyl-3-yl)-2-oxo-4-trifluoromethyl-1,2-dihydro-pyridine-3-carbonitrile;

1-(2,4-Difluoro-benzyl)-6-(5'-ethyl-3'-methanesulfonyl-biphenyl-3-yl)-2-oxo-4-trifluoromethyl-1,2-dihydro-pyridine-3-carbonitrile;

1-(2,4-Difluoro-benzyl)-6-(3'-ethanesulfonyl-5'-isopropyl-biphenyl-3-yl)-2-oxo-4-trifluoromethyl-1,2-dihydro-pyridine-3-carbonitrile; and 1-(2,4-Difluoro-benzyl)-6-(3'-methanesulfonyl-5'-trifluoromethyl-biphenyl-3-yl)-2-oxo-4-trifluoromethyl-1,2-dihydro-pyridine-3-carbonitrile, or a pharmaceutically acceptable salt of any of the foregoing.

24. The compound of claim 21 wherein:

n is 0;

m is 1 or 2;

$R^1$ is benzyl optionally substituted with one or more substituents independently selected from alkyl, halo or haloalkyl;

$R^2$ is cyano;

$R^3$ is trifluoromethyl;

each $R^5$ is independently selected from the group consisting of alkyl, —$R^7$—C(O)$R^{11}$, —$R^7$—C(O)O$R^8$ or —$R^7$—C(O)N($R^8$)$_2$;

$R^6$ is a direct bond;

each $R^7$ is a direct bond;

each $R^8$ is independently hydrogen, alkyl, aryl or aralkyl; and $R^{11}$ is hydrogen, alkyl, aryl, aralkyl, cycloalkyl, cycloalkylalkyl, heterocyclyl, heterocyclylalkyl, pyrrolidinyl or piperidinyl.

25. The compound of claim 24 selected from the group consisting of the following:

6-(3'-Acetyl-biphenyl-3-yl)-1-(2,4-difluoro-benzyl)-2-oxo-4-trifluoromethyl-1,2-dihydro-pyridine-3-carbonitrile;

6-(4'-Acetyl-biphenyl-3-yl)-1-(2,4-difluoro-benzyl)-2-oxo-4-trifluoromethyl-1,2-dihydro-pyridine-3-carbonitrile;

3'-[5-Cyano-1-(2,4-difluoro-benzyl)-6-oxo-4-trifluoromethyl-1,6-dihydro-pyridin-2-yl]-biphenyl-3-carboxylic acid amide;

3'-[5-Cyano-1-(2,4-difluoro-benzyl)-6-oxo-4-trifluoromethyl-1,6-dihydro-pyridin-2-yl]-biphenyl-4-carboxylic acid amide;

3'-[5-Cyano-1-(2,4-difluoro-benzyl)-6-oxo-4-trifluoromethyl-1,6-dihydro-pyridin-2-yl]-biphenyl-3-carboxylic acid dimethylamide;

3'-[5-Cyano-1-(2,4-difluoro-benzyl)-6-oxo-4-trifluoromethyl-1,6-dihydro-pyridin-2-yl]-biphenyl-4-carboxylic acid dimethylamide;

1-(2,4-Difluoro-benzyl)-2-oxo-6-[3'-(pyrrolidine-1-carbonyl)-biphenyl-3-yl]-4-trifluoromethyl-1,2-dihydro-pyridine-3-carbonitrile;

1-(2,4-Difluoro-benzyl)-2-oxo-6-[4'-(piperidine-1-carbonyl)-biphenyl-3-yl]-4-trifluoromethyl-1,2-dihydro-pyridine-3-carbonitrile;

3'-[5-Cyano-1-(2,4-difluoro-benzyl)-6-oxo-4-trifluoromethyl-1,6-dihydro-pyridin-2-yl]-biphenyl-3-carboxylic acid ethylamide;

3'-[5-Cyano-1-(2,4-difluoro-benzyl)-6-oxo-4-trifluoromethyl-1,6-dihydro-pyridin-2-yl]-biphenyl-4-carboxylic acid methylamide;

3'-[5-Cyano-1-(2,4-difluoro-benzyl)-6-oxo-4-trifluoromethyl-1,6-dihydro-pyridin-2-yl]-biphenyl-4-carboxylic acid phenylamide;

3'-[5-Cyano-1-(2,4-difluoro-benzyl)-6-oxo-4-trifluoromethyl-1,6-dihydro-pyridin-2-yl]-biphenyl-4-carboxylic acid benzylamide;

{3'-[5-Cyano-1-(2,4-difluoro-benzyl)-6-oxo-4-trifluoromethyl-1,6-dihydro-pyridin-2-yl]-biphenyl-3-yl}-acetic acid;

{4'-[5-Cyano-1-(2,4-difluoro-benzyl)-6-oxo-4-trifluoromethyl-1,6-dihydro-pyridin-2-yl]-biphenyl-3-yl}-acetic acid;

{3'-[5-Cyano-1-(2,4-difluoro-benzyl)-6-oxo-4-trifluoromethyl-1,6-dihydro-pyridin-2-yl]-biphenyl-4-yl}-acetic acid;

{4'-[5-Cyano-1-(2,4-difluoro-benzyl)-6-oxo-4-trifluoromethyl-1,6-dihydro-pyridin-2-yl]-biphenyl-4-yl}-acetic acid;

{3-Chloro-3'-[5-cyano-1-(2,4-difluoro-benzyl)-6-oxo-4-trifluoromethyl-1,6-dihydro-pyridin-2-yl]-biphenyl-4-yl}-acetic acid methyl ester; and {3-Chloro-3'-[5-cyano-1-(2,4-difluoro-benzyl)-6-oxo-4-trifluoromethyl-1,6-dihydro-pyridin-2-yl]-biphenyl-4-yl}-acetic acid, or a pharmaceutically acceptable salt of any of the foregoing.

26. The compound of claim 21 wherein:

n is 0;

m is 0-2;

$R^2$ is cyano;

$R^3$ is trifluoromethyl;

each $R^5$ is independently selected from the group consisting of halo, alkyl, alkenyl, haloalkyl or —$R^7$—O$R^8$;

$R^6$ is a direct bond, a straight or branched alkenylene chain or a straight or branched alkynylene chain;

$R^7$ is a direct bond; and $R^8$ is hydrogen or alkyl.

27. The compound of claim 26 selected from the group consisting of the following:

6-(3',5'-Bis-trifluoromethyl-biphenyl-3-yl)-1-(2,4-difluoro-benzyl)-2-oxo-4-trifluoromethyl-1,2-dihydro-pyridine-3-carbonitrile;

6-(3',5'-Bis-trifluoromethyl-biphenyl-4-yl)-1-(2,4-difluoro-benzyl)-2-oxo-4-trifluoromethyl-1,2-dihydro-pyridine-3-carbonitrile;

6-(3'-Chloro-4'-ethoxy-biphenyl-3-yl)-1-(2,4-difluoro-benzyl)-2-oxo-4-trifluoromethyl-1,2-dihydro-pyridine-3-carbonitrile;

1-(2,4-Difluoro-benzyl)-6-(3',4'-dimethoxy-biphenyl-4-yl)-2-oxo-4-trifluoromethyl-1,2-dihydro-pyridine-3-carbonitrile;

6-(3'-Chloro-4'-ethoxy-biphenyl-4-yl)-1-(2,4-difluoro-benzyl)-2-oxo-4-trifluoromethyl-1,2-dihydro-pyridine-3-carbonitrile;

1-(2,4-Difluoro-benzyl)-2-oxo-6-(3-phenylethynyl-phenyl)-4-trifluoromethyl-1,2-dihydro-pyridine-3-carbonitrile;

1-(2,4-Difluoro-benzyl)-2-oxo-6-(4-phenylethynyl-phenyl)-4-trifluoromethyl-1,2-dihydro-pyridine-3-carbonitrile;

1-(2,4-Difluoro-benzyl)-2-oxo-6-[3-((E)-styryl)-phenyl]-4-trifluoromethyl-1,2-dihydro-pyridine-3-carbonitrile; and 1-(2,4-Difluoro-benzyl)-2-oxo-6-[4-((E)-styryl)-phenyl]-4-trifluoromethyl-1,2-dihydro-pyridine-3-carbonitrile, or a pharmaceutically acceptable salt of any of the foregoing.

28. The compound of claim 21 wherein:

n is 0;

m is 1 or 2;

$R^2$ is cyano;

$R^3$ is trifluoromethyl;

each $R^5$ is independently selected from the group consisting of nitro, —$R^7$—$N(R^8)_2$, —$R^7$—$OR^8$ or —$R^7$—$N(R^8)C(O)OR^{10}$;

$R^6$ is a direct bond;

each $R^7$ is a direct bond;

each $R^8$ is independently selected from hydrogen or alkyl; and $R^{10}$ is alkyl.

29. The compound of claim 28 selected from the group consisting of the following:

6-(3'-Amino-biphenyl-3-yl)-1-(2,4-difluoro-benzyl)-2-oxo-4-trifluoromethyl-1,2-dihydro-pyridine-3-carbonitrile;

1-(2,4-Difluoro-benzyl)-6-(4'-ethoxy-3'-nitro-biphenyl-3-yl)-2-oxo-4-trifluoromethyl-1,2-dihydro-pyridine-3-carbonitrile;

6-(3'-Amino-4'-ethoxy-biphenyl-3-yl)-1-(2,4-difluoro-benzyl)-2-oxo-4-trifluoromethyl-1,2-dihydro-pyridine-3-carbonitrile; and {3'-[5-Cyano-1-(2,4-difluoro-benzyl)-6-oxo-4-trifluoromethyl-1,6-dihydro-pyridin-2-yl]-4-ethoxy-biphenyl-3-yl}-carbamic acid tert-butyl ester, or a pharmaceutically acceptable salt of any of the foregoing.

30. A method of reducing cholesterol levels in a subject in need thereof, comprising administering an effective amount of a compound of claim 1, or a pharmaceutically acceptable salt thereof.

31. A method of increasing cholesterol efflux from cells of a subject, comprising administering an effective amount of a compound of claim 1, or a pharmaceutically acceptable salt thereof.

32. A method of increasing the expression of ATP-Binding Cassette (ABC1) in the cells of a subject, comprising administering an effective amount of a compound of claim 1, or a pharmaceutically acceptable salt thereof.

33. A method of reducing cholesterol levels in a subject in need thereof, comprising administering an effective amount of a compound of claim 1.

34. A pharmaceutical composition comprising a pharmaceutically acceptable excipient and a compound of claim 1.

* * * * *

SEQUENCE LISTING

```
<160> NUMBER OF SEQ ID NOS: 27

<210> SEQ ID NO 1
<211> LENGTH: 1723
<212> TYPE: DNA
<213> ORGANISM: Rattus norvegicus

<400> SEQUENCE: 1
taatgtccag ggctccagga agagatgtcc ttgtggctgg aggccgcagt gcctgatgtt      60
tctcctgact ctgcaacgga gttgtggaag acagaacctc aagatgcagg agaccaggga     120
ggcaacactt gcatccttag ggaggaagcc aggatgcccc aatcaactgg gggtgcttta     180
aggatagggt tggagtcatc cgagcctaca gccctgctcc ccagggcaga gaccctccca     240
gagcctacag aacttcgtcc acagaagcgg aaaaagggc cagcccccaa aatgctgggg     300
aacgagctat gcagtgtatg tggggacaag gcctctgcgt tccattacaa tgtgctgagc     360
tgcgagggct gcaagggatt cttccgccgc agtgtcatca agggagcacg ctacatttgc     420
catagcggtg gccactgccc catggacacc tacatgcggc ggaaatgcca ggagtgtcgc     480
cttcgcaaat gccgccacgc aggcatgagg gaggagtgtg tcttatcaga agaacagatc     540
cgcttgaaga aactgaagcg tcaagaagag gagcaggctc aagccacatc ggtgtcccca     600
agggtttcct caccgcccca ggtcctgcca cagctcagcc cagaacaact gggcatgatt     660
gagaagttgg tggctgccca gcaacagtgt aacaggcgct ccttctctga ccgacttcga     720
gtcacgcctt ggcccattgc acccgaccct cagagccggg aagcccgcca acagcgcttt     780
gcccacttta ctgagctggc catcgtgtcc gtgcaggaga ttgttgactt tgccaaacag     840
ctccctggct tcctacagct gagcagggag gaccagatcg ccttgctgaa gacctctgcg     900
atcgaggtga tgcttctgga gacatcgcgg aggtacaacc ctgggagtga gagcatcacc     960
ttcctcaagg atttcagtta caaccgggaa gactttgcca aagcagggct gcaggtggag    1020
ttcattaacc ccatctttga gttctccaga tccatgaatg aactgcaact caatgatgct    1080
gaatttgctc tgctcatagc catcagcatc ttctctgcag accggcccaa cgtgcaggac    1140
cagctccaag tagagagact gcaacacaca tatgtggagg ccctgcatgc ctatgtctcc    1200
atcaaccacc cccacgaccg actgatgttc ccacggatgc taatgaagct ggtgagcctc    1260
cggactttga gcagcgtcca ttcagagcaa gtgtttgcac ttcgcctgca ggacaaaaaa    1320
```

-continued

```
cttccccctc tgctctccga gatctgggat gtccacgaat gactgtttct ccgtgtcctc    1380
tgtgttggcc acgcagctga agcttactga ctgcttccta gaggtggagc agactgagga    1440
gggcaaacat tcctgggcgc tgggtgaaag agacccttgc atggcactaa agagagtcaa    1500
agggttgggt gttttgtggc tgctgggcag ttggggacct actaacgttg tatgccatct    1560
gaaggccttg ttgacccaac caaataaact agccaggaga gccactttgt gcagggttct    1620
tcaggccctg cccaaaaaaa aaaaaaaaaa acgactaacg ttgtatgcca tctgaaggcc    1680
ttgttgaccc aaccaaataa actagccagg agagccactt tgt                     1723

<210> SEQ ID NO 2
<211> LENGTH: 445
<212> TYPE: PRT
<213> ORGANISM: Rattus norvegicus

<400> SEQUENCE: 2

Met Ser Leu Trp Leu Glu Ala Ala Val Pro Asp Val Ser Pro Asp Ser
1               5                   10                  15

Ala Thr Glu Leu Trp Lys Thr Glu Pro Gln Asp Ala Gly Asp Gln Gly
                20                  25                  30

Gly Asn Thr Cys Ile Leu Arg Glu Ala Arg Met Pro Gln Ser Thr
            35                  40                  45

Gly Gly Ala Leu Arg Ile Gly Leu Glu Ser Ser Glu Pro Thr Ala Leu
        50                  55                  60

Leu Pro Arg Ala Glu Thr Leu Pro Glu Pro Thr Glu Leu Arg Pro Gln
65                  70                  75                  80

Lys Arg Lys Lys Gly Pro Ala Pro Lys Met Leu Gly Asn Glu Leu Cys
                85                  90                  95

Ser Val Cys Gly Asp Lys Ala Ser Ala Phe His Tyr Asn Val Leu Ser
                100                 105                 110

Cys Glu Gly Cys Lys Gly Phe Phe Arg Arg Ser Val Ile Lys Gly Ala
            115                 120                 125

Arg Tyr Ile Cys His Ser Gly Gly His Cys Pro Met Asp Thr Tyr Met
130                 135                 140

Arg Arg Lys Cys Gln Glu Cys Arg Leu Arg Lys Cys Arg His Ala Gly
145                 150                 155                 160

Met Arg Glu Glu Cys Val Leu Ser Glu Glu Gln Ile Arg Leu Lys Lys
                165                 170                 175

Leu Lys Arg Gln Glu Glu Glu Gln Ala Gln Ala Thr Ser Val Ser Pro
            180                 185                 190

Arg Val Ser Ser Pro Pro Gln Val Leu Pro Gln Leu Ser Pro Glu Gln
        195                 200                 205

Leu Gly Met Ile Glu Lys Leu Val Ala Ala Gln Gln Gln Cys Asn Arg
    210                 215                 220

Arg Ser Phe Ser Asp Arg Leu Arg Val Thr Pro Trp Pro Ile Ala Pro
225                 230                 235                 240

Asp Pro Gln Ser Arg Glu Ala Arg Gln Gln Arg Phe Ala His Phe Thr
                245                 250                 255

Glu Leu Ala Ile Val Ser Val Gln Glu Ile Val Asp Phe Ala Lys Gln
            260                 265                 270

Leu Pro Gly Phe Leu Gln Leu Ser Arg Glu Asp Gln Ile Ala Leu Leu
        275                 280                 285

Lys Thr Ser Ala Ile Glu Val Met Leu Leu Glu Thr Ser Arg Arg Tyr
    290                 295                 300
```

```
Asn Pro Gly Ser Glu Ser Ile Thr Phe Leu Lys Asp Phe Ser Tyr Asn
305                 310                 315                 320

Arg Glu Asp Phe Ala Lys Ala Gly Leu Gln Val Glu Phe Ile Asn Pro
            325                 330                 335

Ile Phe Glu Phe Ser Arg Ser Met Asn Glu Leu Gln Leu Asn Asp Ala
        340                 345                 350

Glu Phe Ala Leu Leu Ile Ala Ile Ser Ile Phe Ser Ala Asp Arg Pro
    355                 360                 365

Asn Val Gln Asp Gln Leu Gln Val Glu Arg Leu Gln His Thr Tyr Val
370                 375                 380

Glu Ala Leu His Ala Tyr Val Ser Ile Asn His Pro Asp Arg Leu
385                 390                 395                 400

Met Phe Pro Arg Met Leu Met Lys Leu Val Ser Leu Arg Thr Leu Ser
            405                 410                 415

Ser Val His Ser Glu Gln Val Phe Ala Leu Arg Leu Gln Asp Lys Lys
        420                 425                 430

Leu Pro Pro Leu Leu Ser Glu Ile Trp Asp Val His Glu
    435                 440                 445
```

<210> SEQ ID NO 3
<211> LENGTH: 1765
<212> TYPE: DNA
<213> ORGANISM: Mus musculus

<400> SEQUENCE: 3

```
ccacgcgtcc gaaagagcct ccagggtgag gagaggaagg agagagatgg aactagaccg      60
gtctgcgggg aaacgcgaca gttttggtag agggacagtg tcttggtaat gtccagggct     120
ccaggaagag atgtccttgt ggctggaggc ctcaatgcct gatgtttctc ctgattctgc     180
aacggagttg tggaagacag aacctcaaga tgcaggagac cagggaggca acacttgcat     240
cctcagggag gaagccagga tgccccagtc aactggggtt gctttaggga tagggttgga     300
gtcagcagag cctacagccc tgctccccag ggcagagacc ctcccagagc cgacagagct     360
tcgtccacaa aagcggaaaa agggcccagc ccccaaaatg ctggggaacg agctgtgcag     420
tgtctgtggg gacaaagcct ctggcttcca ttacaacgtg ctgagctgcg agggctgcaa     480
gggattcttc cgccgcagtg tcatcaaggg agcacgctat gtctgccaca gcggtggcca     540
ctgccccatg gacacctaca tgcggcggaa atgccaggag tgtcgacttc gcaaatgccg     600
ccaggcaggc atgagggagg agtgtgtgct gtcagaagaa cagatccgct tgaagaaact     660
gaagcggcaa gaagaggaac aggctcaagc cacttcggtg tccccaaggg tgtcctcacc     720
tcctcaagtc ctgccacagc tcagcccaga gcagctgggc atgatcgaga gctggtggc     780
tgcccagcaa cagtgtaaca ggcgctcctt ctcagaccgc ctgcgcgtca cgccttggcc     840
cattgcaccc gaccctcaga gccgggaagc ccgacaacag cgctttgccc actttactga     900
gctggccatc gtgtccgtgc aggagattgt tgactttgcc aaacagctcc ctggcttcct     960
acagctcagc agggaggacc agatcgcctt gctgaagacc tctgcaatcg aggtcatgct    1020
tctggagacg tcacggaggt acaaccccgg cagtgagagc atcaccttcc tcaaggactt    1080
cagttacaac cgggaagact tgccaaagc agggctgcag gtggagttca tcaaccccat    1140
ctttgagttc tccagagcca tgaatgagct gcaactcaat gatgctgagt ttgctctgct    1200
cattgccatc agcatcttct ctgcagaccg gcccaacgtg caggaccagc tccaagtaga    1260
gaggctgcaa cacacatatg tggaggccct gcacgcctac gtctccatca accacccca    1320
cgacccactg atgttcccac ggatgctaat gaagctggtg agcctccgta ctttgagcag    1380
```

-continued

```
cgtccattca gagcaagtgt ttgcccttcg cctgcaggac aaaaagcttc cccctctgct    1440
gtctgagatc tgggatgtcc acgagtgact gtttcaccgt gtcctttgtg ttggccacat    1500
ggcgaaggct cactgactgc ttcccacggg tggagcagac tgagaagggc agacattcct    1560
gggagctggg tgaaggagag agccttgcgt agcattaagg gagagtcaac aggttgggtg    1620
ttttctggct gctgggcagt tgggatctac taacgttgta taccatctga agaccttgtt    1680
gacccaacca aataaactag ccaggagagc cactttgtgc agggttcttc agggccccgc    1740
ccaaaaaaaa aaaaaaaaaa aaaaa                                          1765

<210> SEQ ID NO 4
<211> LENGTH: 445
<212> TYPE: PRT
<213> ORGANISM: Mus musculus

<400> SEQUENCE: 4
```

Met Ser Leu Trp Leu Glu Ala Ser Met Pro Asp Val Ser Pro Asp Ser
1               5                   10                  15

Ala Thr Glu Leu Trp Lys Thr Glu Pro Gln Asp Ala Gly Asp Gln Gly
            20                  25                  30

Gly Asn Thr Cys Ile Leu Arg Glu Glu Ala Arg Met Pro Gln Ser Thr
        35                  40                  45

Gly Val Ala Leu Gly Ile Gly Leu Glu Ser Ala Glu Pro Thr Ala Leu
    50                  55                  60

Leu Pro Arg Ala Glu Thr Leu Pro Glu Pro Thr Glu Leu Arg Pro Gln
65                  70                  75                  80

Lys Arg Lys Lys Gly Pro Ala Pro Lys Met Leu Gly Asn Glu Leu Cys
                85                  90                  95

Ser Val Cys Gly Asp Lys Ala Ser Gly Phe His Tyr Asn Val Leu Ser
            100                 105                 110

Cys Glu Gly Cys Lys Gly Phe Phe Arg Arg Ser Val Ile Lys Gly Ala
        115                 120                 125

Arg Tyr Val Cys His Ser Gly Gly His Cys Pro Met Asp Thr Tyr Met
    130                 135                 140

Arg Arg Lys Cys Gln Glu Cys Arg Leu Arg Lys Cys Arg Gln Ala Gly
145                 150                 155                 160

Met Arg Glu Glu Cys Val Leu Ser Glu Glu Gln Ile Arg Leu Lys Lys
                165                 170                 175

Leu Lys Arg Gln Glu Glu Glu Gln Ala Gln Ala Thr Ser Val Ser Pro
            180                 185                 190

Arg Val Ser Ser Pro Pro Gln Val Leu Pro Gln Leu Ser Pro Glu Gln
        195                 200                 205

Leu Gly Met Ile Glu Lys Leu Val Ala Ala Gln Gln Gln Cys Asn Arg
    210                 215                 220

Arg Ser Phe Ser Asp Arg Leu Arg Val Thr Pro Trp Pro Ile Ala Pro
225                 230                 235                 240

Asp Pro Gln Ser Arg Glu Ala Arg Gln Gln Arg Phe Ala His Phe Thr
                245                 250                 255

Glu Leu Ala Ile Val Ser Val Gln Glu Ile Val Asp Phe Ala Lys Gln
            260                 265                 270

Leu Pro Gly Phe Leu Gln Leu Ser Arg Glu Asp Gln Ile Ala Leu Leu
        275                 280                 285

Lys Thr Ser Ala Ile Glu Val Met Leu Leu Glu Thr Ser Arg Arg Tyr
    290                 295                 300

```
Asn Pro Gly Ser Glu Ser Ile Thr Phe Leu Lys Asp Phe Ser Tyr Asn
305                 310                 315                 320

Arg Glu Asp Phe Ala Lys Ala Gly Leu Gln Val Glu Phe Ile Asn Pro
            325                 330                 335

Ile Phe Glu Phe Ser Arg Ala Met Asn Glu Leu Gln Leu Asn Asp Ala
        340                 345                 350

Glu Phe Ala Leu Leu Ile Ala Ile Ser Ile Phe Ser Ala Asp Arg Pro
    355                 360                 365

Asn Val Gln Asp Gln Leu Gln Val Glu Arg Leu Gln His Thr Tyr Val
370                 375                 380

Glu Ala Leu His Ala Tyr Val Ser Ile Asn His Pro His Asp Pro Leu
385                 390                 395                 400

Met Phe Pro Arg Met Leu Met Lys Leu Val Ser Leu Arg Thr Leu Ser
            405                 410                 415

Ser Val His Ser Glu Gln Val Phe Ala Leu Arg Leu Gln Asp Lys Lys
        420                 425                 430

Leu Pro Pro Leu Leu Ser Glu Ile Trp Asp Val His Glu
    435                 440                 445
```

<210> SEQ ID NO 5
<211> LENGTH: 1528
<212> TYPE: DNA
<213> ORGANISM: Homo sapiens

<400> SEQUENCE: 5

```
cagtgccttg gtaatgacca gggctccaga aagagatgtc cttgtggctg ggggcccctg      60
tgcctgacat tcctcctgac tctgcggtgg agctgtggaa gccaggcgca caggatgcaa     120
gcagccaggc ccagggaggc agcagctgca tcctcagaga ggaagccagg atgccccact     180
ctgctggggg tactgcaggg gtgggctgga ggctgcagag cccacagcc ctgctcacca      240
gggcagagcc cccttcagaa cccacagaga tccgtccaca aaagcggaaa aaggggccag     300
cccccaaaat gctggggaac gagctatgca gcgtgtgtgg ggacaaggcc tcgggcttcc     360
actacaatgt tctgagctgc gagggctgca agggattctt ccgccgcagc gtcatcaagg     420
gagcgcacta catctgccac agtggcggcc actgccccat ggacacctac atgcgtcgca     480
agtgccagga gtgtcggctt cgcaaatgcc gtcaggctgg catgcgggag agtgtgtcc      540
tgtcagaaga acagatccgc tgaagaaac tgaagcggca agaggaggaa caggctcatg      600
ccacatcctt gccccccagg cgttcctcac ccccccaaat cctgcccag ctcagcccgg      660
aacaactggg catgatcgag aagctcgtcg ctgcccagca acagtgtaac cggcgctcct     720
tttctgaccg gcttcgagtc acgccttggc ccatggcacc agatccccat agccgggagg     780
cccgtcagca gcgctttgcc cacttcactg agctggccat cgtctctgtg caggagatag     840
ttgactttgc taaacagcta cccggcttcc tgcagctcag ccgggaggac cagattgccc     900
tgctgaagac ctctgcgatc gaggtgatgc ttctggagac atctcggagg tacaaccctg     960
ggagtgagag tatcaccttc ctcaaggatt tcagttataa ccgggaagac tttgccaaag    1020
cagggctgca agtggaattc atcaaccca tcttcgagtt ctccagggcc atgaatgagc    1080
tgcaactcaa tgatgccgag tttgccttgc tcattgctat cagcatcttc tctgcagacc    1140
ggcccaacgt gcaggaccag ctccaggtgg agaggctgca gcacacatat gtggaagccc    1200
tgcatgccta cgtctccatc accatccc atgaccgact gatgttccca cggatgctaa     1260
tgaaactggt gagcctccgg accctgagca gcgtccactc agagcaagtg tttgcactgc    1320
gtctgcagga caaaaagctc ccaccgctgc tctctgagat ctgggatgtg cacgaatgac    1380
```

```
tgttctgtcc ccatattttc tgttttcttg gccggatggc tgaggcctgg tggctgcctc    1440
ctagaagtgg aacagactga aagggcaaa cattcctggg agctgggcaa ggagatcctc    1500
ccgtggcatt aaaagagagt caaagggt                                      1528
```

<210> SEQ ID NO 6
<211> LENGTH: 447
<212> TYPE: PRT
<213> ORGANISM: Homo sapiens

<400> SEQUENCE: 6

```
Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Arg Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300

Arg Tyr Asn Pro Gly Ser Glu Ser Ile Thr Phe Leu Lys Asp Phe Ser
305                 310                 315                 320

Tyr Asn Arg Glu Asp Phe Ala Lys Ala Gly Leu Gln Val Glu Phe Ile
                325                 330                 335

Asn Pro Ile Phe Glu Phe Ser Arg Ala Met Asn Glu Leu Gln Leu Asn
            340                 345                 350
```

```
Asp Ala Glu Phe Ala Leu Leu Ile Ala Ile Ser Ile Phe Ser Ala Asp
        355                 360                 365

Arg Pro Asn Val Gln Asp Gln Leu Gln Val Glu Arg Leu Gln His Thr
    370                 375                 380

Tyr Val Glu Ala Leu His Ala Tyr Val Ser Ile His His Pro His Asp
385                 390                 395                 400

Arg Leu Met Phe Pro Arg Met Leu Met Lys Leu Val Ser Leu Arg Thr
                405                 410                 415

Leu Ser Ser Val His Ser Glu Gln Val Phe Ala Leu Arg Leu Gln Asp
            420                 425                 430

Lys Lys Leu Pro Pro Leu Leu Ser Glu Ile Trp Asp Val His Glu
        435                 440                 445

<210> SEQ ID NO 7
<211> LENGTH: 1959
<212> TYPE: DNA
<213> ORGANISM: Rattus norvegicus

<400> SEQUENCE: 7
ggaattcggc acgagcagca agcgctgttg ctccgagcta ctcccaggct tctgaagtta    60
cttctgaagt gctgtggagg agcaatcacc ggtgcggaca cagagctccc gcctcccaca   120
gccatttcca gggtaacgaa gtaggagacc ccctcctgcg acccccctcac gatcgccggt   180 gcagtcatga gccccgcctc ccctggtgc acggagaggg gcggggcctg gaacgaggct   240
gcttcgtgac ccactatgtc ttcccccaca agttctctgg acactccctt gcctgggaat   300
ggttctcccc agcccagtac ctcctccact tcacccacta ttaaggagga ggtacaggag   360
actgatccac ctccaggctc tgaagggtcc agctctgcct acatcgtgga gccagaggat   420
gaacctgagc gcaagcggaa gaagggtccg gccccgaaga tgctgggcca tgagctgtgc   480
cgcgtgtgcg gggacaaggc ctcgggcttc cactacaatg tgctcagttg tgaaggctgc   540
aaaggcttct tccggcgtag cgtggtccat ggtgggggccg ggcgctatgc ctgtcgggggc   600 agcggaacct gccagatgga tgccttcatg cggcgcaagt gccagctctg cagactgcgc   660
aagtgcaagg aggctggcat gcgggagcag tgcgtgcttt ctgaggagca gattcggaag   720
aaaaagattc agaagcagca acagcagcag ccaccgcccc cgactgagcc agcatccggt   780
agctcagccc ggcctgcagc ctcccctggc acttcggaag caagtagcca gggctccggg   840
gaaggagagg gcatccagct gacagcggct caggagctga tgatccaaca gttagttgcc   900
gtgcagctgc agtgcaacaa gcgatctttc tccgaccagc ctaaagtcac gccctggccc   960
ttgggtgcag accctcagtc ccgagacgct cgtcagcaac gctttgccca cttcactgag  1020
ctagccatca tctcagtcca ggagatcgtg gacttcgcca agcaggtgcc aggggttcctg  1080 cagctgggcc gggaggacca gatcgccctc ctgaaggcat ccaccatcga gatcatgttg  1140
ctagagacag ccagacgcta caaccacgag acagagtgca tcacgttcct gaaggacttc  1200
acctacagca aggacgactt ccaccgtgca ggcttgcagg tggagttcat caatcccatc  1260
tttgagttct ctcgggctat gcgtcggctg ggcctagacg atgcagagta tgccttgctc  1320
attgccatca acatcttctc agcggaccgg cctaatgtgc aggagcccag ccgtgtggag  1380
gctctgcagc agcccctatgt ggaggccctc ctctcctaca cgaggatcaa gcggccgcag  1440
gaccagctgc gcttcccacg aatgctcatg aagctggtga gcctgcgcac cctcagctcc  1500
gtgcactcgg agcaggtttt cgcattgcgt ctccaggaca agaagctgcc gcctttgctg  1560
tccgagatct gggatgtgca tgagtagggg ccgccacaag tgccccagcc ttggtggtgt  1620
```

```
ctacttgcag atggacgctt cctttgcctt tcctggggtg ggaggacact gtcacagccc   1680
agtcccctgg gctcgggctg agcgagtggc agttggcact agaaggtccc accccacccg   1740
ctgagtcttc caggagtggt gagggtcaca ggccctagcc tctgatcttt accagctgcc   1800
cttcctcccg agcttacacc tcagcctacc acaccatgca ccttgagtgg agagaggtta   1860
gggcaggtgg ctccccacag ttgggagacc acaggccccc tcttctgccc cttttattta   1920
ataaaaaaaa taaataaaaa taaagctcgt gccgaattc                          1959
```

<210> SEQ ID NO 8
<211> LENGTH: 443
<212> TYPE: PRT
<213> ORGANISM: Rattus norvegicus

<400> SEQUENCE: 8

```
Met Ser Ser Pro Thr Ser Ser Leu Asp Thr Pro Leu Pro Gly Asn Gly
1               5                   10                  15

Ser Pro Gln Pro Ser Thr Ser Ser Ser Pro Thr Ile Lys Glu Glu
            20                  25                  30

Val Gln Glu Thr Asp Pro Pro Gly Ser Glu Gly Ser Ser Ser Ala
        35                  40                  45

Tyr Ile Val Glu Pro Glu Asp Glu Pro Glu Arg Lys Arg Lys Lys Gly
50                  55                  60

Pro Ala Pro Lys Met Leu Gly His Glu Leu Cys Arg Val Cys Gly Asp
65                  70                  75                  80

Lys Ala Ser Gly Phe His Tyr Asn Val Leu Ser Cys Glu Gly Cys Lys
                85                  90                  95

Gly Phe Phe Arg Arg Ser Val Val His Gly Gly Ala Gly Arg Tyr Ala
            100                 105                 110

Cys Arg Gly Ser Gly Thr Cys Gln Met Asp Ala Phe Met Arg Arg Lys
        115                 120                 125

Cys Gln Leu Cys Arg Leu Arg Lys Cys Lys Glu Ala Gly Met Arg Glu
    130                 135                 140

Gln Cys Val Leu Ser Glu Glu Gln Ile Arg Lys Lys Lys Ile Gln Lys
145                 150                 155                 160

Gln Gln Gln Gln Gln Pro Pro Pro Thr Glu Pro Ala Ser Gly Ser
                165                 170                 175

Ser Ala Arg Pro Ala Ala Ser Pro Gly Thr Ser Glu Ala Ser Ser Gln
            180                 185                 190

Gly Ser Gly Glu Gly Glu Gly Ile Gln Leu Thr Ala Ala Gln Glu Leu
        195                 200                 205

Met Ile Gln Gln Leu Val Ala Val Gln Leu Gln Cys Asn Lys Arg Ser
    210                 215                 220

Phe Ser Asp Gln Pro Lys Val Thr Pro Trp Pro Leu Gly Ala Asp Pro
225                 230                 235                 240

Gln Ser Arg Asp Ala Arg Gln Arg Phe Ala His Phe Thr Glu Leu
                245                 250                 255

Ala Ile Ile Ser Val Gln Glu Ile Val Asp Phe Ala Lys Gln Val Pro
            260                 265                 270

Gly Phe Leu Gln Leu Gly Arg Glu Asp Gln Ile Ala Leu Leu Lys Ala
        275                 280                 285

Ser Thr Ile Glu Ile Met Leu Leu Glu Thr Ala Arg Arg Tyr Asn His
    290                 295                 300

Glu Thr Glu Cys Ile Thr Phe Leu Lys Asp Phe Thr Tyr Ser Lys Asp
305                 310                 315                 320
```

Asp Phe His Arg Ala Gly Leu Gln Val Glu Phe Ile Asn Pro Ile Phe
            325                 330                 335

Glu Phe Ser Arg Ala Met Arg Arg Leu Gly Leu Asp Asp Ala Glu Tyr
        340                 345                 350

Ala Leu Leu Ile Ala Ile Asn Ile Phe Ser Ala Asp Arg Pro Asn Val
            355                 360                 365

Gln Glu Pro Ser Arg Val Glu Ala Leu Gln Gln Pro Tyr Val Glu Ala
    370                 375                 380

Leu Leu Ser Tyr Thr Arg Ile Lys Arg Pro Gln Asp Gln Leu Arg Phe
385                 390                 395                 400

Pro Arg Met Leu Met Lys Leu Val Ser Leu Arg Thr Leu Ser Ser Val
                405                 410                 415

His Ser Glu Gln Val Phe Ala Leu Arg Leu Gln Asp Lys Lys Leu Pro
            420                 425                 430

Pro Leu Leu Ser Glu Ile Trp Asp Val His Glu
            435                 440

<210> SEQ ID NO 9
<211> LENGTH: 1964
<212> TYPE: DNA
<213> ORGANISM: Mus musculus

<400> SEQUENCE: 9
ggcgaagtta cttttgcttt tcgctcagca agcgctgttg cttcgagcta ctcccaggct      60
tctgaagtta cttccaaagt gctgtggagg cacaatcacc ggtgcggaca cagaggcaac     120
tctcgcctcc cacggccgtt ccagggcaa cagagtcgga ccccctgc gacccccctc       180
ccgatcgccg gtgcagtcat gagccccgcc tcccctggt gcacgagag gggcgggcc       240
tggaacaagc aggctgcttc gtgacccact atgtcttccc ccacaagttc tctggacact      300
cccgtgcctg gaatggttc tcctcagccc agtacctccg ccacgtcacc cactattaag      360
gaagaggggc aggagactga tcctcctcca ggctctgaag ggtccagctc tgcctacatc      420
gtggtcatct tagagccaga ggatgagcct gagcgcaagc ggaagaaggg gccggccccg     480
aagatgctgg gccatgagct gtgccgcgtg tgcggagaca aggcctcggg cttccactac     540
aacgtgctca gctgtgaagg ctgcaaaggc ttcttccggc gcagtgtggt ccacggtggg     600
gccgggcgct atgcctgtcg gggcagcgga acctgccaga tggatgcctt catgcggcgc     660
aagtgccagc tctgccggct cgcaagtgc aaggaggctg gcatgcggga gcagtgcgtg      720
ctctctgagg agcagattcg gaagaaaagg attcagaagc agcaacagca gcagccacca     780
ccccatctg agccagcagc cagcagctca ggccggccag cggcctcccc tggcacttcg     840
gaagcaagca gccagggctc cggggaagga gagggcatcc agctgaccgc ggctcaggag     900
ctgatgatcc agcagttagt tgccgcgcag ctgcagtgca acaaacgatc tttctccgac     960
cagcccaaag tcacgccctg gccctgggt gcagaccctc agtcccgaga tgcccgtcag    1020
caacgctttg cccacttcac cgagctagcc atcatctcgg tccaggagat tgtggacttt    1080
gccaagcagg tgccagggtt cttgcagttg gccgggagg accagatcgc cctcctgaag    1140
gcgtccacca ttgagatcat gttgctagaa acagccagac gctacaacca cgagacagaa    1200
tgcatcacgt tcctgaagga cttcacctac agcaaggac acttccaccg tgcaggcttg    1260
caggtggaat tcatcaatcc catcttcgag ttctcgcggg ccatgcggcg gctgggcctg    1320
gacgatgcag agtatgcctt gcttatcgcc atcaacatct ctcagccga tcggcctaat    1380
gtgcaggagc ccagccgtgt ggaggccctg cagcagccat acgtggaggc gctcctctcc    1440

-continued

```
tacacgagga tcaagcgccc acaggaccag ctccgcttcc cacgcatgct catgaagctg    1500
gtgagcctgc gcaccctcag ctccgtgcac tcggagcagg tctttgcatt gcgactccag    1560
gacaagaagc tgccgccctt gctgtccgag atctgggatg tgcacgagta ggggcagcca    1620
caagtgcccc agccttggtg gtgtcttctt gaagatggac tcttcacctc tcctcctggg    1680
gtgggaggac attgtcacgg cccagtccct cgggctcagc ctcaaactca gcggcagttg    1740
gcactagaag gccccacccc acccattgag tcttccaaga gtggtgaggg tcacaggtcc    1800
tagcctctga ccgttcccag ctgccctccc acccacgctt acacctcagc ctaccacacc    1860
atgcaccttg agtggagaga ggttagggca ggtggccccc cacagttggg agaccacagg    1920
ccctctcttc tgccccttttt atttaataaa aaaacaaaaa taaa                    1964
```

<210> SEQ ID NO 10
<211> LENGTH: 446
<212> TYPE: PRT
<213> ORGANISM: Mus musculus

<400> SEQUENCE: 10

```
Met Ser Ser Pro Thr Ser Ser Leu Asp Thr Pro Val Pro Gly Asn Gly
1               5                   10                  15

Ser Pro Gln Pro Ser Thr Ser Ala Thr Ser Pro Thr Ile Lys Glu Glu
            20                  25                  30

Gly Gln Glu Thr Asp Pro Pro Gly Ser Glu Gly Ser Ser Ser Ala
        35                  40                  45

Tyr Ile Val Val Ile Leu Glu Pro Glu Asp Glu Pro Glu Arg Lys Arg
50                  55                  60

Lys Lys Gly Pro Ala Pro Lys Met Leu Gly His Glu Leu Cys Arg Val
65                  70                  75                  80

Cys Gly Asp Lys Ala Ser Gly Phe His Tyr Asn Val Leu Ser Cys Glu
                85                  90                  95

Gly Cys Lys Gly Phe Phe Arg Arg Ser Val Val His Gly Gly Ala Gly
            100                 105                 110

Arg Tyr Ala Cys Arg Gly Ser Gly Thr Cys Gln Met Asp Ala Phe Met
        115                 120                 125

Arg Arg Lys Cys Gln Leu Cys Arg Leu Arg Lys Cys Lys Glu Ala Gly
130                 135                 140

Met Arg Glu Gln Cys Val Leu Ser Glu Glu Gln Ile Arg Lys Lys Arg
145                 150                 155                 160

Ile Gln Lys Gln Gln Gln Gln Pro Pro Pro Ser Glu Pro Ala
                165                 170                 175

Ala Ser Ser Ser Gly Arg Pro Ala Ala Ser Pro Gly Thr Ser Glu Ala
            180                 185                 190

Ser Ser Gln Gly Ser Gly Glu Gly Glu Gly Ile Gln Leu Thr Ala Ala
        195                 200                 205

Gln Glu Leu Met Ile Gln Gln Leu Val Ala Ala Gln Leu Gln Cys Asn
210                 215                 220

Lys Arg Ser Phe Ser Asp Gln Pro Lys Val Thr Pro Trp Pro Leu Gly
225                 230                 235                 240

Ala Asp Pro Gln Ser Arg Asp Ala Arg Gln Gln Arg Phe Ala His Phe
                245                 250                 255

Thr Glu Leu Ala Ile Ile Ser Val Gln Glu Ile Val Asp Phe Ala Lys
            260                 265                 270

Gln Val Pro Gly Phe Leu Gln Leu Gly Arg Glu Asp Gln Ile Ala Leu
        275                 280                 285
```

-continued

```
Leu Lys Ala Ser Thr Ile Glu Ile Met Leu Leu Glu Thr Ala Arg Arg
    290                 295                 300

Tyr Asn His Glu Thr Glu Cys Ile Thr Phe Leu Lys Asp Phe Thr Tyr
305                 310                 315                 320

Ser Lys Asp Asp Phe His Arg Ala Gly Leu Gln Val Glu Phe Ile Asn
                325                 330                 335

Pro Ile Phe Glu Phe Ser Arg Ala Met Arg Arg Leu Gly Leu Asp Asp
            340                 345                 350

Ala Glu Tyr Ala Leu Leu Ile Ala Ile Asn Ile Phe Ser Ala Asp Arg
        355                 360                 365

Pro Asn Val Gln Glu Pro Ser Arg Val Glu Ala Leu Gln Gln Pro Tyr
    370                 375                 380

Val Glu Ala Leu Leu Ser Tyr Thr Arg Ile Lys Arg Pro Gln Asp Gln
385                 390                 395                 400

Leu Arg Phe Pro Arg Met Leu Met Lys Leu Val Ser Leu Arg Thr Leu
                405                 410                 415

Ser Ser Val His Ser Glu Gln Val Phe Ala Leu Arg Leu Gln Asp Lys
            420                 425                 430

Lys Leu Pro Pro Leu Leu Ser Glu Ile Trp Asp Val His Glu
        435                 440                 445
```

<210> SEQ ID NO 11
<211> LENGTH: 2010
<212> TYPE: DNA
<213> ORGANISM: Homo sapiens

<400> SEQUENCE: 11

```
caagaagtgg cgaagttacc tttgagggta tttgagtagc ggcggtgtgt caggggctaa      60
agaggaggac gaagaaaagc agagcaaggg aacccagggc aacaggagta gttcactccg     120
cgagaggccg tccacgagac ccccgcgcgc aggcatgagc cccgcccccc acgcatgagc     180
cccgcccccc gctgttgctt ggagaggggc gggacctgga gagaggctgc tccgtgaccc     240
caccatgtcc tctcctacca cgagttccct ggatacccc ctgcctggaa atggcccccc      300
tcagcctggc gccccttctt cttcacccac tgtaaaggag gagggtccgg agccgtggcc     360
cgggggtccg gaccctgatg tcccaggcac tgatgaggcc agctcagcct gcagcacaga     420
ctgggtcatc ccagatcccg aagaggaacc agagcgcaag cgaaagaagg gcccagcccc     480
gaagatgctg ggccacgagc tttgccgtgt ctgtggggac aaggcctccg gcttccacta     540
caacgtgctc agctgcgaag gctgcaaggg cttcttccgg cgcagtgtgg tccgtggtgg     600
ggccaggcgc tatgcctgcc ggggtggcgg aacctgccag atggacgctt catgcggcg      660
caagtgccag cagtgccggc tgcgcaagtg caaggaggca gggatgaggg agcagtgcgt     720
cctttctgaa gaacagatcc ggaagaagaa gattcggaaa cagcagcagc aggagtcaca     780
gtcacagtcg cagtcacctg tggggccgca ggcagcagca agctcagcct ctgggcctgg     840
ggcttcccct ggtggatctg aggcaggcag ccagggctcc ggggaaggcg agggtgtcca     900
gctaacagcg gctcaagaac taatgatcca gcagttggtg gcggcccaac tgcagtgcaa     960
caaacgctcc ttctccgacc agcccaaagt cacgcccctgg ccctgggcg cagaccccca    1020
gtcccgagat gcccgccagc aacgctttgc ccacttcacg gagctggcca tcatctcagt    1080
ccaggagatc gtggacttcg ctaagcaagt gcctggtttc ctgcagctgg gccgggagga    1140
ccagatcgcc ctcctgaagg catccactat cgagatcatg ctgctagaga cagccaggcg    1200
ctacaaccac gagacagagt gtatcacctt cttgaaggac ttcacctaca gcaaggacga    1260
```

-continued

```
cttccaccgt gcaggcctgc aggtggagtt catcaacccc atcttcgagt tctcgcgggc   1320
catgcggcgg ctgggcctgg acgacgctga gtacgccctg ctcatcgcca tcaacatctt   1380
ctcggccgac cggcccaacg tgcaggagcc gggccgcgtg gaggcgttgc agcagccta   1440 cgtggaggcg ctgctgtcct acacgcgcat caagaggccg caggaccagc tgcgcttccc   1500
gcgcatgctc atgaagctgg tgagcctgcg cacgctgagc tctgtgcact cggagcaggt   1560
cttcgccttg cggctccagg acaagaagct gccgcctctg ctgtcggaga tctgggacgt   1620
ccacgagtga ggggctggcc acccagcccc acagccttgc ctgaccaccc tccagcagat   1680
agacgccggc accccttcct cttcctaggg tggaaggggc cctgggcgag cctgtagacc   1740
tatcggctct catcccttgg gataagcccc agtccaggtc caggaggctc cctccctgcc   1800
cagcgagtct tccagaaggg gtgaaagggt tgcaggtccc gaccactgac ccttcccggc   1860
tgccctccct ccccagctta cacctcaagc ccagcacgca gcgtaccttg aacagaggga   1920
ggggaggacc catggctctc ccccctagc ccgggagacc aggggccttc ctcttcctct   1980
gcttttattt aataaaaata aaaacagaaa                                    2010
```

<210> SEQ ID NO 12
<211> LENGTH: 461
<212> TYPE: PRT
<213> ORGANISM: Homo sapiens

<400> SEQUENCE: 12

```
Met Ser Ser Pro Thr Thr Ser Ser Leu Asp Thr Pro Leu Pro Gly Asn
1               5                   10                  15

Gly Pro Pro Gln Pro Gly Ala Pro Ser Ser Ser Pro Thr Val Lys Glu
            20                  25                  30

Glu Gly Pro Glu Pro Trp Pro Gly Gly Pro Asp Pro Asp Val Pro Gly
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
            100                 105                 110

Arg Ser Val Val Arg Gly Gly Ala Arg Arg Tyr Ala Cys Arg Gly Gly
        115                 120                 125

Gly Thr Cys Gln Met Asp Ala Phe Met Arg Arg Lys Cys Gln Gln Cys
    130                 135                 140

Arg Leu Arg Lys Cys Lys Glu Ala Gly Met Arg Glu Gln Cys Val Leu
145                 150                 155                 160

Ser Glu Glu Gln Ile Arg Lys Lys Lys Ile Arg Lys Gln Gln Gln Gln
                165                 170                 175

Glu Ser Gln Ser Gln Ser Gln Ser Pro Val Gly Pro Gln Gly Ser Ser
            180                 185                 190

Ser Ser Ala Ser Gly Pro Gly Ala Ser Pro Gly Gly Ser Glu Ala Gly
        195                 200                 205

Ser Gln Gly Ser Gly Glu Gly Glu Gly Val Gln Leu Thr Ala Ala Gln
    210                 215                 220

Glu Leu Met Ile Gln Gln Leu Val Ala Ala Gln Leu Gln Cys Asn Lys
225                 230                 235                 240
```

```
Arg Ser Phe Ser Asp Gln Pro Lys Val Thr Pro Trp Pro Leu Gly Ala
            245                 250                 255
Asp Pro Gln Ser Arg Asp Ala Arg Gln Gln Arg Phe Ala His Phe Thr
        260                 265                 270
Glu Leu Ala Ile Ile Ser Val Gln Glu Ile Val Asp Phe Ala Lys Gln
    275                 280                 285
Val Pro Gly Phe Leu Gln Leu Gly Arg Glu Asp Gln Ile Ala Leu Leu
290                 295                 300
Lys Ala Ser Thr Ile Glu Ile Met Leu Leu Glu Thr Ala Arg Arg Tyr
305                 310                 315                 320
Asn His Glu Thr Glu Cys Ile Thr Phe Leu Lys Asp Phe Thr Tyr Ser
                325                 330                 335
Lys Asp Asp Phe His Arg Ala Gly Leu Gln Val Glu Phe Ile Asn Pro
            340                 345                 350
Ile Phe Glu Phe Ser Arg Ala Met Arg Arg Leu Gly Leu Asp Asp Ala
        355                 360                 365
Glu Tyr Ala Leu Leu Ile Ala Ile Asn Ile Phe Ser Ala Asp Arg Pro
    370                 375                 380
Asn Val Gln Glu Pro Gly Arg Val Glu Ala Leu Gln Gln Pro Tyr Val
385                 390                 395                 400
Glu Ala Leu Leu Ser Tyr Thr Arg Ile Lys Arg Pro Gln Asp Gln Leu
                405                 410                 415
Arg Phe Pro Arg Met Leu Met Lys Leu Val Ser Leu Arg Thr Leu Ser
            420                 425                 430
Ser Val His Ser Glu Gln Val Phe Ala Leu Arg Leu Gln Asp Lys Lys
        435                 440                 445
Leu Pro Pro Leu Leu Ser Glu Ile Trp Asp Val His Glu
    450                 455                 460

<210> SEQ ID NO 13
<211> LENGTH: 2070
<212> TYPE: DNA
<213> ORGANISM: Rattus norvegicus

<400> SEQUENCE: 13
ctgagttctg agcgtctaca gcgaaagtgc tgggctttgg aaaggagacc tgggctccga      60
atcctctcag ggccttggac gtctctgacc caaaacaatc caaggttctt atttgaagac     120
caccatccca gaagcacatt ctcgagttga aaagttggag tggtgttcga atgaatctg      180
attgggccct cccatttaca agccacggac gagtttgctc tttctgaaaa cttatttgga     240
gtgctaacag agcacgcggc aggtcctctg ggcagaatc tggacttgga atcgtactcc      300
ccatacaaca atgtgcagtt tcctcaagtt cagccacaga tctcctcctc gtcctattat     360
tccaacctgg gtttctaccc gcaacaaccg gaagactggt actctcctgg actctatgaa     420
ctcaggcgaa tgcccactga gagtgtgtac caggagagaa ctgaggtatc cgagatgcct     480
gtgacaaaga agccgcgaat ggccgcctca tcggcgggaa gaataaaagg ggatgagctg     540
tgtgtggtct gcggagacag ggcctctggg taccattaca acgcgctcac ctgcgagggc     600
tgcaaaggtt tcttccgaag aagcatcacc aaaaacgccg tgtacaagtg taagaacggg     660
ggcaactgcg tgatggatat gtacatgcgt cggaagtgcc aggattgccg gctaaggaag     720
tgcagagaga tgggaatgtt ggctgaatgt ttgttaactg aaattcagtg taaatctaaa     780
cggctaagga aaaatgtgaa gcagcatgcg gatcagacag tgaatgagga cagcgaaggg     840
cgtgacttgc ggcaagtgac ctccacgacc aagctatgca gggagaaaac tgaactcact     900
```

-continued

```
gtagaccagc agaccctcct ggattatatt atggactcat acagcaaaca gagaatgcca   960
caggagatca caaataaaat cttaaaagaa gaatttagtg cagaagaaaa ttttctcata  1020
ttaacagaaa tggctaccag tcacgtacag attctcgtag aattcacaaa aagacttcca  1080
gggtttcaga cactggacca cgaagaccag attgctttgc tcaaagggtc cgcagtcgag  1140
gccatgttcc ttcgttcagc ggagattttc aataagaaac ttcctgccgg acacgcagac  1200
ctgttggaag aaagaattcg aaagagcggc atctccgatg agtacataac cccgatgttt  1260
agtttctata aaagtgtcgg ggagctgaaa atgacccagg aagagtacgc tctgctcaca  1320
gcaattgtca tcctctctcc agacagacaa tacataaagg atagagaggc agtggagaag  1380
cttcaggagc ctctgctcga tgtcctacaa aaactctgca agatctacca gcccgagaac  1440
cctcagcatt tcgcctgcct cctgggtcgc ctgacagaac tccggacatt caaccatcac  1500
cacgctgaga tgctgatgtc ttggagggtg aatgaccaca agttcacccc gctcctctgt  1560
gagatctggg atgtgcagtg aaggacacgg ggagaggcta gctccttgtc ctcctcagag  1620
cagcaacctg gtattggact tcccttcttt tcatttgtac caggtctcac tcaagaatct  1680
caatgaatat ttatgtggca attatacaat tcccacaact gtaaatacag gctccataga  1740
attgcttccc ctacactgta ttttacaagg cttcgggaaa ccccactgac acgcccttt  1800 tgcctcatta aatcaattgt tacttcaatt ttgtcaactg agctagggac cgcctcgttt  1860
tatcctccat gcggcaacat tatatatata tatattttat caaatagctg ttttctcttc  1920
cttttttttt tttttttttt tcggagctgg ggactgaacc cagggccttg cgcttgctag  1980
gcaagcgctc taccactgag ctaaatcccc aaccctatt aaatagctgt tttcaactga  2040
gacaataaac tgaacgtaat gccaagagaa                                   2070
```

<210> SEQ ID NO 14
<211> LENGTH: 469
<212> TYPE: PRT
<213> ORGANISM: Rattus norvegicus

<400> SEQUENCE: 14

```
Met Asn Leu Ile Gly Pro Ser His Leu Gln Ala Thr Asp Glu Phe Ala
1               5                   10                  15

Leu Ser Glu Asn Leu Phe Gly Val Leu Thr Glu His Ala Ala Gly Pro
            20                  25                  30

Leu Gly Gln Asn Leu Asp Leu Glu Ser Tyr Ser Pro Tyr Asn Asn Val
        35                  40                  45

Gln Phe Pro Gln Val Gln Pro Gln Ile Ser Ser Ser Ser Tyr Tyr Ser
    50                  55                  60

Asn Leu Gly Phe Tyr Pro Gln Gln Pro Glu Asp Trp Tyr Ser Pro Gly
65                  70                  75                  80

Leu Tyr Glu Leu Arg Arg Met Pro Thr Glu Ser Val Tyr Gln Gly Glu
                85                  90                  95

Thr Glu Val Ser Glu Met Pro Val Thr Lys Lys Pro Arg Met Ala Ala
            100                 105                 110

Ser Ser Ala Gly Arg Ile Lys Gly Asp Glu Leu Cys Val Val Cys Gly
        115                 120                 125

Asp Arg Ala Ser Gly Tyr His Tyr Asn Ala Leu Thr Cys Glu Gly Cys
    130                 135                 140

Lys Gly Phe Phe Arg Arg Ser Ile Thr Lys Asn Ala Val Tyr Lys Cys
145                 150                 155                 160

Lys Asn Gly Gly Asn Cys Val Met Asp Met Tyr Met Arg Arg Lys Cys
                165                 170                 175
```

```
Gln Asp Cys Arg Leu Arg Lys Cys Arg Glu Met Gly Met Leu Ala Glu
                180                 185                 190

Cys Leu Leu Thr Glu Ile Gln Cys Lys Ser Lys Arg Leu Arg Lys Asn
            195                 200                 205

Val Lys Gln His Ala Asp Gln Thr Val Asn Glu Asp Ser Glu Gly Arg
210                 215                 220

Asp Leu Arg Gln Val Thr Ser Thr Thr Lys Leu Cys Arg Glu Lys Thr
225                 230                 235                 240

Glu Leu Thr Val Asp Gln Gln Thr Leu Leu Asp Tyr Ile Met Asp Ser
                245                 250                 255

Tyr Ser Lys Gln Arg Met Pro Gln Glu Ile Thr Asn Lys Ile Leu Lys
                260                 265                 270

Glu Glu Phe Ser Ala Glu Asn Phe Leu Ile Leu Thr Glu Met Ala
                275                 280                 285

Thr Ser His Val Gln Ile Leu Val Glu Phe Thr Lys Arg Leu Pro Gly
                290                 295                 300

Phe Gln Thr Leu Asp His Glu Asp Gln Ile Ala Leu Leu Lys Gly Ser
305                 310                 315                 320

Ala Val Glu Ala Met Phe Leu Arg Ser Ala Glu Ile Phe Asn Lys Lys
                325                 330                 335

Leu Pro Ala Gly His Ala Asp Leu Leu Glu Glu Arg Ile Arg Lys Ser
                340                 345                 350

Gly Ile Ser Asp Glu Tyr Ile Thr Pro Met Phe Ser Phe Tyr Lys Ser
                355                 360                 365

Val Gly Glu Leu Lys Met Thr Gln Glu Glu Tyr Ala Leu Leu Thr Ala
370                 375                 380

Ile Val Ile Leu Ser Pro Asp Arg Gln Tyr Ile Lys Asp Arg Glu Ala
385                 390                 395                 400

Val Glu Lys Leu Gln Glu Pro Leu Leu Asp Val Leu Gln Lys Leu Cys
                405                 410                 415

Lys Ile Tyr Gln Pro Glu Asn Pro Gln His Phe Ala Cys Leu Leu Gly
                420                 425                 430

Arg Leu Thr Glu Leu Arg Thr Phe Asn His His His Ala Glu Met Leu
                435                 440                 445

Met Ser Trp Arg Val Asn Asp His Lys Phe Thr Pro Leu Leu Cys Glu
450                 455                 460

Ile Trp Asp Val Gln
465

<210> SEQ ID NO 15
<211> LENGTH: 2218
<212> TYPE: DNA
<213> ORGANISM: Homo sapiens

<400> SEQUENCE: 15
acgagactct ctcctcctcc tcacctcatt gtctccccga cttatcctaa tgcgaaattg      60
gattctgagc atttgtagca aaatcgctgg gatctggaga ggaagactca gtccagaatc     120
ctcccagggc cttgaaagtc catctctgac ccaaaacaat ccaaggaggt agaagacatc     180
gtagaaggag tgaaagaaga aagaagagact tagaaacata gctcaaagtg aacactgctt     240
ctcttagttt cctggatttc ttctggacat ttcctcaaga tgaaacttca gacactttgg     300 agttttttt gaagaccacc ataaagaaag tgcatttcaa ttgaaaaatt tggatgggat      360
caaaaatgaa tctcattgaa cattcccatt tacctaccac agatgaattt tcttttctg     420
```

-continued

```
aaaatttatt tggtgtttta acagaacaag tggcaggtcc tctgggacag aacctggaag    480
tggaaccata ctcgcaatac agcaatgttc agtttcccca agttcaacca cagatttcct    540
cgtcatccta ttattccaac ctgggtttct accccagca gcctgaagag tggtactctc    600
ctggaatata tgaactcagg cgtatgccag ctgagactct ctaccaggga gaaactgagg    660
tagcagagat gcctgtaaca agaagcccc gcatgggcgc gtcagcaggg aggatcaaag    720
gggatgagct gtgtgttgtt tgtggagaca gagcctctgg ataccactat aatgcactga    780
cctgtgaggg gtgtaaaggt ttcttcagga gaagcattac caaaaacgct gtgtacaagt    840
gtaaaaacgg gggcaactgt gtgatggata tgtacatgcg aagaaagtgt caagagtgtc    900
gactaaggaa atgcaaagag atgggaatgt tggctgaatg cttgttaact gaaattcagt    960
gtaaatctaa gcgactgaga aaaaatgtga agcagcatgc agatcagacc gtgaatgaag    1020
acagtgaagg tcgtgacttg cgacaagtga cctcgacaac aaagtcatgc agggagaaaa    1080
ctgaactcac cccagatcaa cagactcttc tacattttat tatggattca tataacaaac    1140
agaggatgcc tcaggaaata acaaataaaa ttttaaaaga gaattcagt gcagaagaaa    1200 attttctcat tttgacggaa atggcaacca atcatgtaca ggttcttgta gaattcacaa    1260
aaaagctacc aggatttcag actttggacc atgaagacca gattgctttg ctgaaagggt    1320
ctgcggttga agctatgttc cttcgttcag ctgagatttt caataagaaa cttccgtctg    1380
ggcattctga cctattggaa gaagaattc gaaatagtgg tatctctgat gaatatataa    1440
cacctatgtt tagttttat aaaagtattg gggaactgaa aatgactcaa gaggagtatg    1500
ctctgcttac agcaattgtt atcctgtctc cagatagaca atacataaag gatagagagg    1560
cagtagagaa gcttcaggag ccacttcttg atgtgctaca aaagttgtgt aagattcacc    1620
agcctgaaaa tcctcaacac tttgcctgtc tcctgggtcg cctgactgaa ttacggacat    1680
tcaatcatca ccacgctgag atgctgatgt catggagagt aaacgaccac aagtttaccc    1740
cacttctctg tgaaatctgg gacgtgcagt gatgggatt acaggggagg ggtctagctc    1800 cttttttctct ctcatattaa tctgatgtat aactttcctt tatttcactt gtacccagtt    1860
tcactcaaga aatcttgatg aatatttatg ttgtaattac atgtgtaact tccacaactg    1920
taaatattgg gctagataga acaactttct ctacattgtg ttttaaaagg ctccagggaa    1980
tcctgcattc taattggcaa gccctgtttg cctaattaaa ttgattgtta cttcaattct    2040
atctgttgaa ctagggaaaa tctcattttg ctcatcttac catattgcat atatttatt    2100 aaagagttgt attcaatctt ggcaataaag caaacataat ggcaacagaa aaaaaaaaa    2160 aaaaaaaaa aaaaaaaaa aaaaaaaaa aaaaaaaaa aaaaaaaaa aaaaaaa         2218
```

```
<210> SEQ ID NO 16
<211> LENGTH: 472
<212> TYPE: PRT
<213> ORGANISM: Homo sapiens

<400> SEQUENCE: 16
```

Met Gly Ser Lys Met Asn Leu Ile Glu His Ser His Leu Pro Thr Thr
1               5                   10                  15

Asp Glu Phe Ser Phe Ser Glu Asn Leu Phe Gly Val Leu Thr Glu Gln
            20                  25                  30

Val Ala Gly Pro Leu Gly Gln Asn Leu Glu Val Glu Pro Tyr Ser Gln
        35                  40                  45

Tyr Ser Asn Val Gln Phe Pro Gln Val Gln Pro Gln Ile Ser Ser Ser
    50                  55                  60

```
Ser Tyr Tyr Ser Asn Leu Gly Phe Tyr Pro Gln Gln Pro Glu Glu Trp
 65                  70                  75                  80

Tyr Ser Pro Gly Ile Tyr Glu Leu Arg Arg Met Pro Ala Glu Thr Leu
                 85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
        115                 120                 125

Val Cys Gly Asp Arg Ala Ser Gly Tyr His Tyr Asn Ala Leu Thr Cys
130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Leu Leu Thr Glu Ile Gln Cys Lys Ser Lys Arg Leu
        195                 200                 205

Arg Lys Asn Val Lys Gln His Ala Asp Gln Thr Val Asn Glu Asp Ser
210                 215                 220

Glu Gly Arg Asp Leu Arg Gln Val Thr Ser Thr Thr Lys Ser Cys Arg
225                 230                 235                 240

Glu Lys Thr Glu Leu Thr Pro Asp Gln Gln Thr Leu Leu His Phe Ile
                245                 250                 255

Met Asp Ser Tyr Asn Lys Gln Arg Met Pro Gln Glu Ile Thr Asn Lys
            260                 265                 270

Ile Leu Lys Glu Glu Phe Ser Ala Glu Glu Asn Phe Leu Ile Leu Thr
        275                 280                 285

Glu Met Ala Thr Asn His Val Gln Val Leu Val Glu Phe Thr Lys Lys
290                 295                 300

Leu Pro Gly Phe Gln Thr Leu Asp His Glu Asp Gln Ile Ala Leu Leu
305                 310                 315                 320

Lys Gly Ser Ala Val Glu Ala Met Phe Leu Arg Ser Ala Glu Ile Phe
                325                 330                 335

Asn Lys Lys Leu Pro Ser Gly His Ser Asp Leu Leu Glu Glu Arg Ile
            340                 345                 350

Arg Asn Ser Gly Ile Ser Asp Glu Tyr Ile Thr Pro Met Phe Ser Phe
        355                 360                 365

Tyr Lys Ser Ile Gly Glu Leu Lys Met Thr Gln Glu Glu Tyr Ala Leu
        370                 375                 380

Leu Thr Ala Ile Val Ile Leu Ser Pro Asp Arg Gln Tyr Ile Lys Asp
385                 390                 395                 400

Arg Glu Ala Val Glu Lys Leu Gln Glu Pro Leu Leu Asp Val Leu Gln
                405                 410                 415

Lys Leu Cys Lys Ile His Gln Pro Glu Asn Pro Gln His Phe Ala Cys
            420                 425                 430

Leu Leu Gly Arg Leu Thr Glu Leu Arg Thr Phe Asn His His His Ala
        435                 440                 445

Glu Met Leu Met Ser Trp Arg Val Asn Asp His Lys Phe Thr Pro Leu
450                 455                 460

Leu Cys Glu Ile Trp Asp Val Gln
465                 470

<210> SEQ ID NO 17
```

<211> LENGTH: 5449
<212> TYPE: DNA
<213> ORGANISM: Homo sapiens

<400> SEQUENCE: 17

| | | | | | |
|---|---|---|---|---|---|
| gcgccggggg | ccgccgcgcc | cgccgcccgc | tgcctgcgcc | gccggccggg | catgagttag | 60 |
| tcgcagacat | ggacaccaaa | catttcctgc | cgctcgattt | ctccacccag | gtgaactcct | 120 |
| ccctcacctc | cccgacgggg | cgaggctcca | tggctgcccc | ctcgctgcac | ccgtccctgg | 180 |
| ggcctggcat | cggctccccg | ggacagctgc | attctcccat | cagcaccctg | agctccccca | 240 |
| tcaacggcat | gggcccgcct | ttctcggtca | tcagctcccc | catgggcccc | cactccatgt | 300 |
| cggtgcccac | cacacccacc | ctgggcttca | gcactggcag | cccccagctc | agctcaccta | 360 |
| tgaaccccgt | cagcagcagc | gaggacatca | agccccccct | gggcctcaat | ggcgtcctca | 420 |
| aggtccccgc | ccaccccctca | ggaaacatgg | cttccttcac | caagcacatc | tgcgccatct | 480 |
| gcggggaccg | ctcctcaggc | aagcactatg | gagtgtacag | ctgcgagggg | tgcaagggct | 540 |
| tcttcaagcg | gacggtgcgc | aaggacctga | cctacacctg | ccgcgacaac | aaggactgcc | 600 |
| tgattgacaa | gcggcagcgg | aaccgtgcc | agtactgccg | ctaccagaag | tgcctggcca | 660 |
| tgggcatgaa | gcgggaagcc | gtgcaggagg | agcggcagcg | tggcaaggac | cggaacgaga | 720 |
| atgaggtgga | gtcgaccagc | agcgccaacg | aggacatgcc | ggtggagagg | atcctggagg | 780 |
| ctgagctggc | cgtggagccc | aagaccgaga | cctacgtgga | ggcaaacatg | gggctgaacc | 840 |
| ccagctcgcc | gaacgaccct | gtcaccaaca | tttgccaagc | agccgacaaa | cagcttttca | 900 |
| ccctggtgga | gtgggccaag | cggatcccac | acttctcaga | gctgccccct | gacgaccagg | 960 |
| tcatcctgct | gcgggcaggc | tggaatgagc | tgctcatcgc | ctccttctcc | caccgctcca | 1020 |
| tcgccgtgaa | ggacgggatc | ctcctggcca | ccggctgca | cgtccaccgg | aacagcgccc | 1080 |
| acagcgcagg | ggtgggcgcc | atctttgaca | gggtgctgac | ggagcttgtg | tccaagatgc | 1140 |
| gggacatgca | gatggacaag | acggagctgg | gctgcctgcg | cgccatcgtc | ctctttaacc | 1200 |
| ctgactccaa | ggggctctcg | aacccggccg | aggtggaggc | gctgagggag | aaggtctatg | 1260 |
| cgtccttgga | ggcctactgc | aagcacaagt | acccagagca | gccgggaagg | ttcgctaagc | 1320 |
| tcttgctccg | cctgccggct | ctgcgctcca | tcgggctcaa | atgcctggaa | catctcttct | 1380 |
| tcttcaagct | catcggggac | acacccattg | acaccttcct | tatggagatg | ctggaggcgc | 1440 |
| cgcaccaaat | gacttaggcc | tgcgggccca | tcctttgtgc | ccaccgtttc | tggccaccct | 1500 |
| gcctggacgc | cagctgttct | tctcagcctg | agccctgtcc | ctgcccttct | ctgcctggcc | 1560 |
| tgtttggact | tgggcaca | gcctgtcact | gctctgccta | agagatgtgt | tgtcaccctc | 1620 |
| cttatttctg | ttactacttg | tctgtggccc | agggcagtgg | cttcctgag | gcagcagcct | 1680 |
| tcgtggcaag | aactagcgtg | agcccagcca | ggcgcctccc | caccgggctc | tcaggacacc | 1740 |
| ctgccacacc | ccacgggggct | tgggcgacta | caggtcttc | gggccccagc | cctggagctg | 1800 |
| caggagttgg | gaacggggct | tttgtttccg | ttgctgttta | tcgatgctgg | ttttcagaat | 1860 |
| tcctgtgtgg | ccctcctgtc | tggagtgaca | tcttcatctg | ctctgaatac | tggtgccag | 1920 |
| ccagcccgtg | acagcttccc | cctaatcagg | aggggacagc | tgggggcgca | agctggtgtg | 1980 |
| tcatcagcaa | agacctcagc | cgcctcgggg | atgagagggg | actcgtgggg | caagcaagct | 2040 |
| gccctgtgct | ctgagtgagg | gggaaggtag | cccctttttc | caaagataac | tcacagtttt | 2100 |
| gccctcgagc | caatgagaac | atgagctgcc | ctctgtgcaa | ggtttcgggg | ccacctccag | 2160 |
| gctgcagggg | cgggtcactc | acccccctgt | tttctctctg | ccttggtgtt | ctggtttcag | 2220 |

```
actcccgact cccgttcag accagagtgc cccggcccct cccagcctg agtcttctcc    2280 ttgctctgcg gggtgggctg aggcttgtcc ttgtttcctg cagggctggc cctggctcgg    2340
gcagggtggg gcatcaccac ctcactggcc ttgctggagg cacagggctc tgcggacctg    2400
cagccatctg tgaggcccgc ggggatggga ggggaggagg gtggcctgtt ggtttccctc    2460 agaggggca ggtggcctgg agagagaggg gctcaggaac tgggagcctc gtgggtgggg    2520
cagatgctcc gcggcctgga gtggctctgc cggggcattg gtgggacccc tgctcaggcc    2580
ttctctctgg ctgccagttg tgtctaaaag actcttggaa tctgagaacc cggagtcgca    2640 gcgcccctcgg gcctgggcca cacgcaggcc ctggtgggac cacccagcct ggtattgtcc    2700
acggacagcg ttgttcaccc agagccttac ttgggagcct cactgaacgc ctgctctggt    2760
tgaaggtggg gtggggcgg ggcttgggc ctccctggct cagcccagtg cggcctggcg    2820
ctcctcccgc aggctctgcc cccgggctcc ggtggtgcgg ggccctctca ggttgaactc    2880
gcctcttttg cactggaagg ccctccctt ggcctgagta cttttcccgt tcacgcctca    2940
gtcccgtgga cccagccttt gtcagtggca ggtgcctgaa cagagggtgg atggggggga    3000
taccggaggg ggtcttgtct tcccagccgc agtctaggaa tgatgcgggg gggtggacgc    3060
cttctccata gtctttcccc acctggagca ggggcttcct cagtggtgag gggagctgcc    3120
tacaggttgg accgggaggc agtggcttgg agaggcagct ttccagcctt ggtggggaag    3180
aaagtgtcca ttctttgcct tcctggagct cccagccaga gctgagctta ggcacccgag    3240
tggagcctgc agctgagtct gtgcccgaga caggctgtca gagattccag aagcctctcc    3300
tccccgccgc cctccacccc tgcctttcag cgttgtggat ccctagaggt ggcccctgc    3360 ccgatccacc gtcctgaggc agagtgttga gcctcatacc tgtaccaggt ccccggccag    3420 ctgggccct cccaggcact gccaggaagc cccagctgcc cctggcgggt gtggtggaaa    3480
tggcaggagg gtgcaggtac tcttggggcc ccagcgtgtgg gagtgcaaaa gacccaacgc    3540
caacacctgg tgccttttgc agccagcgcc cacccatccg tgcccggacc cttgggaatg    3600
cccgcggctc cagaggaaaa agcccaggga cggggcctcc gttgcggggg gtcggctgct    3660
tcttgggaac tttgtcgttt ccggcgctgg ctggctggct ggctgtaaag cactgaagcc    3720
ccccggccgc caacccctga agcagaacc tggcctccct ggccacagca gccttaccca    3780
ccgctctacg tgtcccggc acttcccgca gccttcccgt cccttttctca tcggccttgt    3840 agttgtacag tgctgttggt ttgaaaaggt gatgtgtggg gagtgcggct catcactgag    3900
tagagaggta gaatttctat ttaaccagac ctgtagtagt attaccaatc cagttcaatt    3960
aaggtgattt tttgtaatta ttattatttt ggtgggacaa tctttaattt tctaaagata    4020
gcactaacat cagctcatta gccacctgtg cctgtccccg ccttggcccg gctgatgaa    4080 gcggcttccc cgcagggccc ccacttccca gtggctgctt cctggggacc cagggcaccc    4140
cggcaccttc aggcacgctc ctcagctggt cacctcccgg ctttgccgtt cagatggggc    4200
tcctgaggct caggagtgaa gatgccacag agccgggctc ccctaggctg cgtcgggcat    4260
gcttggaagc tggcctgcca ggaccttcca ccctgggggcc tgtgtcagcc gccgccctc    4320 cgcaccctgg aagcacacgg cctctgggaa ggacagccct gaccttcggt tttccgagca    4380
cggtgtttcc caagaattct gggctggcgg cctggtggca gtgctggaga tgaccccgag    4440
cccctccccg tggggcaccc aggagggccc tgccggaatg tgcagcctgt gggtagtcgg    4500
ctggtgtccc tgtcgtggag ctggggtgcg tgatctggtg ctcgtccacg caggtgtgtg    4560
gtgtaaacat gtatgtgctg tacagagaga cgcgtgtgga gagagccgca caccagcgcc    4620
```

```
acccaggaaa ggcggagcgg ttaccagtgt tttgtgttta ttttttaatca agacgtttcc    4680 cctgttttcc tataaatttg cttcgtgtaa gcaagtacat aaggaccctc ctttggtgaa    4740
atccgggttc gaatgaatat ctcaaggcag gagatgcatc tattttaaga tgctttggag    4800
cagacagctt tagccgttcc caatccttag caatgcctta gctgggacgc atagctaata    4860
ctttagagag gatgacagat ccataaagag agtaaagata agagaaaatg tctaaagcat    4920
ctggaaaggt aaaaaaaaaa aatctatttt tgtacaaatg taattttatc cctcatgtat    4980
acttggatat ggcgggggga gggctgggac tgtttcgttt ctgcttctag agattgaggt    5040
gaaagcttcg tccgagaaac gccaggacag acgatggcag aggagagggc tcctgtgacg    5100
gcggcgaggc ttgggaggaa accgccgcaa tgggggtgtc ttccctcggg gcaggagggt    5160
gggcctgagg ctttcaaggg ttttcttccc tttcgagtaa ttttttaaagc cttgctctgt    5220 tgtgtcctgt tgccggctct ggccttcctg tgactgactg tgaagtggct tctccgtacg    5280
attgtctctg aaacatcgtg gcctcaggtg ccagggtttg atggacagta gcattagaat    5340
tgtggaaaag gaacacgcaa agggagaagt gtgagaggag aaacaaaata tgagcgttta    5400
aaatacatcg ccattcagtt cgttaaaaaa aaaaaaaaaa aaaaaaaaa                5449
```

```
<210> SEQ ID NO 18
<211> LENGTH: 462
<212> TYPE: PRT
<213> ORGANISM: Homo sapiens

<400> SEQUENCE: 18

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240
```

```
Ala Val Glu Pro Lys Thr Glu Thr Tyr Val Glu Ala Asn Met Gly Leu
            245                 250                 255
Asn Pro Ser Ser Pro Asn Asp Pro Val Thr Asn Ile Cys Gln Ala Ala
        260                 265                 270
Asp Lys Gln Leu Phe Thr Leu Val Glu Trp Ala Lys Arg Ile Pro His
    275                 280                 285
Phe Ser Glu Leu Pro Leu Asp Asp Gln Val Ile Leu Leu Arg Ala Gly
290                 295                 300
Trp Asn Glu Leu Leu Ile Ala Ser Phe Ser His Arg Ser Ile Ala Val
305                 310                 315                 320
Lys Asp Gly Ile Leu Leu Ala Thr Gly Leu His Val His Arg Asn Ser
                325                 330                 335
Ala His Ser Ala Gly Val Gly Ala Ile Phe Asp Arg Val Leu Thr Glu
            340                 345                 350
Leu Val Ser Lys Met Arg Asp Met Gln Met Asp Lys Thr Glu Leu Gly
        355                 360                 365
Cys Leu Arg Ala Ile Val Leu Phe Asn Pro Asp Ser Lys Gly Leu Ser
    370                 375                 380
Asn Pro Ala Glu Val Glu Ala Leu Arg Glu Lys Val Tyr Ala Ser Leu
385                 390                 395                 400
Glu Ala Tyr Cys Lys His Lys Tyr Pro Glu Gln Pro Gly Arg Phe Ala
                405                 410                 415
Lys Leu Leu Leu Arg Leu Pro Ala Leu Arg Ser Ile Gly Leu Lys Cys
            420                 425                 430
Leu Glu His Leu Phe Phe Phe Lys Leu Ile Gly Asp Thr Pro Ile Asp
        435                 440                 445
Thr Phe Leu Met Glu Met Leu Glu Ala Pro His Gln Met Thr
    450                 455                 460

<210> SEQ ID NO 19
<211> LENGTH: 1330
<212> TYPE: DNA
<213> ORGANISM: Homo sapiens

<400> SEQUENCE: 19
ttggggttgt gctccaggga tggcctttca catagactgc agtgtaaatg acagcctctg      60
gaatgtgcat tgcagggcct tgcttagtgg tagggaatga tttccatcac ttctgtgaca     120
ttctgcttcc caataagtct tcctgtgact ccctatttc ccccatccca gattaactca      180
acagtgtcac tccctggggg tgggtctggc ccccctgaag atgtgaagcc accagtctta     240
ggggtccggg gcctgcactg tccacccccct ccaggtggcc ctgggggctgg caaacggcta     300 tgtgcaatct gcggggacag aagctcaggc aaacactacg gggtttacag ctgtgagggt     360
tgcaagggct tcttcaaacg caccatccgc aaagacctta catactcttg ccggacaac     420 aaagactgca cagtggacaa cgccagcggg aaccgctgtc agtactgccg ctatcagaag     480
tgcctggcca ctggcatgaa gagggaggcg gtacaggagg agcgtcagcg gggaaaggac     540
aaggatgggg atggggaggg gctggggga gcccccgagg agatgcctgt ggacaggatc     600
ctggaggcag agcttgctgt ggaacagaag agtgaccagg gcgttgaggg tcctggggga     660 accggggta gcggcagcag cgtgagtgtt gggtcaatc cactctcctt cgtgatgggg     720
gttgggggag gcagtctagg tctgttctac atcccctccc cctcctttcc cctcataacc     780
ttcctaacac tacttgggac tggaggtgct gccaaacaag gtctttcaaa catctgaggt     840
ggatgtgata gctccttctg tctccactcc ccaaacaacc cactggcaga accataggca     900
```

-continued

```
tgtcccaaat aaataattgt ttgcactaat gccagaagag aagactcact tacagggatt      960
ggtttggatg gggctcacag gaagactata tgtaaggagg gggtgtcaaa agcctcttac     1020
aagggggctc ccagcatatc tcaaaatctt ccataactct tacccccgtc ccctgcagcc     1080
aaatgaccct gtgactaaca tctgtcaggc agctgacaaa cagctattca cgcttgttga     1140
gtgggcgaag aggatcccac acttttcctc cttgcctctg gatgatcagg tcatattgct     1200
gcgggcaggt cagtgacctt ggatcccttt gacttcttga catttgaccc ctctttgact     1260
tcccgatctt tagtgacccc agtggcctta ccttgcgtac ccaggagcc aaacttgctg     1320 acctcgccac                                                            1330
```

<210> SEQ ID NO 20
<211> LENGTH: 246
<212> TYPE: PRT
<213> ORGANISM: Homo sapiens

<400> SEQUENCE: 20

```
Met Ile Ser Ile Thr Ser Val Thr Phe Cys Phe Pro Ile Ser Leu Pro
1               5                   10                  15

Val Thr Ser Leu Phe Pro Pro Ser Gln Ile Asn Ser Thr Val Ser Leu
            20                  25                  30

Pro Gly Gly Gly Ser Gly Pro Pro Glu Asp Val Lys Pro Pro Val Leu
        35                  40                  45

Gly Val Arg Gly Leu His Cys Pro Pro Pro Gly Gly Pro Gly Ala
    50                  55                  60

Gly Lys Arg Leu Cys Ala Ile Cys Gly Asp Arg Ser Ser Gly Lys His
65                  70                  75                  80

Tyr Gly Val Tyr Ser Cys Glu Gly Cys Lys Gly Phe Phe Lys Arg Thr
                85                  90                  95

Ile Arg Lys Asp Leu Thr Tyr Ser Cys Arg Asp Asn Lys Asp Cys Thr
            100                 105                 110

Val Asp Lys Arg Gln Arg Asn Arg Cys Gln Tyr Cys Arg Tyr Gln Lys
        115                 120                 125

Cys Leu Ala Thr Gly Met Lys Arg Glu Ala Val Gln Glu Glu Arg Gln
    130                 135                 140

Arg Gly Lys Asp Lys Asp Gly Asp Gly Glu Gly Ala Gly Gly Ala Pro
145                 150                 155                 160

Glu Glu Met Pro Val Asp Arg Ile Leu Glu Ala Glu Leu Ala Val Glu
                165                 170                 175

Gln Lys Ser Asp Gln Gly Val Glu Gly Pro Gly Gly Thr Gly Gly Ser
            180                 185                 190

Gly Ser Ser Val Ser Val Gly Val Asn Pro Leu Ser Phe Val Met Gly
        195                 200                 205

Val Gly Gly Gly Ser Leu Gly Leu Phe Tyr Ile Pro Ser Pro Ser Phe
    210                 215                 220

Pro Leu Ile Thr Phe Leu Thr Leu Leu Gly Thr Gly Gly Ala Ala Lys
225                 230                 235                 240

Gln Gly Leu Ser Asn Ile
                245
```

<210> SEQ ID NO 21
<211> LENGTH: 1827
<212> TYPE: DNA
<213> ORGANISM: Homo sapiens

<400> SEQUENCE: 21

```
gtagcggtga cggcggcggc ggcggcggcg gcagcattat gcgtgattac tgacaggcac      60
cagctgctgc cgccacagcc gtctcaaacg cactatgtgg actctccgat ctagaggcag     120
attcctgact aatcccagag ggctggccca gcctgtgctc ccgggctgc taggaagcga      180
tgaccactct tgttagccca agttgaagaa agccgggctg tgcctgggag ccgagagagg     240
cggtaatatt tagaagctgc acaggagagg aacatgaact gacgagtaaa catgtatgga     300
aattattctc acttcatgaa gtttcccgca ggctatggag gctcccctgg ccacactggc     360
tctacatcca tgagcccatc agcagccttg tccacaggga agccaatgga cagccacccc     420
agctacacag atacccagt gagtgcccca cggactctga gtgcagtggg gaccccctc      480
aatgccctgg ctctccata tcgagtcatc acctctgcca tgggcccacc ctcaggagca     540
cttgcagcgc tccaggaat caacttggtt gccccaccca gctctcagct aaatgtggtc     600
aacagtgtca gcagttcaga ggacatcaag cccttaccag gcttccgg gattggaaac      660
atgaactacc catccaccag ccccggatct ctggttaaac acatctgtgc catctgtgga     720
gacagatcct caggaaagca ctacggggta tacagttgtg aaggctgcaa agggttcttc     780
aagaggacga taaggaagga cctcatctac acgtgtcggg ataataaaga ctgcctcatt     840
gacaagcgtc agcgcaaccg ctgccagtac tgtcgctatc agaagtgcct tgtcatgggc     900
atgaagaggg aagctgtgca agaagaaaga cagaggagcc gagagcgagc tgagagtgag     960
gcagaatgtg ctaccagtgg tcatgaagac atgcctgtgg agaggattct agaagctgaa    1020
cttgctgttg aaccaaagac agaatcctat ggtgacatga atatggagaa ctcgacaaat    1080
gaccctgtta ccaacatatg tcatgctgct gacaagcagc ttttcaccct cgttgaatgg    1140
gccaagcgta ttccccactt ctctgacctc accttggagg accaggtcat tttgcttcgg    1200
gcagggtgga tgaattgct gattgcctct ttctcccacc gctcagtttc cgtgcaggat    1260
ggcatccttc tggccacggg tttacatgtc caccggagca gtgcccacag tgctggggtc    1320
ggctccatct ttgacagagt cctaactgag ctggtttcca aaatgaaaga catgcagatg    1380
gacaagtcgg aactgggatg cctgcgagcc attgtactct taacccaga tgccaagggc    1440
ctgtccaacc cctctgaggt ggagactctg cgagagaagg tttatgccac ccttgaggcc    1500
tacaccaagc agaagtatcc ggaacagcca ggcaggtttg ccaagctgct gctgcgcctc    1560
ccagctctgc gttccattgg cttgaaatgc ctggagcacc tcttcttctt caagctcatc    1620
ggggacaccc ccattgacac cttcctcatg gagatgttgg agaccccgct gcagatcacc    1680
tgagccccac cagccacagc ctccccaccc aggatgaccc ctgggcaggt gtgtgtggac    1740
cccacccctg cactttcctc cacctcccac cctgaccccc ttcctgtccc caaaatgtga    1800
tgcttataat aaagaaaacc tttctac                                       1827
```

<210> SEQ ID NO 22
<211> LENGTH: 463
<212> TYPE: PRT
<213> ORGANISM: Homo sapiens

<400> SEQUENCE: 22

```
Met Tyr Gly Asn Tyr Ser His Phe Met Lys Phe Pro Ala Gly Tyr Gly
1               5                   10                  15

Gly Ser Pro Gly His Thr Gly Ser Thr Ser Met Ser Pro Ser Ala Ala
            20                  25                  30

Leu Ser Thr Gly Lys Pro Met Asp Ser His Pro Ser Tyr Thr Asp Thr
        35                  40                  45
```

```
Pro Val Ser Ala Pro Arg Thr Leu Ser Ala Val Gly Thr Pro Leu Asn
 50                  55                  60

Ala Leu Gly Ser Pro Tyr Arg Val Ile Thr Ser Ala Met Gly Pro Pro
 65                  70                  75                  80

Ser Gly Ala Leu Ala Pro Pro Gly Ile Asn Leu Val Ala Pro Pro
                 85                  90                  95

Ser Ser Gln Leu Asn Val Val Asn Ser Val Ser Ser Glu Asp Ile
                100                 105                 110

Lys Pro Leu Pro Gly Leu Pro Gly Ile Gly Asn Met Asn Tyr Pro Ser
                115                 120                 125

Thr Ser Pro Gly Ser Leu Val Lys His Ile Cys Ala Ile Cys Gly Asp
130                 135                 140

Arg Ser Gly Lys His Tyr Gly Val Tyr Ser Cys Glu Gly Cys Lys
145                 150                 155                 160

Gly Phe Phe Lys Arg Thr Ile Arg Lys Asp Leu Ile Tyr Thr Cys Arg
                165                 170                 175

Asp Asn Lys Asp Cys Leu Ile Asp Lys Arg Gln Arg Asn Arg Cys Gln
                180                 185                 190

Tyr Cys Arg Tyr Gln Lys Cys Leu Val Met Gly Met Lys Arg Glu Ala
                195                 200                 205

Val Gln Glu Glu Arg Gln Arg Ser Arg Glu Arg Ala Glu Ser Glu Ala
210                 215                 220

Glu Cys Ala Thr Ser Gly His Glu Asp Met Pro Val Glu Arg Ile Leu
225                 230                 235                 240

Glu Ala Glu Leu Ala Val Glu Pro Lys Thr Glu Ser Tyr Gly Asp Met
                245                 250                 255

Asn Met Glu Asn Ser Thr Asn Asp Pro Val Thr Asn Ile Cys His Ala
                260                 265                 270

Ala Asp Lys Gln Leu Phe Thr Leu Val Glu Trp Ala Lys Arg Ile Pro
                275                 280                 285

His Phe Ser Asp Leu Thr Leu Glu Asp Gln Val Ile Leu Leu Arg Ala
                290                 295                 300

Gly Trp Asn Glu Leu Leu Ile Ala Ser Phe Ser His Arg Ser Val Ser
305                 310                 315                 320

Val Gln Asp Gly Ile Leu Leu Ala Thr Gly Leu His Val His Arg Ser
                325                 330                 335

Ser Ala His Ser Ala Gly Val Gly Ser Ile Phe Asp Arg Val Leu Thr
                340                 345                 350

Glu Leu Val Ser Lys Met Lys Asp Met Gln Met Asp Lys Ser Glu Leu
                355                 360                 365

Gly Cys Leu Arg Ala Ile Val Leu Phe Asn Pro Asp Ala Lys Gly Leu
370                 375                 380

Ser Asn Pro Ser Glu Val Glu Thr Leu Arg Glu Lys Val Tyr Ala Thr
385                 390                 395                 400

Leu Glu Ala Tyr Thr Lys Gln Lys Tyr Pro Glu Gln Pro Gly Arg Phe
                405                 410                 415

Ala Lys Leu Leu Leu Arg Leu Pro Ala Leu Arg Ser Ile Gly Leu Lys
                420                 425                 430

Cys Leu Glu His Leu Phe Phe Phe Lys Leu Ile Gly Asp Thr Pro Ile
                435                 440                 445

Asp Thr Phe Leu Met Glu Met Leu Glu Thr Pro Leu Gln Ile Thr
450                 455                 460
```

<210> SEQ ID NO 23

<211> LENGTH: 2081
<212> TYPE: DNA
<213> ORGANISM: Mus musculus

<400> SEQUENCE: 23

```
gtcacagcct aggctttgct ggggacctga gaaacgctgc cgccaagttg aagttcaagg      60
ccctgccttc cctgtgaact gacgtttgtg gctggtcaag ttcgggaaca agacgttgtc     120
atcacagctt agcgctctgt ggcctgcctg gccacatcca tccaacatgg tggacacaga     180
gagccccatc tgtcctctct ccccactgga ggcagatgac ctggaaagtc ccttatctga     240
agaattctta caagaaatgg gaaacattca agagatttct cagtccatcg gtgaggagag     300
ctctggaagc tttggttttg cagactacca gtacttagga agctgtccgg gctccgaggg     360
ctctgtcatc acagacaccc tctctccacg ttccagccct tcctcagtca gctgccccgt     420
gatccccgcc agcacggacg agtccccgg cagtgccctg aacatcgagt gtcgaatatg     480
tgggacaag gcctcagggt accactacg agttcacgca tgtgaaggct gtaagggctt     540
ctttcggcga actattcggc tgaagctggt gtacgacaag tgtgatcgga gctgcaagat     600
tcagaagaag aaccggaaca atgccagta ctgccgtttt cacaagtgcc tgtctgtcgg     660
gatgtcacac aatgcaattc gctttggaag aatgccaaga tctgaaaaag caaaactgaa     720
agcagaaatt cttacctgtg aacacgacct gaaagattcg gaaactgcag acctcaaatc     780
tctgggcaag agaatccacg aagcctacct gaagaacttc aacatgaaca aggtcaaggc     840
ccgggtcata ctcgcgggaa agaccagcaa caacccgcct tttgtcatac atgcatggga     900
gaccttgtgt atggccgaga gacgcttgt ggccaagatg gtggccaacg cgtcgaaga     960
caaagaggca gaggtccgat tcttccactg ctgccagtgc atgtccgtgg agaccgtcac    1020
ggagctcaca gaatttgcca aggctatccc aggctttgca acttggact tgaacgacca    1080
agtcaccttg ctaaagtacg gtgtgtatga agccatcttc acgatgctgt cctccttgat    1140
gaacaaagac gggatgctga tcgcgtacgg caatggcttt atcacacgcg agttccttaa    1200
gaacctgagg aagccgttct gtgacatcat ggaacccaag tttgacttcg ctatgaagtt    1260
caatgcctta gaactggatg acagtgacat ttccctgttt gtggctgcta taatttgctg    1320
tggagatcgg cctggcctt taaacatagg ctacattgag aagttgcagg aggggattgt    1380
gcacgtgctt aagctccacc tgcagagcaa ccatccagat gacccttcc tcttcccaaa    1440
gctccttcaa aaaatggtgg accttcggca gctggtcacg gagcatgcgc agctcgtaca    1500
ggtcatcaag aagaccgagt ccgacgcagc gctgcaccca ctgttgcaag atctacag    1560
agacatgtac tgatctttcc tgagatggca ggccattacc actgttcagg acctccgag    1620
gcctgcggcc ccatacagga gagcaggat ttgcacagag gcctccctc ctacgcttgg    1680
ggatgaagag gctgagcgt aggtaatgcg ggctctcccc acatcctttc tgaatgggca    1740
cttctaagac tacctgctac cgaaatgggg gtgatcggag gctaatagga ttcagacagt    1800
gacagacaac ggcagtcccc agtctggtct taaccggccc aatgttaatc aatgcacagc    1860
actctacgtt gcgtttataa ttcgccatta attaacgggt aacctcgaag tctgagcggt    1920
ctgttccctt cctgccaccc ttctggctat gtgcactctc ttaaatccct gaaaactaat    1980
ctgcactttt taacctttga aaacctacaa gtcaaggtgt ggcccaaggt tagccattta    2040
aatgtggcaa aaaaaaaaaa aaaaaaaaaa aaaaaaaa a                          2081
```

<210> SEQ ID NO 24
<211> LENGTH: 468
<212> TYPE: PRT

<213> ORGANISM: Mus musculus

<400> SEQUENCE: 24

```
Met Val Asp Thr Glu Ser Pro Ile Cys Pro Leu Ser Pro Leu Glu Ala
1               5                   10                  15

Asp Asp Leu Glu Ser Pro Leu Ser Glu Glu Phe Leu Gln Glu Met Gly
            20                  25                  30

Asn Ile Gln Glu Ile Ser Gln Ser Ile Gly Glu Glu Ser Ser Gly Ser
        35                  40                  45

Phe Gly Phe Ala Asp Tyr Gln Tyr Leu Gly Ser Cys Pro Gly Ser Glu
    50                  55                  60

Gly Ser Val Ile Thr Asp Thr Leu Ser Pro Arg Ser Ser Pro Ser Ser
65                  70                  75                  80

Val Ser Cys Pro Val Ile Pro Ala Ser Thr Asp Glu Ser Pro Gly Ser
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Leu Lys Asp Ser Glu Thr Ala Asp Leu Lys Ser Leu Gly Lys
        195                 200                 205

Arg Ile His Glu Ala Tyr Leu Lys Asn Phe Asn Met Asn Lys Val Lys
210                 215                 220

Ala Arg Val Ile Leu Ala Gly Lys Thr Ser Asn Asn Pro Pro Phe Val
225                 230                 235                 240

Ile His Asp Met Glu Thr Leu Cys Met Ala Glu Lys Thr Leu Val Ala
                245                 250                 255

Lys Met Val Ala Asn Gly Val Glu Asp Lys Glu Ala Glu Val Arg Phe
            260                 265                 270

Phe His Cys Cys Gln Cys Met Ser Val Glu Thr Val Thr Glu Leu Thr
        275                 280                 285

Glu Phe Ala Lys Ala Ile Pro Gly Phe Ala Asn Leu Asp Leu Asn Asp
290                 295                 300

Gln Val Thr Leu Leu Lys Tyr Gly Val Tyr Glu Ala Ile Phe Thr Met
305                 310                 315                 320

Leu Ser Ser Leu Met Asn Lys Asp Gly Met Leu Ile Ala Tyr Gly Asn
                325                 330                 335

Gly Phe Ile Thr Arg Glu Phe Leu Lys Asn Leu Arg Lys Pro Phe Cys
            340                 345                 350

Asp Ile Met Glu Pro Lys Phe Asp Phe Ala Met Lys Phe Asn Ala Leu
        355                 360                 365

Glu Leu Asp Asp Ser Asp Ile Ser Leu Phe Val Ala Ala Ile Ile Cys
370                 375                 380

Cys Gly Asp Arg Pro Gly Leu Leu Asn Ile Gly Tyr Ile Glu Lys Leu
385                 390                 395                 400

Gln Glu Gly Ile Val His Val Leu Lys Leu His Leu Gln Ser Asn His
```

405                 410                 415
Pro Asp Asp Thr Phe Leu Phe Pro Lys Leu Leu Gln Lys Met Val Asp
            420                 425                 430

Leu Arg Gln Leu Val Thr Glu His Ala Gln Leu Val Gln Val Ile Lys
        435                 440                 445

Lys Thr Glu Ser Asp Ala Ala Leu His Pro Leu Leu Gln Glu Ile Tyr
    450                 455                 460

Arg Asp Met Tyr
465

<210> SEQ ID NO 25
<211> LENGTH: 1323
<212> TYPE: DNA
<213> ORGANISM: Mus musculus

<400> SEQUENCE: 25
atggaacagc cacaggagga gacccctgag gcccgggaag aggagaaaga ggaagtggcc      60
atgggtgacg gagccccgga gctcaatggg ggaccagaac acacgcttcc ttccagcagc     120
tgtgcagacc tctcccagaa ttcctcccct tcctccctgc tggaccagct gcagatgggc     180
tgtgatgggg cctcaggcgg cagcctcaac atggaatgtc gggtgtgcgg ggacaaggcc     240
tcgggcttcc actacgggt ccacgcgtgc gaggggtgca agggcttctt ccgccggaca     300
atccgcatga agctcgagta tgagaagtgc gatcggatct gcaagatcca gaagaagaac     360
cgcaacaagt gtcagtactg ccgcttccag aagtgcctgg cactcggcat gtcgcacaac     420
gctatccgct ttggacggat gccggacggc gagaagagga gctggtggc ggggctgact      480 gccagcgagg ggtgccagca caaccccag ctggccgacc tgaaggcctt ctctaagcac      540
atctacaacg cctacctgaa aaacttcaac atgaccaaaa agaaggcccg gagcatcctc     600
accggcaagt ccagccacaa cgcacccttt gtcatccacg acatcgagac actgtgcag      660 gcagagaagg gcctggtgtg gaaacagctg gtgaacgggc tgccgcccta caacgagatc     720
agtgtgcacg tgttctaccg ctgccagtcc accacagtgg agacagtccg agagctcacc     780
gagttcgcca gaacatccc caacttcagc agcctcttcc tcaatgacca ggtgacccct     840
ctcaagtatg gcgtgcacga ggccatcttt gccatgctgg cctccatcgt caacaaagac     900
gggctgctgg tggccaacgg cagtggcttc gtcacccacg agttcttgcg aagtctccgc     960
aagcccttca gtgacatcat tgagcccaag ttcgagtttg ctgtcaagtt caatgcgctg    1020
gagctcgatg acagtgacct ggcgctcttc atcgcggcca tcattctgtg tggagaccgg    1080
ccaggcctca tgaatgtgcc ccaggtagaa gccatccagg acaccattct gcgggctcta    1140
gaattccatc tgcaggtcaa ccaccctgac agccagtacc tcttcccaa gctgctgcag    1200 aagatggcag acctgcggca gctggtcact gagcatgccc agatgatgca gtggctaaag    1260
aagacggaga gtgagacctt gctgcacccc ctgctccagg aaatctacaa ggacatgtac    1320
taa                                                                  1323

<210> SEQ ID NO 26
<211> LENGTH: 440
<212> TYPE: PRT
<213> ORGANISM: Mus musculus

<400> SEQUENCE: 26

Met Glu Gln Pro Gln Glu Glu Thr Pro Glu Ala Arg Glu Glu Glu Lys
1               5                   10                  15

Glu Glu Val Ala Met Gly Asp Gly Ala Pro Glu Leu Asn Gly Gly Pro

```
                    20                  25                  30
Glu His Thr Leu Pro Ser Ser Cys Ala Asp Leu Ser Gln Asn Ser
                35                  40                  45

Ser Pro Ser Ser Leu Leu Asp Gln Leu Gln Met Gly Cys Asp Gly Ala
 50                  55                  60

Ser Gly Gly Ser Leu Asn Met Glu Cys Arg Val Cys Gly Asp Lys Ala
 65                  70                  75                  80

Ser Gly Phe His Tyr Gly Val His Ala Cys Glu Gly Cys Lys Gly Phe
                85                  90                  95

Phe Arg Arg Thr Ile Arg Met Lys Leu Glu Tyr Glu Lys Cys Asp Arg
                100                 105                 110

Ile Cys Lys Ile Gln Lys Lys Asn Arg Asn Lys Cys Gln Tyr Cys Arg
                115                 120                 125

Phe Gln Lys Cys Leu Ala Leu Gly Met Ser His Asn Ala Ile Arg Phe
                130                 135                 140

Gly Arg Met Pro Asp Gly Glu Lys Arg Lys Leu Val Ala Gly Leu Thr
145                 150                 155                 160

Ala Ser Glu Gly Cys Gln His Asn Pro Gln Leu Ala Asp Leu Lys Ala
                165                 170                 175

Phe Ser Lys His Ile Tyr Asn Ala Tyr Leu Lys Asn Phe Asn Met Thr
                180                 185                 190

Lys Lys Lys Ala Arg Ser Ile Leu Thr Gly Lys Ser Ser His Asn Ala
                195                 200                 205

Pro Phe Val Ile His Asp Ile Glu Thr Leu Trp Gln Ala Glu Lys Gly
210                 215                 220

Leu Val Trp Lys Gln Leu Val Asn Gly Leu Pro Pro Tyr Asn Glu Ile
225                 230                 235                 240

Ser Val His Val Phe Tyr Arg Cys Gln Ser Thr Thr Val Glu Thr Val
                245                 250                 255

Arg Glu Leu Thr Glu Phe Ala Lys Asn Ile Pro Asn Phe Ser Ser Leu
                260                 265                 270

Phe Leu Asn Asp Gln Val Thr Leu Leu Lys Tyr Gly Val His Glu Ala
                275                 280                 285

Ile Phe Ala Met Leu Ala Ser Ile Val Asn Lys Asp Gly Leu Leu Val
                290                 295                 300

Ala Asn Gly Ser Gly Phe Val Thr His Glu Phe Leu Arg Ser Leu Arg
305                 310                 315                 320

Lys Pro Phe Ser Asp Ile Ile Glu Pro Lys Phe Glu Phe Ala Val Lys
                325                 330                 335

Phe Asn Ala Leu Glu Leu Asp Asp Ser Asp Leu Ala Leu Phe Ile Ala
                340                 345                 350

Ala Ile Ile Leu Cys Gly Asp Arg Pro Gly Leu Met Asn Val Pro Gln
                355                 360                 365

Val Glu Ala Ile Gln Asp Thr Ile Leu Arg Ala Leu Glu Phe His Leu
                370                 375                 380

Gln Val Asn His Pro Asp Ser Gln Tyr Leu Phe Pro Lys Leu Leu Gln
385                 390                 395                 400

Lys Met Ala Asp Leu Arg Gln Leu Val Thr Glu His Ala Gln Met Met
                405                 410                 415

Gln Trp Leu Lys Lys Thr Glu Ser Glu Thr Leu Leu His Pro Leu Leu
                420                 425                 430

Gln Glu Ile Tyr Lys Asp Met Tyr
                435                 440
```

-continued

```
<210> SEQ ID NO 27
<211> LENGTH: 68
<212> TYPE: DNA
<213> ORGANISM: Artificial Sequence
<220> FEATURE:
<223> OTHER INFORMATION: GAL4 Upstream Activating Sequence used in the
      LXRalpha or LXRbeta-LBD-Gal4 fusion
<220> FEATURE:
<221> NAME/KEY: misc_feature
<222> LOCATION: (4)..(4)
<223> OTHER INFORMATION: n = A or G
<220> FEATURE:
<221> NAME/KEY: misc_feature
<222> LOCATION: (5)..(6)
<223> OTHER INFORMATION: n = A, C, T or G
<220> FEATURE:
<221> NAME/KEY: misc_feature
<222> LOCATION: (7)..(7)
<223> OTHER INFORMATION: n = A or G
<220> FEATURE:
<221> NAME/KEY: misc_feature
<222> LOCATION: (9)..(9)
<223> OTHER INFORMATION: n = C or T
<220> FEATURE:
<221> NAME/KEY: misc_feature
<222> LOCATION: (10)..(10)
<223> OTHER INFORMATION: n = A, C, T or G
<220> FEATURE:
<221> NAME/KEY: misc_feature
<222> LOCATION: (11)..(11)
<223> OTHER INFORMATION: n = C or T
<220> FEATURE:
<221> NAME/KEY: misc_feature
<222> LOCATION: (12)..(12)
<223> OTHER INFORMATION: n = A, C, T or G
<220> FEATURE:
<221> NAME/KEY: misc_feature
<222> LOCATION: (14)..(14)
<223> OTHER INFORMATION: n = A, C, T or G
<220> FEATURE:
<221> NAME/KEY: misc_feature
<222> LOCATION: (21)..(21)
<223> OTHER INFORMATION: n = A or G
<220> FEATURE:
<221> NAME/KEY: misc_feature
<222> LOCATION: (22)..(23)
<223> OTHER INFORMATION: n = A, C, T or G
<220> FEATURE:
<221> NAME/KEY: misc_feature
<222> LOCATION: (24)..(24)
<223> OTHER INFORMATION: n = A or G
<220> FEATURE:
<221> NAME/KEY: misc_feature
<222> LOCATION: (26)..(26)
<223> OTHER INFORMATION: n = C or T
<220> FEATURE:
<221> NAME/KEY: misc_feature
<222> LOCATION: (27)..(27)
<223> OTHER INFORMATION: n = A, C, T or G
<220> FEATURE:
<221> NAME/KEY: misc_feature
<222> LOCATION: (28)..(28)
<223> OTHER INFORMATION: n = C or T
<220> FEATURE:
<221> NAME/KEY: misc_feature
<222> LOCATION: (29)..(29)
<223> OTHER INFORMATION: n = A, C, T or G
<220> FEATURE:
<221> NAME/KEY: misc_feature
<222> LOCATION: (31)..(31)
<223> OTHER INFORMATION: n = A, C, T or G
<220> FEATURE:
<221> NAME/KEY: misc_feature
<222> LOCATION: (38)..(38)
<223> OTHER INFORMATION: n = A or G
<220> FEATURE:
<221> NAME/KEY: misc_feature
<222> LOCATION: (39)..(40)
<223> OTHER INFORMATION: n = A, C, T or G
```

```
<220> FEATURE:
<221> NAME/KEY: misc_feature
<222> LOCATION: (41)..(41)
<223> OTHER INFORMATION: n = A or G
<220> FEATURE:
<221> NAME/KEY: misc_feature
<222> LOCATION: (43)..(43)
<223> OTHER INFORMATION: n = C or T
<220> FEATURE:
<221> NAME/KEY: misc_feature
<222> LOCATION: (44)..(44)
<223> OTHER INFORMATION: n = A, C, T or G
<220> FEATURE:
<221> NAME/KEY: misc_feature
<222> LOCATION: (45)..(45)
<223> OTHER INFORMATION: n = C or T
<220> FEATURE:
<221> NAME/KEY: misc_feature
<222> LOCATION: (46)..(46)
<223> OTHER INFORMATION: n = A, C, T or G
<220> FEATURE:
<221> NAME/KEY: misc_feature
<222> LOCATION: (48)..(48)
<223> OTHER INFORMATION: n = A, C, T or G
<220> FEATURE:
<221> NAME/KEY: misc_feature
<222> LOCATION: (55)..(55)
<223> OTHER INFORMATION: n = A or G
<220> FEATURE:
<221> NAME/KEY: misc_feature
<222> LOCATION: (56)..(57)
<223> OTHER INFORMATION: n = A, C, T or G
<220> FEATURE:
<221> NAME/KEY: misc_feature
<222> LOCATION: (58)..(58)
<223> OTHER INFORMATION: n = A or G
<220> FEATURE:
<221> NAME/KEY: misc_feature
<222> LOCATION: (60)..(60)
<223> OTHER INFORMATION: n = C or T
<220> FEATURE:
<221> NAME/KEY: misc_feature
<222> LOCATION: (61)..(61)
<223> OTHER INFORMATION: n = A, C, T or G
<220> FEATURE:
<221> NAME/KEY: misc_feature
<222> LOCATION: (62)..(62)
<223> OTHER INFORMATION: n = C or T
<220> FEATURE:
<221> NAME/KEY: misc_feature
<222> LOCATION: (63)..(63)
<223> OTHER INFORMATION: n = A, C, T or G
<220> FEATURE:
<221> NAME/KEY: misc_feature
<222> LOCATION: (65)..(65)
<223> OTHER INFORMATION: n = A, C, T or G

<400> SEQUENCE: 27
cggnnnncnn nncnccgcgg nnnncnnnnc nccgcggnnn ncnnnncncc gcggnnnncn    60 nnncnccg                                                             68
```